United States Patent

Nakamura et al.

Patent Number: 5,556,852
Date of Patent: *Sep. 17, 1996

[54] N-ACRYLOYLPIPERAZINE COMPOUNDS

[75] Inventors: Norio Nakamura; Nobuyuki Ohkawa; Takeshi Oshima; Masaaki Miyamoto; Yasuteru Iijima, all of Tokyo, Japan

[73] Assignee: Sankyo Company, Limited, Tokyo, Japan

[ * ] Notice: The term of this patent shall not extend beyond the expiration date of Pat. No. 5,369,106.

[21] Appl. No.: 320,445

[22] Filed: Oct. 7, 1994

Related U.S. Application Data

[62] Division of Ser. No. 973,086, Nov. 6, 1992, Pat. No. 5,369,106, which is a division of Ser. No. 751,871, Aug. 28, 1991, Pat. No. 5,192,766, which is a continuation-in-part of Ser. No. 514,523, Apr. 25, 1990, abandoned.

[30] Foreign Application Priority Data

Apr. 28, 1989 [JP] Japan ..................... 1-111295

[51] Int. Cl.$^6$ .................. A01N 43/62; A01N 43/60; C07D 741/04
[52] U.S. Cl. .................. 514/218; 514/253; 514/255; 540/575; 544/384; 544/387; 544/391; 544/400
[58] Field of Search .................. 514/218, 253, 514/255; 540/575; 544/406, 384, 391, 387

[56] References Cited

U.S. PATENT DOCUMENTS

| | | | |
|---|---|---|---|
| 4,788,206 | 11/1988 | Guthrie et al. | 514/346 |
| 4,794,183 | 12/1988 | Nakamura et al. | 546/22 |
| 4,891,363 | 1/1990 | Nakamura et al. | 514/94 |
| 5,068,340 | 11/1991 | Nakamura et al. | 548/119 |

FOREIGN PATENT DOCUMENTS

| | | |
|---|---|---|
| 0284359 | 9/1988 | European Pat. Off. . |
| 0298466 | 1/1989 | European Pat. Off. . |
| 60-193966 | 10/1985 | Japan . |

*Primary Examiner*—C. Warren Ivy
*Assistant Examiner*—Raymond Covington
*Attorney, Agent, or Firm*—Frishauf, Holtz, Goodman, Langer & Chick, P.C.

[57] ABSTRACT

Compounds of formula (I):

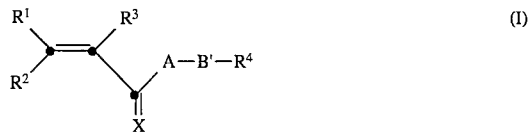

wherein $R^1$ and $R^2$ is each $-R^5$, $-CH=CH-R^5$ or $-C\equiv C-R^5$, wherein $R^5$ is optionally substituted aryl or aromatic heterocyclic; $R^3$ is hydrogen, alkyl, cyano or $-R^5$; X is oxygen or sulfur A is 1,4-piperazin-1,4-diyl or a 1,4-homopiperazin-1,4-diyl; B' is alkylene, carbonyl, thiocarbonyl, sulfinyl or sulfonyl: and $R^4$ is optionally substituted phenyl and pharmaceutically acceptable salts thereof have valuable PAF antagonist activity.

5 Claims, No Drawings

N-ACRYLOYLPIPERAZINE COMPOUNDS

This is a division of application Ser. No. 07/973,086 filed Nov. 6, 1992, now U.S. Pat. No. 5,369,106 which is a division of application Ser. No. 07/751,871 filed Aug. 28, 1991 (now U.S. Pat. No. 5,192,766), which is a continuation-in-part of application Ser. No. 07/514,523 filed Apr. 25, 1990 (abandoned).

BACKGROUND TO THE INVENTION

The present invention relates to a series of novel N-acryloylpiperazine derivatives which have PAF antagonist activity and provides processes for preparing these deriviatives, as well as methods and compositions using them for the treatment of various diseases and disorders arising from the imbalances in the PAF system in the mammalian, e.g. human, body.

The abbreviation "PAF" as used herein means, as is conventional "platelet activating factor".

Natural PAF, at least as isolated from mammalian tissues, is a mixture of from 2 to 5 phospholipids, the number depending upon the nature of the original tissue. The formulae of the major constituents of PAF are now well know. Natural PAF is levorotatory and the various components of natural PAF may be identified, for examples as: $1-C_{16:0}=PAF$ where the alkoxy group at the PAF 1-position is a hexadecyloxy group; $1-C_{18:0}=PAF$ where the alkoxy group at the PAF 1-position is an octadecyloxy group; or $1-C_{18:1}=PAF$ where the alkoxy group at the PAF 1-position is a 9-(Z)-octadecenyloxy group. The convention used above for identifying the constituents of PAF gives the rotation first (l, in the above examples), followed by the number of carbon atoms in the 1-alkoxy group, and finally the number of double bonds.

PAF exhibits effect, from which it derives its name. It has, however, in recent years been seen to be a potentially crucial mediator in a wide variety of pathological processes. Thus, it also has a hypotensive effect and increases vasopermeability; it is believed to be an active agent in the induction of the shock state (for example endotoxin-induced shock or anaphylactic shock) and to act as a mediator of inflammatory disease. It has also been found to play an important role in nephritis, myocardial infarction, angina pectoris, asthma, cardiac and systemic anaphylaxis, gastric and intestinal ulceration, psoriasis and immune and renal disorders. In addition, it is believed that PAF antagonists may be useful for prophylaxis of rejection in organ transplantation.

It is not, therefore, surprising that, as a result, PAF antagonists have been investigated with a view to developing new types of treatment for the above pathologies, and notably new types of anti-shock agent and anti-inflammatory agent. Accordingly, various compounds have been investigated in an attempt to find such PAF antagonists, and, currently, several compounds are known as PAF antagonists. Although the chemical structure of known PAF antagonists varies widely, and there appears to be no obvious common factor linking all of their chemical structures, in general, known materials having PAF-antagonist activity may be classified according to their chemical structure as either PAF type or non-PAF type compounds. The compounds of the present invention are non-PAF type compounds, and specifically are compounds containing an N-acryloylpiperazine or N-acryloylhomopiperazine system.

Amongst known such compounds which have structures similar to those of the compounds of present invention and which are said to have similar types of activities are:

the pentadienylamido compounds disclosed, inter alia, in U.S. Pat. No. 4,788,206;

the alkenyl-, alkenoyl- or thioalkenoyl- amido compounds disclosed, inter alia, in European Patent Publication No. 298 466; and the polycycloalkylcarbonyl- piperazine or homopiperazine compounds disclosed, inter alia, in European Patent Publication No. 284 359.

Also known are the N-nicotinoylpiperazine derivatives of Japanese Patent Application Kokai No. Sho. 60-193966, but these are only disclosed to have peripheral vasodilating and anti-hypertensive activities, and there is no suggestion that the compounds are PAF antagonists.

The compounds of the prior art referred to above all have structures different from those of the compounds of the present invention, although, in some cases, the prior compounds may share elements of the structures of the compounds of the present invention. In particular, none of the prior compounds is an N-acryloylpiperazine or N-acryloylhomopiperazine compound.

We have now discovered a series of new N-acryloylpiperazine and N-acryloylhomopiperazine derivatives which have excellent PAF antagonist activity and many of which have shown an excellent and wholly unexpected stability, even when administered orally, to give a high blood concentration. The activities of many of the compounds of the present invention have shown indications of being substantially better than those of the compounds of the prior art, including those referred to above and having structures similar to those of the compounds of the present invention.

BRIEF SUMMARY OF INVENTION

Accordingly, it is an object of the present invention to provide a series of new N-acryloylpiperazine derivatives as a new composition of matter.

It is a further, and more specific, object of the invention to provide such N-acryloylpiperazine derivatives having improved PAF antagonist activity and preferably stability on oral administration to a mammal.

It is a still further object of the invention to provide compositions containing these compounds and methods using them for the treatment and prophylaxis of PAF-related diseases and disorders.

Other objects and advantages will become apparent as the description proceeds.

In accordance with the present invention, there are provided as new compounds those acryloylpiperazine and acryloylhomopiperazine compounds having the formula (I):

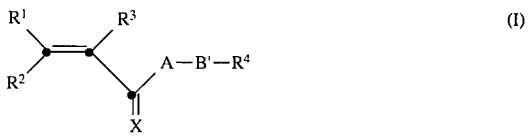

wherein:

R¹ and R² are the same or different, and each represents a group having the formula —R⁵, —CH=CH—R⁵ or —C≡C—R⁵, wherein R⁵ represents a $C_6$–$C_{14}$ carbocyclic aryl group which is unsubstituted or has at least one substituent selected from the group consisting of substituents (a), defined below, or an aromatic heterocyclic group having from 5 to 14 ring atoms, of which from 1 to 5 are hetero-atoms selected from the group consisting of nitrogen, oxygen and sulfur hetero-atoms, said heterocyclic group being unsubstituted or having at least one substituent selected from the group consisting of substituents (a), defined below;

$R^3$ represents a hydrogen atom, a $C_1$-$C_6$ alkyl group, a cyano group, or a group having the formula —$R^5$ in which $R^5$ is as defined above;

X represents an oxygen atom or a sulfur atom;

A represents a 1,4-piperazin-1,4-diyl group or a 1,4-homopiperazin-1,4-diyl group;

B' represents a $C_1$-$C_6$ alkylene group, a carbonyl group, a thiocarbonyl group, a sulfinyl group or a sulfonyl group;

$R^4$ represents an unsubstituted phenyl group or a substituted phenyl group having from 1 to 5 substituents selected from the group consisting of substituents (a) and substituents (b), defined below;

substituents (a):

$C_1$-$C_{22}$ alkyl groups; $C_1$-$C_{22}$ alkoxy groups; $C_1$-$C_6$ haloalkyl groups; hydroxy groups; $C_1$-$C_4$ alkylenedioxy groups; $C_1$-$C_{22}$ aliphatic carboxylic acyloxy groups; substituted $C_1$-$C_6$ aliphatic carboxylic acyloxy groups having at least one substituent selected from the group consisting of substituents (c), defined below; $C_7$-$C_{15}$ carbocyclic aromatic carboxylic acyloxy groups; substituted $C_7$-$C_{15}$ carbocyclic aromatic carboxylic acyloxy groups having at least one substituent selected from the group consisting of substituents (d), defined below; $C_8$-$C_{15}$ aralkyloxycarbonyloxy groups in which the aryl part is unsubstituted or has at least one substituent selected from the group consisting of substituents (d) defined below; $C_1$-$C_6$, alkanesulfonyloxy groups in which the alkane part is unsubstituted or has at least one substituent selected from the group consisting of substituents (c), defined below; arylsulfonyloxy groups in which the aryl part is unsubstituted or has at least one substituent selected from the group consisting of substituents (d), defined below; halogen atoms; and nitro groups;

substituents (b):

$C_1$-$C_6$ alkylsulfonyl groups; $C_1$-$C_6$ alkylsulfinyl groups; and $C_1$-$C_6$ alkylthio groups;

substituents (c):

$C_1$-$C_6$ alkyl groups; $C_1$-$C_6$ haloalkyl groups; halogen atoms; $C_1$-$C_6$ alkoxy groups; and ($C_1$-$C_6$ alkanoyloxy)methoxycarbonyl groups;

substituents (d):

$C_1$-$C_6$, alkyl groups; $C_1$-$C_6$ alkoxy groups; halogen atoms; unsubstituted $C_6$-$C_{10}$ aryl groups; nitro groups; and ($C_1$-$C_6$ alkoxy)carbonyl groups;

and pharmaceutically acceptable salts thereof.

The invention also provides a pharmaceutical composition for the treatment or prophylaxis of PAF-related diseases and disorders, comprising at least one PAP antagonist in combination with a pharmaceutically acceptable carrier or diluent, wherein the PAF antagonist is selected from the group consisting of compounds of formula (I), as defined above, and pharmaceutically acceptable salts thereof.

The invention still further provides a method of treating a PAF-mediated pathology in a mammal susceptible to such pathology, which may be a human being, by administering to said mammal an effective amount of at least one PAF antagonist selected from the group consisting of a compound of formula (I), as defined above, and pharmaceutically acceptable salts thereof.

The invention still further provides a method for the treatment or prophylaxis of psoriasis, nephritis, asthma, inflammation or shock comprising administering an amount of at least one PAF antagonist to an animal (which may be a mammal, e.g. human) sufficient to effect treatment or prophylaxis of psoriasis, nephritis, asthma, inflammation or shock, wherein said PAF antagonist is selected from the group consisting of a compound of formula (I), as defined above and pharmaceutically acceptable salts thereof.

The invention also provides processes for the preparation of the compounds of the present invention, which are described in greater detail hereafter.

DETAILED DESCRIPTION OF INVENTION

In the compounds of the present invention $R^1$ and $R^2$ are the same or different and each represents a group of formula —$R^5$, —CH=CH—$R^5$ or —C≡C—$R^5$, where $R^5$ is as defined above.

Where $R^5$ represents an aryl group, this is a carbocyclic aryl group which has from 6 to 14, preferably from 6 to 12 and more preferably from 6 to 10, ring carbon atoms, and which may be substituted or unsubstituted. Where the group is substituted, the substituents are selected from the group consisting of substituents (a), defined above and exemplified below. Examples of such unsubstituted groups include the phenyl and naphthyl (1- or 2-naphthyl) groups, preferably the phenyl group.

It is believed that the nature of the substituents on the phenyl groups represented by $R^5$, which may be or may be included in the groups represented by $R^1$ and $R^2$, may have a significant effect on the efficacy of the compounds of the present invention, although the exact nature of this effect has not been fully elucidated. In general, we prefer those compounds where $R^1$ and/or $R^2$ represents a group $R^5$ and more prefer those where $R^1$ and/or $R^2$ represents a group $R^5$ where $R^5$ represents an aryl group; most preferably one of the groups represented by $R^5$ is a substituted phenyl group and the other is an unsubstituted phenyl group or a substituted phenyl group. Still more preferably, in the group $R^5$ represented by or included in the group represented by $R^1$, there is an electron-donating substituent (e.g. a methoxy group) or an electron-withdrawing substituent (e.g. a chlorine atom) on the aryl group; and, in the group $R^5$ represented by or included in the group represented by $R^2$, there is no substituent, an alkyl substituent or an electron-withdrawing substituent on the aryl group. This applies even when $R^1$ and/or $R^2$ represents a group of formula —CH=CH—$R^5$ or —C≡C—$R^5$, but these compounds are most preferred when $R^1$ and $R^2$ are different and both represent a group of formula —$R^5$.

Where $R^2$ represents a substituted phenyl group, it is preferably substituted at least at the meta-position.

Examples of groups and atoms which may be included within substituents (a) are:

$C_1$-$C_{22}$ alkyl groups, which may be straight or branched chain groups, such as the methyl, ethyl, propyl, isopropyl, buryl, isobutyl, sec-butyl, t-butyl, pentyl, isopentyl, 2-methylbutyl, neopentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, t-pentyl, isohexyl, 1-methylpentyl, heptyl, 1-methylhexyl, 2-methylhexyl, 5-methylhexyl, 3-ethylpentyl, octyl, 2-methylheptyl, 5-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3, 5-dimethylnonyl, 3-propyloctyl, 5-ethyl-4-methyloctyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl and docosyl groups, preferably a straight or branched chain alkyl group having from 1 to 6 carbon atoms, and more preferably a straight or branched chain alkyl group having from 1 to 4 carbon atoms;

$C_1$–$C_{22}$ alkoxy groups which nay be straight or branched chain groups, such as the methoxy, ethoxy, propoxy, isopropoxy, butoxy, isobutoxy, sec-butoxy, t-butoxy, pentoxy, isopentoxy, 2-methylbutoxy, neopentoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, t-pentoxy, isohexyloxy, 1-methylpentoxy, heptyloxy, 1-methylhexyloxy, 2-methylhexyloxy, 5-methylhexyloxy, 3-ethylpentoxy, octyloxy, 2-methylheptyloxy, 5-methylheptyloxy, 2-ethylhexyloxy, 2-ethyl-3-methylpentoxy, 3-ethyl-2-methylpentoxy, nonyloxy, 2-methyloctyloxy, 7-methyloctyloxy, 4-ethylhexyloxy, 3-ethyl-2-methylhexyloxy, 2-ethyl- 1-methylhexyloxy, decyloxy, 2-methylnonyl oxy, 8-methylnonyloxy, 5-ethyloctyloxy, 3-ethyl-2-methylheptyloxy, 3,3-diethylhexyloxy, undecyloxy, 2-methyldecyloxy, 9-methyldecyloxy, 4-ethylnonyloxy, 3,5-dimethylnonyloxy, 3-propyloctyloxy, 5-ethyl-4-methyloctyloxy, dodecyloxy, 1-methylundecyloxy, 10-methylundecyloxy, 3-ethyldecyloxy, 5-propylnonyloxy, 3,5-diethyloctyloxy, tridecyloxy, 11-methyldodecyloxy, 7-ethylundecyloxy, 4-propyldecyloxy, 5-ethyl-3-methyldecyloxy, 3-pentyloctyloxy, tetradecyloxy, 12-methyltridecyloxy, 8-ethyldodecyloxy, 6-propylundecyloxy, 4-butyldecyloxy, 2-pentylnonyloxy, pentadecyloxy, 13-methyltetradecyloxy, 10-ethyltridecyloxy, 7-propyldodecyloxy, 5-ethyl-3-methyldodecyloxy, 4-pentyldecyloxy, hexadecyloxy, 14-methylpentadecyloxy, 6-ethyltetradecyloxy, 4-propyltridecyloxy, 2-butyldodecyloxy, heptadecyloxy, 15-methylhexadecyloxy, 7-ethylpentadecyloxy, 3-propyltetradecyloxy, 5-pentyldodecyloxy, octadecyloxy, 16-methylheptadecyloxy, 5-propylpentadecyloxy, nonadecyloxy, 17-methyloctadecyloxy, 4-ethylheptadecyloxy, icosyloxy, 18-methylnonadecyloxy, 3-ethyloctadecyloxy, henicosyl and docosyl groups, preferably a straight or branched chain alkoxy group having from 1 to 6 carbon atoms, and more preferably a straight or branched chain alkoxy group having from 1 to 4 carbon atoms;

$C_1$–$C_6$ haloalkyl groups, in which the alkyl part may be any one of those alkyl groups exemplified above, and is more preferably a $C_1$–$C_4$ alkyl group, and the halogen atom may be a fluorine, chlorine, bromine or iodine atom, preferably a fluorine or chlorine atom, such as the fluoromethyl, trifluoromethyl, difluoromethyl, dichloromethyl, dibromomethyl, trichloromethyl, 2,2,2-trichloroethyl, 2,2,2-trifluoroethyl, 2-haloethyl (e.g. 2-chloroethyl, 2-fluoroethyl, 2-bromoethyl or 2-iodoethyl), 2,2-dibromoethyl, 2,2,2-tribromoethyl, pentafluoroethyl, 4-chlorobutyl, 4-bromobutyl and 4-fluorobutyl groups, preferably the trifluoromethyl, trichloromethyl and pentafluoroethyl groups;

hydroxy groups;

$C_1$–$C_4$ alkylenedioxy groups in which the alkylene part may be a straight or branched chain group; examples include the methylenedioxy, dimethylenedioxy, trimethylenedioxy, tetramethylenedioxy, ethylidenedioxy and isopropylidenedioxy groups, of which the methylenedioxy group is preferred;

unsubstituted $C_1$–$C_{22}$ aliphatic carboxylic acyloxy groups, in which the acyl part may contain one or more carbon-carbon double or triple bonds or may be free from such bonds, and in the case of the unsaturated groups, the number of carbon atoms is preferably from 3 to 6; examples of such groups include the alkanoyloxy groups, such as the formyloxy, acetoxy, propionyloxy, butyryloxy, isobutyryloxy, pivaloyloxy, valeryloxy, isovaleryloxy, octanoyloxy, nonylcarbonyloxy, decylcarbonyloxy, 3-methylnonylcarbonyloxy, 8-methylnonylcarbonyloxy, 3-ethyloctylcarbonyloxy, 3,7-dimethyloctylcarbonyloxy, undecylcarbonyloxy, dodecylcarbonyloxy, tridecylcarbonyloxy, tetradecylcarbonyloxy, pentadecylcarbonyloxy, hexadecylcarbonyloxy, 1-methylpentadecyl carbonyl oxy, 14-methylpentadecylcarbonyloxy, 13,13-dimethyltetradecylcarbonyloxy, heptadecylcarbonyloxy, 15-methylhexadecylcarbonyloxy, octadecylcarbonyloxy, 1-methylheptadecyclcarbonyloxy, nonadecylcarbonyloxy, icosylcarbonyloxy, and henicosylcarbonyloxy groups; unsaturated analogs of these alkanoyloxy groups, especially the $C_3$–$C_6$ alkenoyloxy and alkynoyloxy groups, such as the (E)-2-methyl-2-butenoyloxy group; alkoxycarbonyloxy groups, especially $C_2$–$C_7$ alkoxycarbonyloxy groups (i.e. the alkoxy part is $C_1$–$C_6$), such as the methoxycarbonyloxy, ethoxycarbonyloxy, t-butoxycarbonyloxy and isobutoxycarbonyloxy groups; such alkoxycarbonyloxy groups having one or more halogen or trialkylsilyl substituents (in which each alkyl group, which may be the same or different, has from 1 to 4 carbon atoms, and in which one such alkyl group may be replaced by a phenyl group), such as the 2,2,2-trichloroethoxycarbonyloxy and 2-trimethylsilylethoxycarbonyloxy groups; and the alkenyloxycarbonyloxy groups, such as the vinyloxycarbonyloxy and allyloxycarbonyloxy groups;

substituted $C_1$–$C_6$ aliphatic carboxylic acyloxy groups having at least one substituent selected from the group consisting of substituents (c), defined above and exemplified more generally below; the acyloxy part may be any of the $C_1$–$C_6$ unsubstituted acyloxy groups exemplified above, and specific examples of the substituted groups include: the halogenated alkanoyloxy groups, such as the chloroacetoxy, dichloroacetoxy, trichloroacetoxy and trifluoroacetoxy groups; the alkoxyalkanoyloxy groups, such as the methoxyacetoxy group; and the ($C_1$–$C_6$ alkanoyloxy)methoxycarbonyl groups, such as the pivaloyloxymethoxycarbonyloxy group;

$C_7$–$C_{15}$, preferably $C_7$–$C_{11}$, carbocyclic aromatic carboxylic acyloxy groups (i.e. an arylcarbonyl group in which the aryl part is $C_6$–$C_{14}$, preferably $C_6$–$C_{10}$), which may be unsubstituted or may have one or more substituents selected from the group consisting of substituents (d), defined above and exemplified more generally below; examples of such unsubstituted groups include the benzoyloxy, α-naphthoyloxy and β-naphthoyloxy groups; the substituted groups may be any of these unsubstituted groups but having at least one, and preferably from 1 to 5, more preferably from 1 to 3, substituents selected from the group consisting of substituents (d); examples of the substituted groups include: halogenated arylcarbonyloxy groups, such as the 2-bromobenzoyloxy and 4-chlorobenzoyloxy groups; arylcarbonyloxy groups substituted by one or more lower (i.e. $C_1$–$C_6$, preferably $C_1$–$C_4$) alkyl groups, such as the 2,4,6-trimethylbenzoyloxy and p-toluoyloxy groups; arylcarbonyloxy groups substituted by one or more lower (i.e. $C_1$–$C_6$, preferably $C_1$–$C_4$) alkoxy groups, such as the 4-anisoyloxy group; arylcarbonyloxy groups substituted by one or more nitro groups, such as the 4-nitrobenzoyloxy and 2-nitrobenzoyloxy groups; arylcarbonyloxy groups substituted by one or more lower (i.e. $C_2$–$C_7$, preferably $C_2$–$C_5$) alkoxycarbonyl groups, such as the 2-(methoxycarbonyl)benzoyloxy group; and arylcarbonyloxy groups substituted by one or more aryl groups, such as the 4-phenylbenzoyloxy group;

$C_8$–$C_{15}$ aralkyloxycarbonyloxy groups in which the aryl part is $C_6$–$C_{10}$ and the alkyl part is correspondingly $C_1$–$C_4$; these groups may be unsubstituted or may have at least one substituent, preferably on the aryl part or parts, selected from the group consisting of substituents (d), defined above and exemplified more generally below, preferably one or two lower alkoxy or nitro groups; the alkyl part is preferably unsubstituted; examples of such unsubstituted groups include the benzyloxycarbonyloxy group; and examples of such substituted groups include the unsubstituted groups referred to but having one or more, preferably from 1 to 5, more preferably from 1 to 3, of substituents (d), such as the 4-methoxybenzyloxycarbonyloxy, 3,4-dimethoxybenzyloxycarbonyloxy, 2-nitrobenzyloxycarbonyloxy and 4-nitrobenzyloxycarbonyloxy groups;

$C_1$–$C_6$ alkanesulfonyloxy groups in which the alkane part is unsubstituted or has at least one substituent selected from the group consisting of substituents (c), defined above and exemplified more generally below, preferably halogen atoms and more preferably fluorine atoms; examples of such groups include the lower (i.e. $C_1$–$C_6$, preferably $C_1$–$C_4$) alkanesulfonyloxy groups, such as the methanesulfonyloxy, ethanesulfonyloxy and 1-propanesulfonyloxy groups; and fluorinated lower alkanesulfonyloxy groups, such as the trifluoromethanesulfonyloxy and pentafluoroethanesulfonyloxy groups;

arylsulfonyloxy groups in which the aryl part is $C_6$–$C_{10}$ and may be unsubstituted or may have at least one substituent selected from the group consisting of substituents (d), defined above and exemplified more generally below; examples of such unsubstituted groups include the benzenesulfonyloxy group, and examples of such substituted groups include the unsubstituted groups referred to but having one or more, preferably from 1 to 5, more preferably from 1 to 3, of substituents (d), such as the p-toluenesulfonyloxy group;

halogen atoms, such as the fluorine, chlorine, bromine and iodine atoms, preferably the fluorine, chlorine and bromine atoms; and nitro groups.

Where substituent (a) is one of the aforementioned acyloxy groups, it may, if desired, be an acyloxy group which is easily hydrolysed in vivo, so as to form a pro-drug, which may be administered as the ester [substituent (a) is the acyloxy group], and is then converted to the free acid [substituent (a) is a hydroxy group], in vivo. Examples of such groups include: the ($C_1$–$C_6$ alkanoyloxy)methoxycarbonyl groups, especially the pivaloyloxymethoxycarbonyloxy group; the alkanesulfonyloxy groups, especially the methanesulfonyloxy, ethanesulfonyloxy and 1-propanesulfonyloxy groups; the fluorinated alkanesulfonyloxy groups, especially the trifluoromethanesulfonyloxy and pentafluoroethanesulfonyloxy groups; and the arylsulfonyloxy groups, especially the benzenesulfonyloxy and p-toluenesulfonyloxy groups.

Examples of groups and atoms included in substituents (c) are:

the $C_1$–$C_6$, preferably $C_1$–$C_4$, alkyl groups, such as those exemplified above in relation to substituents (a);

the $C_1$–$C_6$, preferably $C_1$–$C_4$, haloalkyl groups, such as those exemplified above in relation to substituents (a), and especially the trifluoromethyl and pentafluoroethyl groups;

halogen atoms, such as the fluorine, chlorine, bromine and iodine atoms, especially the chlorine and fluorine atoms;

the $C_1$–$C_6$, preferably $C_1$–$C_4$, alkoxy groups such as those exemplified above in relation to substituents (a), and especially the methoxy group; and the ($C_1$–$C_6$, alkanoyloxy)methoxycarbonyl groups such as the formyloxymethoxycarbonyl, acetoxymethoxycarbonyl, propionyloxymethoxycarbonyl, butyryloxymethoxycarbonyl, isobutyryloxymethoxycarbonyl, pivaloyloxymethoxycarbonyl, valeryloxymethoxycarbonyl and isovaleryloxymethoxycarbonyl groups, especially the pivaloyloxymethoxycarbonyloxy group.

Examples of groups and atoms included in substituents (d) are:

the $C_1$–$C_6$, preferably $C_1$–$C_4$, alkyl groups, such as those exemplified above in relation to substituents (a);

the $C_1$–$C_6$, preferably $C_1$–$C_4$, alkoxy groups, such as those exemplified above in relation to substituents (a), and especially the methoxy group;

halogen atoms, such as the fluorine, chlorine, bromine and iodine atoms, especially the chlorine and fluorine atoms;

$C_6$–$C_{10}$ aryl groups which are not substituted, such as the phenyl or naphthyl groups;

the nitro group; and $C_2$–$C_7$ alkoxycarbonyl groups (i.e. the alkoxy part is $C_1$–$C_6$), such as the methoxycarbonyl, ethoxycarbonyl, t-butoxycarbonyl and isobutoxycarbonyl groups.

Examples of aromatic heterocyclic groups which may be represented by $R^5$ include aromatic 5- to 14-membered heterocyclic groups, which may be be monocyclic or condensed rang polycyclic groups, and whose ring atoms include from 1 to 5, preferably from 1 to 3, sulfur and/or oxygen and/or nitrogen atoms. Such groups have at least one ring having aromatic character, and, where there are two or more rings, these preferably, but not necessarily, all have aromatic character. Where the group is a condensed ring system, at least one of the rings must be a heterocyclic ring, and the other or others may be heterocyclic or non-heterocyclic, e.g. a benzene ring. Examples of such groups include the furyl, thienyl, pyrrolyl, pyrazolyl, imidazolyl, oxazolyl, isoxazolyl, isothiazolyl, thiazolyl, 1,2,3-oxadiazolyl, triazolyl, tetrazolyl, thiadiazolyl, pyridyl, pyridazinyl, pyrimidinyl, pyrazinyl, indolyl, indazolyl, purinyl, quinolyl, isoquinolyl, phthalazinyl, naphthyridinyl, quinoxalinyl, quinazolinyl, cinnolinyl, pteridinyl, carbazolyl, carbolinyl, phenanthridinyl and acridinyl groups. Of these, we prefer the aromatic 5- to 10-membered heterocyclic groups, which may optionally be condensed, having 1 or 2 sulfur and/or oxygen and/or nitrogen atoms, and more preferably the furyl, thienyl, oxazolyl, isoxazolyl, thiazolyl, pyridyl, quinolyl and isoquinolyl groups.

We most prefer that $R^1$ should represent a substituted phenyl group having at least one of the aforementioned alkyl, alkoxy or halogen substituents and that $R^2$ should represent an unsubstituted phenyl group or a substituted phenyl group having at least one substituent selected from the group consisting of the aforementioned alkyl, haloalkyl and halogen substituents.

Examples of the $C_1$–$C_6$ alkyl groups which may be represented by $R^3$ include those groups referred to above in relation to the alkyl groups which may be included within substituents (a), of which the straight and branched chain alkyl groups having 1 to 4 carbon atoms are preferred.

$R^3$ may also represent any of the groups defined and exemplified above for $R^5$, or it may represent a cyano group or a hydrogen atom, but it is preferably a hydrogen atom.

X may represent an oxygen or sulfur atom, but is preferably an oxygen atom.

Where B' represents an alkylene group, this has from 1 to 6 carbon atoms, and examples include the methylene, methylmethylene, ethylene, propylene, trimethylene, tetramethylene, 1-methyltrimethylene, 2-methyltrimethylene, 3-methyltrimethylene, pentamethylene and hexamethylene groups, of which the methylene, ethylene, trimethylene and tetramethylene groups are preferred.

B' may also represent a carbonyl group, a thiocarbonyl (>C=S) group, a sulfonyl (>$SO_2$) group or a sulfinyl (>SO) group. Most preferably B represents a carbonyl group.

$R^4$ represents a phenyl group which may be unsubstituted or may have at least one substituent selected from the group consisting of substituents (a) and (b). Substituents (a) are both defined and exemplified above. Substituents (b) are defined above, and examples include:

lower alkylsulfonyl groups, which may have from 1 to 6, preferably from 1 to 4, carbon atoms in the alkyl part thereof, and which may be a straight or branched chain group such as those exemplified in relation to the alkyl group which may be included in substituents (a); examples of preferred such alkanesulfonyl groups include the methanesulfonyl, ethanesulfonyl, propanesulfonyl, isopropanesulfonyl, butanesulfonyl, isobutanesulfonyl, sec-butanesulfonyl, t-butanesulfonyl, pentanesulfonyl, isopentanesulfonyl, 2-methylbutanesulfonyl, neopentanesulfonyl, hexanesulfonyl, 4-methylpentanesulfonyl, 3-methylpentanesulfonyl, 2-methylpentanesulfonyl, 3,3-dimethylbutanesulfonyl, 2,2-dimethylbutanesulfonyl, 1,1-dimethylbutanesulfonyl, 1,2-dimethylbutanesulfonyl, 1,3-dimethylbutanesulfonyl and 2,3-dimethylbutanesulfonyl groups, of which the straight and branched chain alkanesulfonyl groups having from 1 to 4 carbon atoms are preferred;

lower alkylsulfinyl groups, which may have from 1 to 6, preferably from 1 to 4, carbon atoms in the alkyl part thereof, which may be a straight or branched chain group such as those exemplified in relation to the alkyl group which may be included in substituents (a); examples of preferred such alkanesulfinyl groups include the methanesulfinyl, ethanesulfinyl, propanesulfinyl, isopropanesulfinyl, butanesulfinyl, isobutanesulfinyl, sec-butanesulfinyl, t-butanesulfinyl, pentanesulfinyl, isopentanesulfinyl, 2-methybutanesulfinyl, neopeneanesulfinyl, hexanesulfinyl, 4-methylpentanesulfinyl, 3-methylpentanesulfinyl, 2-methylpentanesulfinyl, 3,3-dimethylbutanesulfinyl, 2,2-dimethylbutanesulfinyl, 1,1-dimethylbutanesulfinyl, 1,2-dimethylbutanesulfinyl, 1,3-dimethylbutanesulfinyl and 2,3-dimethylbutanesulfinyl groups, of which the straight and branched chain alkanesulfinyl groups having from 1 to 4 carbon atoms are preferred; and lower alkylthio groups, which may have from 1 to 6, preferably from 1 to 4, carbon atoms in the alkyl part thereof, which may be straight or branched chain group such as those exemplified in relation to the alkyl group which may be included in substituents (a); examples of preferred such alkylthio groups include the methylthio, ethylthio, propylthio, isopropylthio, butylthio, isobutylthio, sec-butylthio, t-butylthio, pentylthio, isopentylthio, 2-methylbutylthio, neopentylthio, hexylthio, 4-methylpentylthio, 3-methylpentylthio, 2-methylpentylthio, 3,3-dimethylbutylthio, 2,2-dimethylbutylthio, 1,1-dimethylbutylthio, 1,2-dimethylbutylthio, 1,3-dimethylbutylthio and 2,3-dimethylbutylthio groups, of which the straight and branched chain alkylthio groups having from 1 to 4 carbon atoms are preferred.

We most prefer those compounds of the present invention in which $R^4$ represents a phenyl group having at least one $C_1$–$C_3$ alkoxy, more preferably methoxy, substituent, and most preferred are those compounds where $R^4$ represents a 3,4-dimethoxyphenyl, 3-methoxyphenyl, 4-methoxyphenyl or 3, 4, 5-trimethoxyphenyl group.

Certain of the compounds of the present invention can form salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. The compounds may include at least one basic nitrogen atom, where B represents a $C_1$–$C_6$ alkylene group, and can, therefore, form acid addition salts. Examples of such acid addition salts include: salts with a mineral acid, especially a hydrogen halide (such as hydrofluoric acid, hydrochloric acid, hydrobromic acid or hydroiodic acid), nitric acid, perchloric acid, sulfuric acid or phosphoric acid; salts with an organic carboxylic acid, such as fumaric acid, succinic acid, citric acid, tartaric acid, oxalic acid, maleic acid or malic acid; salts with a sulfonic acid, especially a lower alkanesulfonic acid (such as methanesulfonic acid, trifluoromethanesulfonic acid or ethanesulfonic acid) or an arylsulfonic acid (such as benzenesulfonic acid or p-toluenesulfonic acid); and salts with an amino acid, such as glutamic acid and aspartic acid.

The compounds of the present invention may contain several asymmetric carbon atoms in their molecules, and can thus form optical isomers having the (R)-configuration or the (S)-configuration. Also, because of the carbon-carbon double bond, they can exist in the form of geometric isomers, i.e. the (Z)-isomer or the (E)-isomer. Although these are all represented herein by a single molecular formula, the present invention includes both the individual, isolated isomers and mixtures, including racemates thereof. Where stereospecific synthesis techniques are employed, individual isomers may be prepared directly; on the other hand, if a mixture of isomers is prepared, the individual isomers may be obtained by conventional resolution techniques.

Of the compounds of the present invention, the following are preferred:

(1) Compounds in which both $R^1$ and $R^2$ are independently selected from the group consisting of groups represented by $-R^5$ (in which $R^5$ is as defined above);

(2) Compounds in which at least one of $R^1$ and $R^2$ represents an aryl group having at least one substituent selected from the group consisting of substituents (a), defined above;

(3) Compounds in which $R^3$ represents a hydrogen atom or a $C_1$-$C_6$ alkyl group;

(4) Compounds in which $R^4$ represents a substituted phenyl group having from 1 to 5 $C_1$-$C_6$ alkoxy substituents;

(5) Compounds in which X represents an oxygen atom;

(6) Compounds in which A represents a 1,4-piperazin-1,4-diyl group.

More preferred are those compounds in which $R^1$ and $R^2$ are as defined in (1) or (2) above, $R^3$ is as defined in (3) above, $R^4$ is as defined in (4) above, X is as defined in (5) above and A is as defined in (6) above.

Still more preferred are those compounds in which:

(7) $R^1$ represents a substituted phenyl group having at least one $C_1$-$C_{22}$ alkyl, $C_1$-$C_{22}$ alkoxy or halogen substituent;

(8) $R^1$ represents a substituted phenyl group having at least one $C_1$-$C_6$ alkyl $C_1$-$C_6$ alkoxy or halogen substituent;

(9) $R^2$ represents an unsubstituted phenyl group or a substituted phenyl group having at least one substituent selected from the group consisting of $C_1$-$C_{22}$ alkyl groups, $C_1$-$C_{22}$ alkoxy groups, $C_1$-$C_6$ haloalkyl groups and halogen atoms;

(10) $R^2$ represents a substituted phenyl group having at least one substituent selected from the group consisting of $C_1$-$C_{22}$ alkyl groups, $C_1$-$C_{22}$ alkoxy groups, $C_1$-$C_6$ haloalkyl groups and halogen atoms;

(11) $R^2$ represents a substituted phenyl group having at least one substituent selected from the group consisting of $C_1$-$C_{22}$ alkyl groups, $C_1$-$C_6$ haloalkyl groups and halogen atoms;

(12) $R^2$ represents a substituted phenyl group having at least one substituent selected from the group consisting of $C_1$-$C_6$ alkyl groups, $C_1$-$C_6$ haloalkyl groups and halogen atoms;

(13) $R^2$ is as defined in any one of (10) to (12) above in which the substituent is at the meta position;

(14) Compounds in which $R^3$ represents a hydrogen atom;

(15) Compounds in which $R^4$ represents a substituted phenyl group having from 1 to 3 $C_1$-$C_6$ alkoxy substituents, more especially from 1 to 3 $C_1$-$C_3$ alkoxy substituents and most especially from 1 to 3 methoxy substituents;

(16) Compounds in which B' represents a carbonyl group.

Most preferred are those compounds in which $R^1$ is as defined in (7) or (8) above, $R^2$ is as defined in any one of (9) to (13) above, $R^3$ is as defined in (14) above, $R^4$ is as defined in (15) above, B is as defined in (16) above, X is as defined in (5) above and A is as defined in (6) above.

Examples of specific compounds of the invention are given in the following formulae (I-1) to (I-3), in which the substituents are as defined in the corresponding one of Tables 1 to 3 [i.e. Table 1 relates to formula (I-1), Table 2 relates to formula (I-2) and so on]. In the Tables, the following abbreviations are used:

| | |
|---|---|
| Bu | butyl |
| iBu | isobutyl |
| sBu | sec-butyl |
| Et | ethyl |
| Hx | hexyl |
| Me | methyl |
| Np | naphthyl |
| Ph | phenyl |
| Pn | pentyl |
| Pr | propyl |
| Pyr | pyridyl |
| Quin | quinolyl |
| Tfm | trifluoromethyl |
| Thi | thienyl |

$$\begin{array}{c}R^1\\ \diagdown\\ C=CH\\ \diagup\\ R^2\end{array} \begin{array}{c}\\ \\ \diagdown\\ N\\ \diagup\\ C\\ \|\\ O\end{array} \begin{array}{c} \\ \\ N-B'-\end{array} \begin{array}{c}OCH_3\\ \\ -OCH_3\\ \\ OCH_3\end{array} \quad (I\text{-}1)$$

$$\begin{array}{c}R^1\\ \diagdown\\ C=CH\\ \diagup\\ R^2\end{array} \begin{array}{c}\\ \\ \diagdown\\ N\\ \diagup\\ C\\ \|\\ O\end{array} \begin{array}{c}\\ \\ N-CO-R^4\end{array} \quad (I\text{-}2)$$

$$\begin{array}{c}R^1\\ \diagdown\\ C=CH\\ \diagup\\ R^2\end{array} \begin{array}{c}\\ \\ \diagdown\\ N\\ \diagup\\ C\\ \|\\ O\end{array} \begin{array}{c}(CH_2)_3\\ \diagdown\\ N-CO-R^4\\ \diagup\end{array} \quad (I\text{-}3)$$

TABLE 1

| Compound No. | $R^1$ | $R^2$ | B' |
|---|---|---|---|
| 1-1 | Ph | Ph | C=O |
| 1-2 | 4-MeOPh | 4-MeOPh | C=O |
| 1-3 | 4-ClPh | 4-ClPh | C=O |
| 1-4 | 2-Thi | 2-Thi | C=O |
| 1-5 | 4-Pyr | 4-Pyr | C=O |
| 1-6 | 2-Np | 2-Np | C=O |
| 1-7 | 1-Np | 1-Np | C=O |
| 1-8 | 3-Pyr | 3-Pyr | C=O |
| 1-9 | 2-Pyr | 2-Pyr | C=O |
| 1-10 | 2-Quin | 2-Quin | C=O |
| 1-11 | PhC≡C— | PhC≡C— | C=O |
| 1-12 | PhCH=CH— | PhCH=CH— | C=O |
| 1-13 | 3-Thi | 3-Thi | C=O |
| 1-14 | 3,4-diMeOPh | 3,4-diMeOPh | C=O |
| 1-15 | 3,4,5-TriMeOPh | 3,4,5-TriMeOPh | C=O |
| 1-16 | Ph | 4-MeOPh | C=O |
| 1-17 | Ph | 4-ClPh | C=O |
| 1-18 | Ph | 2-Thi | C=O |
| 1-19 | Ph | 4-Pyr | C=O |
| 1-20 | Ph | 2-Np | C=O |
| 1-21 | Ph | 1-Np | C=O |
| 1-22 | Ph | 3-Pyr | C=O |
| 1-23 | Ph | 2-Pyr | C=O |
| 1-24 | Ph | 2-Quin | C=O |
| 1-25 | Ph | PhC≡C— | C=O |
| 1-26 | Ph | PhCH=CH— | C=O |
| 1-27 | Ph | 3-Thi | C=O |
| 1-28 | Ph | 3,4-diMeOPh | C=O |
| 1-29 | Ph | 3,4,5-TriMeOPh | C=O |
| 1-30 | 4-MeOPh | 4-ClPh | C=O |

TABLE 1-continued

| Compound No. | R¹ | R² | B' |
|---|---|---|---|
| 1-31 | 4-MeOPh | 2-Thi | C=O |
| 1-32 | 3-MeOPh | 4-Pyr | C=O |
| 1-33 | 4-MeOPh | 2-Np | C=O |
| 1-34 | 4-MeOPh | 1-Np | C=O |
| 1-35 | 4-MeOPh | 3-Pyr | C=O |
| 1-36 | 4-MeOPh | 2-Pyr | C=O |
| 1-37 | 4-MeOPh | 2-Quin | C=O |
| 1-38 | 4-MeOPh | PhC≡C— | C=O |
| 1-39 | 4-MeOPh | PhCH=CH— | C=O |
| 1-40 | 4-MeOPh | 3-Thi | C=O |
| 1-41 | 4-MeOPh | 3,4-diMeOPh | C=O |
| 1-42 | 4-MeOPh | 3,4,5-TriMeOPh | C=O |
| 1-43 | 4-ClPh | 2-Thi | C=O |
| 1-44 | 4-ClPh | 4-Pyr | C=O |
| 1-45 | 4-ClPh | 2-Np | C=O |
| 1-46 | 4-ClPh | 1-Np | C=O |
| 1-47 | 2-ClPh | 3-Pyr | C=O |
| 1-48 | 3-ClPh | 2-Pyr | C=O |
| 1-49 | 4-ClPh | 2-Quin | C=O |
| 1-50 | 4-ClPh | PhC≡C— | C=O |
| 1-51 | 4-ClPh | PhCH=CH— | C=O |
| 1-52 | 4-ClPh | 3-Thi | C=O |
| 1-53 | 4-ClPh | 3,4-diMeOPh | C=O |
| 1-54 | 4-ClPh | 3,4,5-TriMeOPh | C=O |
| 1-55 | 2-Thi | 4-Pyr | C=O |
| 1-56 | 2-Thi | 2-Np | C=O |
| 1-57 | 2-Thi | 1-Np | C=O |
| 1-58 | 2-Thi | 3-Pyr | C=O |
| 1-59 | 2-Thi | 2-Pyr | C=O |
| 1-60 | 2-Thi | 2-Quin | C=O |
| 1-61 | 2-Thi | PhC≡C— | C=O |
| 1-62 | 2-Thi | PhCH=CH— | C=O |
| 1-63 | 2-Thi | 3-Thi | C=O |
| 1-64 | 2-Thi | 3,4-diMeOPh | C=O |
| 1-65 | 2-Thi | 3,4,5-TriMeOPh | C=O |
| 1-66 | 4-Pyr | 2-Np | C=O |
| 1-67 | 4-Pyr | 1-Np | C=O |
| 1-68 | 4-Pyr | 3-Pyr | C=O |
| 1-69 | 4-Pyr | 2-Pyr | C=O |
| 1-70 | 4-Pyr | 2-Quin | C=O |
| 1-71 | 4-Pyr | PhC≡C— | C=O |
| 1-72 | 4-Pyr | PhCH=CH— | C=O |
| 1-73 | 4-Pyr | 3-Thi | C=O |
| 1-74 | 4-Pyr | 3,4-diMeOPh | C=O |
| 1-75 | 4-Pyr | 3,4,5-TriMeOPh | C=O |
| 1-76 | 2-Np | 1-Np | C=O |
| 1-77 | 2-Np | 3-Pyr | C=O |
| 1-78 | 2-Np | 2-Pyr | C=O |
| 1-79 | 2-Np | 2-Quin | C=O |
| 1-80 | 2-Np | PhC≡C— | C=O |
| 1-81 | 2-Np | PhCH=CH— | C=O |
| 1-82 | 2-Np | 3-Thi | C=O |
| 1-83 | 2-Np | 3,4-diMeOPh | C=O |
| 1-84 | 2-Np | 3,4,5-TriMeOPh | C=O |
| 1-85 | 1-Np | 3-Pyr | C=O |
| 1-86 | 1-Np | 2-Pyr | C=O |
| 1-87 | 1-Np | 2-Quin | C=O |
| 1-88 | 1-Np | PhC≡C— | C=O |
| 1-89 | 1-Np | PhCH=CH— | C=O |
| 1-90 | 1-Np | 3-Thi | C=O |
| 1-91 | 1-Np | 3,4-diMeOPh | C=O |
| 1-92 | 1-Np | 3,4,5-TriMeOPh | C=O |
| 1-93 | 3-Pyr | 2-Pyr | C=O |
| 1-94 | 3-Pyr | 2-Quin | C=O |
| 1-95 | 3-Pyr | PhC≡C— | C=O |
| 1-96 | 3-Pyr | PhCH=CH— | C=O |
| 1-97 | 3-Pyr | 3-Thi | C=O |
| 1-98 | 3-Pyr | 3,4-diMeOPh | C=O |
| 1-99 | 3-Pyr | 3,4,5-TriMeOPh | C=O |
| 1-100 | 2-Pyr | 2-Quin | C=O |
| 1-101 | 3-Pyr | PhC≡C— | C=O |
| 1-102 | 2-Pyr | PhCH=CH— | C=O |
| 1-103 | 3-Pyr | 3-Thi | C=O |
| 1-104 | 2-Quin | PhC≡C— | C=O |
| 1-105 | 2-Quin | PhCH=CH— | C=O |
| 1-106 | 2-Quin | 3-Thi | C=O |
| 1-107 | 2-Quin | 3,4-diMeOPh | C=O |
| 1-108 | 2-Quin | 3,4,5-TriMeOPh | C=O |
| 1-109 | PhC≡C— | PhCH=CH— | C=O |
| 1-110 | PhC≡C— | 3-Thi | C=O |
| 1-111 | PhC≡C— | 3,4-diMeOPh | C=O |
| 1-112 | PhC≡C— | 3,4,5-TriMeOPh | C=O |
| 1-113 | PhCH=CH— | 3-Thi | C=O |
| 1-114 | PhCH=CH— | 3,4-diMeOPh | C=O |
| 1-115 | PhCH=CH— | 3,4,5-TriMeOPh | C=O |
| 1-116 | Ph | Ph | C=S |
| 1-117 | 4-MeOPh | 4-MeOPh | C=S |
| 1-118 | 4-ClPh | 4-ClPh | C=S |
| 1-119 | 2-Thi | 2-Thi | C=S |
| 1-120 | 4-FPh | 4-FPh | C=S |
| 1-121 | 2-Np | 2-Np | C=S |
| 1-122 | 1-Np | 1-Np | C=S |
| 1-123 | 3-Pyr | 3-Pyr | C=S |
| 1-124 | 2-Pyr | 2-Pyr | C=S |
| 1-125 | 2-Quin | 2-Quin | C=S |
| 1-126 | PhC≡C— | PhC≡C— | C=S |
| 1-127 | PhCH=CH— | PhCH=CH— | C=S |
| 1-128 | 3-Thi | 3-Thi | C=S |
| 1-129 | Ph | 4-MeOPh | C=S |
| 1-130 | Ph | 4-ClPh | C=S |
| 1-131 | Ph | 2-Thi | C=S |
| 1-132 | Ph | 4-Pyr | C=S |
| 1-133 | Ph | 2-Np | C=S |
| 1-134 | Ph | 1-Np | C=S |
| 1-135 | Ph | 3-Pyr | C=S |
| 1-136 | Ph | 2-Pyr | C=S |
| 1-137 | Ph | 2-Quin | C=S |
| 1-138 | Ph | PhC≡C— | C=S |
| 1-139 | Ph | PhCH=CH— | C=S |
| 1-140 | Ph | 3-Thi | C=S |
| 1-141 | 4-MeOPh | 4-ClPh | C=S |
| 1-142 | 2-MeOPh | 2-Thi | C=S |
| 1-143 | 3-MeOPh | 4-Pyr | C=S |
| 1-144 | 4-MeOPh | 2-Np | C=S |
| 1-145 | 4-MeOPh | 1-Np | C=S |
| 1-146 | 4-MeOPh | 3-Pyr | C=S |
| 1-147 | 4-MeOPh | 2-Pyr | C=S |
| 1-148 | 4-MeOPh | 2-Quin | C=S |
| 1-149 | 4-MeOPh | PhC≡C— | C=S |
| 1-150 | 4-MeOPh | PhCH=CH— | C=S |
| 1-151 | 4-MeOPh | 3-Thi | C=S |
| 1-152 | 4-ClPh | 2-Thi | C=S |
| 1-153 | 4-ClPh | 4-Pyr | C=S |
| 1-154 | 3-ClPh | 2-Np | C=S |
| 1-155 | 3-ClPh | 1-Np | C=S |
| 1-156 | 2-ClPh | 3-Pyr | C=S |
| 1-157 | 3-ClPh | 2-Pyr | C=S |
| 1-158 | 4-ClPh | 2-Quin | C=S |
| 1-159 | 4-ClPh | PhC≡C— | C=S |
| 1-160 | 4-ClPh | PhCH=CH— | C=S |
| 1-161 | 4-ClPh | 3-Thi | C=S |
| 1-162 | 2-Thi | 4-Pyr | C=S |
| 1-163 | 2-Thi | 2-Np | C=S |
| 1-164 | 2-Thi | 1-Np | C=S |
| 1-165 | 2-Thi | 3-Pyr | C=S |
| 1-166 | 2-Thi | 2-Pyr | C=S |
| 1-167 | 2-Thi | 2-Quin | C=S |
| 1-168 | 2-Thi | PhC≡C— | C=S |
| 1-169 | 2-Thi | PhCH=CH— | C=S |
| 1-170 | 2-Thi | 3-Thi | C=S |
| 1-171 | 4-Pyr | 2-Np | C=S |
| 1-172 | 4-Pyr | 1-Np | C=S |
| 1-173 | 4-Pyr | 3-Pyr | C=S |
| 1-174 | 4-Pyr | 2-Pyr | C=S |
| 1-175 | 4-Pyr | 2-Quin | C=S |
| 1-176 | 4-Pyr | PhC≡C— | C=S |
| 1-177 | 4-Pyr | PhCH=CH— | C=S |
| 1-178 | 4-Pyr | 3-Thi | C=S |
| 1-179 | 2-Np | 1-Np | C=S |
| 1-180 | 2-Np | 3-Pyr | C=S |
| 1-181 | 2-Np | 2-Pyr | C=S |
| 1-182 | 2-Np | 2-Quin | C=S |

TABLE 1-continued

| Compound No. | R¹ | R² | B' |
|---|---|---|---|
| 1-183 | 2-Np | PhC≡C— | C=S |
| 1-184 | 2-Np | PhCH=CH— | C=S |
| 1-185 | 2-Np | 3-Thi | C=S |
| 1-186 | 1-Np | 3-Pyr | C=S |
| 1-187 | 1-Np | 2-Pyr | C=S |
| 1-188 | 1-Np | 2-Quin | C=S |
| 1-189 | 1-Np | PhC≡C— | C=S |
| 1-190 | 1-Np | PhCH=CH— | C=S |
| 1-191 | 1-Np | 3-Thi | C=S |
| 1-192 | 3-Pyr | 2-Pyr | C=S |
| 1-193 | 3-Pyr | 2-Quin | C=S |
| 1-194 | 3-Pyr | PhC≡C— | C=S |
| 1-195 | 3-Pyr | PhCH=CH— | C=S |
| 1-196 | 3-Pyr | 3-Thi | C=S |
| 1-197 | 2-Pyr | 2-Quin | C=S |
| 1-198 | 3-Pyr | PhC≡C— | C=S |
| 1-199 | 2-Pyr | PhCH=CH— | C=S |
| 1-200 | 3-Pyr | 3-Thi | C=S |
| 1-201 | 2-Quin | PhC≡C— | C=S |
| 1-202 | 2-Quin | PhCH=CH— | C=S |
| 1-203 | 2-Quin | 3-Thi | C=S |
| 1-204 | PhC≡C— | PhCH=CH— | C=S |
| 1-205 | PhC≡C— | 3-Thi | C=S |
| 1-206 | PhCH=CH— | 3-Thi | C=S |
| 1-207 | Ph | Ph | SO₂ |
| 1-208 | 4-MeOPh | 4-MeOPh | So₂ |
| 1-209 | 4-ClPh | 4-ClPh | SO₂ |
| 1-210 | 2-Thi | 2-Thi | SO₂ |
| 1-211 | 4-Pyr | 4-Pyr | SO₂ |
| 1-212 | 2-Np | 2-Np | SO₂ |
| 1-213 | 1-Np | 1-Np | SO₂ |
| 1-214 | 3-Pyr | 3-Pyr | SO₂ |
| 1-215 | 2-Pyr | 2-Pyr | SO |
| 1-216 | 2-Quin | 2-Quin | SO₂ |
| 1-217 | PhC≡C— | PhC≡C— | SO₂ |
| 1-218 | PhCH=CH— | PhCH=CH— | SO₂ |
| 1-219 | 3-Thi | 3-Thi | SO₂ |
| 1-220 | Ph | 4-MeOPh | SO₂ |
| 1-221 | Ph | 4-ClPh | SO₂ |
| 1-222 | Ph | 2-Thi | SO₂ |
| 1-223 | Ph | 4-Pyr | SO₂ |
| 1-224 | Ph | 2-Np | SO₂ |
| 1-225 | Ph | 1-Np | SO₂ |
| 1-226 | Ph | 3-Pyr | SO₂ |
| 1-227 | Ph | 2-Pyr | SO₂ |
| 1-228 | Ph | 2-Quin | SO₂ |
| 1-229 | Ph | PhC≡C— | SO₂ |
| 1-230 | Ph | PhCH=CH— | SO₂ |
| 1-231 | Ph | 3-Thi | SO₂ |
| 1-232 | 4-MeOPh | 4-ClPh | SO₂ |
| 1-233 | 2-MeOPh | 2-Thi | SO₂ |
| 1-234 | 3-MeOPh | 4-Pyr | SO₂ |
| 1-235 | 4-MeOPh | 2-Np | SO₂ |
| 1-236 | 4-MeOPh | 1-Np | SO₂ |
| 1-237 | 4-MeOPh | 3-Pyr | SO₂ |
| 1-238 | 4-MeOPh | 2-Pyr | SO₂ |
| 1-239 | 4-MeOPh | 2-Quin | SO₂ |
| 1-240 | 4-MeOPh | PhC≡C— | SO₂ |
| 1-241 | 4-MeOPh | PhCH=CH— | SO₂ |
| 1-242 | 4-MeOPh | 3-Thi | SO₂ |
| 1-243 | 4-ClPh | 2-Thi | SO₂ |
| 1-244 | 4-ClPh | 4-Pyr | SO₂ |
| 1-245 | 4-ClPh | 2-Np | SO₂ |
| 1-246 | 4-ClPh | 1-Np | SO₂ |
| 1-247 | 2-ClPh | 3-Pyr | SO₂ |
| 1-248 | 3-ClPh | 2-Pyr | SO₂ |
| 1-249 | 4-ClPh | 2-Quin | SO₂ |
| 1-250 | 4-ClPh | PhC≡C— | SO₂ |
| 1-251 | 4-ClPh | PhCH=CH— | SO₂ |
| 1-252 | 4-ClPh | 3-Thi | SO₂ |
| 1-253 | 2-Thi | 4-Pyr | SO₂ |
| 1-254 | 2-Thi | 2-Np | SO₂ |
| 1-255 | 2-Thi | 1-Np | SO₂ |
| 1-256 | 2-Thi | 3-Pyr | SO₂ |
| 1-257 | 2-Thi | 2-Pyr | SO₂ |
| 1-258 | 2-Thi | 2-Quin | SO₂ |
| 1-259 | 2-Thi | PhC≡C— | SO₂ |
| 1-260 | 2-Thi | PhCH=CH— | SO₂ |
| 1-261 | 2-Thi | 3-Thi | SO₂ |
| 1-262 | 4-Pyr | 2-Np | SO₂ |
| 1-263 | 4-Pyr | 1-Np | SO₂ |
| 1-264 | 4-Pyr | 3-Pyr | SO₂ |
| 1-265 | 4-Pyr | 2-Pyr | SO₂ |
| 1-266 | 4-Pyr | 2-Quin | SO₂ |
| 1-267 | 4-Pyr | PhC≡C— | SO₂ |
| 1-268 | 4-Pyr | PhCH=CH— | SO |
| 1-269 | 4-Pyr | 3-Thi | SO₂ |
| 1-270 | 2-Np | 1-Np | SO₂ |
| 1-271 | 2-Np | 3-Pyr | SO₂ |
| 1-272 | 2-Np | 2-Pyr | SO₂ |
| 1-273 | 2-Np | 2-Quin | SO₂ |
| 1-274 | 2-Np | PhC≡C— | SO₂ |
| 1-275 | 2-Np | PhCH=CH— | SO₂ |
| 1-276 | 2-Np | 3-Thi | SO₂ |
| 1-277 | 1-Np | 3-Pyr | SO₂ |
| 1-278 | 1-Np | 2-Pyr | SO₂ |
| 1-279 | 1-Np | 2-Quin | SO₂ |
| 1-280 | 1-Np | PhC≡C— | SO₂ |
| 1-281 | 1-Np | PhCH=CH— | SO |
| 1-282 | 1-Np | 3-Thi | SO₂ |
| 1-283 | 3-Pyr | 2-Pyr | SO₂ |
| 1-284 | 3-Pyr | 2-Quin | SO₂ |
| 1-285 | 3-Pyr | PhC≡C— | SO₂ |
| 1-286 | 3-Pyr | PhCH=CH— | SO₂ |
| 1-287 | 3-Pyr | 3-Thi | SO₂ |
| 1-288 | 2-Pyr | 2-Quin | SO₂ |
| 1-289 | 3-Pyr | PhC≡C— | SO₂ |
| 1-290 | 2-Pyr | PhCH=CH— | SO₂ |
| 1-291 | 3-Pyr | 3-Thi | SO₂ |
| 1-292 | 2-Quin | PhC≡C— | SO₂ |
| 1-293 | 2-Quin | PhCH=CH— | SO₂ |
| 1-294 | 2-Quin | 3-Thi | SO₂ |
| 1-295 | PhC≡C— | PhCH=CH— | SO₂ |
| 1-296 | PhC≡C— | 3-Thi | SO₂ |
| 1-297 | PhCH=CH— | 3-Thi | SO₂ |
| 1-298 | Ph | Ph | CH₂ |
| 1-299 | 4-MeOPh | 4-MeOPh | CH₂ |
| 1-300 | 4-ClPh | 4-ClPh | CH₂ |
| 1-301 | 2-Thi | 2-Thi | CH₂ |
| 1-302 | 4-Pyr | 4-Pyr | CH₂ |
| 1-303 | 2-Np | 2-Np | CH₂ |
| 1-304 | 1-Np | 1-Np | CH₂ |
| 1-305 | 3-Pyr | 3-Pyr | CH₂ |
| 1-306 | 2-Pyr | 2-Pyr | SO |
| 1-307 | 2-Quin | 2-Quin | CH₂ |
| 1-308 | PhC≡C— | PhC≡C— | CH₂ |
| 1-309 | PhCH=CH— | PhCH=CH— | CH₂ |
| 1-310 | 3-Thi | 3-Thi | CH₂ |
| 1-311 | 3,4-diMeOPh | 3,4-diMeOPh | CH₂ |
| 1-312 | 3,4,5-TriMeOPh | 3,4,5-TriMeOPh | CH₂ |
| 1-313 | Ph | 4-MeOPh | CH₂ |
| 1-314 | Ph | 4-ClPh | CH₂ |
| 1-315 | Ph | 2-Thi | CH₂ |
| 1-316 | Ph | 4-Pyr | CH₂ |
| 1-317 | Ph | 2-Np | CH₂ |
| 1-318 | Ph | 1-Np | CH₂ |
| 1-319 | Ph | 3-Pyr | CH₂ |
| 1-320 | Ph | 2-Pyr | CH₂ |
| 1-321 | Ph | 2-Quin | CH₂ |
| 1-322 | Ph | PhC≡C— | CH₂ |
| 1-323 | Ph | PhCH=CH— | CH₂ |
| 1-324 | Ph | 3-Thi | CH₂ |
| 1-325 | Ph | 3,4-diMeOPh | CH₂ |
| 1-326 | Ph | 3,4,5-TriMeOPh | CH₂ |
| 1-327 | 4-MeOPh | 4-ClPh | CH₂ |
| 1-328 | 2-MeOPh | 2-Thi | CH₂ |
| 1-329 | 3-MeOPh | 4-Pyr | CH₂ |
| 1-330 | 4-MeOPh | 2-Np | CH₂ |
| 1-331 | 4-MeOPh | 1-Np | CH₂ |
| 1-332 | 4-MeOPh | 3-Pyr | CH₂ |
| 1-333 | 4-MeOPh | 2-Pyr | CH₂ |
| 1-334 | 4-MeOPh | 2-Quin | CH₂ |

TABLE 1-continued

| Compound No. | R¹ | R² | B' |
|---|---|---|---|
| 1-335 | 4-MeOPh | PhC≡C— | CH₂ |
| 1-336 | 4-MeOPh | PhCH=CH— | CH₂ |
| 1-337 | 4-MeOPh | 3-Thi | CH₂ |
| 1-338 | 4-MeOPh | 3,4-diMeOPh | CH₂ |
| 1-339 | 4-MeOPh | 3,4,5-TriMeOPh | CH₂ |
| 1-340 | 4-ClPh | 2-Thi | CH₂ |
| 1-341 | 4-ClPh | 4-Pyr | CH₂ |
| 1-342 | 3-ClPh | 2-Np | CH₂ |
| 1-343 | 3-ClPh | 1-Np | CH₂ |
| 1-344 | 2-ClPh | 3-Pyr | CH₂ |
| 1-345 | 3-ClPh | 2-Pyr | CH₂ |
| 1-346 | 4-ClPh | 2-Quin | CH₂ |
| 1-347 | 4-ClPh | PhC≡C— | CH₂ |
| 1-348 | 4-ClPh | PhCH=CH— | CH₂ |
| 1-349 | 4-ClPh | 3-Thi | CH₂ |
| 1-350 | 4-ClPh | 3,4-diMeOPh | CH₂ |
| 1-351 | 4-ClPh | 3,4,5-TriMeOPh | CH₂ |
| 1-352 | 2-Thi | 4-Pyr | CH₂ |
| 1-353 | 2-Thi | 2-Np | CH₂ |
| 1-354 | 2-Thi | 1-Np | CH₂ |
| 1-355 | 2-Thi | 3-Pyr | CH₂ |
| 1-356 | 2-Thi | 2-Pyr | CH₂ |
| 1-357 | 2-Thi | 2-Quin | CH₂ |
| 1-358 | 2-Thi | PhC≡C— | CH₂ |
| 1-359 | 2-Thi | PhCH=CH— | CH₂ |
| 1-360 | 2-Thi | 3-Thi | CH₂ |
| 1-361 | 2-Thi | 3,4-diMeOPh | CH₂ |
| 1-362 | 2-Thi | 3,4,5-TriMeOPh | CH₂ |
| 1-363 | 4-Pyr | 2-Np | CH₂ |
| 1-364 | 4-Pyr | 1-Np | CH₂ |
| 1-365 | 4-Pyr | 3-Pyr | CH₂ |
| 1-366 | 4-Pyr | 2-Pyr | CH₂ |
| 1-367 | 4-Pyr | 2-Quin | CH₂ |
| 1-368 | 4-Pyr | PhC≡C— | CH₂ |
| 1-369 | 4-Pyr | PhCH=CH— | CH₂ |
| 1-370 | 4-Pyr | 3-Thi | CH₂ |
| 1-371 | 4-Pyr | 3,4-diMeOPh | CH₂ |
| 1-372 | 4-Pyr | 3,4,5-TriMeOPh | CH₂ |
| 1-373 | 2-Np | 1-Np | CH₂ |
| 1-374 | 2-Np | 3-Pyr | CH₂ |
| 1-375 | 2-Np | 2-Pyr | CH₂ |
| 1-376 | 2-Np | 2-Quin | CH₂ |
| 1-377 | 2-Np | PhC≡C— | CH₂ |
| 1-378 | 2-Np | PhCH=CH— | CH₂ |
| 1-379 | 2-Np | 3-Thi | CH₂ |
| 1-380 | 2-Np | 3,4-diMeOPh | CH₂ |
| 1-381 | 2-Np | 3,4,5-TriMeOPh | CH₂ |
| 1-382 | 1-Np | 3-Pyr | CH₂ |
| 1-383 | 1-Np | 2-Pyr | CH₂ |
| 1-384 | 1-Np | 2-Quin | CH₂ |
| 1-385 | 1-Np | PhC≡C— | CH₂ |
| 1-386 | 1-Np | PhCH=CH— | CH₂ |
| 1-387 | 1-Np | 3-Thi | CH₂ |
| 1-388 | 1-Np | 3,4-diMeOPh | CH₂ |
| 1-389 | 1-Np | 3,4,5-TriMeOPh | CH₂ |
| 1-390 | 3-Pyr | 2-Pyr | CH₂ |
| 1-391 | 3-Pyr | 2-Quin | CH₂ |
| 1-392 | 3-Pyr | PhC≡C— | CH₂ |
| 1-393 | 3-Pyr | PhCH=CH— | CH₂ |
| 1-394 | 3-Pyr | 3-Thi | CH₂ |
| 1-395 | 3-Pyr | 3,4-diMeOPh | CH₂ |
| 1-396 | 3-Pyr | 3,4,5-TriMeOPh | CH₂ |
| 1-397 | 2-Pyr | 2-Quin | CH₂ |
| 1-398 | 3-Pyr | PhC≡C— | CH₂ |
| 1-399 | 2-Pyr | PhCH=CH— | CH₂ |
| 1-400 | 2-Pyr | 3-Thi | CH₂ |
| 1-401 | 2-Quin | PhC≡C— | CH₂ |
| 1-402 | 2-Quin | PhCH=CH— | CH₂ |
| 1-403 | 2-Quin | 3-Thi | CH₂ |
| 1-404 | 2-Quin | 3,4-diMeOPh | CH₂ |
| 1-405 | 2-Quin | 3,4,5-TriMeOPh | CH₂ |
| 1-406 | PhC≡C— | PhCH=CH— | CH₂ |
| 1-407 | PhC≡C— | 3-Thi | CH₂ |
| 1-408 | PhC≡C— | 3,4-diMeOPh | CH₂ |
| 1-409 | PhC≡C— | 3,4,5-TriMeOPh | CH₂ |
| 1-410 | PhCH=CH— | 3-Thi | CH₂ |
| 1-411 | 3-MeOPh | 3-MeOPh | C=O |
| 1-412 | 3-MeOPh | 4-MeOPh | C=O |
| 1-413 | 2-MeOPh | 2-MeOPh | C=O |
| 1-414 | 2-MeOPh | 3-MeOPh | C=O |
| 1-415 | 2-MeOPh | 4-MeOPh | C=O |
| 1-416 | 2-ClPh | 2-ClPh | C=O |
| 1-417 | 2-ClPh | 3-ClPh | C=O |
| 1-418 | 2-ClPh | 4-ClPh | C=O |
| 1-419 | 3-ClPh | 3-ClPh | C=O |
| 1-420 | 3-ClPh | 4-ClPh | C=O |
| 1-421 | 2-MePh | 2-MePh | C=O |
| 1-422 | 2-MePh | 3-MePh | C=O |
| 1-423 | 2-MePh | 4-MePh | C=O |
| 1-424 | 3-MePh | 3-MePh | C=O |
| 1-425 | 3-MePh | 4-MePh | C=O |
| 1-426 | 3-TfmPh | 3-TfmPh | C=O |
| 1-427 | 3-TfmCH₂Ph | 3-TfmCH₂Ph | C=O |
| 1-428 | 2-PrOPh | 2-PrOPh | C=O |
| 1-429 | 2-PrOPh | 3-PrOPh | C=O |
| 1-430 | 2-PrOPh | 4-PrOPh | C=O |
| 1-431 | 3-PrOPh | 3-PrOPh | C=O |
| 1-432 | 3-PrOPh | 4-PrOPh | C=O |
| 1-433 | 4-PrOPh | 4-PrOPh | C=O |
| 1-434 | 3-sBuOPh | 3-sBuOPh | C=O |
| 1-435 | 4-sBuOPh | 4-sBuOPh | C=O |
| 1-436 | 3-iBuOPh | 3-iBuOPh | C=O |
| 1-437 | 4-iBuOPh | 4-iBuOPh | C=O |
| 1-438 | 2-EtPh | 2-EtPh | C=O |
| 1-439 | 2-EtPh | 3-EtPh | C=O |
| 1-440 | 2-EtPh | 4-EtPh | C=O |
| 1-441 | 3-EtPh | 3-EtPh | C=O |
| 1-442 | 3-EtPh | 4-EtPh | C=O |
| 1-443 | 4-EtPh | 4-EtPh | C=O |
| 1-444 | 2-PrPh | 2-PrPh | C=O |
| 1-445 | 2-PrPh | 3-PrPh | C=O |
| 1-446 | 2-PrPh | 4-PrPh | C=O |
| 1-447 | 3-PrPh | 3-PrPh | C=O |
| 1-448 | 3-PrPh | 4-PrPh | C=O |
| 1-449 | 4-PrPh | 4-PrPh | C=O |
| 1-450 | 3-iBuPh | 3-iBuPh | C=O |
| 1-451 | 3-iBuPh | 4-iBuPh | C=O |
| 1-452 | 2-ClPh | Ph | C=O |
| 1-453 | 2-ClPh | 3-MeOPh | C=O |
| 1-454 | 2-ClPh | 4-MeOPh | C=O |
| 1-455 | 2-ClPh | 3-PrOPh | C=O |
| 1-456 | 2-ClPh | 4-PrOPh | C=O |
| 1-457 | 2-ClPh | 3-BuOph | C=O |
| 1-458 | 2-ClPh | 4-BuOPh | C=O |
| 1-459 | 2-ClPh | 3-MePh | C=O |
| 1-460 | 2-ClPh | 4-MePh | C=O |
| 1-461 | 2-ClPh | 3-TfmPh | C=O |
| 1-462 | 2-ClPh | 3,4-diMeOPh | C=O |
| 1-463 | 2-ClPh | 3-MeO-4-PrOPh | C=O |
| 1-464 | 2-ClPh | 3,4-diPrOPh | C=O |
| 1-465 | 2-ClPh | 3,4-diClPh | C=O |
| 1-466 | 3-ClPh | Ph | C=O |
| 1-467 | 3-ClPh | 3-MeOPh | C=O |
| 1-468 | 3-ClPh | 4-MeOPh | C=O |
| 1-469 | 3-ClPh | 3-PrOPh | C=O |
| 1-470 | 3-ClPh | 4-PrOPh | C=O |
| 1-471 | 3-ClPh | 3-iBuOPh | C=O |
| 1-472 | 3-ClPh | 4-iBuOPh | C=O |
| 1-473 | 3-ClPh | 2-MePh | C=O |
| 1-474 | 3-ClPh | 3-MePh | C=O |
| 1-475 | 3-ClPh | 4-MePh | C=O |
| 1-476 | 3-ClPh | 3-TfmPh | C=O |
| 1-477 | 3-ClPh | 3-EtPh | C=O |
| 1-478 | 3-ClPh | 4-EtPh | C=O |
| 1-479 | 3-ClPh | 3-PrPh | C=O |
| 1-480 | 3-ClPh | 4-PrPh | C=O |
| 1-481 | 3-ClPh | 2,3-diMeOPh | C=O |
| 1-482 | 3-ClPh | 3,4-diMeOPh | C=O |
| 1-483 | 3-ClPh | 4-MeO-3-PrOPh | C=O |
| 1-484 | 3-ClPh | 3,4-diPrOPh | C=O |
| 1-485 | 3-ClPh | 2,3-diClPh | C=O |
| 1-486 | 3-ClPh | 3,4-diClPh | C=O |

TABLE 1-continued

| Compound No. | R¹ | R² | B' |
| --- | --- | --- | --- |
| 1-487 | 4-ClPh | 3-MeOPh | C=O |
| 1-488 | 4-ClPh | 4-MeOPh | C=O |
| 1-489 | 4-ClPh | 3-PrOPh | C=O |
| 1-490 | 4-ClPh | 4-PrOPh | C=O |
| 1-491 | 4-ClPh | 3-iBuOPh | C=O |
| 1-492 | 4-ClPh | 4-iBuOPh | C=O |
| 1-493 | 4-ClPh | 2,3-diClPh | C=O |
| 1-494 | 2,3-diClPh | Ph | C=O |
| 1-495 | 2,3-diClPh | 3-MeOPh | C=O |
| 1-496 | 2,3-diClPh | 4-MeOPh | C=O |
| 1-497 | 2,3-diClPh | 3-PrOPh | C=O |
| 1-498 | 2,3-diClPh | 4-PrOPh | C=O |
| 1-499 | 2,3-diClPh | 3-sBuOPh | C=O |
| 1-500 | 2,3-diClPh | 4-sBuOPh | C=O |
| 1-501 | 2,3-diClPh | 3,4-diMeOPh | C=O |
| 1-502 | 2,3-diClPh | 3-MePh | C=O |
| 1-503 | 2,3-diClPh | 4-MePh | C=O |
| 1-504 | 2,3-diClPh | 3-EtPh | C=O |
| 1-505 | 2,3-diClPh | 4-EtPh | C=O |
| 1-506 | 2,3-diClPh | 3-PrPh | C=O |
| 1-507 | 2,3-diClPh | 4-PrPh | C=O |
| 1-508 | 2,3-diClPh | 3-iBuOPh | C=O |
| 1-509 | 2,3-diClPh | 4-iBuOPh | C=O |
| 1-510 | 3,4-diClPh | Ph | C=O |
| 1-511 | 3,4-diClPh | 2-MeOPh | C=O |
| 1-512 | 3,4-diClPh | 3-MeOPh | C=O |
| 1-513 | 3,4-diClPh | 4-MeOPh | C=O |
| 1-514 | 3,4-diClPh | 3-PrOPh | C=O |
| 1-515 | 3,4-diClPh | 4-PrOPh | C=O |
| 1-516 | 3,4-diClPh | 3-iBuOPh | C=O |
| 1-517 | 3,4-diClPh | 4-iBuOPh | C=O |
| 1-518 | 3,4-diClPh | 3-MePh | C=O |
| 1-519 | 3,4-diClPh | 4-MePh | C=O |
| 1-520 | 3,4-diClPh | 3-PrPh | C=O |
| 1-521 | 3,4-diClPh | 4-PrPh | C=O |
| 1-522 | 3,4-diClPh | 3-iBuPh | C=O |
| 1-523 | 3,4-diClPh | 4-iBuPh | C=O |
| 1-524 | 3-FPh | 3-FPh | C=O |
| 1-525 | 4-FPh | 4-FPh | C=O |
| 1-526 | 3-FPh | Ph | C=O |
| 1-527 | 3-FPh | 4-FPh | C=O |
| 1-528 | 3-FPh | 3-MeOPh | C=O |
| 1-529 | 3-FPh | 4-MeOPh | C=O |
| 1-530 | 3-FPh | 3-PrOPh | C=O |
| 1-531 | 3-FPh | 4-PrOPh | C=O |
| 1-532 | 3-FPh | 3-iBuOPh | C=O |
| 1-533 | 3-FPh | 4-iBuOPh | C=O |
| 1-534 | 3-FPh | 3-MePh | C=O |
| 1-535 | 3-FPh | 4-MePh | C=O |
| 1-536 | 3-FPh | 3,4-diMePh | C=O |
| 1-537 | 3-FPh | 3-TfmPh | C=O |
| 1-538 | 3-FPh | 3-EtPh | C=O |
| 1-539 | 3-FPh | 4-PrPh | C=O |
| 1-540 | 3-FPh | 4-iBuPh | C=O |
| 1-541 | 3-FPh | 3,4-diMeOPh | C=O |
| 1-542 | 3-FPh | 2-ClPh | C=O |
| 1-543 | 3-FPh | 3-ClPh | C=O |
| 1-544 | 3-FPh | 4-ClPh | C=O |
| 1-545 | 3-FPh | 2,3-diClPh | C=O |
| 1-546 | 3-FPh | 3,4-diClPh | C=O |
| 1-547 | 3-FPh | 4-PrPh | C=O |
| 1-548 | 3-FPh | 4-iBuPh | C=O |
| 1-549 | 4-FPh | Ph | C=O |
| 1-550 | 4-FPh | 3,4-diClPh | C=O |
| 1-551 | 4-FPh | 3,4-diMeOPh | C=O |
| 1-552 | 4-FPh | 3,4,5-triMeOPh | C=O |
| 1-553 | 4-FPh | 3-MePh | C=O |
| 1-554 | 4-FPh | 4-MePh | C=O |
| 1-555 | 4-FPh | 3,4-diMePh | C=O |
| 1-556 | 3-TfmPh | Ph | C=O |
| 1-557 | 3-TfmPh | 3-MeOPh | C=O |
| 1-558 | 3-TfmPh | 4-MeOPh | C=O |
| 1-559 | 3-TfmPh | 3-PrOPh | C=O |
| 1-560 | 3-TfmPh | 4-PrOPh | C=O |
| 1-561 | 3-TfmPh | 3-iBuOPh | C=O |
| 1-562 | 3-TfmPh | 4-iBuOPh | C=O |
| 1-563 | 3-TfmPh | 3-MePh | C=O |
| 1-564 | 3-TfmPh | 4-MePh | C=O |
| 1-565 | 3-TfmPh | 2,3-diMePh | C=O |
| 1-566 | 3-TfmPh | 3,4-diMePh | C=O |
| 1-567 | 3-TfmPh | 3-EtPh | C=O |
| 1-568 | 3-TfmPh | 4-EtPh | C=O |
| 1-569 | 3-TfmPh | 3-PrPh | C=O |
| 1-570 | 3-TfmPh | 4-PrPh | C=O |
| 1-571 | 3-TfmPh | 3-iBuPh | C=O |
| 1-572 | 3-TfmPh | 4-iBuPh | C=O |
| 1-573 | 3-TfmPh | 2,3-diMeOPh | C=O |
| 1-574 | 3-TfmPh | 3,4-diMeOPh | C=O |
| 1-575 | 2-MePh | Ph | C=O |
| 1-576 | 2-MePh | 3,4-diMePh | C=O |
| 1-577 | 2-MePh | 3,4-diMeOPh | C=O |
| 1-578 | 2-MePh | 3-PrPh | C=O |
| 1-579 | 2-MePh | 4-iBuPh | C=O |
| 1-580 | 3-MePh | Ph | C=O |
| 1-581 | 3-MePh | 1-Np | C=O |
| 1-582 | 3-MePh | 2-Np | C=O |
| 1-583 | 3-MePh | 3,4-diMePh | C=O |
| 1-584 | 3-MePh | 3-EtPh | C=O |
| 1-585 | 3-MePh | 4-EtPh | C=O |
| 1-586 | 3-MePh | 3-PrPh | C=O |
| 1-587 | 3-MePh | 4-PrPh | C=O |
| 1-588 | 3-MePh | 3-iBuPh | C=O |
| 1-589 | 3-MePh | 4-iBuPh | C=O |
| 1-590 | 3-MePh | 3,4-diMeOPh | C=O |
| 1-591 | 3-MePh | 3-MeOPh | C=O |
| 1-592 | 3-MePh | 4-MeOPh | C=O |
| 1-593 | 3-MePh | 3-PrOPh | C=O |
| 1-594 | 3-MePh | 4-PrOPh | C=O |
| 1-595 | 3-MePh | 3-iBuOPh | C=O |
| 1-596 | 3-MePh | 4-iBuOPh | C=O |
| 1-597 | 4-MePh | Ph | C=O |
| 1-598 | 4-MePh | 3,4-diMeOPh | C=O |
| 1-599 | 4-MePh | 3-MeOPh | C=O |
| 1-600 | 4-MePh | 4-MeOPh | C=O |
| 1-601 | 4-MePh | 3,4-diPrOPh | C=O |
| 1-602 | 4-MePh | 3-MeO-4-PrOPh | C=O |
| 1-603 | 3-MeO-4-PrOPh | Ph | C=O |
| 1-604 | 3-MeO-4-PrOPh | 2-Np | C=O |
| 1-605 | 3-MeO-4-PrOPh | 3-Np | C=O |
| 1-606 | 3,4-diPrOPh | Ph | C=O |
| 1-607 | 3-MeOPh | Ph | C=O |
| 1-608 | 3-PrOPh | Ph | C=O |
| 1-609 | 4-PrOPh | Ph | C=O |
| 1-610 | 3-iBuOPh | Ph | C=O |
| 1-611 | 4-iBuOPh | Ph | C=O |
| 1-612 | 3-EtPh | Ph | C=O |
| 1-613 | 3-EtPh | 1-Np | C=O |
| 1-614 | 3-EtPh | 2-Np | C=O |
| 1-615 | 3-PrPh | Ph | C=O |
| 1-616 | 3-PrPh | 1-Np | C=O |
| 1-617 | 3-PrPh | 2-Np | C=O |
| 1-618 | 3-iBuPh | Ph | C=O |
| 1-619 | 3-iBuPh | 1-Np | C=O |
| 1-620 | 3-iBuPh | 2-Np | C=O |
| 1-621 | 3,4-diMePh | Ph | C=O |
| 1-622 | Ph | 3-MeO-4-EtOPh | C=O |
| 1-623 | Ph | 3-MeO-4-EtOPh | C=S |
| 1-624 | Ph | 3-MeO-4-EtOPh | CH₂ |
| 1-625 | Ph | 3-MeO-4-PrOPh | C=S |
| 1-626 | Ph | 3-MeO-4-PrOPh | CH₂ |
| 1-627 | Ph | 3-MeO-4-BuOPh | C=O |
| 1-628 | Ph | 3-MeO-4-PnOPh | C=O |
| 1-629 | Ph | 3-MeO-4-HxOPh | C=O |
| 1-630 | Ph | 3-EtO-4-MeOPh | C=O |
| 1-631 | Ph | 3-PrO-4-MeOPh | C=O |
| 1-632 | Ph | 3-BuO-4-MeOPh | C=O |
| 1-633 | Ph | 3-PnO-4-MeOPh | C=O |
| 1-634 | Ph | 3-HxO-4-MeOPh | C=O |
| 1-635 | Ph | 3,4-diMeOPh | C+S |
| 1-636 | Ph | 3,4-diMeOPh | CH₂ |
| 1-637 | Ph | 3,4-diEtOPh | C=O |
| 1-638 | Ph | 3,4-diPrOPh | C=S |

TABLE 1-continued

| Compound No. | R¹ | R² | B' |
|---|---|---|---|
| 1-639 | Ph | 3,4-diPrOPh | CH₂ |
| 1-640 | Ph | 3,4-diBuOPh | C=O |
| 1-641 | Ph | 4-EtOPh | C=O |
| 1-642 | Ph | 4-BuOPh | C=O |
| 1-643 | Ph | 4-PnOPh | C=O |
| 1-644 | Ph | 4-HxOPh | C=O |
| 1-645 | Ph | 3-MeOPh | C=O |
| 1-646 | Ph | 3-EtOPh | C=O |
| 1-647 | Ph | 3-BuOPh | C=O |
| 1-648 | Ph | 3-BuPh | C=O |
| 1-649 | Ph | 4-BuPh | C=O |
| 1-650 | Ph | 3-PnPh | C=O |
| 1-651 | Ph | 3-HxPh | C=O |
| 1-652 | Ph | 3,4-diEtPh | C=O |
| 1-653 | Ph | 3,4-diPrPh | C=O |
| 1-654 | Ph | 3,4-diBuPh | C=O |
| 1-655 | 3-BuOPh | 3-BuOPh | C=O |
| 1-656 | 4-ClPh | 2,3-diMeOPh | C=O |
| 1-657 | 2,3-diClPh | 3-BuPh | C=O |
| 1-658 | 2,3-diClPh | 4-BuPh | C=O |
| 1-659 | 3,4-diClPh | 3-EtPh | C=O |
| 1-660 | 3,4-diClPh | 4-EtPh | C=O |
| 1-661 | 3,4-diClPh | 3-BuPh | C=O |
| 1-662 | 3,4-diClPh | 4-BuPh | C=O |
| 1-663 | 3,4-diClPh | 4-MeOPh | C=S |
| 1-664 | 3,4-diClPh | 4-MeOPh | CH₂ |
| 1-665 | 3,4-diClPh | 4-PrOPh | C=S |
| 1-666 | 3,4-diClPh | 3-PrOPh | CH₂ |
| 1-667 | 3,4-diClPh | 3-BuOPh | C=O |
| 1-668 | 3,4-diClPh | 4-BuOPh | C=O |
| 1-669 | 3,4-diClPh | 3,4-diMeOPh | C=O |
| 1-670 | 3-TfmPh | 3-EtOPh | C=O |
| 1-671 | 3-TfmPh | 4-EtOPh | C=O |
| 1-672 | 3-TfmPh | 3-BuOPh | C=O |
| 1-673 | 3-TfmPh | 3-PnOPh | C=O |
| 1-674 | 3-TfmPh | 3-HxOPh | C=O |
| 1-675 | 3-TfmPh | 4-BuOPh | C=O |
| 1-676 | 3-TfmPh | 4-PnOPh | C=O |
| 1-677 | 3-TfmPh | 4-HxOPh | C=O |
| 1-678 | 3-TfmPh | 4-BuPh | C=O |
| 1-679 | 3-TfmPh | 3-EtO-4-MeOPh | C=O |
| 1-680 | 3-TfmPh | 3-PrO-4-MeOPh | C=O |
| 1-681 | 3-TfmPh | 3-BuO-4-MeOPh | C=O |
| 1-682 | 3-TfmPh | 3-PnO-4-MeOPh | C=O |
| 1-683 | 3-TfmPh | 3-HxO-4-MeOPh | C=O |
| 1-684 | 3-TfmPh | 3-MeO-4-EtOPh | C=O |
| 1-685 | 3-TfmPh | 3-MeO-4-PrOPh | C=O |
| 1-686 | 3-TfmPh | 3-MeO-4-PrOPh | C=S |
| 1-687 | 3-TfmPh | 3-MeO-4-PrOPh | CH₂ |
| 1-688 | 3-TfmPh | 3-MeO-4-BuOPh | C=O |
| 1-689 | 3-TfmPh | 3-MeO-4-PnOPh | C=O |
| 1-690 | 3-TfmPh | 3-MeO-4-HxOPh | C=O |
| 1-691 | 3-TfmPh | 3,4-diMeOPh | C=S |
| 1-692 | 3-TfmPh | 3,4-diMeOPh | CH₂ |
| 1-693 | 3-TfmPh | 3,4-diPrOPh | C=O |
| 1-694 | 3-TfmPh | 3,4-diPrOPh | C=O |
| 1-695 | 3-TfmPh | 3,4-diPrOPh | CH=S |
| 1-696 | 3-TfmPh | 3,4-diPrOPh | CH₂ |
| 1-697 | 3-TfmPh | 3,4-diBuOPh | C=O |
| 1-698 | 3-MePh | 3-MePh | C=S |
| 1-699 | 3-MePh | 3-MePh | CH₂ |
| 1-700 | 3-MePh | 3-BuPh | C=O |
| 1-701 | 3-MePh | 4-BuPh | C=O |
| 1-702 | 3-MePh | 3-EtOPh | C=O |
| 1-703 | 3-MePh | 4-EtOPh | C=O |
| 1-704 | 3-MePh | 3-BuOPh | C=O |
| 1-705 | 3-MePh | 3-PnOPh | C=O |
| 1-706 | 3-MePh | 3-HxOPh | C=O |
| 1-707 | 3-MePh | 4-BuOPh | C=O |
| 1-708 | 3-MePh | 4-PnOPh | C=O |
| 1-709 | 3-MePh | 4-HxOPh | C=O |
| 1-710 | 3-MePh | 3-MeO-4-PrOPh | C=O |
| 1-711 | 3-MePh | 3-MeO-4-PrOPh | C=S |
| 1-712 | 3-MePh | 3-MeO-4-PrOPh | CH₂ |
| 1-713 | 3-MePh | 3-MeO-4-EtOPh | C=O |
| 1-714 | 3-MePh | 3-MeO-4-BuOPh | C=O |
| 1-715 | 3-MePh | 3-MeO-4-PnOPh | C=O |
| 1-716 | 3-MePh | 3-MeO-4-HxOPh | C=O |
| 1-717 | 3-MePh | 3-EtO-4-MeOPh | C=O |
| 1-718 | 3-MePh | 3-PrO-4-MeOPh | C=O |
| 1-719 | 3-MePh | 3-BuO-4-MeOPh | C=O |
| 1-720 | 3-MePh | 3-PnO-4-MeOPh | C=O |
| 1-721 | 3-MePh | 3-HxO-4-MeOPh | C=O |
| 1-722 | 3-MePh | 3,4-diMeOPh | C=S |
| 1-723 | 3-MePh | 3,4-diMeOPh | CH₂ |
| 1-724 | 3-MePh | 3,4-diEtOPh | C=O |
| 1-725 | 3-MePh | 3,4-diPrOPh | C=O |
| 1-726 | 3-MePh | 3,4-diBuOPh | C=O |
| 1-727 | 3,4-methylenedioxyPh | Ph | C=O |
| 1-728 | 3,4-methylenedioxyPh | 3-ClPh | C=O |
| 1-729 | 3,4-methylenedioxyPh | 3,4-diClPh | C=O |
| 1-730 | 3,4-methylenedioxyPh | 3-MePh | C=O |
| 1-731 | 3,4-methylenedioxyPh | 3-TfmPh | C=O |
| 1-732 | 3-ClPh | 3-EtOPh | C=O |
| 1-733 | 3-ClPh | 4-EtOPh | C=O |
| 1-734 | 3-ClPh | 3-BuOPh | C=O |
| 1-735 | 3-ClPh | 3-PnOPh | C=O |
| 1-736 | 3-ClPh | 3-HxOPh | C=O |
| 1-737 | 3-ClPh | 4-BuOPh | C=O |
| 1-738 | 3-ClPh | 4-PnOPh | C=O |
| 1-739 | 3-ClPh | 4-HxOPh | C=O |
| 1-740 | 3-ClPh | 3-MeO-4-PrOPh | C=O |
| 1-741 | 3-ClPh | 3-MeO-4-PrOPh | C=S |
| 1-742 | 3-ClPh | 3-MeO-4-PrOPh | CH₂ |
| 1-743 | 3-ClPh | 3-MeO-4-EtOPh | C=O |
| 1-744 | 3-ClPh | 3-MeO-4-PnOPh | C=O |
| 1-745 | 3-ClPh | 3-MeO-4-HxOPh | C=O |
| 1-746 | 3-ClPh | 3-EtO-4-MeOPh | C=O |
| 1-747 | 3-ClPh | 3-BuO-4-MeOPh | C=O |
| 1-748 | 3-ClPh | 3-PnO-4-MeOPh | C=O |
| 1-749 | 3-ClPh | 3-HxO-4-MeOPh | C=O |
| 1-750 | 3-ClPh | 3,4-diMeOPh | C=S |
| 1-751 | 3-ClPh | 3,4-diMeOPh | CH₂ |
| 1-752 | 3-ClPh | 3,4-diEtOPh | C=O |
| 1-753 | 3-ClPh | 3,4-diPrOPh | C=S |
| 1-754 | 3-ClPh | 3,4-diPrOPh | CH₂ |
| 1-755 | 3-ClPh | 3,4-diBuOPh | C=O |
| 1-756 | 3-ClPh | 3-BuPh | C=O |
| 1-757 | 3-ClPh | 4-BuPh | C=O |
| 1-758 | 1-Np | 3-ClPh | C=O |
| 1-759 | 2-Np | 3-ClPh | C=O |
| 1-760 | 1-Np | 3,4-diClPh | C=O |
| 1-761 | 2-Np | 3,4-diClPh | C=O |
| 1-762 | 1-Np | 3-TfmPh | C=O |
| 1-763 | 2-Np | 3-TfmPh | C=O |
| 1-764 | 3-BrPh | 3-BrPh | C=O |
| 1-765 | 3-BrPh | 3-MeOPh | C=O |
| 1-766 | 3-BrPh | 3-EtOPh | C=O |
| 1-767 | 3-BrPh | 3-PrOPh | C=O |
| 1-768 | 3-BrPh | 3-BuOPh | C=O |
| 1-769 | 3-BrPh | 3-PnOPh | C=O |
| 1-770 | 3-BrPh | 3-HxOPh | C=O |
| 1-771 | 3-BrPh | 4-MeOPh | C=O |
| 1-772 | 3-BrPh | 4-EtOPh | C=O |
| 1-773 | 3-BrPh | 4-PrOPh | C=O |
| 1-774 | 3-BrPh | 4-BuOPh | C=O |
| 1-775 | 3-BrPh | 4-PnOPh | C=O |
| 1-776 | 3-BrPh | 4-HxOPh | C=O |
| 1-777 | 3-BrPh | 3-MeO-4-EtOPh | C=O |
| 1-778 | 3-BrPh | 3-MeO-4-PrOPh | C=O |
| 1-779 | 3-BrPh | 3-MeO-4-BuOPh | C=O |
| 1-780 | 3-BrPh | 3-EtO-4-MeOPh | C=O |
| 1-781 | 3-BrPh | 3-PrO-4-MeOPh | C=O |
| 1-782 | 3-BrPh | 3-BuO-4-MeOPh | C=O |
| 1-783 | 3-BrPh | 3,4-diEtOPh | C=O |
| 1-784 | 3-BrPh | 3,4-diPrOPh | C=O |
| 1-785 | 3-BrPh | 3-MePh | C=O |
| 1-786 | 3-BrPh | 3-EtPh | C=O |
| 1-787 | 3-BrPh | 4-MePh | C=O |
| 1-788 | 3-BrPh | 4-EtPh | C=O |
| 1-789 | 3-BrPh | 1-Np | C=O |
| 1-790 | 3-BrPh | 2-Np | C=O |

TABLE 1-continued

| Compound No. | R¹ | R² | B' |
|---|---|---|---|
| 1-791 | 3,5-diClPh | 3-MeOPh | C=O |
| 1-792 | 3,5-diClPh | 3-PrOPh | C=O |
| 1-793 | 3,5-diClPh | 4-MeOPh | C=O |
| 1-794 | 3,5-diClPh | 4-PrOPh | C=O |
| 1-795 | 3,5-diClPh | 3-EtPh | C=O |
| 1-796 | 3,5-diClPh | 4-EtPh | C=O |
| 1-797 | 3,5-diClPh | 3-PrPh | C=O |
| 1-798 | 3,5-diClPh | 4-PrPh | C=O |
| 1-799 | 3,5-diClPh | 4-EtOPh | C=O |
| 1-800 | 3,5-diClPh | 3,4-diCH₃O-Ph | C=O |
| 1-801 | 2,3-diClPh | 4-EtOPh | C=O |
| 1-802 | 2,5-diClPh | 3-CH₃OPh | C=O |
| 1-803 | 2,5-diClPh | 4-CH₃OPh | C=O |
| 1-804 | 2,5-diClPh | 3-EtOPh | C=O |
| 1-805 | 2,5-diClPh | 4-EtOPh | C=O |
| 1-806 | 2,5-diClPh | 3-PrOPh | C=O |
| 1-807 | 2,5-diClPh | 4-PrOPh | C=O |
| 1-808 | 2,5-diClPh | 4-CH₃Ph | C=O |
| 1-809 | 2,5-diClPh | 3-EtPh | C=O |
| 1-810 | 2,5-diClPh | 4-PrPh | C=O |
| 1-811 | 2,5-diClPh | 3,4-diCH₃O-Ph | C=O |
| 1-812 | 2,6-diClPh | 3-CH₃OPh | C=O |
| 1-813 | 2,6-diClPh | 4-CH₃OPh | C=O |
| 1-814 | 2,6-diClPh | 3-EtOPh | C=O |
| 1-815 | 2,6-diClPh | 4-EtOPh | C=O |
| 1-816 | 2,6-diClPh | 3-PrOPh | C=O |
| 1-817 | 2,6-diClPh | 4-PrOPh | C=O |
| 1-818 | 2,6-diClPh | 3,4-diCH₃O-Ph | C=O |
| 1-819 | 2,6-diClPh | 4-CH₃Ph | C=O |
| 1-820 | 2,6-diClPh | 4-EtPh | C=O |
| 1-821 | 2,6-diClPh | 4-PrPh | C=O |
| 1-822 | 2,4-diClPh | 3-CH₃OPh | C=O |
| 1-823 | 2,4-diClPh | 4-CH₃OPh | C=O |
| 1-824 | 2,4-diClPh | 3-EtOPh | C=O |
| 1-825 | 2,4-diClPh | 4-EtOPh | C=O |
| 1-826 | 2,4-diClPh | 3-PrOPh | C=O |
| 1-827 | 2,4-diClPh | 4-PrOPh | C=O |
| 1-828 | 2,4-diClPh | 3,4-diCH₃O-Ph | C=O |
| 1-829 | 2,4-diClPh | 4-CH₃Ph | C=O |
| 1-830 | 2,4-diClPh | 4-EtPh | C=O |
| 1-831 | 2,4-diClPh | 4-PrPh | C=O |
| 1-832 | 3,5-diCH₃Ph | 4-CH₃OPh | C=O |
| 1-833 | 3,5-diCH₃Ph | 4-EtOPh | C=O |
| 1-834 | 3,5-diCH₃Ph | 4-PrOPh | C=O |
| 1-835 | 3,5-diCH₃Ph | 3,4-diCH₃O-Pb | C=O |
| 1-836 | 3,5-diCH₃Ph | 4-CH₃Ph | C=O |
| 1-837 | 3,5-diCH₃Ph | 4-EtPh | C=O |
| 1-838 | 3,5-diCH₃Ph | 4-PrPh | C=O |
| 1-839 | 3,5-diCH₃Ph | 3-ClPh | C=O |
| 1-840 | 3,5-diCH₃Ph | 4-ClPh | C=O |
| 1-841 | 3,5-diCH₃Ph | 3-FPh | C=O |
| 1-842 | 3,5-diCH₃Ph | 4-FPh | C=O |
| 1-843 | 3,5-diCH₃Ph | 3-BrPh | C=O |
| 1-844 | 3,5-diCH₃Ph | 4-BrPh | C=O |
| 1-845 | 3,5-diCF₃Ph | 4-CH₃OPh | C=O |
| 1-846 | 3,5-diCF₃Ph | 4-EtOPh | C=O |
| 1-847 | 3,5-diCF₃Ph | 40PrOPh | C=O |
| 1-848 | 3,5-diCF₃Ph | 3,4-diCF₃O-Ph | C=O |
| 1-849 | 3,5-diCF₃Ph | 4-CH₃Ph | C=O |
| 1-850 | 3,5-diCF₃Ph | 4-EtPh | C=O |
| 1-851 | 3,5-diCF₃Ph | 4-PrPh | C=O |
| 1-852 | 3,5-diCF₃Ph | 3-ClPh | C=O |
| 1-853 | 3,5-diCF₃Ph | 4-ClPh | C=O |
| 1-854 | 3,5-diCF₃Ph | 3-FPh | C=O |
| 1-855 | 3,5-diCF₃Ph | 4-FPh | C=O |
| 1-856 | 3,5-diCF₃Ph | 3-BrPh | C=O |
| 1-857 | 3,5-diCF₃Ph | 4-BrPh | C=O |
| 1-858 | 3,4-diFPh | 4-CH₃OPh | C=O |
| 1-859 | 3,4-diFPh | 4-EtOPh | C=O |
| 1-860 | 3,4-diFPh | 3-PrOPh | C=O |
| 1-861 | 3,4-diFPh | 3-CH₃Ph | C=O |
| 1-862 | 3,4-diFPh | 3-EtPh | C=O |
| 1-863 | 3,4-diFPh | 4-PrPh | C=O |
| 1-864 | 3,4-diFPh | 3-ClPh | C=O |
| 1-865 | 3,4-diFPh | 4-ClPh | C=O |
| 1-866 | 3-Cl-5-F-Ph | 4-CH₃OPh | C=O |
| 1-867 | 3-Cl-5-F-Ph | 4-EtOPh | C=O |
| 1-868 | 3-Cl-5-F-Ph | 4-EtPh | C=O |
| 1-869 | 3-Cl-5-F-Ph | 4-PrPh | C=O |
| 1-870 | 3,4-diBrPh | 4-CH₃OPh | C=O |
| 1-871 | 3-FPh | 4-EtPh | C=O |
| 1-872 | 3-FPh | 4-EtOPh | C=O |
| 1-873 | 3-Cl-5-CH₃Ph | 4-CH₃OPh | C=O |
| 1-874 | 3-Cl-5-CH₃Ph | 4-EtOPh | C=O |
| 1-875 | 3-Cl-5-CH₃Ph | 4-EtPh | C=O |
| 1-876 | 3-Cl-5-CH₃Ph | 4-PrPh | C=O |

TABLE 2

| Compound No. | R¹ | R² | R⁴ |
|---|---|---|---|
| 2-1 | 3-ClPh | 3-ClPh | 3,4-diMeOPh |
| 2-2 | 4-ClPh | 4-ClPh | 3,4-diMeOPh |
| 2-3 | 3-ClPh | 2,3-diClPh | 3,4-diMeOPh |
| 2-4 | 3-ClPh | 3,4-diClPh | 3,4-diMeOPh |
| 2-5 | 4-ClPh | 2,3-diClPh | 3,4-diMeOPh |
| 2-6 | 3-ClPh | 3-MeOPh | 3,4-diMeOPh |
| 2-7 | 3-ClPh | 4-MeOPh | 3,4-diMeOPh |
| 2-8 | 3-ClPh | 3,4-diMeOPh | 3,4-diMeoPh |
| 2-9 | 3-ClPh | 3-MeO-3-PrOPh | 3,4-diMeOPh |
| 2-10 | 2,3-diClPh | 3-MeOPh | 3,4-diMeOPh |
| 2-11 | 2,3-diClPh | 4-MeOPh | 3,4-diMeOPh |
| 2-12 | 2,3-diClPh | 3-MePh | 3,4-diMeOPh |
| 2-13 | 2,3-diClPh | 4-MePh | 3,4-diMeOPh |
| 2-14 | 3,4-diClPh | 3-MeOPh | 3,4-diMeOPh |
| 2-15 | 3,4-diClPh | 4-MeOPh | 3,4-diMeOPh |
| 2-16 | 3,4-diClPh | 4-PrOPh | 3,4-diMeOPh |
| 2-17 | 3,4-diClPh | 4-iBuOPh | 3,4-diMeOPh |
| 2-18 | 3,4-diClPh | 3-MePh | 3,4-diMeOPh |
| 2-19 | 3,4-diClPh | 4-MePh | 3,4-diMeOPh |
| 2-20 | 3,4-diClPh | 4-iBuPh | 3,4-diMeOPh |
| 2-21 | 3-MePh | 3-MePh | 3,4-diMeOPh |
| 2-22 | 3-MePh | 4-MePh | 3,4-diMeOPh |
| 2-23 | 3-MePh | 4-MeOPh | 3,4-diMeOPh |

TABLE 2-continued

| Compound No. | R¹ | R² | R⁴ |
| --- | --- | --- | --- |
| 2-24 | 3-MePh | 3-PrOPh | 3,4-diMeOPh |
| 2-25 | 3-MePh | 4-PrOPh | 3,4-diMeOPh |
| 2-26 | 3-MePh | 3-iBuOPh | 3,4-diMeOPh |
| 2-27 | 3-MePh | 4-iBuOPh | 3,4-diMeOPh |
| 2-28 | 3-MePh | 3,4-diMePh | 3,4-diMeOPh |
| 2-29 | 3-MePh | 3,4-diMeOPh | 3,4-diMeOPh |
| 2-30 | 3-MePh | 3,4-diPrOPh | 3,4-diMeOPh |
| 2-31 | 3-MePh | 3-MeO-4-PrOPh | 3,4-diMeOPh |
| 2-32 | 3-TfmPh | 3-ClPh | 3,4-diMeOPh |
| 2-33 | 3-TfmPh | 4-ClPh | 3,4-diMeOPh |
| 2-34 | 3-TfmPh | 3-MeOPh | 3,4-diMeOPh |
| 2-35 | 3-TfmPh | 4-MeOPh | 3,4-diMeOPh |
| 2-36 | 3-TfmPh | 3-PrOPh | 3,4-diMeOPh |
| 2-37 | 3-TfmPh | 4-PrOPh | 3,4-diMeOPh |
| 2-38 | 3-TfmPh | 3-iBuOPh | 3,4-diMeOPh |
| 2-39 | 3-TfmPh | 4-iBuOPh | 3,4-diMeOPh |
| 2-40 | 3-TfmPh | 3,4-diMeOPh | 3,4-diMeOPh |
| 2-41 | 3-ClPh | 3-ClPh | 3-MeOPh |
| 2-42 | 3-ClPh | 4-ClPh | 3-MeOPh |
| 2-43 | 3-CtPh | 3-MeOPh | 3-MeOPh |
| 2-44 | 3-ClPh | 4-MeOPh | 3-MeOPh |
| 2-45 | 3-ClPh | 3,4-diMeOPh | 3-MeOPh |
| 2-46 | 3,4-diClPh | 4-MeOPh | 3-MeOPh |
| 2-47 | 3,4-diClPh | 4-PrOPh | 3-MeOPh |
| 2-48 | 3,4-diClPh | 4-iBuOPh | 3-MeOPh |
| 2-49 | 3-MePh | 3-MeOPh | 3-MeOPh |
| 2-50 | 3-MePh | 4-MeOPh | 3-MeOPh |
| 2-51 | 3-MePh | 4-PrOPh | 3-MeOPh |
| 2-52 | 3-MePh | 4-iBuOPh | 3-MeOPh |
| 2-53 | 3-MePh | 3,4-diMeOPh | 3-MeOPh |
| 2-54 | 3-MePh | 3,4-diClPh | 3-MeOPh |
| 2-55 | 3-MePh | 3,4-diMePh | 3-MeOPh |
| 2-56 | 3-TfmPh | 4-MeOPh | 3-MeOPh |
| 2-57 | 3-TfmPh | 4-PrOPh | 3-MeOPh |
| 2-58 | 3-TfmPh | 4-iBuOPh | 3-MeOPh |
| 2-59 | 3-TfmPh | 3,4-diMeOPh | 3-MeOPh |
| 2-60 | 3-TfmPh | 3,4-diClPh | 3-MeOPh |
| 2-61 | 3-TfmPh | 3,4-diMePh | 3-MeOPh |
| 2-62 | 3-ClPh | 3-ClPh | 4-MeOPh |
| 2-63 | 3-ClPh | 4-ClPh | 4-MeOPh |
| 2-64 | 3-ClPh | 3-MeOPh | 4-MeOPh |
| 2-65 | 3-ClPh | 4-MeOPh | 4-MeOPh |
| 2-66 | 3-ClPh | 3,4-diMeOPh | 4-HcOPh |
| 2-67 | 3,4-diClPh | 4-MeOPh | 4-MeOPh |
| 2-68 | 3,4-diClPh | 4-PrOPh | 4-MeOPh |
| 2-69 | 3,4-diClPh | 4-iBuOPh | 4-MeOPh |
| 2-70 | 3-MePh | 3-MeOPh | 4-MeOPh |
| 2-71 | 3-MePh | 4-MeOPh | 4-MeOPh |
| 2-72 | 3-MePh | 4-PrOPh | 4-McOPh |
| 2-73 | 3-MePh | 4-iBuOPh | 4-McOPh |
| 2-74 | 3-MePh | 3,4-diMeOPh | 4-McOPh |
| 2-75 | 3-MePh | 3,4-diClPh | 4-McOPh |
| 2-76 | 3-MePh | 3,4-diMePh | 4-McOPh |
| 2-77 | 3-TfmPh | 4-MeOPh | 4-McOPh |
| 2-78 | 3-TfmPh | 4-PrOPh | 4-McOPh |
| 2-79 | 3-TfmPh | 4-iBuOPh | 4-McOPh |
| 2-80 | 3-TfmPh | 3,4-diMeOPh | 4-McOPh |
| 2-81 | 3-TfmPh | 3,4-diClPh | 4-McOPh |
| 2-82 | 3-TfmPh | 3,4-diMePh | 4-MeOPh |
| 2-83 | Ph | 3,4-diMeOPh | 3,4-diMeOPh |
| 2-84 | Ph | 3,4-diMeOPh | 3-MeOPh |
| 2-85 | Ph | 3,4-diMeOPh | 4-MeOPh |
| 2-86 | Ph | 3,4-diPrOPh | 3,4-diMeOPh |
| 2-87 | Ph | 3,4-diPrOPh | 3-MeOPh |
| 2-88 | Ph | 3,4-diPrOPh | 4-MeOPh |
| 2-89 | Ph | 3-MeO-4-PrOPh | 3,4-diMeoph |
| 2-90 | Ph | 3-MeO-4-PrOPh | 3-MeOPh |
| 2-91 | Ph | 3-MeO-4-PrOPh | 4-MeOPh |
| 2-92 | 3-ClPh | 3,4-diPrOPh | 3,4-diMeOPh |
| 2-93 | 3-ClPh | 3,4-diPrOPh | 3-MeOPh |
| 2-94 | 3-ClPh | 3,4-diPrOPh | 4-MeOPh |
| 2-95 | 3-ClPh | 3-PrO-4-MeOPh | 3,4-diMeOPh |
| 2-96 | 3-ClPh | 3-PrO-4-MeOPh | 3-MeOPh |
| 2-97 | 3-ClPh | 3-PrO-4-MeOPh | 4-MeOPh |
| 2-98 | 3-MePh | 3-PrO-4-MeOPh | 3,4-diMeOPh |
| 2-99 | 3-MePh | 3-PrO-4-MeOPh | 3-MeOPh |

TABLE 2-continued

| Compound No. | R¹ | R² | R⁴ |
|---|---|---|---|
| 2-100 | 3-MePh | 3-PrO-4-MeOPh | 4-MeOPh |
| 2-101 | 3-TfmPh | 3-MeO-4-PrOPh | 3,4-diMeOPh |
| 2-102 | 3-TfmPh | 3-MeO-4-PrOPh | 3-MeOPh |
| 2-103 | 3-TfmPh | 3-MeO-4-PrOPh | 4-MeOPh |
| 2-104 | 3-TfmPh | 3-PrO-4-MeOPh | 3,4-diMeOPh |
| 2-103 | 3-TfmPh | 3-PrO-4-MeOPh | 3-MeOPh |
| 2-106 | 3-TfmPh | 3-PrO-4-MeOPh | 4-MeOPh |
| 2-107 | 3-TfmPh | 3,4-diPrOPh | 3,4-diMeOPh |
| 2-108 | 3-TfmPh | 3,4-diPrOPh | 3-MeOPh |
| 2-109 | 3-TfmPh | 3,4-diPrOPh | 4-MeOPh |
| 2-110 | 3,4-diMeOPh | Ph | 3,5-diMeO-4-PrSPh |
| 2-111 | 3,4-diMeOPh | Ph | 4-MeSPh |
| 2-112 | 3-MeO-4-PrOPh | Ph | 3-MeS-4,5-diMeOPh |
| 2-113 | 3-MeO-4-PrOPh | 3-MePh | 3,4,5-triMePh |
| 2-114 | 3-MeO-4-PrOPh | 3-MePh | 3,4,5-triEtPh |
| 2-115 | 3-MeO-4-PrOPh | 3-ClPh | 3,4-diEtPh |
| 2-116 | 3-MeO-4-PrOPh | 3-TfmPh | 4-EtPh |
| 2-117 | 4-PrOPh | 3,4-diClPh | 4-ClPh |
| 2-118 | 4-PrOPh | 3-MePh | 3,4-diClPh |
| 2-119 | 3-PrOPh | 3-TfmPh | 3-ClPh |
| 2-120 | 3-ClPh | 3-ClPh | 3-Cl-4-MePh |
| 2-121 | 3-MePh | 3-MePh | 3-Me-4-ClPh |
| 2-122 | 3-MePh | 3-MePh | Ph |
| 2-123 | 3-MeOPh | Ph | 2-TfmPh |
| 2-124 | 3-EtOPh | Ph | 3-TfmPh |
| 2-125 | 4-MeOPh | Ph | 4-TfmPh |
| 2-126 | 4-EtOPh | Ph | 3,4,5-triTfmPh |
| 2-127 | 3,4-diMeOPh | Ph | 2-TfmPh |
| 2-128 | 3,4-diEtOPh | Ph | 3-TfmPh |
| 2-129 | 3-MeOPh | 4-ClPh | 4-TfmPh |
| 2-130 | 3-EtOPh | 4-BrPh | 3,4,5-triTfmPh |
| 2-131 | 4-MeOPh | 4-FPh | 2-TfmPh |
| 2-132 | 4-EtOPh | 4-ClPh | 3-TfmPh |
| 2-133 | 3,4-diMeOPh | 4-FPh | 4-TfmPh |
| 2-134 | 3,4-diEtOPh | 4-BrPh | 3,4,5-triTfmPh |
| 2-135 | 3-MeOPh | 4-MePh | 2-TfmPh |
| 2-136 | 3-EtOPh | 4-MePh | 3-TfmPh |
| 2-137 | 4-MeOPh | 4-MePh | 4-TfmPh |
| 2-138 | 4-EtOPh | 4-MePh | 3,4,5-TriTfmPh |
| 2-139 | 3,4-diMeOPh | 4-MePh | 2-TfmPh |
| 2-140 | 3,4-diEtOPh | 4-MePh | 3-TfmPh |
| 2-141 | 3-MeOPh | 4-TfmPh | 4-TfmPh |
| 2-142 | 3-EtOPh | 4-TfmPh | 3,4,5-triTfmPh |
| 2-143 | 4-MeOPh | 4-TfmPh | 2-TfmPh |
| 2-144 | 4-EtOPh | 4-TfmPh | 3-TfmPh |
| 2-145 | 3,4-diMeOPh | 4-TfmPh | 4-TfmPh |
| 2-146 | 3,4-diEtOPh | 4-TfmPh | 3,4,5-triTfmPh |
| 2-147 | 3-MeOPh | 3,4-diClPh | 2-TfmPh |
| 2-148 | 3-EtOPh | 3,4-diFPh | 3-TfmPh |
| 2-149 | 4-MeOPh | 3,4-diFPh | 4-TfmPh |
| 2-150 | 4-EtOPh | 3,4-diClPh | 3,4,5-triTfmPh |
| 2-151 | 3,4-diMeOPh | 3,4-diClPh | 2-TfmPh |
| 2-152 | 3,4-diEtOPh | 3,4-diFPh | 3-TfmPh |
| 2-153 | 3-MeOPh | Ph | 2-EtOPh |
| 2-154 | 3-EtOPh | Ph | 3-EtOPh |
| 2-155 | 4-MeOPh | Ph | 4-EtOPh |
| 2-156 | 4-EtOPh | Ph | 2,3,4-triEtOPh |
| 2-157 | 3,4-diMeOPh | Ph | 2-HOPh |
| 2-158 | 3,4-diEtOPh | Ph | 3-HOPh |
| 2-159 | 3-MeOPh | 4-ClPh | 4-HOPh |
| 2-160 | 3-EtOPh | 4-BrPh | 3,4,5-triHOPh |
| 2-161 | 4-MeOPh | 4-FPh | 2-MeSPh |
| 2-162 | 4-EtOPh | 4-ClPh | 3-MeSPh |
| 2-163 | 3,4-diMeOPh | 4-FPh | 4-MeSPh |
| 2-164 | 3,4-diEtOPh | 4-BrPh | 3,4,5-triMeSPh |
| 2-165 | 3-MeOPh | 4-MePh | 3,4,5-triEtSPh |
| 2-166 | 3-EtOPh | 4-MePh | 2-EtOPh |
| 2-167 | 4-MeOPh | 4-MePh | 3-EtOPh |
| 2-168 | 4-EtOPh | 4-MePh | 4-EtOPh |
| 2-169 | 3,4-diMeOPh | 4-MePh | 2,3,4-triEtOPh |
| 2-170 | 3,4-diEtOPh | 4-MePh | 2-HOPh |
| 2-171 | 3-MeOPh | 4-TfmPh | 3-HOPh |
| 2-172 | 3-EtOPh | 4-TfmPh | 4-HCPh |
| 2-173 | 4-MeOPh | 4-TfmPh | 3,4,5-triHOPh |
| 2-174 | 4-EtOPh | 4-TfmPh | 2-MeSPh |
| 2-175 | 3,4-diMeOPh | 4-TfmPh | 3-MeSPh |

TABLE 2-continued

| Compound No. | R¹ | R² | R⁴ |
|---|---|---|---|
| 2-176 | 3,4-diEtOPh | 4-TfmPh | 4-MeSPh |
| 2-177 | 3-MeOPh | 3,4-diClPh | 3,4,5-triMeSPh |
| 2-178 | 3-EtOPh | 3,4-diFPh | 3,4,5-triEtSPh |
| 2-179 | 4-MeOPh | 3,4-diFPh | 2-EtOPh |
| 2-180 | 4-EtOPh | 3,4-diClPh | 3-EtOPh |
| 2-181 | 3,4-diMeOPh | 3,4-diClPh | 4-EtOPh |
| 2-182 | 3,4-diEtOPh | 3,4-diFPh | 3,4,5-triEtOPh |
| 2-183 | 3-MeOPh | Ph | 2-ClPh |
| 2-184 | 3-EtOPh | Ph | 3-ClPh |
| 2-185 | 4-MeOPh | Ph | 4-ClPh |
| 2-186 | 4-EtOPh | Ph | 3,4,5-triClPh |
| 2-187 | 3,4-diMeOPh | Ph | 2-FPh |
| 2-188 | 3,4-diEtOPh | Ph | 3-FPh |
| 2-189 | 3-MeOPh | 4-ClPh | 4-FPh |
| 2-190 | 3-EtOPh | 4-BrPh | 3,4,5-triFPh |
| 2-191 | 4-MeOPh | 4-FPh | 2-BrPh |
| 2-192 | 4-EtOPh | 4-ClPh | 3-BrPh |
| 2-193 | 3,4-diMeOPh | 4-FPh | 4-BrPh |
| 2-194 | 3,4-diEtOPh | 4-BrPh | 3,4,5-triBrPh |
| 2-195 | 3-MeOPh | 4-MePh | 2-ClPh |
| 2-196 | 3-EtOPh | 4-MePh | 3-ClPh |
| 2-197 | 4-MeOPh | 4-MePh | 4-ClPh |
| 2-198 | 4-EtOPh | 4-MePh | 3,4,5-triClPh |
| 2-199 | 3,4-diMeOPh | 4-MePh | 2-FPh |
| 2-200 | 3,4-diEtOPh | 4-MePh | 3-FPh |
| 2-201 | 3-MeOPh | 4-TfmPh | 4-FPh |
| 2-202 | 3-EtOPh | 4-TfmPh | 3,4,5-triFPh |
| 2-203 | 4-MeOPh | 4-TfmPh | 2-BrPh |
| 2-204 | 4-EtOPh | 4-TfmPh | 3-BrPh |
| 2-205 | 3,4-diMeOPh | 4-TfmPh | 4-BrPh |
| 2-206 | 3,4-diEtOPh | 4-TfmPh | 3,4,5-tri-BrPh |
| 2-207 | 3-MeOPh | 3,4-diClPh | 2-ClPh |
| 2-208 | 3-EtOPh | 3,4-diFPh | 3-ClPh |
| 2-209 | 4-MeOPh | 3,4-diFPh | 4-ClPh |
| 2-210 | 4-EtOPh | 3,4-diClPh | 3,4,5-triClPh |
| 2-211 | 3,4-di-MeOPh | 3,4-diClPh | 2-FPh |
| 2-212 | 3,4-diEtOPh | 3,4-diFPh | 3-FPh |

TABLE 3

| Compound No. | R¹ | R² | R⁴ |
|---|---|---|---|
| 3-1 | Ph | 3,4-diMeOPh | 3,4,5-triMeOPh |
| 3-2 | 3-ClPh | 3,4-diMeOPh | 3,4,5-triMeOPh |
| 3-3 | 3-TfmPh | 3,4-diMeOPh | 3,4,5-triMeOPh |
| 3-4 | 3-MePh | 3,4-diMeOPh | 3,4,5-triMeOPh |
| 3-5 | 4-MeOPh | 3,4-diClPh | 3,4,5-triMeOPh |
| 3-6 | 4-MeOPh | 3,4-diMePh | 3,4,5-triMeOPh |
| 3-7 | 3-ClPh | 3-ClPh | 3,4,5-triMeOPh |
| 3-8 | 3-MePh | 3-MePh | 3,4,5-triMeOPh |
| 3-9 | 3-ClPh | 3-PrOPh | 3,4,5-triMeOPh |
| 3-10 | 3-ClPh | 4-i-BuOPh | 3,4,5-triMeOPh |
| 3-11 | 3-MePh | 4-PrOPh | 3,4,5-triMeOPh |
| 3-12 | 3-MePh | 4-iBuOPh | 3,4,5-triMeOPh |
| 3-13 | 3,4-diClPh | 4-PrOPh | 3,4,5-triMeOPh |
| 3-14 | 3,4-diClPh | 4-iBuOPh | 3,4,5-triMeOPh |
| 3-15 | 3,4-diClPh | 4-MePh | 3,4,5-triMeOPh |
| 3-16 | 3,4-diClPh | 4-iBuOPh | 3,4,5-triMeOPh |
| 3-17 | Ph | 3,4-diMeOPh | 3,4-diMeOPh |
| 3-18 | 3-ClPh | 3,4-diMeOPh | 3,4-diMeOPh |
| 3-19 | 3-TfmPh | 3,4-diMeOPh | 3,4-diMeOPh |
| 3-20 | 3-MePh | 3,4-diMeOPh | 3,4-diMeOPh |
| 3-21 | 4-MeOPh | 3,4-diClPh | 3,4-diMeOPh |
| 3-22 | 4-MeOPh | 3,4-diMePh | 3,4-diMeOPh |
| 3-23 | 3-ClPh | 3-ClPh | 3,4-diMeOPh |
| 3-24 | 3-MePh | 3-MePh | 3,4-diMeOPh |
| 3-25 | 3-ClPh | 4-PrOPh | 3,4-diMeOPh |
| 3-26 | 3-ClPh | 4-i-BuOPh | 3,4-diMeOPh |
| 3-27 | 3-MePh | 4-PrOPh | 3,4-diMeOPh |
| 3-28 | 3-MePh | 4-iBuOPh | 3,4-diMeOPh |
| 3-29 | 3,4-diClPh | 4-PrOPh | 3,4-diMeOPh |
| 3-30 | 3,4-diClPh | 4-iBuOPh | 3,4-diMeOPh |
| 3-31 | 3,4-diClPh | 4-MePh | 3,4-diMeOPh |
| 3-32 | 3,4-diClPh | 4-iBuOPh | 3,4-diMeOPh |
| 3-33 | Ph | 3,4-diMeOPh | 4-MeOPh |
| 3-34 | 3-ClPh | 3,4-diMeOPh | 4-MeOPh |
| 3-35 | 3-TfmPh | 3,4-diMeOPh | 4-MeOPh |
| 3-36 | 3-MePh | 3,4-diMeOPh | 4-MeOPh |
| 3-37 | 4-MeOPh | 3,4-diClPh | 4-MeOPh |
| 3-38 | 4-MeOPh | 3,4-diMePh | 4-MeOPh |
| 3-39 | 3-ClPh | 3-ClPh | 4-MeOPh |
| 3-40 | 3-MePh | 3-MePh | 4-MeOPh |
| 3-41 | 3-ClPh | 3-PrOPh | 4-MeOPh |
| 3-42 | 3-ClPh | 4-i-BuOPh | 4-MeOPh |
| 3-43 | 3-MePh | 4-PrOPh | 4-MeOPh |
| 3-44 | 3-MePh | 4-iBuOPh | 4-MeOPh |
| 3-45 | 3,4-diClPh | 4-PrOPh | 4-MeOPh |
| 3-46 | 3,4-diClPh | 4-iBuOPh | 4-MeOPh |
| 3-47 | 3,4-diClPh | 4-MePh | 4-MeOPh |
| 3-48 | 3,4-diClPh | 4-iBuOPh | 4-MeOPh |
| 3-49 | Ph | 3-MeO-4-PrOPh | 3,4,5-triMeOPh |
| 3-50 | Ph | 3,4-diPrOPh | 3,4,5-triMeOPh |
| 3-51 | Ph | 3-PrO-4-MeOPh | 3,4,5-triMeOPh |
| 3-52 | 3-ClPh | 3-MeO-4-PrOPh | 3,4,5-triMeOPh |
| 3-53 | 3-ClPh | 3-PrO-4-MeOPh | 3,4,5-triMeOPh |
| 3-54 | 3-ClPh | 3,4-diPrOPh | 3,4,5-triMeOPh |
| 3-55 | 3-ClPh | 3-MeOPh | 3,4,5-triMeOPh |
| 3-56 | 3-MePh | 3-MeO-4-PrOPh | 3,4,5-triMeOPh |
| 3-57 | 3-MePh | 3-PrO-4-MeOPh | 3,4,5-triMeOPh |
| 3-58 | 3-MePh | 3,4-diPrOPh | 3,4,5-triMeOPh |
| 3-59 | 3-TfmPh | 3-MeO-4-PrOPh | 3,4,5-triMeOPh |
| 3-60 | 3-TfmPh | 3-PrO-4-MeOPh | 3,4,5-triMeOPh |

TABLE 3-continued

| Compound No. | R¹ | R² | R⁴ |
|---|---|---|---|
| 3-61 | 3-TfmPh | 3,4-diPrOPh | 3,4,5-triMeOPh |
| 3-62 | 3-BrPh | 3-MeO-4-PrOPh | 3,4,5-triMeOPh |
| 3-63 | 3-BrPh | 3-PrO-4-MeOPh | 3,4,5-triMeOPh |
| 3-64 | 3-BrPh | 3,4-diPrOPh | 3,4,5-triMeOPh |
| 3-65 | 3-BrPh | 3-MeOPh | 3,4,5-triMeOPh |
| 3-66 | 3-BrPh | 3-PrOPh | 3,4,5-triMeOPh |
| 3-67 | 3-BrPh | 4-MeOPh | 3,4,5-triMeOPh |
| 3-68 | 3-BrPh | 4-EtOPh | 3,4,5-triMeOPh |
| 3-69 | 3-BrPh | 4-PrOPh | 3,4,5-triMeOPh |
| 3-70 | 3-BrPh | 4-BuOPh | 3,4,5-triMeOPh |
| 3-71 | 3-TfmPh | 3-MeOPh | 3,4,5-triMeOPh |
| 3-72 | 3-TfmPh | 4-MeOPh | 3,4,5-triMeOPh |
| 3-73 | 3-TfmPh | 3-PrOPh | 3,4,5-triMeOPh |
| 3-74 | 3-TfmPh | 4-PrOPh | 3,4,5-triMeOPh |
| 3-75 | 3-FPh | 3-MeOPh | 3,4,5-triMeOPh |
| 3-76 | 3-FPh | 4-MeOPh | 3,4,5-triMeOPh |
| 3-77 | 3-FPh | 3-PrOPh | 3,4,5-triMeOPh |
| 3-78 | 3-FPh | 4-PrOPh | 3,4,5-triMeOPh |
| 3-79 | 3,5-diClPh | 3-MeOPh | 3,4,5-triMeOPh |
| 3-80 | 3,5-diClPh | 4-MeOPh | 3,4,5-triMeOPh |
| 3-81 | 3,5-diClPh | 3-PrOPh | 3,4,5-triMeOPh |
| 3-82 | 3,5-diClPh | 4-PrOPh | 3,4,5-triMeOPh |
| 3-83 | 3-ClPh | 4-CH₃O-Ph | 3,4,5-triCH₃OPh |
| 3-84 | 2,3-diClPh | 4-CH₃O—Ph | 3,4,5-triCH₃OPh |
| 3-85 | 2,4-diClPh | 4-CH₃O—Ph | 3,4,5-triCH₃OPh |
| 3-86 | 2,5-diClPh | 4-CH₃O—Ph | 3,4,5-triCH₃OPh |
| 3-87 | 2,6-diClPh | 4-CH₃O—Ph | 3,4,5-triCH₃OPh |
| 3-88 | 3,6-diClPh | 4-CH₃O—Ph | 3,4,5-triCH₃OPh |

Of the compounds listed above, the preferred compounds are Compounds Nos. 1-1, 1-2, 1-3, 1-4, 1-6, 1-14, 1-16, 1-17, 1-18, 1-19, 1-20, 1-25, 1-26, 1-28, 1-29, 1-30, 1-41, 1-45, 1-46, 1-53, 1-76, 1-83, 1-91, 1-116, 1-117, 1-118, 1-120, 1-129, 1-130, 1-133, 1-134, 1-141, 1-154, 1-155, 1-207, 1-220, 1-298, 1-300, 1-313, 1-325, 1-327, 1-342, 1-343, 1-388, 1-411, 1-412, 1-419, 1-420, 1-424, 1-425, 1-426, 1-431, 1-433, 1-441, 1-445, 1-452, 1-453, 1-454, 1-455, 1-456, 1-457, 1-458, 1-459, 1-460, 1-461, 1-462, 1-463, 1-466, 1-467, 1-468, 1-469, 1-470, 1-471, 1-472, 1-473, 1-474, 1-475, 1-476, 1-477, 1-478, 1-479, 1-480, 1-481, 1-482, 1-483, 1-484, 1-485, 1-486, 1-487, 1-488, 1-489, 1-490, 1-491, 1-492, 1-496, 1-498, 1-501, 1-505, 1-507, 1-510, 1-511, 1-512, 1-513, 1-514, 1-515, 1-516, 1-517, 1-518, 1-519, 1-520, 1-521, 1-522, 1-523, 1-524, 1-525, 1-528, 1-529, 1-530, 1-531, 1-536, 1-537, 1-539, 1-541, 1-546, 1-551, 1-552, 1-553, 1-556, 1-557, 1-558, 1-559, 1-560, 1-561, 1-562, 1-563, 1-564, 1-565, 1-566, 1-567, 1-568, 1-569, 1-570, 1-571, 1-572, 1-573, 1-574, 1-580, 1-581, 1-582, 1-583, 1-584, 1-585, 1-586, 1-587, 1-588, 1-589, 1-590, 1-591, 1-592, 1-593, 1-594, 1-595, 1-596, 1-598, 1-601, 1-602, 1-603, 1-604, 1-605, 1-606, 1-607, 1-608, 1-609, 1-610, 1-611, 1-612, 1-616, 1-621, 1-622, 1-632, 1-624, 1-625, 1-626, 1-627, 1-628, 1-629, 1-630, 1-631, 1-632, 1-633, 1-634, 1-635, 1-636, 1-637, 1-638, 1-639, 1-640, 1-641, 1-642, 1-643, 1-644, 1-645, 1-646, 1-647, 1-649, 1-650, 1-651, 1-652, 1-655, 1-659, 1-660, 1-661, 1-662, 1-663, 1-664, 1-665, 1-666, 1-667, 1-668, 1-669, 1-670, 1-671, 1-672, 1-673, 1-674, 1-675, 1-676, 1-677, 1-678, 1-679, 1-680, 1-681, 1-682, 1-683, 1-684, 1-685, 1-686, 1-687, 1-688, 1-689, 1-690, 1-691, 1-692, 1-693, 1-694, 1-695, 1-696, 1-697, 1-698, 1-699, 1-700, 1-701, 1-702, 1-703, 1-704, 1-705, 1-706, 1-707, 1-708, 1-709, 1-710, 1-711, 1-712, 1-713, 1-714, 1-715, 1-716, 1-717, 1-718, 1-719, 1-720, 1-721, 1-722, 1-723, 1-724, 1-725, 1-726, 1-727, 1-728, 1-729, 1-730, 1-731, 1-732, 1-733, 1-734, 1-735, 1-736, 1-737, 1-738, 1-739, 1-740, 1-741, 1-742, 1-743, 1-744, 1-745, 1-746, 1-747, 1-748, 1-749, 1-750, 1-751, 1-752, 1-753, 1-754, 1-755, 1-756, 1-757, 1-758, 1-759, 1-760, 1-761, 1-762, 1-763, 1-764, 1-766, 1-771, 1-772, 1-773, 1-774, 1-777, 1-778, 1-779, 1-780, 1-781, 1-782, 1-783, 1-784, 1-785, 1-787, 1-788, 1-789, 1-790, 1-799, 1-801, 1-803, 1-805, 1-807, 1-809, 1-810, 1-813, 1-815, 1-817, 1-820, 1-821, 1-823, 1-825, 1-832, 1-833, 1-845, 1-846, 1-850, 1-851, 1-858, 1-859, 1-860, 1-862, 1-863, 1-866, 1-867, 1-871, 1-872, 1-873, 1-874, 1-875, 1-876, 2-1, 2-7, 2-8, 2-9, 2-15, 2-16, 2-19, 2-21, 2-23, 2-24, 2-25, 2-29, 2-30, 2-31, 2-32, 2-35, 2-37, 2-41, 2-44, 2-45, 2-46, 2-47, 2-51, 2-53, 2-57, 2-59, 2-62, 2-65, 2-66, 2-67, 2-68, 2-70, 2-72, 2-74, 2-75, 2-77, 2-78, 2-80, 2-83, 2-84, 2-85, 2-86, 2-87, 2-88, 2-89, 2-90, 2-91, 2-92, 2-93, 2-94, 2-101, 2-102, 2-103, 2-1-4, 2-107, 2-108, 2-109, 2-110, 2-112, 2-163, 3-1, 3-2, 3-3, 3-4, 3-5, 3-6, 3-7, 3-8, 3-9, 3-11, 3-3-13, 3-18, 3-19, 3-23, 3-25, 3-29, 3-34, 3-35, 3-37, 3-49, 3-50, 3-51, 3-52, 3-54, 3-56, 3-58, 3-59, 3-61, 3-62, 3-64, 3-67 and 3-68.

The more preferred compounds are Compounds Nos. 1-28, 1-53, 1-419, 1-424, 1-425, 1-431, 1-441, 1-445, 1-453, 1-454, 1-455, 1-456, 1-461, 1-462, 1-463, 1-464, 1-467, 1-468, 1-469, 1-470, 1-472, 1-475, 1-476, 1-478, 1-480, 1-482, 1-483, 1-484, 1-486, 1-510, 1-512, 1-513, 1-514, 1-515, 1-517, 1-519, 1-521, 1-524, 1-529, 1-531, 1-541, 1-546, 1-558, 1-560, 1-568, 1-570, 1-574, 1-581, 1-582, 1-585, 1-587, 1-590, 1-592, 1-594, 1-598, 1-603, 1-606, 1-609, 1-622, 1-627, 1-628, 1-631, 1-632, 1-637, 1-660, 1-668, 1-670, 1-671, 1-675, 1-679, 1-680, 1-681, 1-684, 1-685, 1-693, 1-694, 1-702, 1-703, 1-707, 1-710, 1-713, 1-714, 1-717, 1-718, 1-719, 1-727, 1-728, 1-730, 1-731, 1-833, 1-737, 1-740, 1-743, 1-746, 1-752, 1-758, 1-759, 1-772, 1-773, 1-777, 1-778, 1-784, 1-799, 1-803, 1-805, 1-813, 1-815, 1-845, 1-858, 1-859, 1-866, 1-867, 1-872, 1-873, 1-874, 1-875, 1-876, 3-2, 3-3, 3-5, 3-49, 3-50, 3-52, 3-54, 3-56 and 3-59.

The most preferred compounds are:

1-28. 1-[3-(3,4-Dimethoxyphenyl)-3-phenylacryloyl)-4-(3,4,5-trimethoxybenzoyl)piperazine;

1-419. 1-[3,3-Bis(3-chlorophenyl)acryloyl]-4-(3,4,5-trimethoxybenzoyl)piperazine;

1-424. 1-[3,3-Bis(3-methylphenyl)acryloyl]-4-(3,4,5-trimethoxybenzoyl)piperazine;

1-426. 1-[3,3-Bis(3-trifluoromethylphenyl)acryloyl]-4-(3,4,5-trimethoxybenzoyl)piperazine;

1-453. 1-[3-(3-Chlorophenyl)-3-(3-methoxyphenyl)acryloyl]-4-(3,4,5-trimethoxybenzoyl)piperazine;

1-454. 1-[3-(2-Chlorophenyl)-3-(4-methoxyphenyl)acryloyl]-4-(3,4,5-trimethoxybenzoyl)piperazine;

1-455. 1-[3-(2-Chlorophenyl)-3-(3-propoxyphenyl)acryloyl]-4-(3,4,5-trimethoxybenzoyl)piperazine;

1-467. 1-[3-(3-Chlorophenyl)-3-(3-methoxyhenyl)acryloyl]-4-(3,4,5-trimethoxybenzoyl)piperazine;

1-468. 1-[3-(3-Chlorophenyl)-3-(4-methoxyphenyl)acryloyl]-4-(3,4,5-trimethoxybenzoyl)piperazine;

1-469. 1-[3-(3-Chlorophenyl)-3-(3-propoxyphenyl)acryloyl]-4-(3,4,5-trimethoxybenzoyl)piperazine;

1-470. 1-[3-(3-Chlorophenyl)-3-(4-propoxyphenyl)acryloyl]-4-(3,4,5-trimethoxybenzoyl)piperazine;

1-482. 1-[3-(3-Chlorophenyl)-3-(3,4-dimethoxyphenyl)acryloyl]-4-(3,4,5-trimethoxybenzoyl)piperazine;

1-483. 1-[3-(3-Chlorophenyl)-3-(4-methoxy-3-propoxyphenyl)acryloyl]-4-(3,4,5-trimethoxybenzoyl)piperazine;

1-484. 1-[3-(3-Chlorophenyl)-3-(3,4-dipropoxyphenyl)acryloyl]-4-(3,4,5-trimethoxybenzoyl)piperazine;

1-513. 1-[3-(3,4-Dichlorophenyl)-3-(4-methoxyphenyl)acryloyl]-4-(3,4,5-trimethoxybenzoyl)piperazine;

1-515. 1-[3-(3,4-Dichlorophenyl)-3-(4-propoxyphenyl)acryloyl]-4-(3,4,5-trimethoxybenzoyl)piperazine;

1-557. 1-[3-(3-Trifluoromethylphenyl)-3-(3-methoxyphenyl)acryloyl]-4-(3,4,5-trimethoxybenzoyl)piperazine;

1-559. 1-[3-(3-Trifluoromethylphenyl)-3-(3-propxyphenyl)acryloyl]- 4-(3,4,5-trimethoxybenzoyl)piperazine;

1-574. 1-[3-(3-Trifluoromethylphenyl)-3-(3,4-dimethoxyphenyl)acryloyl]- 4-(3,4,5-trimethoxybenzoyl)piperazine;

1-590. 1-[3-(3-Methylphenyl)-3-(3,4-dimethoxyphenyl)acryloyl]-4-(3,4,5-trimethoxybenzoyl)piperazine;

1-594. 1-[3-(3-Methylphenyl)-3-(4-propoxyphenyl)acryloyl]-4-(3,4,5-trimethoxybenzoyl)piperazine;

1-603. 1-[3-(3-Methoxy-4-propoxyphenyl)-3-phenylacryloyl]-4-(3,4,5-trimethoxybenzoyl)piperazine;

1-606. 1-[3-(3,4-Dipropoxyphenyl)-3-phenylacryloyl]-4-(3,4,5-trimethoxybenzoyl)piperazine;

1-622. 1-[3-(4-Ethoxy-3-methoxyphenyl)-3-phenylacryloyl]-4-(3,4,5-trimethoxybenzoyl)piperazine;

1-627. 1-[3-(4-Butoxy-3-methoxyphenyl)-3-phenylacryloyl]-4-(3,4,5-trimethoxybenzoyl)piperazine;

1-685. 1-[3-(3-Methoxy-4-propoxyphenyl)-3-(3-trifluoromethylphenyl)acryloyl]-4-(3,4,5-trimethoxybenzoyl)piperazine;

1-710. 1-[3-(3-Methoxy-4-propoxyphenyl)-3-(3-methylphenyl)acryloyl]-4-(3,4,5-trimethoxybenzoyl)piperazine;

1-740. 1-[3-(3-Chlorophenyl)-3-(4-methoxy-4-methoxy-4-propoxyphenyl)acryloyl]-4-(3,4,5-trimethoxybenzoyl)piperazine;

1-743. 1-[3-(3-Chlorophenyl)-3-(4-ethoxy-3-methoxyphenyl)acryloyl]-4-(3,4,5-trimethoxybenzoyl)piperazine;

1-799. 1-[3-(3,5-Dichlorophenyl)-3-(4-ethoyxphenyl)acryloyl]-4-(3,4,5-trimethoxybenzoyl)piperazine;

1-803. 1-[3-(2,5-dichlorophenyl)-3-(4-methoxyphenyl)acryloyl]-4-(3,4,5-trimethoxybenzoyl)piperazine;

1-805. 1-[3-(2,5-Dichlorophenyl)-3-(4-ethoxyphenyl)acryloyl]-4-(3,4,5-trimethoxybenzoyl)piperazine;

1-858. 1-[3-(3,5-Difluorophenyl)-3-(4methoxyphenyl)acryloyl]-4-(3,4,5-trimethoxybenzoyl)piperazine;

1-859. 1-[3-(3,5-Difluorophenyl)-3-(4-ethoxyphenyl)acryloyl]-4-(3,4,5-trimethoxybenzoyl)piperazine;

1-872. 1-[3-(3-Fluorophenyl)-3-(4-ethoxyphenyl)acryloyl]-4-(3,4,5-trimethoxybenzoyl)piperazine;

1-873. 1-[3-(3-Chloro-5-methylphenyl)-3-(4-methoxyphenyl)acryloyl]-4-(3,4,5-trimethoxybenzoyl)piperazine;

1-874 and 1-[3-(3-Chloro-5-methylphenyl)-3-(4-ethoxyphenyl)acryloyl]-4-(3,4,5-trimethoxybenzoyl)piperazine.

The N-acryloylpiperazine derivatives of the present invention can be prepared by the procedures described below.

Where it is desired to prepare any compound of present invention which has a thiocarbonyl group in molecule, it can, in general, be prepared by any of reactions described below from the corresponding starting material also having a thiocarbonyl group in its molecule. Alternatively, it can also be prepared first synthesizing the corresponding compound having a carbonyl group in its molecule and then reacting carbonyl compound with a reagent which converts the carbonyl group into a thiocarbonyl group, such as Lawesson's Reagent [which consists mainly of [2,4-bis-(4-methoxyphenyl)-1,3-dithia-2,4-diphosphetane-2,4-disulfide] by conventional means. If the compound has two carbonyl groups in its molecule, selective conversion of these two carbonyl groups into either two thiocarbonyl groups or one thiocarbonyl group is possible by selection of the reaction conditions.

In general terms, the compounds of the present invention may be prepared by reacting a compound of formula (II):

with a compound of formula (III):

$$Z^2—B'—R^4 \quad (III)$$

(in which one of $Z^1$ and $Z^2$ represents a group represented by Y and the other represents a group of formula —A—H; Y represents a nucleophilic leaving group; and $R^1$, $R^2$, $R^3$, $R^4$, X, A and B' are as defined above).

Examples of nucleophilic leaving groups which may be represented by Y include: halogen atoms, such as the chlorine, bromine or iodine atoms; azide groups; and lower alkoxycarbonyloxy groups in which the alkoxy part has from 1 to 4, preferably 1 or 2, carbon atoms, such as the methoxycarbonyloxy and ethoxycarbonyloxy groups.

More specifically, examples of preferred methods of preparing the compounds of the present invention are as illustrated in the following Methods A and B.

Method A:

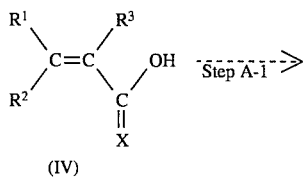

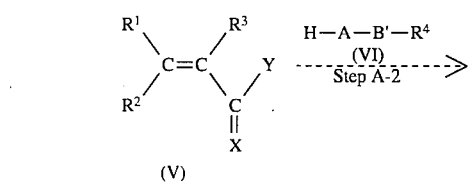

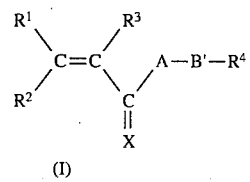

In these formulae, $R^1$, $R^2$, $R^3$, $R^4$, X, A, B' and Y are as defined above.

In Step A-1 the carboxylic acid derivative of formula (IV) is converted to an activated derivative thereof of formula (V).

This activation may be carried out using conventional techniques, which will, of course, depend on the nature of the active derivative of formula (V) to be prepared. For example, where it is desired to prepare an acyl halide compound, a phosphorus chloride (such as phosphorus pentachloride or phosphorus trichloride) or a sulfuric acid derivative (such as thionyl chloride) is reacted with the carboxylic acid of formula (IV). Where it is desired to prepare an acyl azide compound, an azidation reagent, such as diphenylphosphorylazide (DPPA), is employed, together with an organic base. Where it is desired to prepare a lower alkoxycarbonyloxy compound, a lower alkyl halocarboxylate, such as ethyl chloroformate, is employed, together with an organic base.

Where an organic base is employed in this reaction, there is no particular limitation on its nature, and any base commonly used for this type of reaction may equally be employed here. Examples of suitable organic bases include: trialkylamines, such as triethylamine and diisopropylethylamine; and cyclic amines, such as N-methylmorpholine, pyridine, 4-(N,N-dimethylamino)pyridine, N,N-dimethylaniline, 1,5-diazabicyclo[4.3.0]nona-5-ene, 1,4-diazabicyclo[2.2.2]octane and 1,8-diazabicyclo[5.4.0]undec-7-ene (DBU).

In Step A-2 the compound of formula (I) of the present invention is prepared by reacting the activated carboxylic acid derivative of formula (V) with the compound of formula (VI). This reaction may take place in the presence or absence of a base and preferably in a solvent.

When the activated carboxylic acid derivative of formula (V) is an acyl halide, a base is preferably employed. There is no particular restriction on the nature of the base employed for this reaction, and any base commonly employed in reactions of this type may equally be employed here. If an inorganic base [for example: an alkali metal carbonate (such as sodium carbonate or potassium carbonate); an alkali metal bicarbonate (such as sodium bicarbonate or potassium bicarbonate); an alkali metal hydride (such as lithium hydride, sodium hydride or potassium hydride); or an alkali metal hydroxide (such as sodium hydroxide, potassium hydroxide or barium hydroxide)] is employed, the preferred solvent is: an ether, such as diethyl ether, tetrahydrofuran, dioxane or dimethoxyethane; an amide, such as dimethylformamide, dimethylacetamide or hexamethylphosphoric triamide; a sulfoxide such as dimethyl sulfoxide; a nitrile such as acetonitrile; water; or a mixture of water with any one or more of the organic solvents mentioned above. If an organic base [such as triethylamine, diisopropylethylamine, N-methylmorpholine, pyridine, 4-(N,N-dimethylamino)pyridine, N,N-dimethylaniline, 1,5-diazabicyclo[4.3.0]nona-5-ene, 1,4-diazabicyclo[2.2.2]octane or 1,8-diazabicyclo[5.4.0]undec-7-ene (DBU)] is employed, the preferred solvent is: an aromatic hydrocarbon, such as benzene, toluene or xylene; an ether, such as diethyl ether, tetrahydrofuran, dioxane or dimethoxyethane; or a halogenated hydrocarbon, especially a halogenated aliphatic hydrocarbon, such as methylene chloride or chloroform.

When the activated carboxylic acid derivative of formula (V) is an acyl azide compound or a lower alkoxycarbonyloxy compound, the organic base mentioned above is not always necessary, because the reaction will proceed even in the absence of the base. However, a base may be employed, if desired. There is no particular restriction on the nature of the solvent to be employed, provided that it has no adverse effect on the reaction or on the reagents involved. Examples of suitable solvents include: aromatic hydrocarbons, such as benzene, toluene or xylene; halogenated hydrocarbons, especially halogenated aliphatic hydrocarbons, such as methylene chloride or chloroform; ethers, such as diethyl ether, tetrahydrofuran, dioxane or dimethoxyethane; amides, such as dimethylformamide, dimethylacetamide or hexamethylphosphoric triamide; sulfoxides, such as dimethyl sulfoxide; and nitriles, such as acetonitrile.

The reaction can take place over a wide range of temperatures, and the precise reaction temperature is not critical to the invention. In general, we find it convenient to carry out the reaction at a temperature from 0° C. to 50° C., preferably at room temperature. The time required for the reaction may also vary widely, depending on many factors, notably the reaction temperature and the nature of the reagents. However, provided that the reaction is effected under the preferred conditions outlined above, a period of from 15 minutes to 1 day will usually suffice.

Certain of the compounds of formula (VI) used in Step A-2 are known {for example, 1-(3,4,5-trimethoxybenzoyl)piperazine, L. Toldy et al., Acta. Chim. Acad. Sci. Hung., 49 (3), 265–285 (1966), and 1-[3,4,5-trimethoxy(thiobenzoyl)]piperazine, C. Farina et al., Eur. Med. Chem. Chimica Therapeutica, 14 (1), 27–31 (1979)}. Otherwise, they can be prepared by the reaction of the compound of formula (VII) with the compound of formula (IX) both of which will be described later, according to Method B.

Method B:

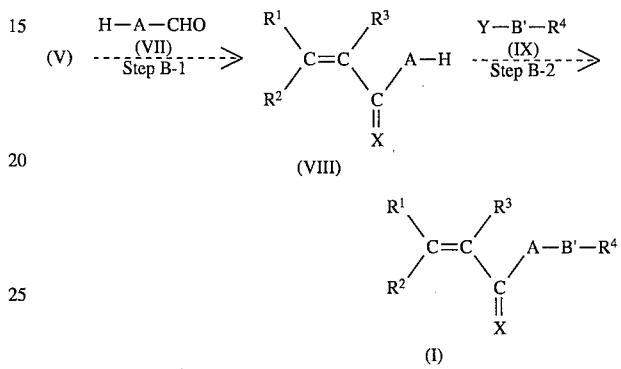

In these formulae, $R^1$, $R^2$, $R^3$, $R^4$, Y, X, A and B' are as defined above.

In Step B-1, a compound of formula (VIII) is prepared by: first, reacting the activated carboxylic acid derivative of formula (V) (prepared as described in Step A-1) with the compound of formula (VII); and then removing the formyl group which is a substituent on the nitrogen atom of the piperazine or homopiperazine ring "A". The reaction in the first part of this Step is essentially the same as and may be carried out under the same conditions as that of Step A-2, and using the same reagents as described therein.

The removal of the formyl group in the latter half of the Step is carried out by treating the formyl compound prepared in the first part of the Step with a base in the presence of a solvent. There is no particular restriction on the nature of the base employed, provided that it does not affect any other part of the compounds in the reaction mixture. The reaction is preferably carried out using as the base: a metal alkoxide, such as sodium methoxide; an alkali metal carbonate, such as sodium carbonate or potassium carbonate; an alkali metal hydroxide, such as sodium hydroxide or potassium hydroxide; aqueous ammonia or concentrated methanolic ammonia. There is no particular restriction on the nature of the solvent employed, provided that it has no adverse effect on the reagents and that it is capable of dissolving the reagents, at least to some extent. Examples of suitable solvents include any of those commonly used for hydrolytic reactions, for example, an organic solvent, such as: an alcohol, e.g. methanol, ethanol or propanol; or an ether, such as tetrahydrofuran or dioxane; also water or a mixture of water with any one or more of the organic solvents mentioned above may be used.

The reaction will take place over a wide range of temperatures, and the precise reaction temperature chosen is not critical to the invention. In general, in order to avoid side reactions, we find it convenient to carry out the reaction at a temperature in the range of from 0° C. to 150° C., preferably at room temperature, although the exact preferred temperature may vary depending upon the starting materials, the base and the reaction solvent. The time required for the reaction may likewise vary widely, depending on many factors, notably the reaction temperature and the nature of the reagents. However, in most cases, a period of from 1 to 24 hours will normally suffice.

In Step B-2, a compound of formula (I) is prepared by reacting a compound of formula (VIII) with a compound of formula (IX) in the presence of a base and in a solvent.

Where B' represents any group other than a lower alkylene group, the reaction is essentially the same as and may be carried out according to the procedure described in Step A-2. When B' represents a lower alkylene group, the base is preferably an alkali metal hydride, such as lithium hydride, sodium hydride or potassium hydride. There is no particular restriction on the nature of the solvent employed, provided that it does not hinder the reaction and that it can dissolve the starting materials at least to some degree. Preferred solvents are: ethers, such as diethyl ether, tetrahydrofuran, dioxane or dimethoxyethane; and amides, such as dimethylformamide, dimethylacetamide or hexamethylphosphoric triamide.

After completion of the reaction, the desired compound from every reaction mentioned above can be collected from the reaction mixture by conventional means. For example, it can be obtained by adding a water-immiscible organic solvent to the reaction mixture, followed by washing with water, and then distilling off the solvent. The compound thus obtained can, if necessary, be further purified by conventional means, such as recrystallization, reprecipitation or the various chromatography techniques, notably column chromatography.

The carboxylic acid derivative of formula (IV), in which X represents an oxygen atom, that is to say the compound of formula (XIII), which is one of the starting materials employed in the process of the present invention may be prepared as illustrated in the following Method C:

Method C:

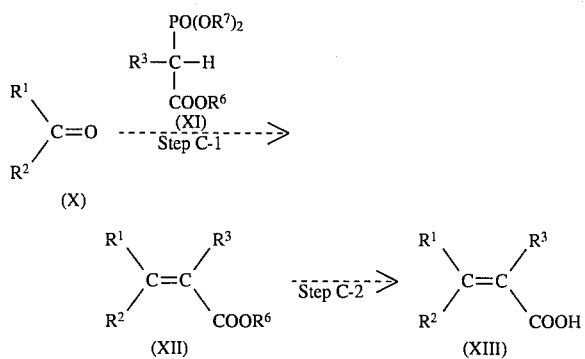

In these formulae, $R^1$, $R^2$ and $R^3$ are as defined above, $R^6$ represents a $C_1$–$C_6$ alkyl group, and $R^7$ represents a $C_1$–$C_6$ alkyl group or an aryl group which may optionally be substituted, as defined above in relation to $R^5$.

In Step C-1, a compound of formula (XII) is prepared by reacting a ketone compound of formula (X) with Horner's reagent, the compound of formula (XI). This reagent can be prepared, for example, by the well known Arbuzov reaction. Step C-1 takes place in the presence of a base and in a solvent.

There is no particular restriction on the nature of the base employed, provided that it has no adverse effect on other parts of the molecule. Examples of suitable bases include: inorganic bases, such as alkali metal hydrides (e. g. lithium hydride, sodium hydride or potassium hydride) and alkali metal hydroxides (e.g. sodium hydroxide, potassium hydroxide or barium hydroxide); organic bases, such as 1,5-diazabicyclo[4.3.0]nona-5-ene, 1,4-diazabicyclo[2.2.2] octane and 1,8-diazabicyclo[5.4.0]undec-7-ene (DBU); and organic metal bases, such as butyllithium and lithium diisopropylamide.

There is no particular restriction on the nature of the solvent employed, provided that it does not hinder the reaction and that it can dissolve the starting materials, at least to some degree. Examples of preferred solvents include: aromatic hydrocarbons, such as benzene, toluene or xylene; ethers, such as diethyl ether, tetrahydrofuran, dioxane or dimethoxyethane; amides, such as dimethylformamide, dimethylacetamide or hexamethylphosphoric triamide; and sulfoxides, such as dimethyl sulfoxide.

In Step C-2, the starting material of formula (XIII) used in the present invention is prepared by removing the group $R^6$, which is the carboxy-protecting group in the compound of formula (XII).

Removal of the protecting group may be carried out by any known reaction for removing groups of this type, for example by treatment with an acid or a base. Examples of suitable acids include hydrochloric acid, sulfuric acid, phosphoric acid and hydrobromic acid. There is no particular restriction on the nature of the base, provided that it does not affect other parts of the compounds in the reaction mixture; however, we prefer to use: alkali metal carbonates, such as sodium carbonate or potassium carbonate; alkali metal hydroxides, such as sodium hydroxide or potassium hydroxide; or concentrated methanolic ammonia. There is likewise no particular restriction on the nature of the solvent, and any solvent commonly used for hydrolytic reactions may equally be used here, provided that it has no adverse effect on any of the reagents and that it is capable of dissolving the reagents, at least to some extent. Examples include: water and mixtures of water with an organic solvent, for example: an alcohol such as methanol, ethanol or propanol; or an ether, such as tetrahydrofuran or dioxane.

The reaction will take place over a wide range of temperatures, and the precise reaction temperature chosen is not critical to the invention, although the preferred temperatures may vary depending on the starting materials and the base employed. In general, we find it convenient to carry out the reaction at a temperature in the range of from 0° C. to 150° C. The time required for the reaction may likewise vary widely, depending on many factors, notably the reaction temperature and the nature of the reagents. However, in most cases, a period of from 1 to 10 hours will normally suffice.

When the substituents $R^1$ and $R^2$ are different, the product will normally be obtained as a mixture of its geometrical isomers. By using chromatography or similar techniques, as is well known, in each of Steps C-1 and C-2, the (E)-form and (Z)-form can be obtained separately, if desired.

In general, the compounds of formula (X), which are starting materials in this reaction, are well known. However, where they are not, they can be prepared, for example, by reacting a compound of formula $R^1$—CHO (in which $R^1$ is as defined above) with a compound of formula $R^2$—MgZ (in which $R^2$ is as defined above and Z represents a halogen atom) or with a compound of formula $R^2$—Li (in which $R^2$ is as defined above), or by reacting a compound of formula $R^2$—CHO (in which $R^2$ is as defined above) with a compound of formula $R^1$—MgZ (in which $R^1$ and Z are as defined above) or with a compound of formula $R^1$—Li (in which $R^1$ is as defined above), followed by oxidizing the alcohol compound thus formed to its corresponding carbonyl compound by conventional means.

Further, by application of the famous Friedel-Crafts reaction, these compounds of formula (X) can be also prepared by reacting a compound of formula $R^1H$ (in which $R^1$ is as defined above) with a compound of formula $R^2$—COZ (in which $R^2$ and Z are as defined above), or by reacting a compound of formula $R^2H$ (in which $R^2$ is as defined-above) with a compound of formula $R^1$—COZ (in which $R^1$ and Z are as defined above).

The following Method D provides an alternative method of preparing a compound of formula (XIII), in which $R^3$ does not represent a hydrogen atom, that is to say a compound of formula (XVI).

Method D:

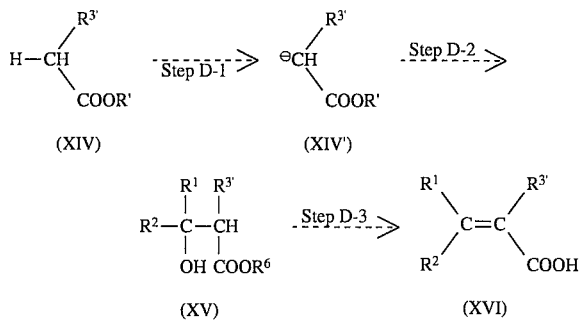

In the above formulae, $R^1$, $R^2$ and $R^6$ are as defined above; $R^{3'}$ represents any of the groups in the definition of $R^3$ other than a hydrogen atom; and R' represents a carboxy-protecting group, which may or may not be the same as the group represented by $R^6$.

In this reaction scheme, the starting material of formula (XVI) of the present invention is prepared by treating a compound of formula (XIV) with a base in the presence of solvent at −78° C.–0° C. to yield an anion of formula (XIV') (Step D-1), which is then reacted, in Step D-2, with a compound of formula (X) (see Method C); this is then treated, in Step D-3, with a dehydrating agent, such as an acid or phosphorus oxychloride, in the presence or absence of a solvent, and then the ester group is hydrolized by conventional means.

In Steps D-1 and D-2, there is no particular restriction on the nature of the solvent to be employed, provided that it has no adverse effect on the reaction or on the reagents involved. Examples of suitable solvents include: aliphatic hydrocarbons, such as hexane and heptane; aromatic hydrocarbons, such as benzene, toluene and xylene; ethers, such as diethyl ether, diisopropyl ether, tetrahydrofuran, dioxane, dimethoxyethane and diethylene glycol dimethyl ether; amides, such as formamide, dimethylformamide, dimethylacetamide and hexamethylphosphoric triamide; and sulfoxides, such as dimethyl sulfoxide and sulfolane.

There is no particular restriction on the nature of the base employed for the reaction of Step D-1, and any base commonly employed in reactions of this type may equally be employed here. Examples of suitable bases include: inorganic bases, such as alkali metal hydrides (e.g. lithium hydride, sodium hydride or potassium hydride); organic bases, such as 1,5-diazabicyclo[4.3.0]nona-5-ene, 1,4-diazabicyclo[2.2.2]octane or 1,8-diazabicyclo[5.4.0]undec-7-ene (DBU); and organic metal bases such as butyllithium and lithium diisopropylamide.

In Step D-2, which is preferably carried out without intermediate isolation of the anion of formula (XIV') produced in Step D-1, the anion is reacted with a compound of formula (X), to give a compound of formula (XV). The reaction is preferably carried out in the same reaction medium and under the same conditions as Step D-1.

Step D-3 consists of the reaction of the resulting compound of formula (XV) with a dehydrating agent, to give the desired compound of formula (XVI). This reaction may take place in the presence or absence of a solvent. There is no particular restriction on the nature of the solvent, where it is employed, provided that it has no adverse effect on the reaction or on the reagents involved. Examples of suitable solvents include: aliphatic hydrocarbons, such as hexane and heptane; aromatic hydrocarbons, such as benzene, toluene and xylene; halogenated hydrocarbons, especially halogenated aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol and methylcellosolve; ketones, such as acetone, methyl ethyl ketone, methyl isobutyl ketone, isophorone and cyclohexanone; nitro compounds, such as nitroethane and nitrobenzene; nitriles, such as acetonitrile and isobutyronitrile; amides, such as formamide, dimethyl formamide, dimethylacetamide and hexamethylphosphoric triamide; and sulfoxides, such as dimethyl sulfoxide and sulfolane.

There is likewise no particular restriction on the nature of the acid employed for this reaction, and any acid commonly employed as a proton donor and classified as a Bronsted acid may equally be employed here. Examples of suitable acids include: organic acids, such as p-toluenesulfonic acid or camphorsulfonic acid; and inorganic acids, such as hydrochloric acid or sulfuric acid.

When an phosphorus oxychloride is employed as the dehydrating reagent, an aprotic solvent should be used. Preferred such solvents include the aliphatic hydrocarbons, aromatic hydrocarbons or halogenated hydrocarbons listed above.

When the substituents $R^1$ and $R^2$ are different, the product will normally be obtained as a mixture of its geometric isomers. By using chromatography or similar techniques, as is well known, the Z-form and the E-form can be obtained separately, if desired.

Alternatively, the starting material of formula (XVI) may be prepared by reacting the compound of formula (X) with a compound of formula:

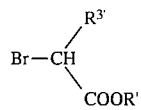

using activated zinc powder in the presence of a solvent according to the same Reformatsky reaction as is reported by Kametani et al. [Yakugakuzassi, 88, 911 (1968)], followed by dehydration and hydrolysis in a similar manner to that described above.

There is no particular restriction on the nature of the solvent to be employed in the Reformatsky reaction, provided that it has no adverse effect on the reaction or on the reagents involved. Examples of suitable solvents include: aliphatic hydrocarbons, such as hexane or heptane; and aromatic hydrocarbons, such as benzene, toluene or xylene, preferably aromatic hydrocarbons.

The reaction can take place over a wide range of temperatures, and the precise reaction temperature is not critical to the invention. In general, we find it convenient to carry out the reaction at a temperature from 0° C. to the boiling point of the reaction medium, preferably at a temperature from 80° C. to 100° C. The time required for the reaction may also vary widely, depending on many factors, notably the reaction temperature, the nature of the reagents, and the nature of the solvent. However, provided that the reaction is effected under the preferred conditions outlined above, a period of from 1 to 24 hours, preferably from 2 to 6 hours, will usually suffice.

An alternative method of preparing the compound of formula (XIII) in which $R^2$ represents a group —$R^5$, as defined above, that is to say a compound of formula (XVIII), is shown in Method E:

Method E:

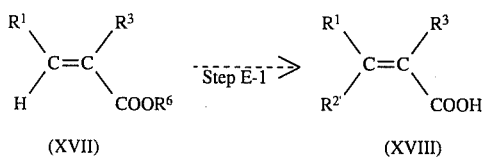

(XVII)            (XVIII)

In these formulae, $R^1$, $R^3$ and $R^6$ are as defined above, and $R^{2'}$ represents a group of formula —$R^5$ as defined above for $R^2$.

In Step E-1, the compound of formula (XVIII) is prepared by reacting the compound of formula (XVII), according to Heck's reaction, with a compound of formula $R^{2'}$—Y (in which $R^{2'}$ and Y are as defined above) in the presence of a palladium salt, such as palladium acetate, in a solvent, and then removing the carboxy-protecting group, $R^6$ as mentioned above There is no particular restriction on the nature of the solvent employed, provided that it does not hinder the reaction and that it can dissolve the starting compounds, at least to some degree. Examples of preferred solvents include: nitriles, such as acetonitrile; aromatic hydrocarbons, such as benzene, toluene and xylene; esters, such as ethyl acetate and propyl acetate; ethers, such as diethyl ether, tetrahydrofuran, dioxane and dimethoxyethane; amides, such as dimethylformamide, dimethylacetamide and hexamethylphosphoric triamide; and sulfoxides, such as dimethyl sulfoxide.

The compound of formula (XVII) used as the starting material can be prepared from a compound of formula $R^1$—CHO (in which $R^1$ is as defined above), using the techniques of Method C or Method D.

An alternative method of preparing a compound of formula (XII) in which $R^3$ represents a hydrogen atom, that is to say a compound of formula (XXI), is shown in Method F:

Method F:

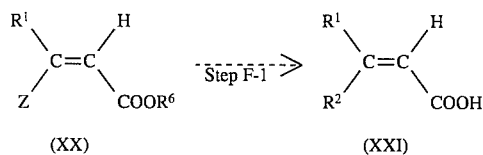

(XX)             (XXI)

In these formulae, $R^1$, $R^2$, $R^6$ and Z are as defined above.

In Step F-1, the compound of formula (XXI) is prepared from the compound of formula (XX).

When $R^2$ is $R^{2'}$ (as defined above), the compound of formula (XXI) is prepared by reacting the compound of formula (XX) with a compound of formula $R^{2'}$—MgZ (in which $R^{2'}$ and Z are as defined above) in the presence of a divalent nickel complex such as bis(diphenylphosphino)ethane nickel (II) chloride in a solvent, followed by removing the carboxy-protecting group, $R^6$, by the procedure mentioned above.

There is no particular restriction on the nature of the solvent employed, provided that it does not hinder the reaction and that it can dissolve the starting compounds, at least to some degree. Examples of preferred solvents include: aromatic hydrocarbons, such as benzene, toluene or xylene; and ethers, such as diethyl ether, tetrahydrofuran, dioxane or dimethoxyethane.

When $R^2$ represents any group other than $R^{2'}$, the compound of formula (XXI) may be prepared by reacting the compound of formula (XX) with a compound of formula $R^5$—CH=CH$_2$ (in which $R^5$ is as defined above) or with a compound of formula $R^5$—C≡CH (in which $R^5$ is as defined above) in the presence of a palladium complex such as bis (triphenylphosphine) palladium (II) chloride in a solvent, followed by removing the carboxy-protecting group, $R^6$.

In the first part of this reaction, the reaction may occasionally be carried out preferably in the presence of an organic base, such as triethylamine.

There is no particular restriction on the nature of the solvent employed in this reaction, provided that does not hinder the reaction and that it can dissolve the starting compounds, at least to some degree. Examples of preferred solvents include: aromatic hydrocarbons, such as benzene, toluene and xylene; halogenated hydrocarbons, especially halogenated aliphatic hydrocarbons, such as methylene chloride and chloroform; ethers, such as diethyl ether, tetrahydrofuran, dioxane and dimethoxyethane; amides, such as dimethylformamide, dimethylacetamide and hexamethylphosphoric triamide; and sulfoxides, such as dimethyl sulfoxide.

The compound of formula (XX) used as the starting material in this reaction can be prepared by the addition of a halogen atom, such as a chlorine or bromine atom, to a compound of formula (XVII) wherein $R^3$ represents a hydrogen atom, followed by removing a hydrogen halide, such as hydrogen bromide or hydrogen chloride, to form a triple bond, and then followed by the addition of a hydrogen halide such as hydrogen bromide.

As will be demonstrated hereafter, the novel N-acryloylpiperazine derivatives of the present invention have an excellent PAF-antagonist activity, and, moreover, have excellent stability on oral administration. Accordingly, these derivatives are expected to be useful for the therapy and prophylaxis of various diseases and disorders in which PAF is thought to be implicated, such as endotoxin-induced shock, anaphylactic shock, nephritis, myocardial infarction, angina pectoris, asthma, psoriasis and gastric ulceration.

The compounds of the invention may be administered orally or parenterally, as required, and may, if desired, be formulated into appropriate pharmaceutical preparations, the nature of which will depend upon the desired route of administration. For example, for oral administration, the compounds may be formulated as tablets, capsules, granules, powders or syrups. For parenteral administration, they may be formulated as injectable solutions or suspensions or as suppositories. Although the preferred dose will vary, depending upon the nature of the disorder, as well as upon the symptoms, age, condition and body weight of the patient and the route of administration, a preferred dose for an adult human patient would normally be expected to be from 0.2 to 50 mg/kg body weight per day, and this could be administered in a single dose or in divided doses.

These preparations can be formulated using any conventional additives such as vehicles, binders, disintegrating agents, lubricants, stabilizers and corrigents, as is well known in the art.

The invention is further illustrated by the following non-limiting Examples. Preparation of certain of the starting materials employed in these Examples is illustrated by the subsequent Preparations. The biological activities of certain of the compounds of the invention are then illustrated in the subsequent Experiments, and these are followed by examples of Formulations of the invention.

EXAMPLE 1

1-(3,3-Diphenylacryloyl)-4-(3,4,5-trimethoxybenzoyl)piperazin 4.164 g of phosphorus pentachloride were added to 90 ml of a methylene chloride solution containing 4.485 g of 3,3-diphenylacrylic acid, which had previously been cooled at 0°–5° C. The reaction mixture was then stirred for one hour at room temperature, after which the solvent was distilled off under reduced pressure. The resulting residue was dissolved in 50 ml of toluene, and then the solvent was once again distilled off under reduced pressure. This procedure comprising dissolution and distillation was repeated once more. 3,3-Diphenylacryloyl chloride was obtained as a white solid. This crude product was immediately used in the next reaction.

0.840 g of sodium bicarbonate dissolved in 15 ml of water was added to 30 ml of a tetrahydrofuran solution containing 1.401 g of 1-(3,4,5-trimethoxybenzoyl)piperazine. 1.214 g of the 3,3-diphenylacryloyl chloride obtained as described above were added to the mixture, in one go, and the resulting mixture was stirred for 30 minutes at room temperature. At the end of this time, 50 ml of methylene chloride were added to the reaction mixture, the organic phase and the aqueous phase were separated from each other, and the aqueous phase was extracted with methylene chloride. The methylene chloride phase and the methylene chloride extract were combined and washed with 10% w/v aqueous hydrochloric acid with a 5% w/v aqueous solution of sodium bicarbonate and with a saturated aqueous solution of sodium chloride, in that order. The methylene chloride solution was dried over anhydrous sodium sulfate, and then the solvent was removed by distillation under reduced pressure. The oily residue (2.70 g) was purified by silica gel flash chromatography. Those fractions which were eluted with a 100:1 by volume mixture of methylene chloride and methanol were collected to afford 2.150 g of the title compound as a white powder. Recrystallization of this from a mixture of ethyl acetate and hexane gave white needles, melting at 148°–150° C.

Nuclear Magnetic Resonance Spectrum (CDCl$_3$, 270 MHz) δ ppm: 2.65–3.80 (8H, multiplet); 3.84 (6H, singlet); 3.85 (3H, singlet): 6.30 (1H, singlet); 6.52 (2H, singlet); 7.2–7.5 (10H, multiplet).

Mass spectrum (m/z): 486 (M$^+$), 291 (M$^+$—C$_{10}$H$_{11}$O$_4$), 279 (M$^+$—C$_{15}$H$_{11}$O), 207 (C$_{15}$H$_{11}$O), 195 (C$_{10}$H$_{11}$O$_4$).

Infrared Absorption Spectrum (CHCl$_3$) ν$_{max}$ cm$^{-1}$: 1630, 1585.

Elemental analysis: Calculated for C$_{29}$H$_{30}$N$_2$O$_5$: C, 71.59%; H, 6.21%; N, 5.76%. Found: C, 71.54%; H, 6.44%; N, 5.71%.

EXAMPLE 2

1-[3,3-Bis(4-methoxyphenyl)acryloyl]-4-(3,4,5-trimethoxybenzoyl)piperazine

Following a procedure similar to that described in Example 1, but using 0.500 g of 3,3-bis(4-methoxyphenyl)acrylic acid. 0.362 g of the title compound was obtained as a powder.

Nuclear Magnetic Resonance Spectrum (CDCl$_3$, 270 MHz) δ ppm: 2.70–3.75 (8H, multiplet); 3.82 (3H, singlet): 3.84 (3H, singlet); 3.85 (9H, singlet); 6.14 (1H, singlet); 6.54 (2H, singlet): 6.80–6.93 (4H, multiplet): 7.18–7.30 (4H, multiplet).

Mass spectrum (m/z): 546 (M$^+$), 351 (M$^+$—C$_{10}$H$_{11}$O$_4$), 279 (M$^+$—C$_{17}$H$_{15}$O$_3$), 267 (C$_{17}$H$_{15}$O$_3$), 195 (C$_{10}$H$_{11}$O$_4$).

Infrared Absorption Spectrum (CHCl$_3$) ν$_{max}$ cm$^{-1}$: 1625, 1605, 1585.

EXAMPLE 3

1-[3,3-Bis(4-chlorophenyl)acryloyl]-4-(3,4,5-trimethoxybenzoyl)piperazine

Following a procedure similar to that described in Example 1, but using 0.500 g of 3,3-bis(4-chlorophenyl)acrylic acid, 0.938 g of the title compound was obtained as a white powder.

Nuclear Magnetic Resonance Spectrum (CDCl$_3$, 270 MHz) δ ppm: 2.90–3.70 (8H, multiplet): 3.86 (9H, singlet); 6.32 (1H, singlet); 6.56 (2H, singlet); 7.15–7.40 (8H, multiplet).

Mass spectrum (m/z): 554 (M$^+$), 359 (M$^+$—C$_{10}$H$_{11}$O$_4$), 279 (M$^+$—C$_{15}$H$_9$Cl$_2$O), 275 (C$_{15}$H$_9$Cl$_2$O); 195 (C$_{10}$H$_{11}$O$_4$).

Infrared Absorption Spectrum (CHCl$_3$) ν$_{max}$ cm$^{-1}$: 1630, 1590.

EXAMPLE 4

1-[3,3-Bis(2-thienyl)acryloyl]-4-(3,4,5-trimethoxybenzoyl)piperazine

Following a procedure similar to that described in Example 1, but using 0.500 g of 3,3-bis(2-thienyl)-acrylic acid, 0.719 g of the title compound was obtained as a white powder.

Nuclear Magnetic Resonance Spectrum (CDCl$_3$, 270 MHz) δ ppm: 2.90–3.75 (8H, singlet); 3.85 (9H, singlet); 6.34 (1H, singlet); 6.57 (2H, singlet); 7.02 (1H, doublet or doublets, J=5.13 & 3.66 Hz); 7.08 (1H, doublet of doublets, J=5.13 & 3.66 Hz); 7.13 (1H, doublet of doublets, J=1.10 & 3.66 Hz); 7.26 (1H, doublet of doublets, J=1.10 & 3.66 Hz); 7.32 (1H, doublet of doublets, J=5.13 & 1.10 Hz); 7.42 (1H, doublet of doublets, J=5.13 & 1.10 Hz).

Mass spectrum (m/z): 498 (M$^+$), 303 (M$^+$—C$_{10}$C$_{11}$O$_4$), 279 (M$^+$—C$_{11}$H$_7$OS$_2$), 219 (C$_{11}$H$_7$OS$_2$), 195 (C$_{10}$H$_{11}$O$_4$).

Infrared Absorption Spectrum (CHCl$_3$) ν$_{max}$ cm$^{-1}$: 1620, 1585.

Elemental analysis: Calculated for C$_{25}$H$_{26}$N$_2$O$_5$S$_2$: C, 60.22%: H, 5.26%: N, 5.62%: S, 12.86%. Found: C, 60.34%: H, 5.43%: N, 5.59%: S, 12.97%.

EXAMPLE 5

1-[(Z)-3-Phenyl-3-(2-thienyl)acryloyl]-4-(3,4,5-trimethoxybenzoyl)piperazine Following a procedure similar to that described in Example 1, but using 0.480 g of (Z)-3-phenyl-3-(2-thienyl)acrylic acid (prepared as described in Preparation 1, Isomer A, melting at 144°–147° C.), 0.703 g of the title compound was obtained as a white powder.

Nuclear Magnetic Resonance Spectrum (CDCl$_3$, 270 MHz) δ ppm: 2.70–3.75 (8H, multiplet); 3.84 (3H, singlet); 3.85 (6H, singlet); 6.41 (1H, singlet); 6.53 (2H, singlet); 6.88 (1H, doublet of doublets, J=3.67 & 1.10 Hz); 6.98 (1H, doublet of doublets, J=5.13 & 3.67 Hz); 7.30 (1H, doublet of doublets, J=5.13 & 1.10 Hz); 7.40 (5H, singlet-like).

Mass spectrum (m/z): 492 (M$^+$), 297 (M$^+$—C$_{10}$H$_{11}$O$_4$), 279 (M$^+$ C$_{13}$H$_9$OS), 213 (C$_{13}$H$_9$OS), 195 (C$_{10}$H$_{11}$O$_4$).

Infrared Absorption Spectrum (CDCl$_3$) $v_{max}$ cm$^{-1}$: 1620, 1585.

Elemental analysis: Calculated for C$_{27}$H$_{28}$N$_2$O$_5$S: C, 65.83%; H, 5.73%; N, 5.69%; S, 6.51%. Found: C, 65.68%; H, 5.97%; N, 5.79%; S, 6.51%.

EXAMPLE 6

1-[(E)-3-Phenyl-3-(4-pyridyl)acryloyl]-4-(3,4,5-trimethoxybenzoyl)piperazine 1 ml of a methylene chloride solution containing 0.330 g of diphenylphosphoryl azide and then 0.280 g of 1-(3,4,5-trimethoxybenzoyl)piperazine were added to 5 ml of a methylene chloride solution containing both 0.224 g of (E)-3-phenyl-3-(4-pyridyl)acrylic acid (prepared as described in Preparation 3) and 0.28 ml of triethylamine. The mixture was then stirred for 4 hours at room temperature, after which the reaction solution was diluted with 20 ml of methylene chloride. It was then washed with a 5% w/v aqueous solution of sodium bicarbonate, followed by a saturated aqueous solution of sodium chloride, and the organic phase was dried over anhydrous sodium sulfate. The solvent was then removed by distillation under reduced pressure, and the oily residue (0.686 g) was purified by silica gel flash chromatography. 0.419 g of the title compound was obtained as a white powder from the fractions eluted with mixtures of methylene chloride and methanol ranging from 100:2 to 100:3 by volume.

Nuclear Magnetic Resonance Spectrum (CDCl$_3$, 60 MHz) δ ppm: 3.05–3.70 (8H, multiplet); 3.84 (9H, multiplet); 6.50 (1H, singlet); 6.58 (2H, singlet); 7.10–7.68 (7H, multiplet); 8.45–8.85 (2H, multiplet).

Mass spectrum (m/z): 487 (M$^+$), 292 (M$^+$—C$_{10}$H$_{11}$O$_4$), 279 (M$^+$—C$_{14}$H$_{10}$NO), 208 (C$_{14}$H$_{10}$NO), 195 (C$_{10}$H$_{11}$O$_4$).

Infrared Absorption Spectrum (CDCl$_3$) $v_{max}$ cm$^{-1}$: 1630.

EXAMPLES 7 TO 56

The following compounds were synthesized from the appropriate starting materials prepared as described in the subsequent Preparations, following the general synthetic method given below.

General synthetic method:

0.793 g (2.88 mmole) of diphenylphosphoryl azide and then 0.449 g (1.60 mmole) of N-(3,4,5-trimethoxybenzoyl)piperazine were added to 7 ml of a methylene chloride solution containing 1.60 mmole of the respective 3,3-disubstituted-acrylic acid derivative (identified by the number of the Preparation shown in which it was prepared) and 0.67 ml (4.80 mmole) of triethylamine. The reaction mixture was then stirred for 3 hours at room temperature, after which it was diluted with 20 ml of methylene chloride. The resulting solution was washed with a saturated aqueous solution of sodium bicarbonate, with 10% w/v aqueous hydrochloric acid and with water, in that order, and the solution was then dried over anhydrous sodium sulfate. The solvent was distilled off, and the residue was subjected to moderate pressure liquid chromatography using two Lobar B columns connected in series. Elution with ethyl acetate removed the less polar impurities from the residue. Next, elution with mixtures of methylene chloride and methanol ranging from 100:1 to 100:2 by volume gave a desired N-(3,3-disubstituted-acryloyl)N-(3,4,5-trimethoxybenzoyl)piperazine derivative, in a yield which varied from 50 to 99%. When the desired compound was obtained in a non-crystalline solid, the compound was pulverized and dried; when it was obtained in a crystalline form, the compound was recrystallized from a suitable solvent (specified in the Example), to afford a sample for biological tests.

EXAMPLE 7

1-[(E)-3-(3,4-Dimethoxyphenyl)cinnamoyl]-4-(3,4,5-trimethoxybenzoyl)piperazine Prepared from (E)-3-(3,4-dimethoxyphenyl)cinnamic acid (prepared as described in Preparation 6) as a powder in a yield of 78%.

Nuclear Magnetic Resonance Spectrum (CDCl$_3$, 270 MHz) δ ppm: 2.70–3.70 (8H, multiplet); 3.81 (3H, singlet); 3.84 (9H, singlet); 3.90 (3H, singlet); 6.25 (1H, singlet); 6.52 (2H, singlet); 6.76–6.88 (3H, multiplet); 7.27–7.42 (5H, multiplet).

Infrared Absorption Spectrum (CHCl$_3$) $v_{max}$ cm$^{-1}$: 1625, 1585, 1515, 1460, 1420, 1330, 1130.

Mass Spectrum (m/z): 546 (M$^+$), 351, 279, 267, 195.

EXAMPLE 8

1-[(Z)-3-(3,4-Dimethoxyphenyl)cinnamoyl]-4-(3,4,5-trimethoxybenzoyl)piperazine Prepared from (Z)-3-(3,4-dimethoxyphenyl)cinnamic acid (prepared as described in Preparation 7) as a powder in a yield of 88%.

Nuclear Magnetic Resonance Spectrum (CDCl$_3$, 270 MHz) δ ppm: 2.80–3.70 (8H, multiplet): 3.85 (3H, singlet); 3.86 (9H, singlet); 3.92 (3H, singlet); 6.22 (1H, singlet); 6.55 (2H, singlet): 6.80 (1H, doublet of doublets, J=8.30 & 1.46 Hz): 6.86 (1H, doublet, J=8.30 Hz): 6.86–6.88 (1H, multiplet): 7.28–7.40 (5H, multiplet).

Infrared Absorption Spectrum (CHCl$_3$) $v_{max}$ cm$^{-1}$: 1630, 1585, 1515, 1460, 1420, 1335, 1130.

Mass Spectrum (m/z): 546 (M$^+$), 351, 279, 267, 195.

EXAMPLE 9

4-(3,4,5-Trimethoxybenzoyl)-1-](E)-3-(3,4,5-trimethoxyphenyl)cinnamoyl]piperazine Prepared from (E)-3-(3,4,5-trimethoxyphenyl)cinnamic acid (prepared as described in Preparation 10) as crystals, melting at 166°–168° C. (after recrystallisation from a mixture of methylene chloride, diethyl ether and hexane), in a yield of 74%.

Nuclear Magnetic Resonance Spectrum (CDCl$_3$, 270 MHz) δ ppm: 2.70–3.70 (8H, multiplet): 3.78 (3H, singlet): 3.846 (9H, singlet): 3.850 (3H, singlet): 3.87 (3H, singlet); 6.26 (1H, singlet): 6.47 (2H, singlet): 6.53 (2H, singlet): 7.28–7.42 (5H, multiplet).

Infrared Absorption Spectrum (CHCl$_3$) $v_{max}$ cm$^{-1}$: 1625, 1585, 1505, 1460, 1415, 1330, 1125.

Mass Spectrum (m/z): 576 (M$^+$), 381. 297, 279, 195.

EXAMPLE 10

4-(3,4,5-Trimethoxybenzoyl)-1-[(Z)-3-(3,4,5,-trimethoxyphenyl)cinnamoyl]piperazine Prepared from (Z)-3-(3,4,5-trimethoxyphenyl)cinnamic acid (prepared as described in Preparation 11) as crystals, melting at 149°–151° C. (after recrystallisation from a mixture of methylene chloride, diethyl ether and hexane), in a yield of 79%.

Nuclear Magnetic Resonance Spectrum (CDCl$_3$, 270 MHz) δ ppm: 2.80–3.70 (8H, multiplet); 3.77 (6H, singlet); 3.85 (3H, singlet); 3.86 (6H, singlet); 3.89 (3H, singlet); 6.25 (1H, singlet); 6.53 (2H, singlet); 6.54 (2H, singlet); 7.28–7.40 (5H, multiplet).

Infrared Absorption Spectrum (CHCl$_3$) ν$_{max}$ cm$^{-1}$: 1630, 1585, 1505, 1460, 1415, 1335, 1125.

EXAMPLE 11

1-[(E)-3-(3-Methoxy-4-propoxyphenyl)cinnamoyl]-4-(3,4,5-trimethoxybenzoyl)piperazine Prepared from (E)-3-(3-methoxy-4-propoxyphenyl)cinnamic acid (prepared as described in Preparation 14) as a powder in a yield of 91%.

Nuclear Magnetic Resonance Spectrum (CDCl$_3$, 270 MHz) δ ppm: 1.04 (3H, triplet, J=7.32 Hz); 1.88 (2H, multiplet); 2.70–3.65 (8H, multiplet); 3.79 (3H, singlet); 3.84 (6H, singlet); 3.85 (3H, singlet); 3.99 (2H, triplet, J=6.83 Hz); 6.24 (1H, singlet); 6.53 (2H, singlet); 6.75–6.85 (3H, multiplet); 7.27–7.43 (5H, multiplet).

Infrared Absorption Spectrum (CHCl$_3$) ν$_{max}$ cm$^{-1}$: 1630, 1600, 1590, 1510, 1460, 1425, 1330, 1130.

Mass Spectrum (m/z); 574 (M$^+$), 531, 379, 295, 279, 195.

EXAMPLE 12

1-[(Z)-3-(3-Methoxy-4-propoxyphenyl)cinnamoyl]-4-(3,4,5-trimethoxybenzoyl)piperazine Prepared from (Z)-3-(3-methoxy-4-propoxyphenyl)cinnamic acid (prepared as described in Preparation 15) as a powder in a yield of 91%.

Nuclear Magnetic Resonance Spectrum (CDCl$_3$, 270 MHz) δ ppm: 1.06 (3H, triplet, J=7.32 Hz); 1.89 (2H, multiplet); 2.80–3.70 (8H, multiplet); 3.78 (3H, singlet); 3.85 (3H, singlet); 3.86 (6H, singlet); 4.00 triplet, J=6.84 Hz); 6.20 (1H, singlet); 6.55 (2H, singlet); 6.78 (1H, doublet of doublets, J=8.30 & 1.46 Hz); 6.85–6.95 (2H, multiplet); 7.27–7.40 (5H, multiplet).

Infrared Absorption Spectrum (CHCl$_3$, ν$_{max}$ cm$^{-1}$: 1630, 1600, 1590, 1515, 1465, 1420, 1335, 1130.

Mass Spectrum (m/z): 574 (M$^+$), 531, 379, 295, 279, 195.

EXAMPLE 13

1-[(E)-3-(3,4Dipropoxyphenyl)cinnamoyl]-4-(3,4,5-trimethoxybenzoyl)piperazine Prepared from (E)3 (3,4-dipropoxyphenyl)cinnamic acid (prepared as described in Preparation 18) as a powder in a yield of 87%.

Nuclear Magnetic Resonance Spectrum (CDCl$_3$, 270 MHz) δ ppm: 1.01 (3H, triplet, J=7.33 Hz); 1.05 (3H, triplet, J=7.33 Hz); 1.85 (4H, multiplet); 2.70–3.70 (8H, multiplet); 3.84 (9H, singlet); 3.84 (9H, singlet); 3.85 (3H, singlet); 3.88 (2H, triplet, J=6.83 Hz); 3.97 (2H, triplet, J=6.84 Hz); 6.23 (1H, singlet); 6.53 (2H, singlet); 6.80 (3H, singlet); 7.25–7.40 (5H, multiplet).

Infrared Absorption Spectrum (CHCl$_3$) ν$_{max}$ cm$^{-1}$: 1625, 1600, 1590, 1510, 1460, 1425, 1330, 1130.

Mass Spectrum (m/z): 602 (M$^+$), 559, 517, 407, 323, 195.

EXAMPLE 14

1-[(Z)-3-(3,4Dipropoxyphenyl)cinnamoyl]-4-(3,4,5-trimethoxybenzoyl)piperazine Prepared from (Z)-3-(3,4-dipropoxyphenyl)cinnamic acid (prepared as described in Preparation 19) as a powder in a yield of 88%.

Nuclear Magnetic Resonance Spectrum (CDCl$_3$, 270 MHz) δ ppm: 1.01 (3H, triplet, J=7.32 Hz); 1.06 (3H, triplet, J=7.32 Hz); 1.70–1.95 (4H, multiplet); 2.70–3.70 (8H, multiplet); 3.85 (9H, singlet); 3.85–3.92 (2H, multiplet); 3.99 (2H, triplet, J=6.84 Hz); 6.19 (1H, multiplet); 6.55 (2H, singlet); 6.75–6.90 (3H, multiplet); 7.28–7.40 (5H, multiplet).

Infrared Absorption Spectrum (CHCl$_3$) ν$_{max}$ cm$^{-1}$: 1630, 1600, 1590, 1510, 1460, 1420, 1330, 1130.

Mass Spectrum (m/z): 602 (M$^+$), 559, 517, 407, 323, 195.

EXAMPLE 15

1-[(E)-3-(4-Chlorophenyl)-3-(3,4-dimethoxyphenyl)acryloyl]-4-(3,4,5-trimethoxybenzoyl)piperazine Prepared from (E)-3-(4-chlorophenyl)-3-(3,4-dimethoxyphenyl)acrylic acid (prepared as described in Preparation 22) as a powder in a yield of 89%.

Nuclear Magnetic Resonance Spectrum (CDCl$_3$, 270 MHz) δ ppm: 2.80–3.70 (8H, multiplet); 3.82 (3H, singlet); 3.86 (9H, singlet); 3.90 (3H, singlet); 6.28 (1H, singlet); 6.56 (2H, singlet); 6.75 (1H, broad singlet); 6.81 (2H, broad singlet); 7.20–7.38 (4H, AB-like multiplet).

Infrared Absorption Spectrum (CHCl$_3$) ν$_{max}$ cm$^{-1}$: 1625, 1585, 1510, 1460, 1420, 1330, 1130.

Mass Spectrum (m/z): 580 (M$^+$, $^{35}$Cl) 385, 301, 279, 195.

EXAMPLE 16

1-[(Z)-3-(4-Chlorophenyl)-3-(3,4-dimethoxyphenyl)acryloyl]-4-(3,4,5-trimethoxybenzoyl)piperazine Prepared from (Z)-3-(4-chlorophenyl)-3-(3,4-dimethoxyphenyl)acrylic acid (prepared as described in Preparation 23) as a powder in a yield of 71%.

Nuclear Magnetic Resonance Spectrum (CDCl$_3$, 270 MHz) δ ppm: 2.80–3.70 (8H, multiplet); 3.80 (3H, singlet); 3.86 (9H, singlet); 3.92 (3H, singlet); 6.20 (1H, singlet); 6.55 (2H, singlet ); 6.78 (1H, doublet of doublets, J=8.25 & 1.95 Hz); 6.86 (1H, doublet, J=8.25 Hz); 6.81–6.87 multiplet); 7.20–7.36 (4H, AB-like multiplet).

Infrared Absorption Spectrum (CHCl$_3$) ν$_{max}$ cm$^{-1}$: 1635, 1595, 1515, 1465, 1425, 1335, 1135.

Mass Spectrum (m/z): 580 (M$^+$, $^{35}$Cl), 385, 301, 279, 195.

EXAMPLE 17

1-[(Z)-3-(3-Chlorophenyl)-3-(3,4-dimethoxyphenyl)acryloyl]-4-(3,4,5-trimethoxybenzoyl)piperazine Prepared from (Z)-3-(3-chlorophenyl)-3-(3,4-dimethoxyphenyl)acrylic acid (prepared as described in Preparation 26) as a powder in a yield of 88%.

Nuclear Magnetic Resonance Spectrum (CDCl$_3$, 270 MHz) δ ppm: 2.80–3.70 (8H, multiplet); 3.82 (3H, singlet); 3.86 (9H, singlet); 3.90 (3H, singlet); 6.29 (1H, singlet); 6.57 (2H, singlet); 6.77 (1H, broad singlet); 6.82 (2H, multiplet); 7.15–7.43 (4H, multiplet).

Infrared Absorption Spectrum (CHCl$_3$) ν$_{max}$ cm$^{-1}$: 1630, 1600, 1590, 1515, 1460, 1420, 1330, 1130.

Mass Spectrum (m/z): 580 (M$^+$, $^{35}$Cl) 385, 301, 279, 195.

EXAMPLE 18

1-[(E)-3-(3-Chlorophenyl)-3-(3,4-dimethoxyphenyl)acryloyl]-4-(3,4,5-trimethoxybenzoyl)piperazine Prepared from (Z)-3-(3-chlorophenyl)-3-(3,4-dimethoxyphenyl)acrylic acid (prepared as described in Preparation 27) as a powder in a yield of 90%.

Nuclear Magnetic Resonance Spectrum (CDCl$_3$, 270 MHz) δ ppm: 2.80–3.70 (8H, multiplet); 3.81 (3H, singlet); 3.86 (9H, singlet); 3.92 (3H, singlet); 6.22 (1H, singlet); 6.55 (2H, singlet); 6.78 (1H, doublet of doublets, J=8.30 & 1.95 Hz); 6.85 (1H, multiplet); 6.87 (1H, doublet, J=8.30 Hz); 7.13–7.38 (4H, multiplet).

Infrared Absorption Spectrum (CHCl$_3$) ν$_{max}$ cm$^{-1}$: 1630, 1590, 1515, 1460, 1420, 1330, 1260, 1130.

Mass Spectrum (m/z): 580 (M$^+$, $^{35}$Cl), 385, 301, 279, 195.

EXAMPLE 19

1-[(E)-3-(4-Chlorophenyl)-3-(2,3-dimethoxyphenyl)acryloyl]-4-(3,4,5-trimethoxybenzoybenzoyl)piperazine Prepared from (E)-3-(4-chlorophenyl)-3-(2,3-dimethoxyphenyl)acrylic acid (prepared as described in Preparation 30) as a powder in a yield of 85%.

Nuclear Magnetic Resonance Spectrum (CDCl$_3$, 270 MHz) δ ppm: 2.80–3.70 (8H, multiplet); 3.57 (3H, singlet); 3.86 (9H, singlet); 3.87 (3H, singlet); 6.17 (1H, singlet); 6.55 singlet); 6.75 (1H, doublet of doublets, J=7.81 & 1.46 Hz); 6.93 doublet of doublets, J=8.30 & 1.46 Hz); 7.04 (1H, triplet, J=8.30 Hz); 7.25 (2H, doublet of multiplets, J=8.79 Hz); 7.29 (2H, doublet of multiplets, J=8.79 Hz).

Infrared Absorption Spectrum (CHCl$_3$) ν$_{max}$ cm$^{-1}$: 1635, 1595, 1470, 1430, 1335, 1135.

Mass Spectrum (m/z): 80 (M$^+$, $^{35}$Cl) 549, 301, 195.

EXAMPLE 20

1-[(Z)-3-(4-Chlorophenyl)-3-(2,3-dimethoxyphenyl)acryloyl]-4-(3,4,5-trimethoxybenzoyl)piperazine Prepared from (Z)-3-(4-chlorophenyl)-3-(2,3-dimethoxyphenyl)acrylic acid (prepared as described in Preparation 31) as a powder in a yield of 94%.

Nuclear Magnetic Resonance Spectrum (CDCl$_3$, 270 MHz) δ ppm: 2.90–3.70 (8H, multiplet); 3.855 (9H, singlet); 3.86 (6H, singlet); 6.38 (1H, singlet); 6.57 (2H, singlet); 6.86 (1H, doublet of doublets. J=8.30 & 1.47 HZ); 6.96 (1H, doubles of doublets, J=8.30 & 1.47 Hz); 7.07 (1H, triplet, J=8.30 Hz); 7.20 (2H, doublet of multiplets. J=8.79 Hz); 7.29 (2H, doublet of multiplets. J=8.79 Hz).

Infrared Absorption Spectrum (CHCl$_3$) ν$_{max}$ cm$^{-1}$: 1630, 1585, 1480, 1420, 1330, 1125.

Mass Spectrum (m/z): 580 (M$^+$, $^{35}$Cl) 549, 301, 195.

EXAMPLE 21

1-[(Z)-3-(4-Chlorophenyl)-3-(4-isobutoxyphenyl)acryloyl]-4-(3,4,5-trimethoxybenzoyl)

Prepared from (Z)-3-(4-chlorophenyl)-3-(4-isobutoxyphenyl)acrylic acid (prepared as described in Preparation 34) as crystals melting at 122°–124° C. (after recrystallisation from a mixture of diethyl ether and hexane), in a yield of 75%.

Nuclear Magnetic Resonance Spectrum (CDCl$_3$, 270 MHz) δ ppm: 1.03 (6H, doublet. J=6.83 Hz); 2.09 (1H, multiplet); 2.80–3.65 (8H, multiplet); 3.73 (2H, doublet. J=6.34 Hz); 3.86 (9H, singlet); 6.26 (1H, singlet); 6.56 (2H, singlet); 6.84 (2H, doublet of multiplets, J=8.30 Hz); 7.17 (2H, doublet of multiplets, J=8.30 Hz); 7.22 (2H, doublet of multiplets, J=8.30 Hz); 7.34 (2H, doublet of multiplets, J=8.30 Hz).

Infrared Absorption Spectrum (CHCl$_3$) ν$_{max}$ cm$^{-1}$: 1625, 1605, 1590, 1510, 1460, 1425, 1330, 1175, 1130.

Mass Spectrum (m/z): 592 (M$^+$, $^{35}$Cl) 535, 397, 313, 279, 257, 195.

EXAMPLE 22

1-[(E)-3-(4-Chlorophenyl)-3-(4-isobutoxyphenyl)acryloyl]-4-(3,4,5-trimethoxybenzoyl)piperazine Prepared from (E)-3-(4-chlorophenyl)-3-(4-isobutoxyphenyl)acrylic acid (prepared as described in Preparation 35) as crystals melting at 128°–129° C. (after recrystallisation from a mixture of diethyl ether and hexane), in a yield of 59%.

Nuclear Magnetic Resonance Spectrum (CDCl$_3$, 270 MHz) δ ppm: 1.04 (6H, doublet, J=6.84 Hz); 2.10 (1H, multiplet); 2.70–3.65 (8H, multiplet); 3.75 (1H, doublet, J=6.35 Hz); 3.84 (6H, singlet); 3.85 (3H, singlet); 6.18 (1H, singlet); 6.54 (2H, singlet); 6.88 (2H, doublet of multiplets, J=8.79 Hz); 7.17 (2H, doublet of multiplets, J=8.79 Hz); 7.21 (2H, doublet of multiplets, J=8.30 Hz); 7.30 (2H, doublet of multiplets, J=8.30 Hz).

Infrared Absorption Spectrum (CHCl$_3$) ν$_{max}$ cm$^{-1}$: 1630, 1605, 1590, 1510, 1490, 1460, 1425, 1330, 1285, 1175, 1130.

Mass Spectrum (m/z); 592 (M$^+$, $^{35}$Cl) 535, 397, 313, 279, 257, 195.

EXAMPLE 23

1-[(Z)-3-(4-Chlorophenyl)-3-(4-propoxyphenyl)acryloyl]-4-(3,4,5-trimethoxybenzoyl)piperazine Prepared from (Z)-3-(4-chlorophenyl)-3-(4-propoxyphenyl)acrylic acid (prepared as described in Preparation 38) as a powder in a yield of 76%.

Nuclear Magnetic Resonance Spectrum (CDCl$_3$, 270 MHz) δ ppm: 1.04 (3H, triplet, J=7.32 Hz); 1.75–1.90 (2H, multiplet); 2.80–3.65 (8H, multiplet); 3.86 (9H, singlet); 3.93 (2H, triplet, J=6.84 Hz); 6.26 (1H, singlet); 6.56 (2H, singlet); 6.85 (2H, doublet of multiplets, J=8.79 Hz); 7.17

(2H, doublet of multiplets, J=8.79 Hz); 7.22 (2H, doublet of multiplets, J=8.79 Hz); 7.34 (2H, doublet of multiplets, J=8.79 Hz).

Infrared Absorption Spectrum (CHCl$_3$) $v_{max}$ cm$^{-1}$: 1630, 1605, 1590, 1510, 1460, 1425, 1330, 1130.

Mass Spectrum (m/z): 578 (M$^+$, $^{35}$Cl) 535, 383, 299, 279, 195.

EXAMPLE 24

1-[(E)-3-(4-Chlorophenyl)-3-(4-propoxyphenyl)acryloyl]-4-(3,4,5,-trimethoxybenzoyl)piperazine Prepared from (E)-3-(4-chlorophenyl)-3-(4-propoxyphenyl)acrylic acid (prepared as described in Preparation 39) as a powder in a yield of 74%.

Nuclear Magnetic Resonance Spectrum (CDCl$_3$, 270 MHz) δ ppm: 1.06 (3H, triplet, J=7.33 Hz); 1.75–1.92 (2H, multiplet); 2.80–3.70 (8H, multiplet); 3.846 (6H, singlet); 3.850 (3H, singlet); 6.18 (1H, singlet); 6.54 (2H, singlet); 6.88 (2H, doublet of multiplets, J=8.78 Hz); 7.17 (2H, doublet of multiplets, J=8.78 Hz); 7.24 (2H, doublet of multiplets, J=8.30 Hz); 7.30 (2H, doublet of multiplets, J=8.30 Hz).

Infrared Absorption Spectrum (CHCl$_3$) $v_{max}$ cm$^{-1}$: 1630, 1605, 1590, 1510, 1460, 1420, 1330, 1130.

Mass Spectrum (m/z): 578 (M$^+$, $^{35}$Cl), 535, 383, 299, 279, 195.

EXAMPLE 25

1-[Bis(4-fluorophenyl)acryloyl]-4-(3,4,5 trimethoxybenzoyl)piperazine

Prepared from 3,3-bis(4-fluorophenyl)acrylic acid as a powder in a yield of 76%.

Nuclear Magnetic Resonance Spectrum (CDCl$_3$ 270 MHz) δ ppm: 2.70–3.70 (8H, multiplet); 3.85 (9H, singlet); 6.27 (1H, singlet); 6.56 (2H, singlet); 6.97–7.13 (4H, multiplet); 7.20–7.33 (4H, multiplet).

Infrared Absorption Spectrum (CHCl$_3$) $v_{max}$ cm$^{-1}$: 1630, 1600, 1585, 1505, 1460, 1420, 1330, 1125.

Mass Spectrum (m/z): 522 (M$^+$), 327, 279, 243, 195.

EXAMPLE 26

1-[(E)-3-(4-fluorophenyl)-3-(3,4,5-trimethoxyphenyl)acryloyl]-4-(3,4,5-trimethoxybenzoyl)piperazine Prepared from (E)-3-(4-fluorophenyl)-3-(3,4,5-trimethoxyphenyl)acrylic acid (prepared as described in Preparation 42) as crystals, melting at 195°–197° C. (after recrystallisation from a mixture of methylene chloride, diethyl ether and hexane), in a yield of 77%.

Nuclear Magnetic Resonance Spectrum (CDCl$_3$, 270 MHz) δ ppm: 2.80–3.70 (8H, multiplet); 3.79 (6H, singlet); 3.86 (9H, singlet); 3.87 (3H, singlet); 6.27 (1H, singlet); 6.45 (2H, singlet); 6.56 (2H, singlet); 7.05–7.13 (2H, multiplet); 7.25–7.33 (2H, multiplet).

Infrared Absorption Spectrum (CHCl$_3$) $v_{max}$ cm$^{-1}$: 1625, 1585, 1505, 1460, 1415, 1330, 1125.

Mass Spectrum (m/z): 594 (M$^+$), 315, 279, 195.

EXAMPLE 27

1-[(Z)-3-(4-Fluorophenyl)-3-(3,4,5-trimethoxyphenyl)acryloyl]-4-(3,4,5-trimethoxybenzoyl)piperazine Prepared from (Z)-3-(4-fluorophenyl)-3-(3,4,5-trimethoxyphenyl)acrylic acid (prepared as described in Preparation 43) as crystals, melting at 130°–132° C. (after recrystallisation from a mixture of methylene chloride and diethyl ether), in a yield of 78%.

Nuclear Magnetic Resonance Spectrum (CDCl$_3$, 270 MHz) δ ppm: 2.80–3.70 (8H, multiplet); 3.77 (6H, singlet); 3.85 (3H, singlet); 3.86 (6H, singlet); 3.89 (3H, singlet); 6.20 (1H, singlet); 6.51 (2H, singlet); 6.54 (2H, singlet); 7.00–7.09 (2H, multiplet); 7.26–7.35 (2H, multiplet).

Infrared Absorption Spectrum (CHCl$_3$) $v_{max}$ cm$^{-1}$: 1625, 1600, 1585, 1505, 1460, 1415, 1125.

Mass Spectrum (m/z): 594 (M$^+$), 315, 279, 195.

EXAMPLE 28

1-[Bis(3,4-dimethoxyphenyl)acryloyl]-4-(3,4,5-trimethoxybenzoyl)piperazine

Prepared from 3,3-bis(3,4-dimethoxyphenyl)acrylic acid as a powder in a yield of 74%.

Nuclear Magnetic Resonance Spectrum (CDCl$_3$, 270 MHz) δ ppm: 2.80–3.70 (8H, multiplet); 3.81 (3H, singlet); 3.82 (3H, singlet); 3.86 (9H, singlet); 3.91 (3H, singlet); 3.92 (3H, singlet); 6.16 (1H, singlet); 6.56 (2H, singlet); 6.80–6.95 (6H, multiplet).

Infrared Absorption Spectrum (CHCl$_3$) $v_{max}$ cm$^{-1}$: 1625, 1600, 1585, 1515, 1460, 1420, 1330, 1250, 1125.

Mass Spectrum (m/z); 606 (M$^+$), 411, 327, 195.

EXAMPLE 29

1-[(E)-3-(3,4-Dimethoxyphenyl)-3-(4-methoxyphenyl)acryloyl]-4-(3,4,5Trimethoxybenzoyl)piperazine Prepared from (E)-3-(3,4-dimethoxyphenyl)-3-(4-methoxyphenyl)acrylic acid (prepared as described in Preparation 46) as a powder in a yield of 54%.

Nuclear Magnetic Resonance Spectrum (CDCl$_3$, 270 MHz) δ ppm: 2.80–3.70 (8H, multiplet); 3.81 (3H, singlet); 3.85 (12H, singlet); 3.90 (3H, singlet); 6.16 (1H, singlet); 6.55 (2H, singlet); 6.76–6.85 (3H, multiplet); 6.89 (2H, doublet of multiplets, J=8.78 Hz); 7.22 (2H, doublet of multiplets, J=8.78 Hz).

Infrared Absorption Spectrum (CHCl$_3$) $v_{max}$ cm$^{-1}$: 1625, 1600, 1585, 1510, 1460, 1420, 1330, 1130.

Mass Spectrum (m/z): 576 (M$^+$), 381, 297, 195.

EXAMPLE 30

1-[(Z)-3-(3,4-Dimethoxyphenyl)-3-(4-methoxyphenyl)acryloyl]-4-(3,4,5-trimethoxybenzoyl)piperazine Prepared from (Z)-3-(3,4-dimethoxyphenyl)-3-(4-methoxyphenyl)acrylic acid (prepared as described in Preparation 47) as a powder in a yield of 73%.

Nuclear Magnetic Resonance Spectrum (CDCl$_3$, 270 MHz) δ ppm: 2.90–3.70 (8H, multiplet); 3.80 (3H, singlet); 3.83 (3H, singlet); 3.86 (9H, singlet); 3.92 (3H, singlet); 6.15 (1H, singlet); 6.55 (2H, singlet); 6.78–6.91 (5H, multiplet); 7.12–7.26 (2H, multiplet).

Infrared Absorption Spectrum (CHCl$_3$) $v_{max}$ cm$^{-1}$: 1625, 1605, 1585, 1510, 1460, 1420, 1330, 1130.

Mass Spectrum (m/z): 576 (M$^+$), 381, 297, 279, 195.

EXAMPLE 31

1-[(Z)-3-(3,4-Dichlorophenyl)-3-(4-methoxyphenyl)
acryloyl]-4-(3,4,5-trimethoxybenzoyl)piperazine Prepared from (Z)-3-(3,4-dichlorophenyl)-3-(4-methoxyphenyl)acrylic acid (prepared as described in Preparation 50) as a powder in a yield of 85%.

Nuclear Magnetic Resonance Spectrum (CDCl$_3$, 270 MHz) δ ppm: 3.10–3.70 (8H, multiplet); 3.83 (3H, singlet); 3.857 (3H, singlet); 3.861 (6H, singlet); 6.32 (1H, singlet); 6.58 (2H, singlet); 6.87 (2H, doublet of multiplets, J=8.79 Hz); 7.13 (1H, doublet of doublets, J=8.30 & 1.95 Hz); 7.18 (2H, doublet of multiplets, J=8.79 Hz); 7.36 (1H, doublet, J=1.95 Hz); 7.45 (1H, doublet, J=8.30 Hz).

Infrared Absorption Spectrum (CHCl$_3$) $v_{max}$ cm$^{-1}$: 1630, 1605, 1585, 1510, 1460, 1420, 1330, 1125.

Mass Spectrum (m/z): 584 (M$^+$, $^{35}$Cl) 389, 305, 279, 195.

EXAMPLE 32

1-[(E)-3-(3,4-Dichlorophenyl)-3-(4-methoxyphenyl)
acryloyl-4-(3,4,5,-trimethoxybenzoyl)piperazine Prepared from (E)-3-(3,4-dichlorophenyl)-3-(4-methoxyphenyl)acrylic acid (prepared as described in Preparation 51) as a powder in a yield of 84%.

Nuclear Magnetic Resonance Spectrum (CDCl$_3$, 270 MHz) δ ppm: 2.80–3.70 (8H, multiplet); 3.85 (12H, singlet); 6.21 (1H, singlet); 6.54 (2H, singlet); 6.90 (2H, doublet of multiplets, J=8.79 Hz); 7.10 (1H, doublet of doublets, J=8.30 & 1.95 Hz); 7.18 (2H, doublet of multiplets, J=8.79 Hz); 7.38 (1H, doublet, J=1.95 Hz); 7.40 (1H, doublet, J=8.30 Hz).

Infrared Absorption Spectrum (CHCl$_3$) $v_{max}$ cm$^{-1}$: 1630, 1605, 1585, 1510, 1460, 1420, 1330, 1130.

Mass Spectrum (m/z): 584 (M$^+$, $^{35}$Cl) 389, 305, 279, 195.

EXAMPLE 33

1-[(E)-3-(3,4-Dimethoxyphenyl)-3-(3-
trifluoromethylphenyl)acryloyl]-4-(3,4,5-
trimethoxybenzoyl)piperazine Prepared from (E)-3-(3,4-dimethoxyphenyl)-3-(3-trifluoromethylphenyl)acrylic acid (prepared as described in Preparation 54) as a powder in a yield of 74%.

Nuclear Magnetic Resonance Spectrum (CDCl$_3$, 270 MHz) δ ppm: 2.90–3.70 (8H, multiplet); 3.82 (3H, singlet); 3.848 (6H, singlet); 3.853 (3H, singlet).; 3.91 (3H, singlet); 6.37 (1H, singlet); 6.56 (2H, singlet); 6.77 (1H, broad singlet); 6.79–6.88 (2H, multiplet); 7.47–7.60 (3H, multiplet); 7.60–7.71 (1H, multiplet).

Infrared Absorption Spectrum (CHCl$_3$) $v_{max}$ cm$^{-1}$: 1625, 1600, 1585, 1510, 1460, 1420, 1325, 1300, 1170, 1125.

Mass Spectrum (m/z): 614 (M$^+$), 419, 335, 307, 279, 195.

EXAMPLE 34

1-[(Z)-3-(3,4-Dimethoxyphenyl)-3-(3-
trifluoromethylphenyl)acryloyl]-4-(3,4,5-
trimethoxybenzoyl)piperazine Prepared from (Z)-3-(3,4-dimethoxyphenyl)-3-(3-trifluoromethylphenyl)acrylic acid (prepared as described in Preparation 55) as a powder in a yield of 50%.

Nuclear Magnetic Resonance Spectrum (CDCl$_3$, 270 MHz) δ ppm: 2.80–3.70 (8H, multiplet); 3.81 (3H, singlet); 3.85 (3H, singlet); 3.86 (6H, singlet); 3.93 (3H, singlet); 6.26 (1H, singlet); 6.56 (2H, singlet); 6.78 (1H, doublet of doublets, J=8.30 & 1.96 Hz); 6.86 (1H, multiplet); 6.87 (1H, doublet, J=8.30 Hz); 7.43–7.53 (2H, multiplet); 7.53–7.67 (2H, multiplet).

Infrared Absorption Spectrum (CDCl$_3$) $v_{max}$ cm$^{-1}$: 1625, 1600, 1585, 1515, 1460, 1420, 1325, 1255, 1165, 1125.

Mass Spectrum (m/z): 614 (M$^+$), 419, 335, 307, 279, 195.

EXAMPLE 35

1-[(E)-3-(3,4-Dimethoxyphenyl)-3-(4-methylphenyl)
acryloyl]-4-(3,4,5-trimethoxybenzoyl)piperazine Prepared from (E)-3-(3,4-dimethoxyphenyl)-3-(4-methylphenyl)acrylic acid (prepared as described in Preparation 58) as a powder in a yield of 89%.

Nuclear Magnetic Resonance Spectrum (CDCl$_3$, 270 MHz) δ ppm; 2.39 (3H, singlet); 2.80–3.70 (8H, multiplet); 3.81 (3H, singlet); 3.848 (6H, singlet); 3.851 (3H, singlet); 3.89 (3H, singlet); 6.20 (1H, singlet); 6.54 (2H, singlet); 6.79 (1H, broad singlet); 6.80–6.90 (2H, multiplet); 7.17 (4H, singlet).

Infrared Absorption Spectrum (CDCl$_3$) $v_{max}$ cm$^{-1}$: 1620, 1600, 1585, 1510, 1460, 1420, 1330, 1125.

Mass Spectrum (m/z): 560 (M$^+$), 365, 281, 279, 195.

EXAMPLE 36

1-[(Z)-3-(3,4-Dimethoxyphenyl)-3-(4-methylphenyl)
acryloyl]-4-(3,4,5-trimethoxybenzoyl)piperazine Prepared from (Z)-3-(3,4-dimethoxyphenyl)-3-(4-methylphenyl)acrylic acid (prepared as described in Preparation 59) as a powder in a yield of 99%.

Nuclear Magnetic Resonance Spectrum (CDCl$_3$, 270 MHz) δ ppm: 2.37 (3H, singlet); 2.80–3.70 (8H, multiplet); 3.80 (3H, singlet); 3.85 (3H, singlet); 3.86 (6H, singlet); 3.91 (3H, singlet); 6.19 (1H, singlet); 6.55 (2H, singlet); 6.80 (1H, doublet of doublets, J=8.30 & 1.46 Hz); 6.84 (1H, multiplet); 6.85 (1H, doublet, J=8.30 Hz); 7.14 (2H, doublet, J=8.30 Hz); 7.19 (2H, doublet, J=8.30 Hz).

Infrared Absorption Spectrum (CDCl3) $v_{max}$ cm$^{-1}$: 1625, 1585, 1510, 1460, 1420, 1330, 1255, 1125.

Mass Spectrum (m/z): 560 (M$^+$), 365, 281, 279, 195.

EXAMPLE 37

1-[(Z)-3-(3,4-Dichlorophenyl)-3-(3-methylphenyl)
acryloyl]-4-(3,4,5-trimethoxybenzoyl)piperazine Prepared from (Z)-3-(3,4-dichlorophenyl)-3-(3-methylphenyl)acrylic acid (prepared as described in Preparation 62) as a powder, in a yield of 91%.

Nuclear Magnetic Resonance Spectrum (CDCl$_3$, 270 MHz) δ ppm: 2.34 (3H, singlet); 2.90–3.70 (8H, multiplet); 3.857 (3H, singlet); 3.862 (6H, singlet); 6.36 (1H, singlet); 6.58 (2H, singlet); 7.00–7.07 (2H, multiplet); 7.13 (1H, doublet of doublets, J=8.30 Hz); 7.16–7.28 (2H, multiplet); 7.36 (1H, doublet, J=1.96 Hz); 7.45 (1H, doublet, J=8.30 Hz).

Infrared Absorption Spectrum (CDCl$_3$) ν$_{max}$ cm$^{-1}$: 1635, 1590, 1465, 1425, 1335, 1130.

Mass Spectrum (m/z): 568 (M$^+$, $^{35}$Cl) 373, 289, 279, 195.

EXAMPLE 38

1-[(E)-3-(3,4-Dichlorophenyl)-3-(3-methylphenyl)acryloyl]-4-(3,4,5-trimethoxybenzoyl)piperazine Prepared from (E)-3-(3,4-dichlorophenyl)-3-(3-methylphenyl)acrylic acid (prepared as described in Preparation 63) as a powder in a yield of 92%.

Nuclear Magnetic Resonance Spectrum (CDCl$_3$, 270 MHz) δ ppm: 2.35 (3H, singlet); 2.70–3.70 (8H, multiplet); 3.84 (6H, singlet); 3.85 (3H, singlet); 6.27 (1H, singlet); 6.53 (2H, singlet); 7.02–7.14 (3H, multiplet); 7.18–7.32 (2H, multiplet); 7.36–7.44 (3H, multiplet).

Infrared Absorption Spectrum (CDCl$_3$) ν$_{max}$ cm$^{-1}$: 1630, 1610, 1590, 1465, 1425, 1335, 1130.

Mass Spectrum (m/z): 568 (M$^+$, $^{35}$Cl) 373, 289, 279, 195.

EXAMPLE 39

1-[(E)-3-(3,4-Dimethoxyphenyl)3-(3-methylphenyl)acryloyl]-4-(3,4,5-trimethoxybenzoyl)piperazine Prepared from (E)-3-(3,4-dimetboxyphenyl)-3-(3-methylphcnyl)acrylic acid (prepared as described in Preparation 66) as a powder in a yield of 83%.

Nuclear Magnetic Resonance Spectrum (CDCl$_3$, 270 MHz) δ ppm: 2.34 (3H, singlet); 2.70–3.70 (8H, multiplet); 3.81 (3H, singlet); 3.846 (6H, singlet); 3.850 (3H, singlet); 3.90 (3H, singlet); 6.21 (1H, singlet); 6.54 (2H, singlet); 6.76–6.88 (3H, multiplet); 7.06–7.13 (2H, multiplet); 7.16–7.30 (2H, multiplet).

Infrared Absorption Spectrum (CDCl$_3$) ν$_{max}$ cm$^{-1}$: 1630, 1605, 1590, 1515, 1465, 1425, 1330, 1130.

Mass Spectzum (m/z): 560 (M$^+$), 365, 281, 279, 195.

EXAMPLE 40

1-[(Z)-3-(3,4-Dimethoxyphenyl)-3-(3-methylphenyl)acryloyl]-4-(3,4,5-trimethoxybenzoyl)piperazine Prepared from (Z)-3-(3,4-dimethoxyphenyl)-3-(3-methylphenyl)acrylic acid (prepared as described in Preparation 67) as a powder in a yield of 83%.

Nuclear Magnetic Resonance Spectrum (CDCl$_3$, 270 MHz) δ ppm: 2.34 (3H, singlet); 2.80–3.70 (8H, multiplet) 3.80 (3H, singlet); 3.85 (3H, singlet); 3.86 (6H, singlet); 3.92 (3H, singlet); 6.20 (1H, singlet); 6.55 (2H, singlet); 6.77–6.90 (3H, multiplet); 7.06–7.28 (4H, multiplet).

Infrared Absorption Spectrum (CDCl$_3$) ν$_{max}$ cm$^{-1}$: 1630, 1600, 1590, 1515, 1465, 1425, 1330, 1260, 1130.

Mass Spectrum (m/z): 560 (M$^+$), 365, 281, 279, 195.

EXAMPLE 41

1-[3,3-Bis(3-chlorophenyl)acryloyl]-4-(3,4,5-trimethoxybenzoyl)piperazine

Prepared from 3,3-bis(3-chlorophenyl)acrylic acid (prepared as described in Preparation 110) as a powder, in a yield of 86%.

Nuclear Magnetic Resonance Spectrum (CDCl$_3$, 270 MHz) δ ppm: 2.80–3.70 (8H, multiplet); 3.86 (9H, singlet); 6.36 (1H, singlet); 6.56 (2H, singlet); 7.10–7.20 (2H, multiplet); 7.27–7.43 (6H, multiplet).

Infrared Absorption Spectrum (CDCl3) ν$_{max}$ cm$^{-1}$: 1630, 1590, 1460, 1420, 1330, 1130.

Mass Specnrum (m/z): 554 (M$^+$, $^{35}$l) 359, 279, 275, 195.

EXAMPLE 42

1-[(Z)-3-(2-Chlorophenyl)-3-(4-methoxyphenyl)acryloyl]-4-(3,4,5-trimethoxybenzoyl)piperazine Prepared from (Z)-3-(2-chlorophenyl)-3-(4-methoxyphenyl)acrylic acid (prepared as described in Preparation 69) as a powder, in a yield of 91%.

Nuclear Magnetic Resonance Spectrum (CDCl$_3$, 270 MHz) δ ppm: 2.80–3.80 (8H, multiplet); 3.81 (3H, singlet); 3.86 (9H, singlet); 6.54 (1H, single:); 6.58 (2H, singlet); 6.85 (2H, doublet of multiplets, J=8.79 Hz); 7.18 (2H, doublet of multiplets, J=8.79 Hz); 7.29–7.45 (4H, multiplet).

Infrared Absorption Spectrum (CDCl$_3$) ν$_{max}$ cm$^{-1}$: 1630, 1605, 1585, 1510, 1460, 1420, 1330, 1130.

Mass Spectrum (m/z): 550 (M$^+$, $^{35}$l) 515, 279, 271, 195.

EXAMPLE 43

1-[(Z)-3-(3-Chlorophenyl)-3-(3-methoxyphenyl)acryloyl]-4-(3,4,5-trimethoxybenzoyl)piperazine Prepared from (Z)-3-(3-chlorophenyl)-3-(3-methoxyphenyl)acrylic acid (prepared as described in Preparation 72) as a powder, in a yield of 81%.

Nuclear Magnetic Resonance Spectrum (CDCl$_3$, 270 MHz) δ ppm: 2.80–3.70 (8H, multiplet); 3.78 (3H, singlet); 3.85 (9H, singlet); 6.35 (1H, singlet); 6.56 (2H, singlet); 6.56–6.94 (3H, multiplet); 7.16–7.40 (5H, multiplet).

Infrared Absorption Spectrum (CDCl$_3$) ν$_{max}$ cm$^{-1}$: 1625, 1600, 1585, 1460, 1420, 1330, 1125.

Mass Spectrum (m/z): 550 (M$^+$, $^{35}$Cl), 355, 279, 271, 195.

EXAMPLE 44

1-[(E)-3-(3-Chlorophenyl)-3-(3-menhoxphenyl)acryloyl]-4-(3,4,5-trimethoxybenzoyl)piperazine Prepared from (E)-3-(3-chlorophenyl)-3-(3-methoxyphenyl)acrylic acid (prepared as described in Preparation 73) as a powder, in a yield of 82%.

Nuclear Magnetic Resonance Spectrum (CDCl$_3$, 270 MHz ) δ ppm: 2.80–3.70 (8H, multiplet); 3.77 (3H, singlet); 3.85 (9H, singlet); 6.29 (1H, singlet); 6.54 (2H, singlet); 6.80–6.87 (2H, multiplet); 6.90–6.97 (1H, multiplet); 7.12–7.19 (1H, multiplet); 7.22–7.37 (4H, multiplet).

Infrared Absorption Spectrum (CDCl$_3$) ν$_{max}$ cm$^{-1}$: 1630, 1600, 1585, 1460, 1420, 1330, 1125.

Mass Spectrum (m/z): 550 (M$^+$, $^{35}$Cl), 355, 279, 271, 195.

EXAMPLE 45

1-[(Z)-3-(3-Chlorophenyl)-3-(4-methoxyphenyl) acryloyl]-4-(3,4,5-trimethoxybenzoyl)piperazine Prepared from (Z)-3-(3-chlorophenyl)-3-(4-methoxyphenyl)acrylic acid (prepared as described in Preparation 76) as a powder, in a yield of 81%.

Nuclear Magnetic Resonance Spectrum (CDCl$_3$, 270 MHz) δ ppm: 2.80–3.70 (8H, multiplet); 3.83 (3H, singlet); 3.85 (9H, singlet); 6.28 (1H, singlet); 6.56 (2H, singlet); 6.86 (2H, doublet of multiplets, J=8.79 Hz); 7.19 (2H, doublet of multiplets, J=8.79 Hz); 7.26–7.40 (4H, multiplet);

Infrared Absorption Spectrum (CDCl$_3$) $v_{max}$ cm$^{-1}$: 1625, 1605, 1585, 1510, 1460, 1420, 1330, 1125.

Mass Spectrum (m/z): 550 (M$^+$, $^{35}$Cl) 355, 279, 271, 195.

EXAMPLE 46

1-[(E)-3-(3-Chlorophenyl)-3-(4-methoxyphenyl) acryloyl]-4-(3,4,5-trimethoxybenzol)piperazine Prepared from (E)-3-(3-chlorophenyl)-3-(4-methoxyphenyl)acrylic acid (prepared as described in Preparation 77) as a powder, in a yield of 82%.

Nuclear Magnetic Resonance Spectrum (CDCl$_3$, 270 MHz) δ ppm: 2.80–3.70 (8H, multiplet); 3.85 (12H, singlet); 6.21 (2H, singlet); 6.55 (2H, singlet); 6.90 (2H, doublet of multiplets, J=8.79 Hz); 7.20 (2H, doublet of multiplets, J=8.79 Hz); 7.12–7.36 (4H, multiplet).

Infrared Absorption spectrum (CDCl 3) $v_{max}$ cm$^{-1}$: 1625, 1600, 1585, 1510, 1460, 1420, 1330, 1125.

Mass Spectrum (m/z): 550 (M$^+$, $^{35}$Cl) 355, 279, 271, 195.

EXAMPLE 47

1-[(Z)-3-(2-Naphthyl)-3-phenylacryloyl]-4-(3,4,5-trimethoxybenzoyl)piperazine

Prepared from (Z)-3-(2-naphthyl)-3-phenylacrylic acid (prepared as described in Preparation 113) as a powder, in a yield of 94%.

Nuclear Magnetic Resonance Spectrum (CDCl$_3$, 270 MHz) δ ppm: 2.50–3.70 (8H, multiplet); 3.77 (3H, singlet); 3.82 (6H, singlet); 6.39 (3H, singlet); 7.28–7.40 (6H, multiplet); 7.46–7.57 (2H, multiplet); 7.78–7.90 (4H, multiplet).

Infrared Absorption Spectrum (CDCl$_3$) $v_{max}$ cm$^{-1}$: 1625, 1600, 1585, 1460, 1425, 1330, 1130.

Mass Spectrum (m/z): 536 (M$^+$), 341, 279, 257, 195.

EXAMPLE 48

1-[(E)-3-(2-Naphthyl)-3-phenylacryloyl]-4-(3,4,5-trimetnoxybenzoyl)piperazine

Prepared from (E)- 3-(2-napthyl)-3-phenylacrylic acid (prepared as described in Preparation 114) as a powder, in a yield of 88%.

Nuclear Magnetic Resonance Spectrum (CDCl$_3$, 270 MHz) δ ppm: 2.60–3.70 (8H, multiplet); 3.85 (9H, singlet); 6.44 (1H, singlet); 6.54 (2H, singlet); 7.30–7.54 (8H, multiplet); 7.71 (1H, broad singlet); 7.74–7.88 (3H, singlet).

Infrared Absorption Spectrum (CDCl$_3$) $v_{max}$ cm$^{-1}$: 1625, 1605, 1595, 1460, 1420, 1330, 1125.

Mass Spectrum (m/z): 536 (M$^+$), 341, 279, 257, 195.

EXAMPLE 49

1-[(Z)-3-(3,4-Dichlorophenyl)-3-(4-propoxyphenyl) acryloyl]-4-(3,4,5-trimethoxybenzoyl)piperazine Prepared from (Z)-3-(3,4-dichlorophenyl)-3-(4-propoxyphenyl)acrylic acid (prepared as described in Preparation 80), as a powder, in a yield of 84%.

Nuclear Magnetic Resonance Spectrum (CDCl$_3$, 270 MHz) δ ppm: 1.04 (3H, triplet, J=7.32 Hz); 1.73–1.90 (2H, multiplet); 3.10–3.70 (8H, multiplet); 3.86 (9H, multiplen); 3.93 (2H, triplet, J=6.35 Hz); 6.31 (1H, singlet); 6.58 (2H, singlet); 6.86 (2H, doublet of multiplets, J=8.79 Hz); 7.13 (1H, doublet of doublets, J=8.30 & 1.46 Hz); 7.17 (2H, doublet of multiplets, J=8.79 Hz); 7.36 (1H, doublet, J=1.46 Hz); 7.45 (1H, doublet, J=8.30 Hz).

Infrared Absorption Spectrum (CDCl$_3$) $v_{max}$ cm$^{-1}$: 1630, 1605, 1590, 1510, 1460, 1420, 1330, 1130.

Mass Spectrum (m/z): 612 (M$^+$, $^{35}$Cl) 569, 417, 333, 279, 195.

EXAMPLE 50

1-[(E)-3-(4-Ethoxy-3-methoxyphenyl)-3-phenylacryloyl]-4-(3,4,5-trimethoxybenzoyl)piperazine Prepared from (E)-3-(4-ethoxy-3-methoxypnenyl)cinnamic acid (prepared as described in Preparation 84), as a powder, in a yield of 93%

Nuclear Magnetic Resonance Spectrum (CDCl$_3$, 270 MHz) δ ppm: 1.47 (3H, triplet, J=6.84 Hz); 2.50–3.70 (8H, multiplet); 3.80 (3H, singlet); 3.84 (9H, singlet); 4.11 (2H, quarter, J=6.84 Hz); 6.25 (1H, singlet); 6.53 (2H, singlet); 6.79 (1H, broad singlet); 6.80 (2H, broad singlet); 7.27–7.34 (2H, multiplet); 7.34–7.41 (3H, multiplet).

Infrared Absorption Spectrum (CDCl3) $v_{max}$ cm$^{-1}$: 1630, 1600, 1590, 1510, 1460, 1420, 1330, 1130.

Mass Spectrum (m/z): 560 (M$^+$), 545, 365, 281, 195.

EXAMPLE 51

1-[(E)-3-(4-Butoxy-3-methoxyohenyl)-3-phenylacryloyl]-4-(3,4,5-trimethoxybenzoyl)piperazine Prepared from (E)-3-(4-butoxy-3-methoxyphenyl)cinnamic acid (prepared as described in Preparation 88), aa a powder, in a yield of 79%

Nuclear Magnetic Resonance Spectrum (CDCl$_3$, 270 MHz) δ ppm: 0.98 (3H, triplet, J=7.32 Hz); 1.45–1.58 (2H, multiplet); 1.75–1.90 (2H, multiplet); 2.60–3.70 (8H, multiplet); 3.79 (3H, singlet); 3.84 (9H, singlet); 6.24 (1H, singlet); 6.53 (2H, singlet); 6.76–6.86 (3H, multiplet); 7.26–7.34 (2H, multiplet); 7.34–7.42 (3H, multiplet).

Infrared Absorption Spectrum (CHCl$_3$) $v_{max}$ cm$^{-1}$: 1625, 1600, 1590, 1510, 1460, 1420, 1330, 1130.

Mass Spectrum (m/z): 588 (M$^+$), 545, 531, 393, 309, 279, 195.

EXAMPLE 52

1-[(Z)-3-(3,4-Dichlorophenyl)-3-(4-ethylphenyl) acryloyl]-4-(3,4,5-trimethoxybenzoyl)piperazine Prepared from (Z)-3-(3,4-dichlorophenyl)-3-(4-ethylphenyl)acrylic acid (prepared as described in Preparation 91), as a powder, in a yield of 81%

Nuclear Magnetic Resonance Spectrum (CDCl$_3$, 270 MHz) δ ppm: 1.25 (3H, triplet, J=7.32 Hz); 2.67 (2H, quartet, J=7.32 Hz); 3.00–3.70 (8H, multiplet); 3.86 (9H, multiplet); 6.36 (1H, singlet); 6.58 (2H, singlet); 7.13 (1H, doublet of doublets, J=8.30 & 1.96 Hz); 7.12–7.22 (4H, multiplet); 7.36 (1H, doublet, J=1.96 Hz); 7.45 (1H, doublet, J=8.30 Hz).

Infrared Absorption Spectrum (CDCl$_3$) ν$_{max}$ cm$^{-1}$: 1630, 1590, 1460, 1420, 1330, 1130.

Mass Spectrum (m/z): 582 (M$^+$, $^{35}$Cl), 387, 303, 279, 195.

EXAMPLE 53

1-[(E)-3-Phenyl-3-(4-propoxyphenyl)acryloyl]-4-(3,4,5-trimethoxybenzoyl)piperazine Prepared from (E)-3-(4-propoxyphenyl)cinnamic acid (prepared as described in Preparation 95), as a powder in a yield of 78%.

Nuclear Magnetic Resonance Spectrum (CDCl$_3$, 60 MHz) δ ppm: 1.03 (3H, triplet, J=7 Hz); 1.50–2.15 (2H, multiplet); 2.80–3.70 (8H, multiplet); 3.83 (9H, singlet); 3.84 (2H, triplet, J=7 Hz); 6.26 (1H, singlet); 6.56 (2H, singlet); 6.86 (2H, doublet of multiplets, J=9 Hz); 7.24 (2H, doublet of multiplets, J=m 9 Hz); 7.25–7.60 (5H, multiplet).

EXAMPLE 54

1-[(E)-3-(3,4-Methylenedioxyphenyl)-3-phenylacryloyl]-4 (3,4,5-trimethoxybenzoyl)piperazine Prepared from (E)-3-(3,4-methylenedioxyphenyl)cinnamic acid (prepared as described in Preparation 96), as a powder, in a yield of 94%

Nuclear Magnetic Resonance Spectrum (CDCl$_3$, 60 MHz) δ ppm: 2.60–3.70 (8H, multiplet); 3.84 (9H, singlet); 5.98 (2H, singlet); 6.23 (1H, singlet); 6.55 (2H, singlet); 6.78 (3H, singlet); 7.20–7.60 (5H, multiplet).

EXAMPLE 55

1-[(E)-3-(3-Methoxy-4-propoxyphenyl)-3-(3-methylphenyl)acryloyl]-4-(3,4,5-trimethoxybenzoyl) piperazine Prepared from (E)-3-(3-methoxy-4-propoxyphenyl)-3-(3-methylphenyl)acrylic acid (prepared as described in Preparation 100), as a powder, in a yield of 69%

Nuclear Magnetic Resonance Spectrum (CDCl$_3$, 270 MHz) δ ppm: 1.04 (3H, triplet, J=7.33 Hz); 1.80–1.95 (2H, multiplet); 2.34 (3H, singlet); 2.70–3.70 (8H, multiplet); 3.80 (3H, singlet); 3.85 (9H, singlet); 3.99 (2H, triplet. J=6.84 Hz); 6.21 (1H, singlet); 6.54 (2H, singlet); 6.80 (3H, broad singlet); 7.05–7.13 (2H, multiplet); 7.16–7.30 (2H, multiplet).

Infrared Absorption Spectrum (CHCl$_3$) ν$_{max}$ cm$^{-1}$: 1630, 1600, 1590, 1510, 1460, 1425, 1330, 1260, 1130.

Mass Spectrum (m/z): 588 (M$^+$), 545, 393, 309, 279, 195.

EXAMPLE 56

1-[3,3-Bis(3-Methylphenyl)acryloyl]-4-(3,4,5-trimethoxybenzoyl)piperazine

Prepared from 3,3-bis(3-methylphenyl)acrylic acid (prepared as described in Preparation 103), as a powder, in a yield of 82%

Nuclear Magnetic Resonance Spectrum (CDCl$_3$, 270 MHz) δ ppm: 2.34 (6H, singlet); 2.60–3.70 (8H, multiplet); 3.84 (9H, singlet); 6.24 (1H, singlet); 6.54 (2H, singlet); 7.02–7.12 (4H, multiplet); 7.13–7.29 (4H, multiplet).

Infrared Absorption Spectrum (CDCl$_3$) ν$_{max}$ cm$^{-1}$: 1630, 1605, 1590, 1460, 1425, 1330, 1130.

Mass Spectrum (m/z): 514 (M$^+$, $^{35}$Cl), 319, 279, 235, 195.

EXAMPLE 57

1-[(E)-3,5-Diphenylpent-2-en-4-ynoyl]-4-(3,4,5,trimethoxybenzoyl)piperazine

Following a procedure similar to that described in Example 1, but using 0.900 g of (E)-3,5-diphenylpent-2-en-4-ynoic acid (prepared as described in Preparation 1.574 g of the title compound was obtained as a powder.

Nuclear Magnetic Resonance Spectrum (CDCl$_3$, 270 MHz) δ ppm: 3,40–4.00 (8H, multiplet); 3.83 (3H, singlet); 3.85 (6H, singlet); 6.59 (2H, singlet); 6.74 (1H, singlet); 7.3–7.8 (10H, multiplet).

Mass spectrum (m/z): 510 (M$^+$), 315, 279, 231, 195.

Infrared Absorption Spectrum (CDCl$_3$) ν$_{max}$ cm$^{-1}$: 1615, 1590, 1490, 1460, 1420, 1330, 1125.

Elemental analysis: Calculated for C$_{31}$H$_{30}$N$_2$O$_5$: C, 72.97%: H, 5.92%: N, 5.49%. Found: C, 72.65%; H, 6.10%: N, 5.45%.

EXAMPLE 58

1-[(2E, 4Z)-3,5-Diphenylpent-2,4-dienoyl]-4-(3,4,5,trimethoxybenzoyl)piperazine 0.025 g of 10% w/w palladium-on-barium sulfate and two drops of quinoline were added to 5ml of a methanol solution containing 0.250 g of 1-[(E)-3,5-diphenylpent-2-en-4-ynoyl]-4-(3,4,5-trimetnoxybenzoyl)piperazine (prepared as described in Example 58). Hydrogen gas was introduced into the reaction mixture at room temperature and at atmospheric pressure. The reaction mixture was then shaken for 15 hours after which the catalyst was filtered off and the solvent was removed by distillation under reduced pressure. The residue was subjected to moderate pressure liquid chromatography using a Lobar B column. 0.153 g of the title compound was obtained as a powder from those fractions eluded with mixtures of methylene chloride and ethyl acetate ranging from 3:2 to 1:3 by volume.

Nuclear Magnetic Resonance Spectrum (CDCl$_3$, 270 MHz) δ ppm: 2.90–3.80 (8H, multiplet); 3.86 (3H, singlet); 3.87 (6H, singlet); 6.38 (1H, broad singlet); 6.58 (2H, singlet); 6.61 (1H, doublet of doublets, J=12.20 & 1.95 Hz).

EXAMPLE 59

1-[3,3-Bis(4-methoxyphenyl)-2-methylacryloyl]-4-(3,4,5-trimethoxybenzoyl)piperazine Following a procedure similar to that described as the general synthetic method of Example 7, 0.673 g of the title compound was obtained as powder from 0.511 g of 3,3-bis(4-methoxyphenyl)-2-methylacrylic acid (prepared as described in Preparation 108).

Nuclear Magnetic Resonance Spectrum (CDCl$_3$, 270 MHz) δ ppm: 2.00 (3H, singlet); 2.95–3.45 (8H, multiplet); 3.80 (3H, singlet); 3.82 (3H, singlet); 3.846 (6H, singlet); 3.851 (3H, singlet); 6.53 (2H, singlet); 6.75–7.20 (8H, multiplet).

Mass spectrum (m/z): 560 (M$^+$); 545, 365, 281, 279, 195.

EXAMPLE 60

1-(3,3-Diphenylacryloyl)-4-(2,4,5-trimenhoxybenzenesulfonyl)piperazine 0.371 g of phosphorus pentachloride was added to 8 ml of a methylene chloride solution containing 0.400 g of 3-phenylcinnamic acid in an ice bath. The reaction solution was then stirred for 1 hour an 0° to 5° C., after which it was condensed by evaporation under reduced pressure. 10 ml of dry toluene were added to the residue, which was then evaporated to dryness under reduced pressure. The residue was dissolved in 5 ml of tetrahydrofuran, and this solution was added to a mixture of 0.564 g of N-(3,4,5-trimethoxybenzenesulfonyl)piperazine (prepared as described in Preparation 109), 0.300 g of sodium bicarbonate, 15 ml of tetrahydrofuran and 7.5 ml of water. The reaction solution was stirred for 30 minutes at room temperature, and then poured into water, after which it was extracted twice with methylene chloride. The combined methylene chloride extracts were washed with 10% w/v aqueous hydrochloric acid, with a saturated aqueous solution of sodium bicarbonate and with a saturated aqueous solution of sodium chloride, in that order. They were then dried over anhydrous sodium sulfate and condensed by evaporation under reduced pressure. The residue was subjected to column chromatography using 20 g of silica gel. 0.750 g of the title compound was obtained as crystals, melting at 163° C.–165° C. (after recrystallization from a mixture of ethyl acetate and hexane), from those fractions eluted with mixtures of methylene chloride and ethyl acetate ranging from 3:2 to 1:3 by volume.

Nuclear Magnetic Resonance Spectrum (CDCl$_3$, 270 MHz) δ ppm: 2.17 (2H, triplet, J=4.76 Hz); 2.81 (2H, triplet, J=4.76 Hz); 3.35 (2H, triplet, J=4.76 Hz); 3.64 (2H, triplet, J=4.76 Hz); 3.92 (6H, singlet); 3.97 (3H, singlet); 6.21 (1H, singlet); 6.80 (2H, singlet); 7.00–7.40 (10H, multiplet).

Mass spectrum (m/z): 522 (M$^+$), 458, 315, 291, 231, 207.

Infrared Absorption Spectrum (CDCl$_3$) ν$_{max}$ cm$^{-1}$: 1630, 1595, 1500, 1460, 1410, 1350, 1315, 1155, 1130.

Elemental analysis: Calculated for C$_{28}$H$_{30}$N$_2$O$_6$S: C, 64.35%; H, 5.79%; N, 5.36%; S, 6.14%. Found: C, 64.60%; H, 5.94%; N, 5.35%; S, 6.27%.

EXAMPLE 61

1-(3-Phenylcinnamoyl)-4-[3,4,5-trimethoxy(thiobenzoyl)]piperazine 0.836 g of phosphorus pentachloride was added to 18 ml of a methylene chloride solution containing 0.900 g of 3-phenylcinnamic acid, in an ice bath. The mixture was then stirred for 1 hour at 0° to 5° C. At the end of this time, the reaction mixture was evaporated to dryness under reduced pressure, and then 20 ml of dry toluene was added to the resulting residue; the mixture was then evaporated to dryness; this procedure was then repeated. The resulting residue was dissolved in 5 ml of tetrahydrofuran, and this solution was added to a mixture of 1.189 g of 1-(3,4,5-trimethoxythiobenzoyl)piperazine, 0.674 g of sodium bicarbonate, 25 ml of tetrahydrofuran and 12.5 ml of water, in an ice bath. The reaction mixture was then stirred for 30 minutes at room temperature, after which it was poured into water and extracted twice with methylene chloride. The methylene chloride extract was washed with 10% w/v aqueous hydrochloric acid, with a saturated aqueous solution of sodium bicarbonate and with water, in than order. In was then dried over anhydrous sodium sulfate and condensed by evaporation under reduced pressure. The residue was subjected to column chromatography through 40 g of silica gel. Those fractions eluted with a 3:1 by volume mixture of methylene chloride and ethyl acetate were collected, and the eluent removed, to give 1.860 g of the title compound as a powder.

Nuclear Magnetic Resonance Spectrum (CDCl$_3$, 270 MHz) δ ppm: 2.84 (1H, broad singlet); 3.23 (1H, broad singlet); 3.39 (1H, broad singlet); 3.51 (2H, broad singlet); 3.69 (1H, broad singlet); 3.76 (1H, broad singlet); 3.82, 3.84 (together 9H, both singlets); 4.17 (1H, broad singlet); 6.27, 6.33 (1H, both singlets); 6.37, 6.44 (2H, both singlets); 7.20–7.50 (10H, multiplet).

Mass spectrum (m/z): 502 (M$^+$), 469, 335, 295, 211, 207, 178, 167.

Infrared Absorption Spectrum (CDCl$_3$) ν$_{max}$ cm$^{-1}$: 1630, 1580, 1460, 1425, 1340, 1280, 1125.

EXAMPLE 62

1-[3,3-Bis(4-methoxypnenyl)acryloyl]-4-[3,4,5-trimethoxy(thiobenzoyl)]piperazine Following a procedure similar to that described in Example 61, but using 0. 400 g of 3,3-bis (4-metoxyphenyl)acrylic acid, 0.596 g of the title compound was obtained as a yellow powder.

Nuclear Magnetic Resonance Spectrum (CDCl$_3$, 270 MHz) δ ppm: 2.96, 3.23, 3,45, 3.51,4.20 (together 8H, 5 broad singlets); 3.82 (6H, singlet); 3.85 (9H, singlet); 6.11, 6.16 (1H, both singlets); 6.38, 6.45 (2H, both singlets); 6.80–6.95 (4H, multiplet); 7.10–7.30 (4H, multiplet).

Mass spectrum (m/z): 562 (M$^+$), 529, 335, 295, 267, 227, 211.

Infrared Absorption Spectrum (CDCl$_3$) ν$_{max}$ cm$^{-1}$: 1625, 1605, 1585, 1510, 1460, 1425, 1340, 1280, 1170, 1125.

Elemental analysis: Calculated for C$_{31}$H$_{34}$N$_2$O$_6$S: C, 66.17%; H, 6.09%; N, 4.98%: S, 5.70%. Found: C, 65.92%; H, 6,37%; N, 4.84%; S, 5.65%.

EXAMPLE 63

1-[3,3-Bis(4-fluorophenyl)]-4-[3,4,5-trimethoxy (thiobenzoyl)]piperazine

Following a procedure similar to that described in Example 61, but using 0. 300 g of 3,3-bis (4-fluorophenyl)acrylic acid, 0.574 g of the title compound was obtained as a yellow powder.

Nuclear Magnetic Resonance Spectrum (CDCl$_3$, 270 MHz) δ ppm: 3.04, 3.25, 3.52, 3.78, 4.21 (together 8H, 5 broad singlets); 3.84 (9H, singlet); 6.28 (1H, broad singlet); 6.45 (2H, singlet); 6.95–7.35 (8H, multiplet).

Mass spectrum (m/z): 538 (M$^+$), 505, 335, 295, 243, 211.

Infrared Absorption Spectrum (CDCl$_3$) ν$_{max}$ cm$^{-1}$: 1630, 1600, 1580, 1505, 1460, 1425, 1340, 1125.

EXAMPLE 64

1-(3-Phenylcinnamoyl)-4-(3,4,5-trimethoxybenzyl) piperazine

Following a procedure similar to that described in Example 61, but using 0.500 g of 3-phenylcinnamic acid and 0.653 g of 1-(3,4,5-trimethoxybenzyl)piperazine, 0.897 g of the title compound was obtained as a powder.

Nuclear Magnetic Resonance Spectrum (CDCl$_3$, 270 MHz) δ ppm: 1.88 (2H, triplet, J=5.13 Hz); 2.25 (2H, triplet, J=5.13 Hz); 3.28 (2H, multiplet); 3.28 (2H, singlet); 3.55 (2H, triplet, J=5.13 Hz); 3.83 (3H, singlet); 3.84 (6H, singlet); 6.30 (1H, singlet); 6.46 (2H, singlet); 7.13–7.47 (10H, multiplet).

Mass spectrum (m/z): 472 (M$^+$), 457, 291, 265, 207, 181.

Infrared Absorption Spectrum (CDCl$_3$) ν$_{max}$ cm$^{-1}$: 1630, 1595, 1460, 1440, 1345, 1125.

EXAMPLE 65

1-[3,3-piphenyl(thioacryloyl)]-4-[3,4,5-trimethoxy (thiobenzoyl)]piperazine

A solution of 1.000 g of 1-(3-phenylcinnamoyl)-4-[3,4,5-trimethoxy(thiobenzoyl)]piperazine (prepared as described in Example 61) in 10 ml of benzene and 0.805 g of Lawesson's Reagent [consisting mainly of [2,4-bis(4-methoxyphenyl)-1,3-dithia- 2,4-diphosphetane-2,4disulfide] was heated under reflux for 2 hours. At the end of this time, the reaction mixture was cooled to room temperature, poured into water and extracted twice with ethyl acetate. The extract was washed with water, dried over anhydrous sodium sulfate, and concentrated by distillation under reduced pressure. The residue was purified by column chromatography through 30 g of silica gel eluted with a 3:1 by volume mixture of hexane and ethyl acetate, to give 1.010 g of the title compound as a yellow powder.

Nuclear Magnetic Resonance Spectrum (CDCl$_3$, 270 MHz) δ ppm: 2.86–4.45 (8H, multiplet); 3.82 & 3.84 (together 9H, each singlet); 6.36 & 6.37 (together 2H, each singlet); 6.66% 6.69 (together 1H, each singlet); 7.15–7.50 (10H, multiplet).

Mass spectrum (m/z): 518 (M$^+$), 485; 351; 307.

Infrared Absorption Spectrum (CDCl$_3$) ν$_{max}$ cm$^{-1}$: 1580, 1475, 1425, 1340, 1285, 1130.

EXAMPLE 66

1-[3,3-Bis(4-methoxyphenyl)thioacryloyl]-4-(3,4,5-trimethoxybenzoyl)piperazine 66 (a) 1-[3,3-Bis(4-methoxyphenyl)acryloyl]piperazine 3,41 ml of diphenylphosphoryl azide and 1.09 ml of 1-formylpiperazine were added to a 60 ml of a methylene chloride solution of 3.00 g of 3,3-bis(4-methoxyphenyl)acrylic acid and 2.94 ml of triethylamine. The reaction mixture was then stirred for 2 hours at room temperature, after which it was poured into a saturated aqueous solution of sodium bicarbonate and extracted twice with methylene chloride. The combined extracts were washed with water, dried over anhydrous sodium sulfate and evaporated under reduced pressure. The residue was dissolved in 80 ml of methanol, and 40 ml of a 10% w/v aqueous solution of sodium hydroxide were added to the resulting solution. The reaction mixture was stirred for 18 hours at room temperature and then poured into water: it was then extracted twice with methylene chloride. The combined extracts were washed with water, dried over anhydrous sodium sulfate and evaporated under reduced pressure. The residue was purified by column chromatography through 80 g of silica gel eluted with mixtures of methylene chloride and methanol ranging from 19:1 to 4:1 by volume to give 3.00 g of 1-[3,3-bis(4-methoxyphenyl)acryloyl]piperazine as a powder.

Nuclear Magnetic Resonance Spectrum (CDCl$_3$, 60 MHz) δ ppm: 2.08 (1H, singlet); 2.20–3.65 (8H, multiplet); 3.80 (6H, singlet); 6.13 (1H, singlet); 6.70–7.40 (8H, multiplet).

66 (b) 1-[3,3-Bis(4-methoxyphenyl)thioacryloyl]piperazine 1.155 g of the 1-[3,3-bis(4-methoxyphenyl)acryloyl]piperazine [prepared as described in step (a) above] were dissolved in 12 ml of benzene, and the resulting solution was heated under reflux for 2 hours with 1.326 g of Lawesson's Reagent. At the end of this time, the reaction mixture was cooled to room temperature, after which it was poured into water and extracted twice with ethyl acetate. The combined extracts were washed with water, dried over anhydrous sodium sulfate, and concentrated by evaporation under reduced pressure. The residue was purified by column chromatography through 30 g of silica gel eluted with a 19:1 by volume mixture of methylene chloride and methanol, to give 1.177 g of 1-[3,3-bis(4-methoxyphenyl)thioacryloyl] piperazine as a powder.

Nuclear Magnetic Resonance Spectrum (CDCl$_3$, 60 MHz) δ ppm: 2.30 (2H, multiplet); 2.80 (2H, multiplet); 2.86 (1H, singlet); 3,48 (2H, multiplet); 3.80 (6H, singlet); 4.16 (2H, multiplet); 6.50 (1H, singlet); 6.70–7.50 (8H, multiplet).

66 (c) 1-[3,3-Bis(4-methoxyphenyl)thioacryloyl]-4-( 3,4,5-trimethoxybenzoyl)piperazine 1.049 g of 1-[3,3-bis(4-methoxyphenyl)thioacryloyl]-piperazine [prepared as described in step (b) above] and 0.29 ml of triethylamine were dissolved in 30 ml of methylene chloride, and 0.157 g of 3,4,5-trimethoxybenzoyl chloride were added, whilst ice-cooling, to the resulting solution. The reaction mixture was then stirred for 1 hour at room temperature, after which it was poured into water and extracted twice with methylene chloride. The combined extracts were washed with 10% w/v aqueous hydrochloric acid, with a saturated aqueous solution of sodium bicarbonate and with water, in that order, after which they were dried over anhydrous sodium sulfate and evaporated under reduced pressure. The residue was purified by column chromatography through 40 g of silica gel and by medium pressure liquid chromatography using a Lobar B column using mixtures of methylene chloride and ethyl acetate ranging from 9:1 no 4:1 by volume as eluent, to give 1.368 g of the title compound as a yellow powder.

Nuclear Magnetic Resonance Spectrum (CDCl$_3$, 270 MHz) δ ppm: 2.75–3.30 (2H, multiplet); 3.40–3.70 (4H, multiplet); 3.83, 3.846 & 3.850 (together 15H, each singlet); 6.53 & 6.55 (together 3H, each singlet); 6.80–6.95 (4H, multiplet); 7.15–7.35 (4H, multiplet).

Mass spectrum (m/z): 562 (M$^+$); 529; 455; 367.

Infrared Absorption Spectrum (CDCl$_3$) ν$_{max}$ cm$^{-1}$: 1630, 1605, 1585, 1510, 1460, 1420, 1330, 1280, 170, 1125.

EXAMPLE 67

1-[3,3,Bis (4-methoxyphenyl)thioacryloyl]-4-[3,4,5,-trimethoxy (thiobenzoyl)]piperazine A procedure similar to that described in Example 65 was repeated, but using 0.790 g of 1-[3,3-Bis(4-methoxyphenyl)thioacryloyl]-4-(3,4,5-trimethoxybenzoyl)piperazine (prepared as described in Example 66), to give 0.792 g of the title compound as a yellow powder.

Nuclear Magnetic Resonance Spectrum (CDCl$_3$, 270 MHz) δ ppm: 2.99, 3,46, 3.56, 3.72, 4.27 & 4.37 (together 8H, 6 broad singlets); 3.82, 3.83 & 3.85 (together 15H, each singlet); 6.39 & 6.46 (together 2H, each singlet); 6.51 &

6.55 (together 1H, each singlet); 6.80–6.95 (4H, multiplet); 7.10–7.37 (4H, multiplet).

Mass spectrum (m/z): 578 (M$^+$); 545; 513; 367.

Infrared Absorption Spectrum (CDCl$_3$) $\nu_{max}$ cm$^{-1}$: 1605, 1580, 1510, 1460, 1425, 1335, 1280, 1170, 1125.

Elemental analysis: Calculated for $C_{31}H_{34}N_2O_5S_2$: C, 69.34%; H, 5.92%; N, 4.84%; S, 11.08%. Found: C, 64.21%; H, 6.19%; N, 4.64%; S, 10.98%.

EXAMPLE 68

1-[3,3-Bis(3-chlorophenyl)acryloyl]-4-(3,4-dimethoxybenzoyl)piperazine 0.44 ml of diphenylphosphoryl azide and 0.545 g of 1-[3,3-bis(3-chlorophenyl)acryloyl]piperazine (prepared as described in Preparation 111) were added to 10 ml of a methylene chloride solution containing 0.25 g of 3,4-dimethoxybenzoic acid and 0.38 ml of triethylamine, and the reaction mixture was stirred for 16 hours at room temperature. At the end of this time, the mixture was washed with 10% w/v aqueous hydrochloric acid, with a saturated aqueous solution of sodium bicarbonate and with water, in that order, after which it was dried over anhydrous sodium sulfate. The solvent was then removed by distillation under reduced pressure, and the resulting residue was purified by medium pressure chromatography using two Lobar B columns eluted with mixtures of hexane and ethyl acetate ranging from 1:2 to 1:4 by volume, to give 0.682 g of the title compound as a white powder.

Nuclear Magnetic Resonance Spectrum (CDCl$_3$, 270 MHz) δ ppm: 2.90–3.70 (8H, multiplet); 3.89 (3H, singlet); 3.90 (3H, singlet); 6.36 (1H, singlet); 6.85 (1H, doublet, J=7.81 Hz); 6.92 (1H, doublet of doublets, J=7.81 & 1.47 Hz); 6.95 (1H, doublet, J=1.47 Hz); 7.10–7.20 (2H, multiplet); 7.24–7.42 (6H, multiplet).

Mass Spectrum (m/z): 524 (M$^+$, $^{35}$Cl) 359, 275, 249, 165.

EXAMPLE 69

1-[3,3-Bis(3-chlorophenyl)acryoyl]-4-(4-methoxybenzoyl)piperazine 0.25 g of p-methoxybenzoyl chloride were added to 10 ml of a methlylene chloride solution containing 0.529 g of 1-[3,3-bis(3-chlorophenyl)acryloyl]piperazine (prepared as described in Preparation 111) and 0.41 ml of triethylamine, whilst ice-cooling, and the mixture was stirred at room temperature for 1 hour. The mixture was then worked up and purified as described it Example 68 to give 0.682 g of the title compound as a powder.

Nuclear Magnetic Resonance Spectrum (CDCl$_3$, 270 MHz) 2.90–3.70 (8H, multiplet); 3.83 (3H, singlet); 6.36 (1H, singlet); 6.90 (1H, doublet of multiplets, J=8.79 Hz); 7.10–7.19 (2H, multiplet); 7.24–7.42 (8H, multiplet).

Mass Spectrum (m/z): 494 (M$^+$, $^{35}$Cl) 359, 275, 219, 135.

Elemental analysis: Calculated for $C_{27}H_2O_3Cl_2$: C, 65.46%; H, 4.88%; N, 5.65%; Cl, 14.31%. Found: C, 65.19%; H, 5.12%; N, 5.64%; Cl, 14.55%.

EXAMPLE 70

1-[(Z)-3-(3-Propoxyphenyl)-3-(3-chlorophenyl)arcyloyl]-4-(3,4,5-trimethoxybenzoyl)piperazine Prepared from the compound of Preparation 123, as a powder, in a yield of 90%.

Nuclear Magnetic Resonance Spectrum (270 MHz. CDCl$_3$) δ ppm: 1.02 (3H, t, J=7.33Hz), 1.70–1.90 (2H, m), 2.80–3.70 (8H, m), 3.86 (9H, s), 3.89 (2H, t, J=6.84 Hz), 6.34 (1H, s), 6.56 (2H, s), 6.76–6.85 (2H, m), 6.87–6.94 (1H, m) 7.16–7.40 (5H, m).

Mass Spectrum (m/z):578 (M$^{30}$, $^{35}$Cl); 383; 299; 279; 257; 195.

Infrared Absorption Spectrum $\nu_{max}$ (CHCl$_3$) cm–1: 1625, 1600, 1585, 1460, 1420, 1330, 1125.

EXAMPLE 71

1-[(Z)-3-(4-Propoxyphenyl)-3-(3-chlorophenyl)acryloyl]-4-(3,4,5-trimethoxybenzoyl)piperazine Prepared from the compound of Preparation 126, as a powder, in a yield of 78%.

Nuclear Magnetic Resonance Spectrum (270 MHz, CDCl$_3$) δ ppm: 1.04 (3H, t, J=7.32Hz), 1.75–1.90 (2H,m), 3.00–3.70 (8H,m), 3.85 (9H,m), 3.95 (2H, t, J=6.35 Hz), 6.28 (1H, s), 6.56 (2H, s), 6.85 (2H, dm, J=8.79 Hz), 7.18 (2H, dm, J=79 Hz), 7.18–7.22 (1H, m), 7.26–7.40 (3H, m).

Mass Spectrum (m/z): 578 (M$^+$, $^{35}$Cl); 535; 515; 383; 299; 279; 195.

Infrared Absorption Spectrum $\nu_{max}$ (CHCl$_3$) cm–1: 1630, 1610, 1590, 1510, 1460, 1425, 1330, 1130.

EXAMPLE 72

1-[(Z)-3-(3-Methexyphenyl)-3-(2-chlorophenyl)acryloyl]-4-( 3,4,5-trimethoxybenzoyl) piperazine Prepared from the compound of Preparation 129, as a powder, in a yield of 77%.

Nuclear Magnetic Resonance Spectrum (270 MHz, CDCl$_3$) δ ppm: 3.00–3.70 (8H, m), 3.78 (3H, s), 3.86 (9H, s), 6.58 (2H, s), 6.61 (1H, s), 6.76–6.80 (1H, m) 6.80–6.91 (2H, m), 7.21–7.44 (8H, m).

Mass Spectrum (m/z): 550 (M$^+$, $^{35}$Cl); 515; 271; 195.

Infrared Absorption Spectrum $\nu_{max}$ (CHCl$_3$) cm–1: 1630, 1590, 1465, 1425, 1330, 1290, 1130.

EXAMPLE 73

1-[(Z)-3-(4-Methoxyphenyl)-3-(3-bromophenyl)acryloyl]-4-(3,4,5-trimethoxybenzoyl)piperazine Prepared from the compound of Preparation 132, as a powder, in a yield of 76%.

Nuclear Magnetic Resonance Spectrum (270 MHz, CDCl$_3$) δ ppm: 2.80–3.70 (8H, m), 3.83 (3H, s), 3.86 (9H, s), 6.28 (1H, s), 6.57 (2H, s), 6.87(2H, dm, J=8.79 Hz), 7.20 (2H, dm, J=8.79 Hz), 7.23–7.30 (2H, m), 7.40–7.46 (1H, m), 7.48–7.57 (1H, m).

Mass Spectrum (m/z): 594 (M$^{30}$, $^{79}$Br); 399; 315; 279; 195.

Infrared Absorption Spectrum $\nu_{max}$ (CDCl$_3$) cm–1: 1630, 1610, 1590, 1515, 1475, 1430, 1335, 1180, 1130.

EXAMPLE 74

1-[(Z)-3-(4-Methoxyphenyl)-3-(3-fluorohertyl)acryloyl]-4-( 3,4,5-trimethoxybenzoyl) piperazine Prepared from the compound of Preparation 138, as a powder, in a yield of 76%.

Nuclear Magnetic Resonance Spectrum (270 MHz, CDCl$_3$) δ ppm: 2.80–3.70 (8H, m), 3.83 (3H, s), 3.85 (9H, s), 6.28 (1H, s), 6.56(2H, s), 6.86 (2H, dm, J=8.79 Hz), 6.94–7.03 (1H, m), 7.04–7.13 (2H, m), 7.20 (2H, dm, J=8.79 Hz), 7.35 (1H, ddd, J=7.81, 7.81, 5.86 Hz).

Mass Spectrum (m/z): 535 (M$^+$); 339; 279; 255; 195.

Infrared Absorption Spectrum ν$_{max}$ (CHCl$_3$) cm–1: 1630, 1610, 1590, 1515, 1465, 1430, 1335, 1180, 1130.

EXAMPLE 75

1-[(Z)-3-(4-Methoxylpheny)-3-(3-trifluoromethylpheny)acryloyl]-4-( 3,4,5-trimethoxybenzoyl)piperazine Prepared from the compound of Preparation 140, as a powder, in a yield of 79%.

Nuclear Magnetic Resonance Spectrum (270 MHz, CDCl$_3$) δ ppm: 2.80–3.70 (8H, m), 3.83 (3H, s), 3.846 (6H, s), 3.851 (3H, s). 6.36 (1H, s), 6.56 (2H, s), 6.87 (2H, dm, J=8.79 Hz), 7.19 (2H, dm, J=8.79 Hz), 7.45–7.58 (3H, m), 7.62–7.69 (1H, m).

Mass Spectrum (m/z):584 (M$^+$); 516; 389; 305; 279; 195.

Infrared Absorption Spectrum ν$_{max}$ (CHCl$_3$) cm–1: 1630, 1605, 1590, 1510, 1460, 1425, 1320, 1180, 1130.

EXAMPLE 76

1-[(E)-3-(3-propoxyphenyl)-3-phenylacryloyl]-4-(3,4,5-trimethoxybenzoyl)piperazine Prepared from the compound of Preparation 143, as a powder, in a yield of 89%.

Nuclear Magnetic Resonance Spectrum (270 MHz, CDCl$_3$) δ ppm: 1.02 (3H, t, J=7.32 Hz), 1.70–1.90 (2H, m), 2.70–3.70 (8H, m), 3.84 (6H, s), 3.85 (3H, s), 3.88 (2H, t, J=6.35 Hz), 6.30 (1H, s), 6.53 (2H, s), 6.78–6.94 (3H, m), 7.19–7.40 (6H, m).

Mass Spectrum (m/z): 544 (M$^+$); 515; 501; 349; 279; 265; 195.

Infrared Absorption Spectrum ν$_{max}$ (CDCl$_3$) cm–1: 1630, 1590, 1460, 1425, 1330, 1280, 1130.

EXAMPLE 77

1-[(Z)-3-(4-Methoxyphenyl)-3-(3,5-dichlorophenyl) acryloyl]-4-( 3,4 5-trimethoxybenzoyl) piperazine Prepared from the compound of Preparation 147, as a powder, in a yield of 88%.

Nuclear Magnetic Resonance Spectrum (270 MHz, CDCl$_3$) δ ppm: 3.00–3.70 (8H, m), 3.83 (3H, s), 3.86 (9H, s), 6.33 (1H, s), 6.59 (2H, s), 6.88 (2H, dm, J=8.78 Hz), 7.17 (2H, d, J=95 Hz), 7.20 (2H, dm, J=8.78 Hz), 7.38 (1H, t, J=1.95 Hz).

Mass Spectrum (m/z): 584 (M$^+$, $^{35}$Cl); 389; 305; 279; 195.

Infrared Absorption Spectrum ν$_{max}$ (CDCl$_3$) cm–1: 1630, 1605, 1590, 1560, 1510, 1460, 1420, 1330, 1180, 1130.

EXAMPLE 78

1-[(Z)-3-(4-Methoxyphenyl)-3-(2,4-dichlorophenyl) acryloyl]-4-( 3,4,5-trimethoxybenzoyl) piperazine Prepared from the compound of Preparation 150, as a powder, in a yield of 93%.

Nuclear Magnetic Resonance Spectrum (270 MHz, CDCl$_3$) δ ppm: 3.00–3.80 (8H, m), 3.81 (3H, s), 3.86 (9H, s), 6.59 (1H, s), 6.61 (2H, s), 6.85 (2H, dm, J=8.79 Hz), 7.16 (2H, ds, J=8.79 Hz), 7.25 (1H, d, J=8.30 Hz), 7.30 (1H, dd, J=8.30, 1.95 Hz), 7.44 (1H, d, J=1.95 Hz).

Mass Spectrum (m/z); 584 (M$^+$, $^{35}$Cl); 549; 305; 279; 195.

Infrared Absorption Spectrum ν$_{max}$ (CHCl$_3$) cm–1: 1630, 1610, 1590, 1515, 1465, 1415, 1335, 1180, 1130.

EXAMPLE 79

1-[(Z)-3-(4-Methoxyphenyl)-3-(2,6-dichlorophenyl) acryloyl]-4-( 3,4,5-trimethoxybenzoyl) piperazine Prepared from the compound of Preparation 152, in a yield of 85%.

Melting point (solvent)=162°–164° C. (CH$_2$Cl$_2$-hexane)

Nuclear Magnetic Resonance Spectrum (270 MHz, CDCl$_3$) δ ppm: 3,40–3.80 (8H, m), 3.82 (3H, s), 3.86 (9H, s), 6.62 (2H, s), 6.78 (1H, s) 6.87 (2H, dm, J=6.83 Hz), 7.20–7.30 (3H, m), 7.32–7.42 (2H, m).

Mass Spectrum (m/z): 584 (M$^+$); 549; 305; 279; 195.

Infrared Absorption Spectrum ν$_{max}$ (CHCl$_3$) cm–1: 1630, 1605, 1590, 1510, 1460, 1420, 1330, 1180, 1130.

EXAMPLE 80

1-[(Z)-3-(4-Methoxyphenyl),3-(2,5-dichlorophenyl)acryloyl]-4-(3,4,5-trimethoxybenzoyl)piperazine Prepared from the compound of Preparation 154, as a powder, in a yield of 85%.

Nuclear Magnetic Resonance Spectrum (270 MHz, CDCl$_3$) δ ppm: 3.10–3.80 (8H, m), 3.82 (3H, s), 3.86 (9H, s), 6.60 (1H, s), 6.61 (2H, s), 6.86(2H, dm, J=8.79 Hz), 7.18 (2H, dm, J=8.79 Hz). 7.26–7.38 (3H, m).

Mass Spectrum (m/z): 584 (M$^+$, $^{35}$Cl); 549; 533; 305; 279; 195.

Infrared Absorption Spectrum ν$_{max}$ (CHCl$_3$) cm–1: 1630, 1605, 1585, 1510, 1460, 1420, 1330, 1175, 1130.

EXAMPLE 81

1-[(Z)-3-(4-Methoxyphenyl)-3-(2,3-dichlorophenyl) acryloyl]-4-( 3,4,5-trimethoxybenzoyl) piperazine Prepared from the compound of Preparation 156, in a yield of 89%.

Melting point (solvent)=119°–122° C. (CH$_2$Cl$_2$-hexane)

Nuclear Magnetic Resonance Spectrum (270 MHz, CDCl$_3$) δ ppm: 3.20–3.80 (8H, m), 3.81 (3H, s), 3.86 (9H, s), 6.58 (1H, br,s), 6.60 (2H, s), 6.85 (2H, dm, J=8.79 Hz), 7.17 (2H, dm, J=8.79 Hz), 7.23–7.31 (2H, m), 7.46–7.53 (1H, m).

Mass Spectrum (m/z): 584 (M$^+$, $^{35}$Cl); 549; 305; 279; 179.

Infrared Absorption Spectrum ν$_{max}$ (CHCl$_3$) cm–1: 1630, 1605, 1585, 1510, 1460, 1420, 1330, 1280, 1175, 1130.

EXAMPLE 82

1-[(Z)-3-(4-Methoxyphenyl)-3-(3,5-dimethylphenyl) acryloyl]-4-( 3,4 5-trimethoxybenzoyl) piperazine Prepared from the compound of Preparation 159, as a powder, in a yield of 75%.

Nuclear Magnetic Resonance Spectrum (270 MHz, CDCl$_3$) δ ppm: 2.29 (6H, s), 2.60–3.70 (8H, m), 3.82 (3H, s), 3.846 (6H, s), 3.850 (3H, s), 6.17 (1H, s), 6.54 (2H, s), 6.85 (2H, dm, J=8.79 Hz), 6.88 (2H, br,s), 7.01 (1H, br,s), 7.21 (2H, dm, J=8.79 Hz).

Mass Spectrum (m/z): 544 (M$^+$); 349; 279; 265; 195.

Infrared Absorption Spectrum ν$_{max}$ (CHCl$_3$) cm−1: 1625, 1605, 1590, 1505, 1460, 1425, 1330, 1175, 1130.

EXAMPLE 83

1-[(Z)-3-(4-Ethylphenyl)-3-(3-chlorophenyl)acryloyl]-4-( 3,4,5-trimethoxybenzoyl)piperazine Prepared from the compound of Preparation 164, as a powder, in a yield of 78%.

Nuclear Magnetic Resonance Spectrum (270 MHz, CDCl$_3$) δ ppm: 1.25 (3H, t, J=7.81 Hz), 2.67 (2H, q, J=7.81 Hz), 2.80–3.70 (BH, m), 3.85 (9H, s), 6.33 (1H, s), 6.56 (2H, s), 7.14–7.23 (5H, m), 7.25–7.29 (1H, m), 7.31 (1H, dd, J=7.82.7–82 Hz), 7.37 (1H, ddd, J=7.82, 1,47, 1.47 Hz).

Mass Spectrum (m/z); 548 (M$^+$) ; 353: 279; 269; 195.

Infrared Absorption Spectrum ν$_{max}$ (CHCl$_3$) cm−1: 1630, 1590, 1465. 1430, 1235, 1130, 985.

EXAMPLE 84

1-[(Z)-3-(4-Methoxyphenyl)-3-(3,5-di-trifluoromethylphenyl)acryloyl]-4-(3,4,5-trimethoxybenzoyl)piperazine Prepared from the compound of Preparation 167, as a powder, in a yield of 77%.

Nuclear Magnetic Resonance Spectrum (270 MHz, CDCl$_3$) δ ppm: 3.20–3.70 (8H, m), 3.84 (3H, s), 3.86 (9H, s), 6.28 (1H, s), 6.59 (2H, s), 6.90(2H, dm, J=8.79 Hz), 7.17 (2H, dm, J=8.79 Hz), 7.70–7.74 (2H, m), 7.88–7.92 (1H, m).

Mass Spectrum (m/z): 652 (M$^+$); 457; 373; 279; 195.

Infrared Absorption Spectrum ν$_{max}$ (CHCl$_3$) cm−1: 1630, 1610, 1590, 1515, 1460, 1425, 1330, 1280, 1180, 1130.

EXAMPLE 85

1-[(Z)-3-(4-Ethoxyphenyl)-3-(3,5-dichlorophenyl)acryloyl]-4-(3,4,5-trimethoxybenzoyl) piperazine Prepared from the compound of Preparation 171, as a powder, in a yield of 82%.

Nuclear Magnetic Resonance Spectrum (270 MHz, CDCl$_3$) δ ppm: 1.43 (3H, t, J=6.841Hz), 3.20–3.70(8H, m), 3.86(9H, s), 4.05(2H, q, J=6.841 Hz), 6.33 (1H, s 6.59(2H, s), 6.86(2H, t, dm, J=8.79Hz), 7.166(2H, d, J=1.95 Hz), 7.167 (2H, dm J=8.79 Hz), 7.38 (1H, t, J=1.95 Hz).

Mass Spectrum (m/z): 598 (M$^+$); 403; 319; 279; 195.

Infrared Absorption Spectrum ν$_{max}$ (CHCl$_3$) cm−1: 1630, 1605, 1590. 1510, 1460, 1420, 1330, 1220, 1175, 1130.

EXAMPLE 86

1-[(Z)-3-(4-Ethylphenyl)-3-(3,5-dichlorophenyl)acryoyl]-4-( 3,4,5-trimethoxybenzoyl)piperazine Prepared from the compound of Preparation 175, as a powder, in a yield of 91%.

Nuclear Magnetic Resonance Spectrum (270 MHz, CDCl$_3$) δ ppm: 1.25 (3H, t,J=7.32 Hz), 2.67 (2H, q,j=t7.32 Hz), 3.00–3.75 (8H, m), 3.86 (9H, s), 6.38(1H, s) 6.59 (2H, s), 7.10–7.26 (4H, m), 7.17 (2H, d, J=1.95 Hz), 7.38 (1H, t, J=1.95 Hz)

Mass Spectrum (m/z): 582 (M$^+$); 387; 303; 279; 195.

Infrared Absorption Spectrum ν$_{max}$ (CHCl$_3$) cm−1: 1630, 1590, 1560, 1460, 1425, 1330, 1220, 1130.

EXAMPLE 87

1-[(Z)-3-(4-Methoxyphenyl)-3-(3,5-difluorophenyl) acryloyl]-4-( 3,4,5-trimethoxybenzoyl) piperazine Prepared from the compound of Preparation 179, as a powder, in a yield of 95%.

Nuclear Magnetic Resonance Spectrum (270 MHz, CDCl$_3$) δ ppm: 3.05–3.75 (8H, m), 3.83 (3H, s), 3.86 (9H, s), 6.33 (1H, s), 6.59 (2H, s), 6.77–6.91 (3H, 6.87 (2H, dm J=8.79 Hz), 7.19 (2H, dm J=8.79 Hz).

Mass Spectrum (m/z): 552 (M$^+$); 357; 279; 273; 195.

Infrared Absorption Spectrum ν$_{max}$ (CHCl$_3$) cm−1: 1625, 1610, 1595, 1515, 1465, 1430, 1335, 1180, 1130.

EXAMPLE 88

1-[(Z)-3-(4-Ethoxyphenyl)-3-(3-fluorophenyl) acryloyl]-4-(3,4,5-trimethoxybenzoyl)piperazine Prepared from the compound of Preparation 185, as a powder, in a yield of 94%.

Nuclear Magnetic Resonance Spectrum (270 MHz, CDCl$_3$) δ ppm: 1.42 (3H, t, J=6.83 Hz), 2.70–3.70 (8H, m), 3.85 (9H, s), 4.05 (2H, q, J=6.83 Hz), 6.28 (1H, s), 6.56 (2H, s), 6.85 (2H, dm, J=8.79 Hz), 6.93–7.03 (1H, m), 7.03–7.13 (2H, m), 7.19 (2H, dm, J=8.79 Hz), 7.35 (1H, ddd, J=7.81, 7.81, 5.86 Hz).

Mass Spectrum (m/z): 548 (M$^+$); 533; 519; 353; 279; 269; 195.

Infrared Absorption Spectrum ν$_{max}$ (CHCl$_3$) cm−1: 1625, 1605, 1585, 1505, 1460, 1420, 1330, 1170, 1125.

EXAMPLE 89

1-[(Z)-3-(4-Methoxyphenyl)-3-(3-chloro-5-methylphenyl)acryloyl]-4-(3,4,5-trimethoxybenzoyl) piperazine Prepared from the compound of Preparation 189, as a powder, in a yield of 91%.

Nuclear Magnetic Resonance Spectrum (270 MHz, CDCl$_3$) δ ppm: 2.33 (3H, s), 2.70–3.70 (8H, m), 3.83 (3H, s), 3.86 (9H, s), 657 (1H, s), 6.57 (2H, s), 6.86 (2H, dm J=8.79 Hz), 6.93–7.11 (2H, m), 7.14–7.25 (1H, m), 7.20 (29, dm, J=8.79 Hz).

Mass Spectrum (m/z): 564 (M$^+$, $^{35}$Cl); 549; 369; 285; 279; 195.

Infrared Absorption Spectrum ν$_{max}$ (CDCl$_3$) cm−1: 1625, 1600, 1585, 1510, 1460, 1420, 1330, 1170, 1125.

EXAMPLE 90

1-[(Z)-3-(4-Ethoxyphenyl)-3-(3-chloro-5-methylphenyl)acryloyl]-4-(3,4,5-trimethoxybenzoyl) piperazine Prepared from the compound of Preparation 193, as a powder, in a yield of 92%.

Nuclear Magnetic Resonance Spectrum (60 MHz, CDCl$_3$) δ ppm: 1.40 (3H, t, J=7 Hz), 2.32 (3H, s), 2.90–3.75 (8H, m), 3.85 (9H, s), 4.04 (2H, q, J=7 Hz), 6.26 (1H, s), 6.59 (2H, s), 6.80–7.40 (3H, m), 6.86 (2H, dm J=9 Hz), 7.22 (2H, q, J=9Hz).

Mass Spectrum (m/z): 578 (M$^+$, $^{35}$Cl); 563; 383; 299; 179; 195.

EXAMPLE 91

1-[(Z)-3-(2-Chlorophenyl)-3-(4-methoxyphenyl)acryloyl]-4-( 4-acetoxy-3,5-dimethoxybenzoyl) piperazine Following the procedure described in Example 68, but using a compound of Preparation 196 (0.600 g) and a compound of Preparation 195 (0.936 g), there was obtained the title compound (1.072 g) as a powder, Melting point: 191°–194° C.

Nuclear Magnetic Resonance Spectrum (270 MHz, CDCl$_3$) δ ppm: 2.34 (3H, s), 2.70–3.70 (8H, m), 3.82 (6H, s), 3.83 (3H, s), 6.28 (1H, s), 6.58 (2H, s), 6.87 (2H, dm, J=8.79 Hz), 7.16–7.23 (3H, m), 7.32 (1H, dd. J=7.32, 7.32 Hz), 7.37 (1H) ddd, J=7.81, 1.95, 1.95 Hz)

Mass Spectrum (m/z): 578 (M$^+$, $^{35}$Cl); 536; 355; 307; 271; 181.

Infrared Absorption Spectrum ν$_{max}$ (CDCl$_3$) cm–1: 1770, 1630, 1600, 1515, 1460, 1430, 1370, 1340, 1285, 1180, 1135.

EXAMPLE 92

1-[(Z)-3-(2-Chlorophenyl)-3-(4-methoxyphenyl)acryloyl]-4-( 3,5-4-hydroxybenzoy) piperazine To a solution of a compound of Example 91 (0.500 g) in methanol (20 ml) was added an aqueous solution saturated with potassium carbonate (10 ml), and the resulting mixture was stirred at room temperature for an hour. The reaction mixture was poured into water and extracted thrice with methylenechloride. The combined extract was washed with water dried and concentrated. The residue was purified by liquid chromatography under medium pressure through two Lobar B columns. Fractions eluted with a 19:1 mixture of ethyl acetate and methanol were collected and worked up to afford the title compound (0.464 g ) as a powder.

Nuclear Magnetic Resonance Spectrum (270 MHz, CDCl$_3$) δ ppm: 3.00–3.70 (8H, m), 3.83 (3H, s), 3.89 (6H, s), 5–72 (l8. s), 6.29 (1H, s), 6.61 (2H, s), 6.87 (2H, dm, J=9.27 Hz), 7.16–7.23 (3H, m), 7.31 (1H, dd, J=8.30, 8.30 Hz), 7.37 (1H, ddd, J=8.30, 1.95, 1.95 Hz).

Mass Spectrum (m/z); 536 (M$^+$); 356; 355; 271; 265; 181.

Infrared Absorption Spectrum ν$_{max}$ (CHCl$_3$) cm–1: 3550, 1630, 1605, 1510, 1460, 1420, 1365, 1330, 1280, 1180, 1115, 980, 830.

EXAMPLE 93

1-[(Z)-3-(4-Methoxyphenyl)-3-(3-trifluoromethyl)acryloyl]4-(3,4,5-trimethoxybenzoyl)hexahyro-1H-1,4-diazepine In a manner similar to that of Example 7, the condensation reaction of a compound of Preparation 140 (0.516 g) with 1-(3,4,5-trimetoxybenzoyl)-homopiperazine (0.471 g) and the work-up of the reaction product were carried out to give the title compound (0.819 g) as a powder.

Nuclear Magnetic Resonance Spectrum (270 MHz, CDCl$_3$) δ ppm: 1.60–2.10 (2H, m), 3.20–3.80 (8H, m), 3.82 (3H, s), 3.83 (3H, s), 3.85 (3H, s), 3.86 (3H, s), 6.46 (1H, br,s), 6.55 (2H, s), 6.81–6.92 (2H, m), 7.14–7.25 (2H, m), 7.40–7.52 (2H, m), 7.52–7.66 (2H, m).

Mass Spectrum (m/z); 598 (M$^+$); 403; 305; 293; 195.

Infrared Absorption Spectrum ν$_{max}$ (CDCl$_3$) cm–1: 1630, 1610, 1590, 1510, 1465, 1420, 1320, 1180, 1130.

PREPARATION 1

(E)- and (Z)-3-Phenyl-3-(2-thienyl)acrylic acids 100 ml of a tetrahydrofuran solution containing 26.30 g of triethyl phosphonoacetate were dropped over a period of 15 minutes at 8°–10° C. into 400 ml of a tetrahydrofuran suspension containing 5.63 g of sodium hydride (as a 55% w/w suspension in mineral oil), in an ice bath. The reaction solution was then stirred for 1 hour at room temperature, after which 22.08 g of 2-benzoylthiophene were added. The reaction mixture was then heated under reflux for 21 hours, poured into 300 ml of water and extracted with ethyl acetate. The extract was dried over anhydrous sodium sulfate and the solvent was distilled off under reduced pressure. 26.56 g of the resulting oily residue were dissolved in 450 ml of methanol, and 150 ml of a 10% w/v aqueous solution of sodium hydroxide were added thereto. The mixture was then stirred for 2 hours at room temperature. At the end of this time, the reaction solution was poured into 500 ml of water and washed with methylene chloride. Sufficient aqueous hydrochloric acid was added to the aqueous phase to adjust the pH to a value of 2, and then the mixture was extracted with methylene chloride. The extract was dried over anhydrous sodium sulfate, and the solvent was distilled off under reduced pressure. The residue was purified by silica gel column chromatography. Elution with a 19:1 by volume mixture of methylene chloride and methanol gave at first 3,415 g of the less polar isomer A [thought to be the (Z)-isomer. Rf: 0.48 (silica gel, developing solvent: a 24:1 by volume mixture of methylene chloride and methanol)], and next 0.789 g of the other more polar isomer B [thought no be the (E)-isomer, Rf: 0.35 (silica gel, developing solvent: a 24:1 by volume mixture of methylene chloride and methanol)].

Isomer A:

Pale brown crystals melting at 144°–147° C.

Nuclear Magnetic Resonance Spectrum (CDCl$_3$, 90 MHz) δ ppm: 6.34 (1H, singlet); 6.80–7.10 (2H, multiplet); 7.15–7.50 (6H, multiplet); 9.93 (1H, broad singlet).

Mass spectrum (m/z): 230 (M$^+$).

Infrared Absorption Spectrum (CDCl$_3$) ν$_{max}$ cm$^{-1}$: 1685, 1610, 1595.

Elemental analysis: Calculated for C$_{13}$H$_{10}$O$_2$S: C, 67.80%; H, 4.38%; S, 13.92%. Found: C, 67.71%; H, 4.12%; N, 13.88%.

Isomer B:

Pale brown crystals, melting at 152°–155° C.

Nuclear Magnetic Resonance Spectrum (CDCl$_3$, 90 MHz) δ ppm: 6.18 (1H, singlet); 6.95–7.15 (1H, multiplet); 7.15–7.55 (7H, multiplet); 10.66 (1H, broad singlet).

Mass spectrum (m/z): 230 (M$^+$).

Infrared Absorption Spectrum (CDCl$_3$) $v_{max}$ cm$^{-1}$: 1690, 1595.

PREPARATION 2

Ethyl (E)- and (Z)-3-phenyl-3-(4-pyridyl)acrylates 100 ml of a tetrahydrofuran solution containing 26.92 g of triethyl phosphonoacetate were dropped over a period of 20 minutes into 400 ml of a tetrahydrofuran suspension containing 5.76 g of sodium hydride (as a 55% w/w suspension in mineral oil), at 8°–10° C. in an ice bath. The reaction solution was then stirred for 1 hour at room temperature, after which 22.00 g of 4-benzoylpyridine were added. After the mixture had been stirred for a further 3 hours, the reaction solution was poured into 300 ml of water and extracted with ethyl acetate. The extract was dried over anhydrous sodium sulfate and then the solvent was distilled off under reduced pressure. The resulting residue was purified by silica gel column chromatography. Elution with mixtures of hexane and methylene chloride ranging from 3:1 to 1:1 by volume gave an first 10.047 g of the less polar isomer C [thought to be the (Z)-isomer. Rf: 0.63 (silica gel. developing solvent: a 49:1 by volume mixture of methylene chloride and methanol)] and next elution with mixtures of hexane and methylene chloride ranging from 1:1 to 0:1 by volume gave 16.603 g of the other more polar isomer D [thought to be the (E)-isomer, Rf: 0.55 (silica gel, developing solvent: a 49:1 by volume mixture of methylene chloride and methanol)].

Isomer C:

Colorless oil.

Nuclear Magnetic Resonance Spectrum (CDCl$_3$, 90 MHz) δ ppm: 1.11 (3H, triplet, J=7.5 Hz); 4.07 (2H quartet J=7.5 Hz); 6.48 (1H, singlet); 7.05–7.55 (7H, multiplet); 8.40–8.90 (2H, multiplet).

Mass spectrum (m/z): 253 (M$^+$), 208 (M$^+$—C$_2$H$_5$O).

Infrared Absorption Spectrum (CDCl$_3$) $v_{max}$ cm$^{-1}$: 1720.

Elemental analysis: Calculated for C$_{16}$H$_{15}$NO$_2$: C, 75.87%; H, 5.97%; S, 5.53%. Found: C, 75.91%; H, 6.26%; N, 5.48%.

Isomer D;

Colorless crystals, melting at 101°–102° C.

Nuclear Magnetic Resonance Spectrum (CDCl$_3$, 90 MHz) δ ppm: 1.12 (3H, triplet, J=7.5 Hz); 4.05 (2H, quartet, J=7.5 Hz); 6.46 (1H, singlet); 7.05–7.50 (7H, multiplet); 8.50–8.85 (2H, multiplet).

Mass spectrum (m/z): 253 (M$^+$), 208 (M$^+$-C$_2$H$_5$O).

Infrared Absorption Spectrum (CDCl$_3$) $v_{max}$ cm$^{-1}$: 1715.

Elemental analysis: Calculated for C$_{16}$H$_{15}$NO$_2$: C, 75.87%; H, 5.97%; S, 5.53%. Found: C, 75.86%; H, 5.86%; N, 5.59%.

PREPARATION 3

(E)-3-phenyl-3-(4-pyridyl)acrylic acid 20 ml of a 10% w/v aqueous solution of sodium hydroxide were added to 35 ml of a methanol solution containing 3,41 g of ethyl (E)-3-phenyl-3-(4-pyridyl)-acrylate (prepared as described in Preparation 2), and the mixture was stirred for 1 hour an room temperature. At the end of this time, the reaction solution was poured into 50 ml of water and washed with methylene chloride. Sufficient hydrochloric acid was added to the aqueous phase to adjust the pH to a value of 2.8. The resulting precipitate was collected, giving 2.131 g of the title compound, as a white powder, melting at 239°–241° C.

Nuclear Magnetic Resonance Spectrum (hexadeuterated dimethyl sulfoxide, 90 MHz) δ ppm: 6.51 (1H, singlet); 7.15–7.55 (7H, multiplet); 8.45–8.80 (2H, multiplet).

Mass Spectrum (m/z): 225 (M$^+$): 180 (M$^+$—COOH).

Infrared Absorption Spectrum (Nujol-trade mark) $v_{max}$ cm$^{-1}$: 1697; 1625; 1602.

PREPARATIONS 4 TO 103

General Synthesis of 3,3-Diphenylacrylic Acid Derivatives According to Beck's Reaction This follows essentially the same method as that reported by Heck et al. [J. Org. Chem. 43, 2952 (1978)], in which a coupling reaction of an (E)-acrylic acid ester having a substituted group, R$^1$, at its 3-position with an iodine compound having a substituted group, R$^2$, was conducted. A mixture of 20 mmole of an (E)-acrylic acid ethyl ester having R$^1$ at its 3-position, 30 mmole of an aryl iodide represented by the general formula R$^2$-I, 4.17 ml of triethylamine, 0.270 g of palladium acetate and 8 ml of acetonitrile was put into a sealed tube, and heated for 18 hours in an oil bath at 100° C. The mixture was stood to allow it to cool, after which it was diluted with 30 ml of ethyl acetate, and then washed with 10% w/v aqueous hydrochloric acid, with a saturated aqueous solution of sodium bicarbonate and with a saturated aqueous solution of sodium chloride, in that order. The organic phase was dried and condensed by evaporation under reduced pressure. The residue was subjected to flash column chromatography using silica gel (about 400 Tyler mesh, 400 g), and medium pressure liquid chromatography using a Lobar C column (Type Si-60). Elution with mixtures of methylene chloride, diethyl ether and hexane ranging from 1:1:5 to 1:1:4 by volume gave separately the (E)-isomer and the (A)-isomer of a 3,3-disubstituted ethyl acrylate. Where two isomers were produced, each is mentioned in a separate Preparation, but the isomer eluded earlier in the chromatographic procedure mentioned above appears in the first of the pair of Preparations. Toluene was employed as the eluent for separation of the isomers of the compounds of Preparations 32/33, and 36/37. The isolated (E)-or (Z)-3,3-diphenylacrylic acid ethyl ester (4 mmole) was dissolved in a mixture of 12 ml of dioxane and 12 ml of methanol, and 5 ml of a 10% w/v aqueous solution of sodium hydroxide were added for hydrolysis. The reaction mixture was stirred for 18 hours an room temperature, and when the solvent was distilled off. The residue was diluted with 20 ml of water and washed with ethyl acetate. Sufficient 10% w/v aqueous hydrochloric acid was added to the aqueous phase to adjust the pH to a value of 2, and then the mixture was extracted twice with methylene chloride. The combined methylene chloride extracts were washed with water and then dried over anhydrous sodium sulfate. The desired 3,3-disubstituted acrylic acid was obtained as a solid. The results are summarized below.

The ester compounds of Preparations 96 and 97 could not, however, be separated by the method described above. Accordingly, they were separated by the following procedure:

The mixture of the compounds of Preparations 96 and 97 was hydrolized as described above. The mixture of the acid compounds thus obtained was then washed with methylene chloride, and the insoluble material was recrystallized from a mixture of diethyl ether and tetrahydrofuran, to give the compound of Preparation 96 (believed to be the E-isomer). The methylene chloride washings were condensed by distillation under reduced pressure, and the residue was recrystallized from a mixture of methylene chloride and hexane, to give the compound of Preparation 97 (believed to be the Z-isomer).

PREPARATION 4

Ethyl (E)-3-(3,4-dimethoxyphenyl)cinnamate

Prepared as an oil in a yield of 14%.

Nuclear Magnetic Resonance Spectrum (CDCl$_3$, 270 MHz) δ ppm: 1.10 (3H, triplet, J=7.32 Hz); 3.82 (3H, singlet); 3.88 (3H, singlet); 4.04 (2H, quartet, J=7.32 Hz); 6.32 (1H, singlet); 6.74–6.84 (2H, multiplet); 6.89 (1H, broad singlet); 7.16–7.25 (2H, multiplet); 7.34–7.42 (2H, multiplet).

Infrared Absorption Spectrum (CHCl$_3$) $v_{max}$ cm$^{-1}$: 1705, 1595, 1580, 1510, 1465, 1160, 1135.

Mass Spectrum (m/z): 312 (M$^+$), 297, 283, 267, 240.

PREPARATION 5

Ethyl (Z)-3-(3,4-dimethoxyphenyl)cinnamate

Prepared as crystals, melting at 93°–95° C. (after recrystallisation from a mixture of diethyl ether and hexane), in a yield of 21%.

Nuclear Magnetic Resonance Spectrum (CDCl$_3$, 270 MHz) δ ppm: 1.16 (3H, triplet, J=7.32 Hz); 3.81 (3H, singlet); 3.92 (3H, singlet); 4.09 (2H, quartet, J=7.32 Hz); 6.29 (1H, singlet); 6.72 (1H, doublet, J=1.95 Hz); 6.82 (1H, doublet of doublets, J=8.30 & 1.95 Hz); 6.88 (1H, doublet, J=8.30 Hz); 7.30–7.14 (8H, multiplet).

Infrared Absorption Spectrum (CHCl$_3$) $v_{max}$ cm$^{-1}$: 1710, 1605, 1585, 1515, 1465, 1445, 1160, 1135.

Mass Spectrum (m/z): 312 (M$^+$), 297, 283, 267, 240.

PREPARATION 6

(E)-3-(3,4-Dimethoxyphenyl)cinnamic acid.

Prepared as crystals, melting at 178°–181° C. (after recrystallisation from a mixture of methylene chloride and hexane), in a yield of 98%.

Nuclear Magnetic Resonance Spectrum (CDCl$_3$, 270 MHz) δ ppm: 3.81 (3H, singlet); 3.88 (3H, singlet); 6.28 (1H, singlet); 6.75–6.83 (2H, multiplet); 6.86 (1H, broad singlet); 7.17–7.25 (2H, multiplet: 7.33–7.43 (3H, multiplet).

Infrared Absorption Spectrum (CHCl$_3$) $v_{max}$ cm$^{-1}$: 2400–3600 (broad), 1690, 1595, 1515, 1260, 1135.

Mass Spectrum (m/z): 284 (M$^+$), 269, 267, 239.

PREPARATION 7

(Z)-3-(3,4-Dimethoxyphenyl)cinnamic acid

Prepared as crystals, melting at 162°–164° C. (after recrystallisation from a mixture of diethyl ether and hexane), in a yield of 99%.

Nuclear Magnetic Resonance Spectrum (CDCl$_3$, 270 MHz) δ ppm: 3.80 (3H, singlet); 3.92 (3H, singlet); 6.26 (1H, singlet); 6.75 (1H, doublet, J=1.95 Hz); 6.80 (1H, doublet of doublets, J=8.30 & 1.95 Hz); 6.87 (1H, doublet, J=8.30 Hz); 7.27–7.43 (5H, multiplet).

Infrared Absorption Spectrum (CHCl$_3$) $v_{max}$ cm$^{-1}$: 400–3600 (broad), 1690, 1605, 1515, 1255, 1135.

Mass Spectrum (m/z): 284 (M$^+$), 269, 267, 239.

PREPARATION 8

Ethyl(E)-3-(3,4,5,-trimethoxyphenyl)cinnamate

Prepared as crystals, melting at 119°–121° C. (after recrystallisation from a mixture of diethyl ether, methylene chloride and hexane), in a yield of 19%.

Nuclear Magnetic Resonance Spectrum (CDCl$_3$, 270 MHz) δ ppm: 1.11 (3H, triplet, J=7.32 Hz); 3.77 (6H, singlet); 3.87 (3H, singlet); 4.05 (2H, quartet, J=7.32 Hz); 6.32 (1H, singlet); 6.51 (2H, singlet), 7.18–7.24 (2H, multiplet); 7.35–7.41 (3H, multiplet).

Infrared Absorption Spectrum (CHCl$_3$) $v_{max}$ cm$^{-1}$: 710, 1615, 1580, 1500, 1460, 1415, 1160, 1125.

Mass Spectrum (m/z): 342 (M$^+$), 327, 313, 299, 297.

PREPARATION 9

Ethyl (Z)-3-(3,4,5-trimethoxyphenyl)cinnamate

Prepared as crystals, melting at 96°–98° C. (after recrystallisation from a mixture of methylene chloride and diethyl ether), in a yield of 35%.

Nuclear Magnetic Resonance Spectrum (CDCl$_3$, 270 MHz) δ ppm: 1.14 (3H, triplet, J=7.33 Hz); 3.80 (6H, singlet); 3.90 (3H, singlet); 4.08 (2H, quartet, J=7.33 Hz); 6.32 (1H, singlet); 6.43 (2H, singlet); 7.31–7.40 (5H, multiplet).

Infrared Absorption Spectrum (CHCl$_3$) $v_{max}$ cm$^{-1}$: 1710, 1610, 1585. 1500, 1460, 1410, 1300, 1170, 1125.

Mass Spectrum (m/z): 342 (M$^+$), 327, 313, 299, 297.

PREPARATION 10

(E)-3-(3,4,5-Trimethoxyphenyl)cinnamic acid

Prepared as crystals, melting at 202°–206° C. (after recrystallisation from a mixture of diethyl ether and methylene chloride), in a yield of 100%.

Nuclear Magnetic Resonance Spectrum (CDCl$_3$, 270 MHz ) δ ppm: 3.76 (6H, singlet); 3.87 (3H, singlet); 6.30 (1H, singlet); 6.49 (2H, singlet); 7.19–7.25 (2H, multiplet); 7.35–7.41 (3H, multiplet).

Infrared Absorption Spectrum (KBr) $v_{max}$ cm$^{-1}$: 2400–3400 (broad), 1688, 1610, 1578, 1502, 1241, 1200, 1129.

Mass Spectrum (m/z); 314 (M$^+$), 299.

PREPARATION 11

(Z)-3-(3,4,5-Trimethoxyphenyl)cinnamic acid

Prepared as crystals, melting at 203°–205° C. (after recrystallisation from a mixture of methylene chloride and hexane), in a yield of 100%.

Nuclear Magnetic Resonance Spectrum (CDCl$_3$, 270 MHz) δ ppm: 3.78 (6H, singlet); 3.91 (3H, singlet); 6.30 (1H, singlet); 6.44 (2H, singlet); 7.28–7.43 (5H, multiplet).

Infrared Absorption Spectrum (CHCl₃) $v_{max}$ cm⁻¹: 2400–3600 (broad), 1690, 1610, 1580, 1500, 1460, 1410, 1365, 1125.

Mass Spectrum (m/z): 314 (M⁺), 299.

PREPARATION 12

Ethyl (E)-3-(3-methoxy-4-propoxyphenyl)cinnamate

Prepared as crystals, melting at 66°–68° C. (after recrystallisation from hexane), in a yield of 24%.

Nuclear Magnetic Resonance Spectrum (CDCl₃, 270 MHz) 1.03 (3H, triplet, J=7.32 Hz); 1.10 (3H, triplet, J=7.33 Hz); 1.80–1.95 (2H, multiplet); 3.81 (3H, singlet); 3.98 (2H, triplet, J=6.84 Hz); 4.03 (2H, quartet, J=7.33 Hz); 6.31 (1H, singlet); 6.77 (1H, singlet); 6.78 (1H, singlet); 6.89 (1H, singlet); 7.16–7.25 (2H, multiplet); 7.35–7.45 (3H, multiplet).

Infrared Absorption Spectrum (CHCl₃) $v_{max}$ cm⁻¹: 1710, 1600, 1520, 1470, 1375, 1260, 1160, 1140.

Mass Spectrum (m/z): 340 (M⁺), 298, 269, 253, 226.

PREPARATION 13

Ethyl (Z)-3-(3-methoxy-4-propoxyphenyl)cinnamate

Prepared as an oil in a yield of 37%.

Nuclear Magnetic Resonance Spectrum (CDCl₃, 270 MHz) δ ppm: 1.05 (3H, triplet, J=7.32 Hz); 1.15 (3H, triplet, J=7.32 Hz); 1.80–2.00 (2H, multiplet); 3.79 (3H, singlet); 4.01 (2H, triplet, J=6.83 Hz); 4.08 (2H, quartet, J=7.32 Hz); 6.27 (1H, singlet); 6.72 (1H, doublet, J=1.95 Hz); 6.78 (1H, doublet of doublets, J=8.30 & 1.95 Hz); 6.87 (1H, doublet, J=8.30 Hz); 7.30–7.42 (8H, multiplet).

Infrared Absorption Spectrum (CHCl₃) $v_{max}$ cm⁻¹: 1710, 1610, 1515, 1470, 1375, 1260, 1170, 1140.

Mass Spectrum (m/z): 340 (M⁺), 298, 269, 253, 226.

PREPARATION 14

(E)-3-(3-Methoxy-4-propoxyphenyl)cinnamic acid

Prepared as crystals, melting at 147°–150° C. (after recrystallisation from a mixture of methylene chloride and hexane), in a yield of 94%.

Nuclear Magnetic Resonance Spectrum (CDCl₃, 270 MHz) δ ppm: 1.03 (3H, triplet, J=7.33 Hz); 1.75–2.00 (2H, multiplet); 3.79 (3H, singlet); 3.98 (2H, triplet, J=6.84 Hz); 6.28 (1H, singlet); 6.73–6.80 (2H, multiplet); 6.85 (1H, broad singlet); 7.15–7.25 (2H, multiplet). 7.33–7.40 (3H, multiplet).

Infrared Absorption Spectrum (CHCl₃) $v_{max}$ cm⁻¹: 2400–3600 (broad), 1690, 1610, 1595, 1580, 1510, 1465, 1260, 1180, 1135.

Mass Spectrum (m/z): 312 (M⁺), 270, 253, 225.

PREPARATION 15

(Z)-3-(3-Methoxy-4-propoxyphenyl)cinnamic acid

Prepared as crystals, melting at 139°–142° C. (after recrystallisation from a mixture of methylene chloride and hexane), in a yield of 93%.

Nuclear Magnetic Resonance Spectrum (CDCl₃, 270 MHz) δ ppm: 1.06 (3H, triplet, J=7.33 Hz); 1.80–2.00 (2H, multiplet); 3.79 (3H, singlet); 4.01 (2H, triplet, J=6.84 Hz); 6.24 (1H, singlet); 6.29–6.79 (2H, multiplet); 6.85 (1H, doublet of doublets, J=8.33 & 1.47 Hz); 7.25–7.45 (5H, multiplet).

Infrared Absorption Spectrum (CDCl₃) $v_{max}$ cm⁻¹: 2400–3600 (broad), 1690, 1600, 1575, 1510, 1465, 1445, 1410, 1250, 1130.

Mass Spectrum (m/z): 312 (M⁺), 270, 253, 225.

PREPARATION 16

Ethyl (E)-3-(3,4-dipropoxyohyphenyl) cinnamate

Prepared as an oil in a yield of 16%.

Nuclear Magnetic Resonance Spectrum (CDCl₃, 270 MHz) δ ppm: 1.01 (3H, triplet, J=7.33 Hz); 1.03 (3H, triplet, J=7.33 Hz); 1.10 (3H, triplet, J=7.33 Hz); 1.70–1.95 (4H, multiplet); 3.90 (2H, triplet, a t 6.83 Hz); 3.96 (2H, triplet, J=6.83 Hz) 4.03 (2H, quartet, J=7.33 Hz); 6.30 (1H, singlet); 6.72–6.80 (2H, multiplet); 6.90 (1H, broad singlet); 7.15–7.25 (2H, multiplet); 7.30–7.45 (3H, multiplet).

Infrared Absorption Spectrum (CHCl₃) $v_{max}$ cm⁻¹: 1705, 1595, 1510, 1470, 1370, 1260, 1160, 1130.

Mass Spectrum (m/z): 368 (M⁺), 326, 323, 284.

PREPARATION 17

Ethyl (Z)-3-(3,4-dipropoxyphenyl)cinnamate

Prepared as an oil in a yield of 25%.

Nuclear Magnetic Resonance Spectrum (CDCl₃, 270 MHz) δ ppm: 1.00 (3H, triplet, J=7.32 Hz); 1.06 (3H, triplet, J=7.32 Hz); 1.15 (3H, triplet, J=7.32 Hz); 1.70–1.95 (4H, multiplet); 3.89 (2H, triplet, J=6.84 Hz); 4.00 (2H, triplet, J=6.84 Hz); 4.08 (2H, quartet, J=7.32 Hz); 6.26 (1H, singlet); 6.73 (1H, doublet, J=1.95 Hz); 6.77 (1H, doublet of doublers, J=8.30 & 1.95 Hz); 6.86 (1H, doublet, J=8.30 Hz); 7.25–7.40 (5H, multiplet).

Infrared Absorption Spectrum (CDCl 3) $v_{max}$ cm⁻¹: 1710, 1605, 1510, 1470, 1445, 1370, 1260, 1160, 1130.

Mass Spectrum (m/z): 368 (M⁺), 326, 323, 284.

PREPARATION 18

(E)-3-(3,4-Dipropoxyphenyl)cinnamic acid

Prepared as crystals, melting at 102°–103° C. (after recrystallisation from a mixture of methylene chloride and hexane), in a yield of 92%.

Nuclear Magnetic Resonance Spectrum (CHCl₃, 270 MHz) δ ppm: 1.00 (3H, triplet, J=7.32 Hz); 1.03 (3H, triplet, J=7.32 Hz); 1.70–1.95 (4H, multiplet); 3.89 (2H, triplet, J=6.83 Hz); 3.96 (2H, triplet, J=6.84 Hz); 6.26 (1H, singlet); 6.74 (1H, doublet of doublets, J=8.30 & 1.96 Hz); 6.78 (1H, doublet, J=8.30 Hz); 6.86 (1H, doublet, J=1.96 Hz); 7.15–7.25 (2H, multiplet); 7.30–7.40 (3H, multiplet).

Infrared Absorption Spectrum (CHCl₃) $v_{max}$ cm⁻¹: 2400–3600 (broad), 1690, 1610, 1595, 1580, 1510, 1425, 1260, 1135.

Mass Spectrum (m/z): 340 (M⁺), 298, 256, 239.

PREPARATION 19

(Z)-3-(3,4-Dipropoxyphenyl)cinnamic acid

Prepared as crystals, melting at 120°–123° C. (after recrystallisation from a mixture of methylene chloride and hexane), in a yield of 94%.

Nuclear Magnetic Resonance Spectrum (CDCl$_3$, 270 MHz) δ ppm: 1.00 (3H, triplet, J=7.33 Hz); 1.06 (3H, triplet, J=7.32 Hz); 1.70–1.95 (4H, multiplet); 3.89 (2H, triplet, J=6.84 Hz); 4.00 (2H, triplet, J=6.84 Hz); 6.23 (1H, singlet); 6.73–6.80 (2H, multiplet); 6.83–6.87 (1H, multiplet); 7.25–7.45 (5H, multiplet).

Infrared Absorption Spectrum (CHCl$_3$) ν$_{max}$ cm$^{-1}$: 2400–3600 (broad), 1695, 1610, 1515, 1260, 1135.

Mass Spectrum (m/z): 340 (M$^+$), 298, 256, 239.

PREPARATION 20

Ethyl (E)-3-(4-chlorophenyl)-3-(3,4-dimethoxyphenyl)acrylate

Prepared as crystals, melting at 83°–84° C. (after recrystallisation from a mixture of diethyl ether and hexane), in a yield of 14%.

Nuclear Magnetic Resonance Spectrum (CDCl$_3$, 270 MHz) δ ppm: 1.15 (3H, triplet, J=7.32 Hz); 3.84 (3H, singlet); 3.89 (3H, singlet); 4.06 (2H, quartet, J=7.32 Hz); 6.31 (1H, singlet); 6.76 (1H, doublet of doublets, J=8.79 & 1.95 Hz); 6.80 (1H, doublet, J=8.79 Hz); 6.86 (1H, doublet, J=1.95 Hz); 7.15 (2H, doublet of multiplets, J=8.79 Hz); 7.36 (2H, doublet of multiplets, J=8.79 Hz).

Infrared Absorption Spectrum (CHCl$_3$) ν$_{max}$ cm$^{-1}$: 1705, 1615, 1595, 1580, 1510, 1460, 1370, 1290, 1160, 1135.

Mass Spectrum (m/z): 346 (M$^+$, $^{35}$Cl) 317, 301, 274.

PREPARATION 21

Ethyl (Z)-3-(4-chlorophenyl)-3-(3,4-dimethoxyphenyl)-arylate

Prepared as crystals, melting at 67°–69° C. (after recrystallisation from a mixture of diethyl ether and hexane), in a yield of 22%.

Nuclear Magnetic Resonance Spectrum (CDCl$_3$, 270 MHz) δ ppm: 1.16 (3H, triplet, J=7.32 Hz); 3.81 (3H, singlet); 3.91 (3H, singlet); 6.26 (1H, singlet); 6.70 (1H, doublet, J=1.95 Hz); 6.79 (1H, doublet of doublets, J=8.30 & 1.95 Hz); 6.88 (1H, doublet, J=8.30 Hz); 7.12–7.40 (4H, multiplet).

Infrared Absorption Spectrum (CHCl$_3$) ν$_{max}$ cm$^{-1}$: 1710, 1600, 1590, 1515, 1490, 1460, 1255, 1170, 1135.

Mass Spectrum (m/z): 346 (M$^+$, $^{35}$Cl) 317, 301, 274.

PREPARATION 22

(E)-3-(4-Chlorophenyl)-3-(3,4-dimethoxyphenyl)acrylic acid

Prepared as crystals, melting at 164°–165° C. (after recrystallisation from a mixture of methylene chloride and hexane), in a yield of 85%.

Nuclear Magnetic Resonance Spectrum (CDCl$_3$, 270 MHZ) δ ppm: 3.83 (3H, singlet); 3.89 (3H, singlet); 6.29 (1H, singlet); 6.76 (1H, doublet of doublets, 2 8.30 & 1.95 Hz); 6.80 (1H, doublet, J=8.30 Hz); 6.84 (1H, doublet, J=1.95 Hz); 7.15 (2H, doublet of multiplets, J=8.30 Hz); 7.35 (2H, doublet of multiplets, J=8.30 Hz).

Infrared Absorption Spectrum (CHCl$_3$) ν$_{max}$ cm$^{-1}$: 2400–3600 (broad), 1690, 1610, 1595, 1515, 1465, 1260, 1175, 1135.

Mass Spectrum (m/z): 318 (M$^+$), 303, 243.

PREPARATION 23

(Z)-3-(4-Chlorophenyl)-3-(3,4,dimethoxyphenyl)acrylic acid

Prepared as crystals, melting at 188°–190° C. (after recrystallisation from a mixture of methylene chloride and hexane), in a yield of 91%.

Nuclear Magnetic Resonance Spectrum (CDCl$_3$, 270 MHz) δ ppm: 3.80 (3H, singlet); 3.92 (3H, singlet); 6.23 (1H, singlet); 6.72 (1H, doublet, J=1.95 Hz); 6.78 (1H, doublet of doublets, J=8.30 & 1.95 Hz); 6.86 (1H, doublet, J=8.30 Hz); 7.23 (2H, doublet of multiplets, J=8.79 Hz); 7.31 (2H, doublet of multiplets, J=8.79 Hz).

Infrared Absorption Spectrum (CHCl$_3$) ν$_{max}$ cm$^{-1}$: 2400–3600 (broad), 1690, 1605, 1585, 1515, 1490, 1465, 1415, 1255, 1135.

Mass Spectrum (m/z): 318 (M$^+$), 303, 243.

PREPARATION 24

Ethyl (Z)-3-(3-chlorophenyl)-3-(3-dimethoxyphenyl)acrylate

Prepared as an oil in a yield of 13%.

Nuclear Magnetic Resonance Spectrum (CDCl$_3$, 60 MHz) δ ppm: 1.11 (3H, triplet, J=7 Hz); 3.83 (3H, singlet); 3.88 (3H, singlet); 4.06 (2H, quartet, J=7 Hz); 6.35 (1H, singlet); 6.75–7.00 (3H, multiplet); 7.00–7.50 (4H, multiplet).

PREPARATION 25

Ethyl (E)-3-(3-chlorophenyl)-3-(3,4-dimethoxyphenyl)acrylate

Prepared as an oil in a yield of 20%.

Nuclear Magnetic Resonance Spectrum (CDCl$_3$, 60 MHz) δ ppm: 1.15 (3H, triplet, J=7 Hz); 3.81 (3H, singlet); 3.90 (3H, singlet); 4.08 (2H, quartet. J=7 Hz); 6.29 (1H, singlet); 6.70–7.00 (3H, multiplet); 7.10–7.45 (4H, multiplet).

PREPARATION 26

(Z)-3-(3-Chlorophenyl)-3-(3,4-dimethoxyphenyl)acrylic acid

Prepared as crystals, melting at 178°–181° C. (after recrystallisation from a mixture of methylene chloride and hexane), in a yield of 90%.

Nuclear Magnetic Resonance Spectrum (CDCl$_3$, 270 MHz) δ ppm: 3.83 (3H, singlet); 3.89 (3H, singlet); 6.30 (1H, singlet); 6.75 (1H, doublet of doublets, J=8.30 & 1.95 Hz) 6.80 (1H, doublet, J=8.30 Hz); 6.85 (1H, doublet, J=1.95 Hz); 7.10 (1H, doublet of triplets, J=7.81 & 1.46 Hz); 7.20 (1H, triplet, J=1.46 Hz); 7.31 (1H, triplet, J=7.81 Hz); 7.36 (1H, doublet of triplets, J=7.81 & 1.46 Hz).

Infrared Absorption Spectrum (CHCl$_3$) ν$_{max}$ cm$^{-1}$: 2400–3600 (broad), 1690, 1600, 1590, 1580, 1510, 1460, 1420, 1255, 1140.

Mass Spectrum (m/z): 318 (M$^+$, $^{35}$Cl) 303

PREPARATION 27

(Z)-3-(3-Chlorophenyl)-3-(3-dimethoxyphenyl)acrylic acid

Prepared as crystals, melting at 158°–160° C. (after recrystallisation from a mixture of methylene chloride and hexane ), in a yield of 91%.

Nuclear Magnetic Resonance Spectrum (CDCl$_3$, 270 MHz) δ ppm: 3.81 (3H, singlet); 3.92 (3H, singlet); 6.23 (1H, singlet); 6.73 (1H, doublet, J=1.95 Hz); 6.78 (1H, doublet of doublets, J=8.30 & 1.95 Hz); 6.87 (1H, doublet, J=8.30 Hz); 7.15–7.40 (4H, multiplet).

Infrared Absorption Spectrum (CDCl$_3$) ν$_{max}$ cm$^{-1}$: 2400–3600 (broad), 1690, 1600, 1580, 1565, 1515, 1460, 1420, 1255, 1135.

Mass Spectrum (m/z): 318 (M$^+$, $^{35}$Cl) 303.

PREPARATION 28

Ethyl (E)-3-(4-Chlorophenyl)-3-(2,3-dimethoxyphenyl)acrylate

Prepared as crystals, melting at 82°–84° C. (after recrystallisation from hexane), in a yield of 4%.

Nuclear Magnetic Resonance Spectrum (CDCl$_3$, 270 MHz) δ ppm: 1.17 (3H, triplet, J=7.32 Hz); 3.39 (3H, singlet); 3.84 (3H, singlet); 4.10 (2H, quartet, J=7.32 Hz); 6.16 (1H, singlet); 6.82 (1H, doublet of doublets, J=8.30 & 1.46 Hz); 6.93 (1H, doublet of doublets, J=8.30 & 1.46 Hz); 7.04 (1H, triplet, J=8.30 Hz); 7.20 (2H, doublet of multiplets, J=8.79 Hz); 7.29 (2H, doublet of multiplets. J=8.79 Hz).

Infrared Absorption Spectrum (CDCl$_3$) ν$_{max}$ cm$^{-1}$: 1715, 1620, 1600, 1580, 1495, 1475, 1430, 1370, 1260, 1170.

Mass Spectrum (m/z): 46 (M$^+$, $^{35}$Cl) 315, 301, 287.

PREPARATION 29

Ethyl (Z)-3-(4-Chlorophenyl)-3-(2,3-dimethoxyphenyl)acrylate

Prepared as crystals, melting at 90°–92° C. (after recrystallisation from hexane), in a yield of 37%.

Nuclear Magnetic Resonance Spectrum (CDCl$_3$, 270 MHz) δ ppm: 1.11 (3H, triplet, J=7.32 Hz); 3.58 (3H, singlet); 3.89 (3H, singlet); 4.04 (2H, quartet, J=7.32 Hz); 6.43 (1H, singlet); 6.69 (1H; doublet of doublets, J=8.30 & 1.47 Hz); 6.95 (1H, doublet of doublets, J=8.30 & 1.47 Hz); 7.08 (1H, triplet, J=8.30 Hz); 7.28 (4H, singlet).

Infrared Absorption Spectrum (CDCl$_3$) ν$_{max}$ cm$^{-1}$: 1720, 1625, 1590, 1580, 1495, 1480, 1430, 1370, 1260, 1170.

Mass Spectrum (m/z): 46 (M$^+$, $^{35}$Cl) 315, 301, 287.

PREPARATION 30

(E)-3-(4-Chlorophenyl)-3-(2,3-dimethoxyphenyl)acrylic acid

Prepared as crystals, melting at 129°–131° C. (after recrystallisation from a mixture of methylene chloride and hexane), in a yield of 98%.

Nuclear Magnetic Resonance Spectrum (CDCl$_3$, 270 MHz) δ ppm: 3.39 (3H, singlet); 3.84 (3H, singlet); 6.16 (1H, singlet); 6.79 (1H, doublet of doublets, J=8.30 & 1.47 Hz); 6.93 (1H, doublet of doublets, J=8.30 & 1.47 Hz); 7.04 (1H, triplet, J=8.30 Hz); 7.20 (1H, doublet of multiplets, J=8.79 Hz); 7.28 (2H, doublet of multiplets, J=8.79 Hz).

Infrared Absorption Spectrum (CDCl$_3$) ν$_{max}$ cm$^{-1}$: 2400–3600 (broad), 1690, 1620, 1600, 1580, 1495, 1475, 1425, 1260.

Mass Spectrum (m/z): 318 (M$^+$, $^{35}$Cl) 287

PREPARATION 31

(Z)-3-(4-Chlorophenyl)-3-(2,3-dimethoxyphenyl)acrylic acid

Prepared as crystals, melting at 147° C. (after recrystallisation from a mixture of methylene chloride and hexane), in a yield of 98%.

Nuclear Magnetic Resonance Spectrum (CDCl$_3$, 270 MHz) δ ppm: 3.57 (3H, singlet); 3 88 (3H, singlet); 6 38 (1H, singlet); 6. 67 (1H, doublet of doublets, J=7.81 & 1.46 Hz); 6. 94 (1H, doublet of doublets, J=7.81 & 1.46 Hz); 7.06 (1H, triplet, J=7.81 Hz); 7.20–7.33 (4H, multiplet).

Infrared Absorption Spectrum (CDCl$_3$) ν$_{max}$ cm$^{-1}$: 2400–3600 (broad), 1695, 1620, 1590, 1580, 1495, 1480, 1425, 1265.

Mass Spectrum (m/z): 318 (M$^+$, $^{35}$Cl) 287

PREPARATION 32

Ethyl (Z)-3-(4-Chlorophenyl)-3-(4-isobutoxyphenyl)acrylate

Prepared as an oil in a yield of 13%.

Nuclear Magnetic Resonance Spectrum (CDCl$_3$, 270 MHz) δ ppm: 1.02 (6H, doublet, J=6.83 Hz); 1.14 (3H, triplet, J=7.32 Hz); 2.00–2.15 (1H, multiplet); 3.72 (doublet, J=6.35 Hz); 4.05 (2H, quartet, J=7.32 Hz); 6.30 (1 singlet); 6.83 (2H, doublet of multiplets, 8.79 Hz); 7.14 (2H, doublet of multiplets, 8.79 Hz); 7.20 (2H, doublet of multiplets, 8.79 Hz); 7.35 doublet of multiplets, 8.79 Hz).

Infrared Absorption Spectrum (CDCl$_3$) ν$_{max}$ cm$^{-1}$: 1710, 1605, 1515, 1495, 1475. 1375, 1280, 1255, 1170.

Mass Spectrum (m/z): 58 (M$^+$, $^{35}$Cl) 313, 302

PREPARATION 33

Ethyl (E)-3-(4-Chlorophenyl)-3-(4-isobutoxyphenyl)acrylate

Prepared as an oil in a yield of 16%.

Nuclear Magnetic Resonance Spectrum (CDCl$_3$, 270 MHz) δ ppm: 1.03 (6H, doublet, J=6.83 Hz); 1.17 (3H, triplet, J=7.32 Hz); 2.00–2.20 (1H, multiplet); 3.74 (2H, doublet, J=6.35 Hz); 4.09 (2H, quartet, J=7.32 Hz); 6.23 (1H, singlet); 6.89 (2H, doublet of multiplets, J=9.28 Hz); 7.11 (2H, doubler of multiplets, J=9.28 Hz); 7.22 (2H, doubler of multiplets, J=8.79 Hz); 7.29 (2H, doubler of multiplets, J=8.79 Hz).

Infrared Absorption Spectrum (CDCl$_3$) ν$_{max}$ cm$^{-1}$: 1710, 1605, 1590, 1510, 1490, 1470, 1370, 1285, 1160.

Mass Spectrum (m/z): 358 (M$^+$, $^{35}$Cl) 313, 302

PREPARATION 34

(Z)-3-(4-Chlorophenyl)-3-(4-isobutoxyphenyl)acrylic acid

Prepared as crystals, melting at 172°–174° C. (after recrystallisation from a mixture of methylene chloride and hexane), in a yield of 80%.

Nuclear Magnetic Resonance Spectrum (CDCl$_3$, 270 MHz) δ ppm: 1.02 (6H, doublet, J=6.83 Hz); 1.95–2.20 (1H, multiplet); 3.72 (2H, doublet, J=6.84 Hz); 6.27 (1H, singlet); 6.83 (2H, doublet of multiplets, J=8.30 Hz); 7.13 (2H, doublet of multiplets, J=8.30 Hz); 7.18 (2H, doublet of multiplets, J=8.79 Hz); 7.34 (2H, doublet of multiplets, J=8.79 Hz).

Infrared Absorption Spectrum (CDCl$_3$) $v_{max}$ cm$^{-1}$: 400–3600 (broad), 1695, 1600, 1590, 1510, 1295, 1250, 1175.

Mass Spectrum (m/z): 330 (M$^+$, $^{35}$Cl) 274, 257.

PREPARATION 35

(E)-3-(4-Chlorophenyl)-3-(4-isobutoxyphenyl)acrylic acid

Prepared as crystals, melting at 150°–152° C. (after recrystallisation from a mixture of methylene chloride and hexane), in a yield of 100%.

Nuclear Magnetic Resonance Spectrum (CDCl3, 270 MHz) δ ppm: 1.04 (6H, doublet, J=6.35 Hz); 2.00–2.20 (1H, multiplet); 3.75 (2H, doublet, J=6.34 Hz); 6.19 (1H, singlet); 6.87 (2H, doublet of multiplets, J=8.79 Hz); 7.12 (2H, double of multiplets, J=8.79 Hz); 7.21 (2H, doublet of multiplets, J=8.78 Hz); 7.30 (2H, doublet of multiplets, J=8.78 Hz).

Infrared Absorption Spectrum (CDCl$_3$) $v_{max}$ cm$^{-1}$: 2400–3600 (broad), 1690, 1610, 1590, 1515, 1290, 1245, 1175.

Mass Spectrum (m/z): 330 (M$^+$, $^{35}$Cl) 274, 257.

PREPARATION 36

Ethyl (Z)-3-(4-Chlorophenyl)-3-(4-propoxyphenyl)acrylate

Prepared as an oil in a yield of 19%.

Nuclear Magnetic Resonance Spectrum (CDCl3, 270 MHz) δ ppm: 1.03 (3H, triplet, J=7.32 Hz); 1.14 (3H, triplet, J=7.33 Hz); 1.74–1.90 (2H, multiplet); 3.92 (2H, triplet, J=6.83 Hz); 4.05 (2H, quartet, J=7.33 Hz); 6.31 (1H, singlet); 6.83 (2H, doublet of multiplets, J=9.28 Hz); 7.14 (1H, doublet of multiplets, J=8.79 Hz); 7.20 (2H, doublet of multiplets, J=9.28 Hz); 7.36 (2H, doublet of multiplets, J=8.79 Hz).

Infrared Absorption Spectrum (CDCl$_3$) $v_{max}$ cm$^{-1}$: 1705, 1600, 1595, 1510, 1370, 1275, 1250, 1160, 1150.

Mass Spectrum (m/z): 44 (M$^+$, $^{35}$Cl) 302, 299, 272, 257, 230.

PREPARATION 37

Ethyl (E)-3-(4-Chlorophenyl)-3-(4-propoxvohenyl)acrylate

Prepared as an oil in a yield of 27%.

Nuclear Magnetic Resonance Spectrum (CDCl$_3$, 270 MHz) δ ppm: 1.05 (3H, triplet, J=7.33 Hz); 1.16 (3H, triplet, J=7.33 Hz); 1.75–1.95 (2H, multiplet); 3.95 (2H, triplet, J=6.84 Hz); 4.09 (2H, quartet, J=7.33 Hz); 6.23 (1H, singlet); 6.89 (2H, doublet of multiplets, J=8.78 Hz) 7.12 (2H, doublet of multiplets, J=8.78 Hz); 7.22 (2H, doublet of multiplets, J=8.79 Hz); 7.29 (2H, doublet of multiplets, J=8.79 Hz).

Infrared Absorption Spectrum (CHCl$_3$) $v_{max}$ cm$^{-1}$: 1710, 1610, 1590, 1510, 1490, 1370, 1290, 1240, 1170, 1150.

Mass Spectrum (m/z): 344 (M$^+$, $^{35}$Cl) 302, 299, 272, 257, 230.

PREPARATION 38

(Z)-3-(4-Chlorophenyl)-3-(4-propoxyphenyl)acrylic acid

Prepared as crystals, melting at 159°–161° C. (after recrystallisation from a mixture of methylene chloride and hexane), in a yield of 96%.

Nuclear Magnetic Resonance Spectrum (CDCl$_3$, 270 MHz) δ ppm: 1.03 (3H, triplet, J=7.32 Hz); 1.70–1.90 (2H, multiplet); 3.93 (2H, triplet, J=6.84 Hz); 6.27 (1H, singlet); 6.83 (2H, doublet of multiplets, J=8.79 Hz); 7.14 (2H, doublet of multiplets, J=8.30 Hz); 7.19 (2H, doublet of multiplets, J=8.79 Hz); 7.34 (2H, doublet of multiplets, J=8.30 Hz).

Infrared Absorption Spectrum (CDCl$_3$) $v_{max}$ cm$^{-1}$: 2400–3600 (broad), 1695, 1600, 1595, 1510, 1280, 1255, 1180.

Mass Spectrum (m/z): 316 (M$^+$, $^{35}$Cl), 274, 257, 229.

PREPARATION 39

(E)-3-(4-Chlorophenyl)-3-(4-propoxyphenyl)acrylic acid

Prepared as crystals, melting at 145°–147° C. (after recrystallisation from a mixture of methylene chloride and hexane), in a yield of 97%.

Nuclear Magnetic Resonance Spectrum (CDCl$_3$, 270 MHz) δ ppm: 1.06 (3H, triplet, J=7.33 Hz); 1.75–1.90 (2H, multiplet); 3.95 (3H, triplet, J=6.35 Hz); 6.19 (1H, singlet); 6.88 (2H, doublet of multiplets, J=8.79 Hz); 7.13 (2H, doublet of multiplets, J=8.79 Hz); 7.21 (2H, doublet of multiplets, J=8.79 Hz) 7.30 (2H, doublet of multiplets, J=8.79 Hz).

Infrared Absorption Spectrum (CDCl$_3$) $v_{max}$ cm$^{-1}$: 2400–3600 (broad), 1690, 1610, 1590, 1510, 1495, 1290, 1270, 1250, 1175.

Mass Spectrum (m/z): 316 (M$^+$, $^{35}$Cl), 274, 257, 229.

PREPARATION 40

Ethyl (E)-3-(4-Fluorophenyl)-3-(3,4,-trimethoxyphenyl) acrylate

Prepared as crystals, melting at 133°–135° C. (after recrystallisation from diethyl ether), in a yield of 22%.

Nuclear Magnetic Resonance Spectrum (CDCl$_3$, 270 MHz) δ ppm: 1.15 (3H, triplet, J=7.32 Hz); 3.78 (6H, singlet); 3.87 (3H, singlet); 4.07 (2H, quartet, J=7.32 Hz); 6.31 (1H, singlet); 6.48 (2H, singlet); 7.03–7.13 (2H, multiplet); 7.17–7.25 (2H, multiplet).

Infrared Absorption Spectrum (CDCl$_3$) $v_{max}$ cm$^{-1}$: 1710, 1605, 1580, 1505, 1465, 1415, 1355, 1165, 1155, 1130.

Mass Spectrum (m/z): 360 (M$^+$), 345, 315.

PREPARATION 41

Ethyl (Z)-3-(4-Fluorophenyl)-3-(3,4,5trimethoxyphenyl)acrylate

Prepared as crystals, melting at 62°–64° C. (after recrystallisation from a mixture of diethyl ether and hexane), in a yield of 37%.

Nuclear Magnetic Resonance Spectrum (CDCl$_3$, 270 MHz) δ ppm: 1–14 (3H, triplet, J=7.33 Hz); 3.80 (6H, singlet); 3.90 (3H, singlet); 4.08 (2H, quartet, J=7.33 Hz); 6.26 (1H, singlet); 6.41 (2H, singlet); 6.98–7.08 (2H, multiplet); 7.27–7.36 (2H, multiplet).

Infrared Absorption Spectrum (CHCl$_3$) $v_{max}$ cm$^{-1}$: 1710, 1600, 1585, 1505, 1465, 1415, 1370, 1310, 1160, 1130.

Mass Spectrum (m/z): 360 (M$^+$), 345, 315.

PREPARATION 42

(E)-3-(4-Fluorophenyl)-3-(3,4,5-trimethoxyphenyl)acrylic acid

Prepared as crystals, melting at 201°–204° C. (after recrystallisation from a mixture of methylene chloride, diethyl ether and hexane), in a yield of 98%.

Nuclear Magnetic Resonance Spectrum (CDCl$_3$, 270 MHz) δ ppm: 3.78 (6H, singlet); 3.87 (3H, singlet); 6.28 (1H, singlet); 6.46 (2H, singlet); 7.02–7.12 (2H, multiplet) 7.12–7.25 (2H, multiplet).

Infrared Absorption Spectrum (CDCl$_3$) $v_{max}$ cm$^{-1}$: 2400–3600 (broad), 1690, 1600, 1580, 1505, 1130.

Mass Spectrum (n/z); 332 (M$^+$), 317.

PREPARATION 43

(Z)-3-(4-Fluorophenyl)-3-(3,4,5-trimethoxyphenyl)acrylic acid

Prepared as crystals, melting at 187°–189° C. (after recrystallisation from a mixture of methylene chloride and hexane), in a yield of 100%.

Nuclear Magnetic Resonance Spectrum (CDCl$_3$, 270 MHz) δ ppm: 3.79 (6H, singlet); 3.91 (3H, singlet); 6.21 (1H, singlet); 6.42 (2H, singlet); 6.99–7.09 (2H, multiplet); 7.27–7.35 (2H, multiplet).

Infrared Absorption Spectrum (CDCl$_3$) $v_{max}$ cm$^{-1}$: 2400–3600 (broad), 1690, 1600, 1585, 1505, 1415, 1125.

Mass Spectrum (m/z); 332 (M$^+$), 317.

PREPARATION 44

Ethyl (E)-3-(3,4-Dimethoxyphenyl)-3-(4-methoxyphenyl)acrylate

Prepared as an oil in a yield of 20%.

Nuclear Magnetic Resonance Spectrum (CDCl$_3$, 270 MHz) 1.16 (3H, triplet J=7.32 Hz); 3.83 (3H, singlet); 3.85 (3H, singlet); 3.89 (3H, singlet); 4.08 (2H, quartet, J=7.32 Hz); 6.23 (1H, singlet); 6.77–6.89 (3H, multiplet); 6.91 (2H, doublet of multiplets, J=8.78 Hz); 7.16 (2H, doublet of multiplets, J=8.78 Hz).

Infrared Absorption Spectrum (CHCl$_3$) $v_{max}$ cm$^{-1}$: 1705, 1605, 1580, 1510, 1465, 1290, 1165, 1135.

Mass Spectrum (m/z): 342 (M$^+$), 313, 297.

PREPARATION 45

Ethyl (Z)-3-(3,4-Dimethoxyphenyl)-3-(4-methoxyphenyl)acrylate

Prepared as an oil in a yield of 30%.

Nuclear Magnetic Resonance Spectrum (CDCl$_3$, 270 MHz) δ ppm: 1.15 (3H, triplet J=7.32 Hz); 3.81 (3H, singlet); 3.85 (3H, singlet); 3.92 (3H, singlet); 4.07 (2H, quartet, J=7.32 Hz); 6.24 (1H, singlet); 6.71 (1H, doublet, J=1.95 Hz); 6.77–6.94 (4H, multiplet); 7.26 (2H, doublet of multiplets, J=8.79 Hz).

Infrared Absorption Spectrum (CDCl$_3$) $v_{max}$ cm$^{-1}$: 1705, 1600, 1510, 1465, 1250, 1170, 1135.

Mass Spectrum (m/z): 342 (M$^+$), 313, 297.

PREPARATION 46

(E)-3-(3,4-Dimethoxyphenyl)-3-(4-methoxyphenyl)acrylic acid

Prepared as crystals, melting at 161°–163° C. (after recrystallisation from a mixture of methylene chloride and hexane), in a yield of 91%.

Nuclear Magnetic Resonance Spectrum (CDCl$_3$, 270 MHz) δ ppm: 3.82 (3H, singlet); 3.85 (3H, singlet); 3.89 (3H, singlet); 6.20 (1H, singlet); 6.74–6.82 (2H, multiplet); 6.84 (1H, broad singlet); 6.89 (2H, doublet of multiplets, J=8.79 Hz); 7.17 (2H, doublet of multiplets, J=8.79 Hz).

Infrared Absorption Spectrum (CDCl$_3$) $v_{max}$ cm$^{-1}$: 2400–3600 (broad), 1685, 1605, 1595, 1510, 1465 1290, 1245, 1170, 1135.

Mass Spectrum (m/z): 314 (M$^+$), 299.

PREPARATION 47

(Z)-3-(3,4-Dimethoxyphenyl)-3-(.4-methoxyphenyl)acrylic acid.

Prepared as crystals, melting at 149°–152° C. (after recrystallisation from a mixture of methylene chloride and hexane), in a yield of 97%.

Nuclear Magnetic Resonance Spectrum (CDCl$_3$, 270 MHz) δ ppm: 3.81 (3H, singlet); 3.83 (3H, singlet); 3.92 (3H, singlet); 6.21 (1H, singlet); 6.74 (1H, doublet, J=1.95 Hz); 6.80 (1H, doublet of doublets 8.30 & 1.95 Hz); 6.82–6.93 (3H, multiplet); 7.14–7.29 (2H, multiplet).

Infrared Absorption Spectrum (CHCl$_3$) $v_{max}$ cm$^{-1}$: 2400–3600 (broad), 1690, 1600, 1515, 1465, 1255, 1175, 1135.

Mass Spectrum (m/z): 314 (M$^+$), 299, 270.

PREPARATION 48

Ethyl (Z)-3-(3,4-Dichlorophenyl)-3-(4-methoxyphenyl)acrylate

Prepared as an oil in a yield of 62%.

Nuclear Magnetic Resonance Spectrum (CDCl$_3$, 60 MHz) δ ppm: 1.15 (3H, triplet, J=7 Hz); 3.80 (3H, singlet); 4.06 (2H, quartet J=7 Hz); 6.35 (1H, singlet); 6.8–7.4 (7H, multiplet).

PREPARATION 49

Ethyl (E)-3-(3,4-Dichlorophenyl)-3-(4-methoxyphenyl) acrylate

Prepared as an oil in a yield of 23%.

Nuclear Magnetic Resonance Spectrum (CDCl$_3$, 60 MHz) δ ppm: 1.16 (3H, triplet, J=7 Hz); 3.84 (3H, singlet); 4.06 (2H, quartet J=7 Hz); 6.23 (1H, singlet); 6.7–7.5 (7H, multiplet).

PREPARATION 50

(Z)-3-(3,4,Dichlorophenyl)-3-(4-methoxyphenyl) acrylic acid

Prepared as crystals, melting at 181°–184° C. (after recrystallisation from a mixture of methylene chloride and hexane), in a yield of 84%.

Nuclear Magnetic Resonance Spectrum (CD$_3$OD, 270 MHz) δ ppm: 3.80 (3H, singlet); 6.36 (1H, singlet); 6.91 (2H, doublet of multiplets, J=9.28 Hz); 7.08 (1H, doublet of doublets, J=8.30 & 1.95 Hz); 7.23 (2H, doublet of multiplets, J=9.28 Hz); 7.31 (1H, doublet, J=1.95 Hz); 7.51 (1H, doublet, J=8.30 Hz).

Infrared Absorption Spectrum (KBr) ν$_{max}$ cm$^{-1}$: 2300–3400 (broad), 1692, 1597, 1585, 1510, 1288, 1254, 1214, 1178, 1162.

Mass Spectrum (m/z): 322 (M$^+$,$^{35}$Cl) 305, 277.

PREPARATION 51

(E)-3-(3,4-Dichlorophenyl)-3-(4-methoxyphenyl) acrylic acid

Prepared as crystals, melting at 193°–196° C. (after recrystallisation from a mixture of methylene chloride and hexane), in a yield of 95%.

Nuclear Magnetic Resonance Spectrum (CD$_3$OD, 270 MHz) δ ppm: 3.83 (3H, singlet); 6.30 (1H, singlet); 6.93 (2H, doublet of multiplets, J=8.79 Hz); 7.12 (2H, doublet of multiplets, J=8.79 Hz); 7.23 (1H, doublet of doublets, J=8.30 & 1.95 Hz); 7.38 (1H, doublet, J=1.95 Hz); 7.50 (1H, doublet, J=8.30 Hz).

Infrared Absorption Spectrum (KBr) ν$_{max}$ cm$^{-1}$: 2300–3400 (broad), 1688, 1662, 1602, 1512, 1407, 1281, 1253, 1207, 1177.

Mass Spectrum (m/z): 322 (M$^+$, $^{35}$Cl) 305, 277.

PREPARATION 52

Ethyl (E)-3-(3,4-Dimethoxyphenyl)-3-(3-trifluoromethylphenyl)acrylane

Prepared as crystals, melting at 72°–74° C. (after recrystallisation from hexane), in a yield of 13%.

Nuclear Magnetic Resonance Spectrum (CDCl$_3$, 270 MHz) δ ppm: 1.08 (3H, triplet, J=7.32 Hz); 3.84 (3H, singlet); 3.89 (3H, singlet); 4.03 (2H, quartet. J=7.32 Hz); 6.37 (1H, singlet); 6.72 (1H, doublet of doublets, J=8.30 & 1.96 Hz); 6.80 (1H, doublet, J=8.30 Hz); 6.87 (1H, doublet, J=1.96 Hz); 7.35–7.70 (4H, multiplet).

Infrared Absorption Spectrum (CHCl$_3$) ν$_{max}$ cm$^{-1}$: 1710, 1595, 1515, 1460, 1370.

Mass Spectrum (m/z): 380 (M$^+$), 361, 335.

PREPARATION 53

Ethyl (Z)-3-(3,4-Dimethoxyphenyl)-3-(3-trifluoromethylphenyl)acrylate

Prepared as an oil in a yield of 16%.

Nuclear Magnetic Resonance Spectrum (CDCl$_3$, 270 MHz) δ ppm: 1.18 (3H, triplet, J=7.32 Hz); 3.82 (3H, singlet); 3.93 (3H, singlet); 4.11 (2H, quartet, J=7.32 Hz); 6.30 (1H, singlet); 6.71 (1H, doublet. J=1.95 Hz); 6.81 (1H, doublet of doublets, J=8.30 & 1.96 Hz); 6.89 (1H, doublet, J=8.30 Hz); 7.40–7.50 (2H, multiplet); 7.57–7.68 (2H, multiplet).

Infrared Absorption Spectrum (CDCl$_3$) ν$_{max}$ cm$^{-1}$: 1710, 1600, 1580, 1515, 1460, 1370, 1325.

Mass Spectrum (m/z): 380 (M$^+$), 361, 335.

PREPARATION 54

(E) -3-(3,4-Dimethoxyphenyl)-3-(3-trifluoromethylphenyl) acrylic acid

Prepared as crystals (melting at 142°–144° C., after recrystallisation from a mixture of methylene chloride and hexane), in a yield of 100%.

PREPARATION 55

(Z)-3-(3,4-Dimethoxyphenyl)-3-(3-trifluoromethylphenyl)acrylic acid

Prepared as crystals (melting at 140°–143° C., after recrystallisation from a mixture of methylene chloride and hexane), in a yield of 100%.

PREPARATION 56

Ethyl (E)-3-(3,4-Dimethoxyphenyl)-3-(4-methylphenyl) acrylate

Prepared as crystals, melting at 75°–77° C. (after recrystallisation from hexane), in a yield of 21%.

Nuclear Magnetic Resonance Spectrum (CDCl$_3$, 270 MHz) δ ppm: 1.14 (3H, triplet, J=7.32 Hz); 2.39 (3H, singlet); 3.83 (3H, singlet); 3.88 (3H, singlet); 4.06 (2H, quartet, J=7.32 Hz); 6.27 (1H, singlet); 6.77 (1H, doublet, J=8.30 Hz); 6.81 (1H, doublet of doublets, J=8.30 & 1.95 Hz); 6.89 (1H, doublet, J=1.95 Hz); 7.01–7.22 (4H, multiplet).

Infrared Absorption Spectrum (CDCl$_3$) ν$_{max}$ cm$^{-1}$: 1705, 1600, 1580, 1510, 1465, 1440, 1370, 1290, 1250, 1160, 1130.

Mass Spectrum (m/z): 326 (M$^+$), 297, 281, 254.

PREPARATION 57

Ethyl (Z)-3-(3,4-Dimethoxyphenyl)-3-(4-methylphenyl) acrylane

Prepared as crystals (melting at 69°–70° C. after recrystallisation from hexane), in a yield of 38%.

Nuclear Magnetic Resonance Spectrum (CDCl$_3$, 270 MHz) δ ppm: 1.16 (3H, triplet, J=7.32 Hz); 2.36 (3H, singlet); 3.81 (3H, singlet); 3.91 (3H, singlet); 4.08 (2H, quartet, J=7.32 Hz); 6.27 (1H, singlet); 6.72 (1H, doublet, J=1.95 Hz); 6.81 (1H, doublet of doublets, J=7.81 & 1.95 Hz); 6.88 (1H, doublet, J=7.81 Hz). 7.13 (2H, doublet of multiplets, J=8.30 Hz); 7.21 (2H, doublet of multiplets, J=m 8.30 Hz).

Infrared Absorption Spectrum (CDCl$_3$) $v_{max}$ cm$^{-1}$: 1710, 1600, 1580, 1510, 1465, 1415, 1370, 1250, 1160, 1135.

Mass Spectrum (m/z): 326 (M$^+$), 297, 281, 254.

PREPARATION 58

(E)-3-(3,4-Dimethoxyphenyl)-3-(4-methylphenyl) acrylic acid

Prepared as crystals, melting at 167°–170° C. (after recrystallisation from a mixture of methylene chloride and hexane), in a yield of 97%.

Nuclear Magnetic Resonance Spectrum (CDCl$_3$, 270 MHz) δ ppm: 2.39 (3H, singlet); 3.88 (3H, singlet); 3.92 (3H, singlet); 6.24 (1H, singlet); 7.79 (1H, multiplet); 6.86 (1H, broad singlet); 7.08–7.22 (4H, multiplet).

Infrared Absorption Spectrum (CDCl$_3$) $v_{max}$ cm$^{-1}$: 2400–3600 (broad), 1690, 1600, 1580, 1510, 1465, 1440, 1420, 1325, 1290, 1250, 1175, 1135.

Mass Spectrum (m/z): 298 (M$^+$), 283.

PREPARATION 59

(Z)-3-(3,4-Dimethoxyphenyl)-3-(4-methylphenyl) acrylic acid

Prepared as crystals, melting at 185°–188° C. (after recrystallisation from a mixture of methylene chloride and hexane), in a yield of 96%.

Nuclear Magnetic Resonance Spectrum (CDCl$_3$, 270 MHz) δ ppm: 2.36 (3H, singlet); 3.80 (3H, singlet); 3.92 (3H, singlet); 6.24 (1H, singlet); 6.75 (1H, doublet, J=1.95 Hz); 6.79 (1H, doublet of doublets, J=m 8.30 & 1.95 Hz); 6.86 (1H, doublet, J=8.30 Hz); 7.10–7.23 (4H, multiplet).

Infrared Absorption Spectrum (CDCl$_3$) $v_{max}$ cm$^{-1}$: 2400–3600 (broad), 1690, 1605, 1515, 1465, 1420, 1260, 1180, 1140.

Mass Spectrum (m/z): 298 (M$^+$), 283.

PREPARATION 60

Ethyl (Z)-3-(3,4-Dichlorophenyl)-3-(3-methylphenyl) acrylane

Prepared as an oil in a yield of 52%.

Nuclear Magnetic Resonance Spectrum (CDCl$_3$, 270 MHz) δ ppm: 1.17 (3H, triplet, J=7.32 Hz); 2.33 (3H, singlet); 4.08 (2H, quartet, J=7.32 Hz); 6.36 (1H, singlet); 7.03–7.13 (3H, multiplet); 7.15–7.23 (2H, multiplet); 7.30 (1H, doublet, J=1.95 Hz); 7.46 (1H, doublet, J=8.30 Hz).

Infrared Absorption Spectrum (CDCl$_3$) $v_{max}$ cm$^{-1}$: 1715, 1620, 1470, 1370, 1280, 1170, 1150.

Mass Spectrum (m/z): 334 (M$^+$, $^{35}$Cl) 305, 289, 262.

PREPARATION 61

Ethyl (E)-3-(3,4-Dichlorophenyl)-3-(3-methylphenyl) acrylate

Prepared as an oil in a yield of 19%.

Nuclear Magnetic Resonance Spectrum (CDCl$_3$, 270 MHz) δ ppm: 1.11 (3H, triplet, J=7.32 Hz); 2.35 (3H, singlet); 4.05 (2H, quartet, J=7.32 Hz); 6.30 (1H, singlet); 6.95–7.05 (2H, multiplet); 7.12 (1H, doublet of doublets, J=8.79 & 1.95 Hz); 7.15–7.32 (2H, multiplet); 7.379 (1H, doublet, J=1.95 Hz); 7.385 (1H, doublet, J=8.79. Hz).

Infrared Absorption Spectrum (CDCl$_3$) $v_{max}$ cm$^{-1}$: 1720, 1620, 1470, 1380, 1370, 1350, 1280, 1250, 1175.

Mass Spectrum (m/z): 334 (M$^+$, $^{35}$Cl) 305, 289, 262.

PREPARATION 62

(Z)-3-(3,4-Dichlorophenyl)-3-(3-methylphenyl)acrylic acid

Prepared as crystals, melting at 163°–165° C. (after recrystallisation from a mixture of methylene chloride and hexane), in a yield of 95%.

Nuclear Magnetic Resonance Spectrum (CDCl$_3$, 270 MHz) δ ppm: 2.33 (3H, singlet); 6.33 (1H, singlet); 7,00–7.10 (3H, multiplet); 7.18–7.28 (2H, multiplet); 7.29 (1H, doublet, J=1.95 Hz); 7.45 (1H, doublet, J=7.81. Hz).

Infrared Absorption Spectrum (CDCl$_3$) $v_{max}$ cm$^{-1}$: 2400–3600 (broad), 1695, 1600, 1585, 1475, 1290, 1125.

Mass Spectrum (m/z): 306 (M$^+$, $^{35}$Cl) 291, 261.

PREPARATION 63

(E)-3-(3,4-Dichlorophenyl)-3-(3-methylphenyl)acrylic acid

Prepared as crystals, melting at 152°–154° C. (after recrystallisation from a mixture of methylene chloride and hexane), in a yield of 92%.

Nuclear Magnetic Resonance Spectrum (CDCl$_3$, 270 MHz) δ ppm: 2.34 (3H, singlet); 6.26 (1H, singlet); 6.94–7.03 (2H, multiplet); 7.09 (1H, doublet of doublets, J=8.30 & 1.95 Hz); 7.18–7.32 (2H, multiplet); 7.35 (1H, doublet, J=1.96 Hz); 7.39 (1H, doublet, J=8.30 Hz).

Infrared Absorption Spectrum (CDCl$_3$) $v_{max}$ cm$^{-1}$: 2400–3600 (broad) 1695, 1620, 1470, 1410, 1285, 1180, 1130.

Mass Spectrum (m/z): 306 (M$^+$, $^{35}$Cl) 291, 261.

PREPARATION 64

Ethyl (E)-3-(3,4-Dimethoxyphenyl)-3-(3-methylphenyl) acrylate

Prepared as an oil in a yield of 23%.

Nuclear Magnetic Resonance Spectrum (CDCl$_3$, 270 MHz) δ ppm: 1.11 (3H, triplet. J=7.32 Hz); 2.36 (3H, singlet); 3.83 (3H, singlet); 3.88 (3H, singlet); 4.04 (2H, quartet, J=7.32 Hz); 6.29 (1H, singlet); 6.75–6.84 (2H, multiplet); 6.90 (1H, broad singlet); 6.94–7.05 (2H, multiplet); 7.15–7.31 (2H, multiplet).

Infrared Absorption Spectrum (CDCl$_3$) $v_{max}$ cm$^{-1}$: 1710, 1600, 1580, 1515, 1470, 1445, 1330, 1295. 1255, 1160, 1145, 1130.

Mass Spectrum (m/z): 326 (M$^+$), 297, 281, 254.

PREPARATION 65

Ethyl
(Z)-3-(3,4-Dimethoxyphenyl)-3-(3-methylphenol)
acrylate

Prepared as an oil in a yield of 33%.

Nuclear Magnetic Resonance Spectrum (CDCl$_3$, 270 MHz) δ ppm: 1.16 (3H, triplet, J=7.33 Hz); 2.33 (3H, singlet); 3.81 (3H, singlet); 3.92 (3H, singlet); 4.08 (2H, quartet, J=7.32 Hz); 6.72 (1H, doublet, J=1.96 Hz); 6.81 (1H, doublet of doublets, J=8.30 & 1.96 Hz); 6.88 (1H, doublet, J=8.30 Hz); 7.07–7.26 (4H, multiplet.

Infrared Absorption Spectrum (CHCl$_3$) $v_{max}$ cm$^{-1}$: 1715, 1610, 1590, 1520, 1470, 1260, 1180, 1160, 1145, 1135.

Mass Spectrum (m/z): 326 (M$^+$), 297, 281, 254.

PREPARATION 66

(E)-3-(3,4-Dimethoxyphenyl)-3-(3-methylphenyl)
acrylic acid

Prepared as crystals, melting at 140°–143° C. (after recrystallisation from a mixture of diethyl ether and hexane), in a yield of 95%.

Nuclear Magnetic Resonance Spectrum (CDCl$_3$, 270 MHz) δ ppm: 2.35 (3H, singlet); 3.82 (3H, singlet); 3.89 (3H, singlet); 6.27 (1H, singlet); 6.74–6.83 (2H, multiplet); 6.87 (1H, broad singlet); 6.99–7.06 (2H, multiplet); 7.15–7.31 (2H, multiplet).

Infrared Absorption Spectrum (CHCl$_3$) $v_{max}$ cm$^{-1}$: 2400–3600 (broad), 1695, 1600, 1580, 1515, 1470, 1260, 1170, 1145, 1130.

Mass Spectrum (m/z): 298 (M$^+$), 283, 253.

PREPARATION 67

(Z)-3-(3,4,Dimethoxyphenyl)-3-(3-methylphenyl)
acrylic acid

Prepared as crystals, melting at 148°–150° C. (after recrystallisation from a mixture of methylene chloride and hexane), in a yield of 96%.

Nuclear Magnetic Resonance Spectrum (CDCl$_3$, 270 MHz) δ ppm: 2.33 (3H, singlet); 3.81 (3H, singlet); 3.92 (3H, singlet); 6.24 (2H, singlet); 6.75 (1H, doublet, J=1.96 Hz); 6.80 (1H, doublet of doublets, J=8.30 & 1.96 Hz); 6.87 (1H, doublet, J=8.30 Hz); 7.05–7.14 (2H, multiplet); 7.16–7.24 (2H, multiplet).

Infrared Absorption Spectrum (CDCl$_3$) $v_{max}$ cm$^{-1}$: 2400–3600 (broad), 1690, 1605, 1585, 1515, 1450, 1440, 1420, 1255, 1175, 1135.

Mass Spectrum (m/z): 298 (M$^+$), 283, 253.

PREPARATION 68

Ethyl
(Z)-3-(2-Chlorophenyl)-3-(4-methoxyphenyl)acrylate

Prepared as an oil in a yield of 81%.

Nuclear Magnetic Resonance Spectrum (CDCl$_3$, 270 MHz) δ ppm: 1.10 (3H, triplet, J=7.33 Hz); 3.81 (3H, singlet); 4.03 (2H, quartet, J=7.33 Hz); 6.48 (1H, singlet); 6.85 (2H, doublet of multiplets, J=9.28 Hz); 7.11–7.20 (1H, multiplet); 7.26 (2H, doublet of multiplets, J=9.28 Hz); 7.26–7.37 (2H, multiplet); 7.40–7.50 (1H, multiplet).

Infrared Absorption Spectrum (CDCl$_3$) $v_{max}$ cm$^{-1}$: 1710, 1605, 1590, 1575, 1515, 1465, 1370, 1355, 1280, 1255, 1160.

Mass Spectrum (m/z): 316 (M$^+$, $^{35}$Cl) 281, 271, 253.

PREPARATION 69

(Z)-3-(2-Chlorophenyl)-3-(4-methoxyphenyl)
acrylic acid

Prepared as crystals, melting at 162°–164° C. (after recrystallisation from a mixture of methylene chloride and hexane), in a yield of 85%.

Nuclear Magnetic Resonance Spectrum (CDCl$_3$, 270 MHz) δ ppm: 3.80 (3H, singlet); 6.44 (1H, singlet); 6.84 (2H, doublet of multiplets, J=8.79 Hz); 7.09–7.16 (1H, multiplet); 7.24 (2H, doublet of multiplets, J=8.79 Hz); 7.26–7.35 (2H, multiplet); 7.37–7.46 (1H, multiplet).

Infrared Absorption Spectrum (CHCl$_3$) $v_{max}$ cm$^{-1}$: 2400–3600 (broad), 1700, 1620, 1605, 1595, 1575, 1515, 1425, 1290, 1260, 1180, 1160.

Mass Spectrum (m/z): 288 (M$^+$, $^{35}$Cl) 253, 238.

PREPARATION 70

Ethyl
(Z)-3-(3-Chlorophenyl)-3-(3-methoxyphenyl)acrylate

Prepared as an oil in a yield of 8%.

Nuclear Magnetic Resonance Spectrum (CDCl$_3$, 270 MHz) δ ppm: 1.13 (3H, triplet, J=7.32 Hz); 3.78 singlet); 4.06 (2H, quartet, J=7.32 Hz); 6.37 (1H, singlet); 6.81 (1H, triplet, J=1.96 Hz); 6.86 (1H, doubled doublet of doublets, J=8.31, 1.96 & 0.9 8 Hz); 6.91 (1H, doubled doublet of doublets, J=8.31, 1.96 & 0.9 8 Hz); 7.10 (1H, doublet of triplets, J=7.81 & 1.95 Hz); 7.20 (1H, triplet, J=1.95 Hz); 7.25 (1H, triplet, J=7.81 Hz); 7.31 (1H, triplet, J=7.81 Hz); 7.35 (1H, doublet of triplets, J=7.81 & 1.95 Hz).

Infrared Absorption Spectrum (CDCl$_3$) $v_{max}$ cm$^{-1}$: 1715, 1620, 1600, 1580, 1490, 1470, 1435, 1370, 1350, 1290, 1280, 1170.

Mass Spectrum (m/z): 316 (M$^+$, $^{35}$Cl) 287, 271, 243, 228.

PREPARATION 71

Ethyl
(E)-3-(3-Chlorophenyl)-3-(3methoxyphenyl)acrylate

Prepared as an oil in a yield of 18%.

Nuclear Magnetic Resonance Spectrum (CDCl$_3$, 270 MHz) δ ppm: 1.12 (3H, triplet, J=7.32 Hz); 3.79 (3H, singlet); 4.06 (2H, quartet, J=7.32 Hz); 6.33 (1H, singlet); 6.72 (1H, doublet of doublets, J=2.44 & 1.46 Hz); 6.79 (1H, doublet of triplets, J=7.81 & 1.46 Hz); 6.93 (1H, doubled doublet of doublets, J=8.30, Hz); 2.44 & 1.46 Hz); 7.18 (1H, doublet of triplets, J=7.32 & 1.46 Hz); 7.22–7.36 (4H, multiplet).

Infrared Absorption Spectrum (CDCl$_3$) $v_{max}$ cm$^{-1}$: 1720, 1620, 1590, 1580, 1570, 1490, 1470, 1430, 1370, 1350, 1290, 1260, 1170.

Mass Spectrum (m/z): 16 (M$^+$, $^{35}$Cl) 287, 271, 243, 228.

PREPARATION 72

(Z)-3-(3-Chlorophenyl)-3-(3-methoxyphenyl)acrylic acid

Prepared as crystals, melting at 115°–117° C. (after recrystallisation from a mixture of methylene chloride and hexane), in a field of 98%.

Nuclear Magnetic Resonance Spectrum (CDCl$_3$, 270 MHz) δ ppm: 3.78 (3H, singlet); 6.35 (1H, singlet); 6.78 (1H, triplet, J=1.47 Hz); 6.84 (1H, doublet of multiplets, J=7.81 Hz); 6.93 (1H, doublet of multiplets, J=7.81 Hz); 7.10 (1H, doublet of triplets, J=7.32 & 1.47 Hz); 7.25 (1H, triplet, J=7.81 Hz); 7.30 (1H, triplet, J=7.32 Hz); 7.36 (lH, doublet of triplets, J=7.33 & 1.47 Hz);

Infrared Absorption Spectrum (CDCl$_3$) $v_{max}$ cm$^{-1}$: 2400–3600 (broad), 1695, 1620, 1600, 1580, 1490, 1435, 1410, 1345, 1290, 1150.

Mass Spectrum (m/z): 288 (M$^+$, $^{35}$Cl) 271, 243.

PREPARATION 73

(E)-3-(3-Chlorophenol)-3-(3-methoxyphenyl)acrylic acid

Prepared as crystals, melting an 140°–142° C. (after recrystallisation from a mixture of methylene chloride and hexane), in a yield of 96%.

Nuclear Magnetic Resonance Spectrum (CDCl$_3$, 270 MHz) δ ppm: 3.79 (3H, singlet); 6.30 (1H, singlet); 6.72 (1H, doublet of doublets, J=2.44 & 1.47 Hz); 6.78 (1H, doublet of multiplets, J=7.32 Hz); 6.93 (1H, doubled doublet of doublets, J=8.30, Hz); 2.44 & 0.97 Hz); 7.16 (1H, doublet of triplets. J=7.81 & 1.47 Hz); 7.23–7.38 (4H, multiplet).

Infrared Absorption Spectrum (CDCl$_3$) $v_{max}$ cm$^{-1}$: 2400–3600 (broad), 1695, 1620, 1600, 1590, 1570, 1490, 1470, 1460, 1430, 1350, 1285.

Mass Spectrum (m/z): 288 (M$^+$, $^{35}$Cl) 271, 243.

PREPARATION 74

Ethyl (E)-3-(3-Chlorophenyl)-3-(4-methoxyohenyl)acrylate

Prepared as an oil in a yield of 10%.

Nuclear Magnetic Resonance Spectrum (CDCl$_3$, 270 MHz) δ ppm: 1.12 (3H, triplet, J=7.32 Hz); 3.82 (3H, singlet); 4.05 (2H, quartet, J=7,32 Hz); 6.32 (1H, singlet); 6.85 (2H, doublet of multiplets, J=9.28 Hz); 7.09 (1H, doublet of triplets, J=7.30 & 1.96 Hz); 7.18–7.39 (5H, multiplet).

Infrared Absorption Spectrum (CDCl$_3$) $v_{max}$ cm$^{-1}$: 1710, 1605, 1600, 1570, 1515, 1465, 1420, 1370, 1350, 1290, 1275, 1255, 1170, 1155.

Mass Spectrum (m/z): 316 (M$^+$, $^{35}$Cl) 287, 271, 244, 228.

PREPARATION 75

Ethyl (E)-3-(3-Chlorophenyl)-3-(4-methoxyphenyl)acrylate

Prepared as an oil in a yield of 14%.

Nuclear Magnetic Resonance Spectrum (CDCl$_3$, 270 MHz) δ ppm: 1.17 (3H, triplet, J=7.32 Hz); 3.84 (3H, singlet); 4.09 (2H, quartet, J=7.32 Hz); 6.25 (1H, singlet); 6.91 (2H, doublet of multiplets, J=8.79 Hz); 7.14 (2H, doublet of multiplets, J=8.79 Hz); 7.15–7.36 (4H, multiplet).

Infrared Absorption Spectrum (CDCl$_3$) $v_{max}$ cm$^{-1}$: 1715, 1610, 1570, 1515, 1470, 1370, 1355, 1295, 1250, 1175.

Mass Spectrum (m/z): 316 (M$^+$, $^{35}$Cl) 287, 271, 244, 228.

PREPARATION 76

(Z)-3-(3-Chlorophenyl)-3-(4-methoxyphenyl)acrylic acid

Prepared as crystals, melting at 158°–160° C. (after recrystallisation from a mixture of methylene chloride and hexane), in a yield of 94%.

Nuclear Magnetic Resonance Spectrum (CDCl$_3$, 270 MHz) δ ppm: 3.82 (3H, singlet); 6.29 (1H, singlet); 6.85 (2H, doublet of multiplets, J=9.28 Hz); 7.09 (2H, doublet of triplets, J=7.30 & 1.46 Hz); 7.16–7.38 (8H, multiplet).

Infrared Absorption Spectrum (CDCl$_3$) $v_{max}$ cm$^{-1}$: 2400–3600 (broad), 1695, 1605, 1590, 1570, 1515, 1425, 1285, 1255, 1180.

Mass Spectrum (m/z): 288 (M$^+$, $^{35}$Cl) 271, 243.

PREPARATION 77

(E)-3-(3-Chlorophenyl)-3-(4-methoxyphenyl)acrylic acid

Prepared as crystals, melting at 119°–120° C. (after recrystallisation from a mixture of methylene chloride and hexane), in a yield of 92%.

Nuclear Magnetic Resonance Spectrum (CDCl$_3$, 270 MHz) δ ppm: 3.85 C3H, singlet); 6.21 (1H, singlet); 6.90 (2H, doublet of multiplets, J=8.79 Hz); 7.15 (2H, doublet of multiplets, J=8.79 Hz); 7.12–7.38 (4H, multiplet).

Infrared Absorption Spectrum (CDCl$_3$) $v_{max}$ cm$^{-1}$: 2400–3600 (broad), 1695, 1610, 1570, 1515, 1420, 1295, 1250, 1180.

Mass Spectrum (m/z): 288 (M$^+$, $^{35}$Cl) 271, 243.

PREPARATION 78

Ethyl (Z)-3-(3,4-Dichlorophenyl)-3 (4-propoxyphenyl)acrylate

Prepared as an oil, in a yield of 4%.

Nuclear Magnetic Resonance Spectrum (CDCl$_3$, 270 MHz) δ ppm: 1.03 (3H, triplet, J=7.32 Hz); 1.16 (3H, triplet. J=7.32 Hz); 1.70–1.90 (2H, multiplet); 3.93 (2H, triplet. J=6.84 Hz); 4.07 (2H, quartet. J=7.32 Hz); 6.32 (1H, singlet); 6.84 (2H, doublet of multiplets, J=8.79 Hz); 7.06 (lH, doublet of doublets, J=8.30 & 1.95 Hz); 7.20 (2H, doublet of multiplets, J=m 8.79 Hz); 7.29 (1H, doublet, J=m 1.95 Hz); 7.45 (1H, doublet, J=8.30 Hz).

Mass Spectrum (m/z): 378 (M$^+$, $^{35}$Cl) 336, 333, 308, 305, 291, 264.

PREPARATION 79

Ethyl (E)-3-(3,4-Dichlorophenyl)-3-(4-propoxyphenyl) acrylate

Prepared as an oil, in a yield of 5%.

Nuclear Magnetic Resonance Spectrum (CDCl$_3$, 270 MHz) δ ppm: 1.05 (3H, triplet, J=7.32 Hz); 1.17 (3H, triplet, J=7.32 Hz); 1.75–1.90 (2H, multiplet); 3.95 (2H, triplet, J=6.35 Hz); 4.09 (2H, quartet, J=7.32 Hz); 6.22 (1H, singlet); 6.90 (2H, doublet of multiplets, J=8.79 Hz); 7.11 (2H, doublet of multiplets, J=8.79 Hz); 7.13 (1H, doublet of doublets, J=8.30 & 1.96 Hz); 7.38 (1H, doublet, J=1.96 Hz); 7.39 (1H, doublet, J=8.30 Hz).

Infrared Absorption Spectrum (CHCl$_3$) $\nu_{max}$ cm$^{-1}$: 1715, 1630, 1515, 1470, 1390, 1370, 1350, 1290, 1280, 1245, 1170.

Mass Spectrum (m/z): 378 (M$^+$, $^{35}$Cl) 336, 333, 308, 305, 291, 264.

PREPARATION 80

(Z)-3-(3,4-Dichlorophenyl)-3-(4-propoxyohenyl)acrylic acid

Prepared as crystals, melting at 161°–163° C. (after recrystallisation from a mixture of methylene chloride and hexane), in a yield of 96%.

Nuclear Magnetic Resonance Spectrum (CDCl$_3$, 270 MHz) δ ppm: 1.03 (3H, triplet, J=7.32 Hz); 1.70–1.90 (2H, multiplet); 3.93 (2H, triplet, J=6.84 Hz); 6.29 (1H, singlet); 6.85 (2H, doublet of multiplets, J=8.79 Hz); 7.06 (1H, doublet of doublets, J=8.30 & 1.95 Hz); 7.19 (2H, doublet of multiplets, J=8.79 Hz); 7.28 (1H, doublet, J=1.95 Hz); 7.45 (1H, doublet, J=8.30 Hz).

Infrared Absorption Spectrum (CDCl$_3$) $\nu_{max}$ cm$^{-1}$: 2400–3600 (broad), 1695, 1605, 1590, 1515, 1475, 1285, 1255, 1180.

Mass Spectrum (m/z): 350 (M$^+$, $^{35}$Cl) 308, 291, 263.

PREPARATION 81

(E)-3-(3,4-Dichlorophenyl)-3-(4-propoxyphenyl)acrylic acid

Prepared as crystals, melting at 155°–157° C. (after recrystallisation from a mixture of methylene chloride and hexane), in a yield of 85%.

PREPARATION 82

Ethyl (E)-3-(4-ethoxy-3-methoxyphenyl)cinnamate

Prepared as crystals, melting at 89°–91° C. (after recrystallization from hexane), in a yield of 21%.

Nuclear Magnetic Resonance Spectrum (CDCl$_3$, 270 MHz) δ ppm: 1.10 (3H, triplet, J=7.32 Hz); 1.46 (3H, triplet, J=7.33 Hz); 3.81 (3H, singlet); 4.03 (2H, quartet, J=7.33 Hz); 4.10 (2H, quartet, J=7.33 Hz); 6.31 (1H, singlet); 6.77 (2H, broad singlet); 6.90 (1H, broad singlet); 7.16–7.25 (2H, multiplet); 7.32–7.41 (3H, multiplet).

Infrared Absorption Spectrum (CHCl$_3$) $\nu_{max}$ cm$^{-1}$: 1710, 1615, 1600, 1580, 1515, 1480, 1470, 1370, 1320, 1290, 1250, 1160, 1135.

Mass Spectrum (m/z): 326 (M$^+$), 297, 281, 253, 226.

PREPARATION 83

Ethyl (Z)-3-(4-ethoxy-3-methoxyphenyl)cinnamate

Prepared as an oil, in a yield of 21%.

Nuclear Magnetic Resonance Spectrum (CDCl$_3$, 270 MHz) δ ppm: 1.15 (3H, triplet, J=7.32 Hz); 1.49 (3H, triplet, J=7.32 Hz); 3.80 (3H, singlet); 4.08 (2H, quartet, J=7.32 Hz); 4.14 (2H, quartet, J=7.32 Hz); 6.28 (1H, singlet); 6.73 (1H, doublet, J=1.95 Hz); 6.79 (1H, doublet of doublets, J=8.30 & 1.95 Hz); 6.87 (1H, doublet, J=8.30 Hz); 7.29–7.40 (8H, multiplet).

Infrared Absorption Spectrum (CDCl$_3$) $\nu_{max}$ cm$^{-1}$: 1710, 1605, 1580, 1515, 1480, 1470, 1450, 1410, 1370, 1355, 1320, 1250, 1160, 1130.

Mass Spectrum (m/z): 326 (M$^+$), 297, 281, 253, 226.

PREPARATION 84

(E)-3-(4-Ethoxy-3-methoxyphenyl)cinnamic acid

Prepared as crystals, melting at 200°–202° C. (after recrystallization from a mixture of tetrahydrofuran and hexane), in a yield of 93%.

Nuclear Magnetic Resonance Spectrum (a 1:1 by volume mixture of CDCl$_3$ and CD$_3$OD, 270 MHz) δ ppm: 1.45 (3H, triplet, J=6.96 Hz); 3.80 (3H, singlet); 4.11 (2H, quartet, J=6.96 Hz); 6.32 (1H, singlet); 6.80 (1H, doublet of doublets, J=8.43 & 1.83 Hz); 6.84 (1H, doublet, J=8.43 Hz); 6.88 (1H, doublet, J=1.83 Hz); 7.18–7.27 (2H, multiplet); 7.32–7.42 (3H, multiplet).

Infrared Absorption Spectrum (KBr) $\nu_{max}$ cm$^{-1}$: 2400–3600 (broad), 1692, 1660, 1605, 1587, 1514, 1479, 1421, 1402, 1324, 1297, 1274, 1255, 1204, 1137.

Mass Spectrum (m/z): 298 (M$^+$), 270, 253, 225.

PREPARATION 85

(Z)-3-(4-Ethoxy-3-methoxyphenyl)cinnamic acid

Prepared as crystals, melting at 133°–135° C. (after recrystallization from a mixture of methylene chloride and hexane), in a yield of 90%.

Nuclear Magnetic Resonance Spectrum (CDCl$_3$, 270 MHz) δ ppm: 1.49 (3H, triplet, J=7.33 Hz); 3.80 (3H, singlet); 4.14 (2H, quartet, J=7.32 Hz); 6.25 (1H, singlet); 6.72–6.86 (3H, multiplet); 7.27–7.43 (8H, multiplet).

Infrared Absorption Spectrum (CDCl$_3$) $\nu_{max}$ cm$^{-1}$: 2400–3600 (broad), 1690, 1605, 1580, 1515, 1470, 1450, 1415, 1255, 1135.

Mass Spectrum (m/z): 298 (M$^+$), 270, 253, 225.

PREPARATION 86

Ethyl (E)-3-(4-butoxy-3-methoxyphenyl)cinnamate

Prepared as an oil, in a yield of 21%.

Nuclear Magnetic Resonance Spectrum (CDCl$_3$, 270 MHz) δ ppm: 1.43–1.54 (2H, multiplet); 1.78–1.86 (2H, multiplet); 3.80 (3H, singlet); 4.02 (2H, triplet, J=6.84 Hz); 4.03 (2H, quartet, J=7.33 Hz); 6.31 (1H, singlet); 6.77 (2H, broad singlet); 6.79 (2H, broad singlet); 7.17–7.24 (2H, multiplet); 7.34–7.41 (3H, multiplet).

Infrared Absorption Spectrum (CDCl$_3$) $\nu_{max}$ cm$^{-1}$: 1710, 1690, 1610, 1595, 1580, 1510, 1465, 1370, 1290, 1270, 1250, 1160, 1135.

Mass Spectrum (m/z): 354 (M$^+$), 309, 298, 269, 253, 226.

PREPARATION 87

Ethyl (Z)-3-(4-butoxy-3-methoxyphenyl)cinnamate

Prepared as an oil, in a yield of 47%.

Nuclear Magnetic Resonance Spectrum (CDCl$_3$, 60 MHz) δ ppm: 0.98 (3H, triplet, J=7 Hz); 1.13 (3H, triplet, J=7 Hz); 1.30–2.20 (4H, multiplet); 3.78 (3H, singlet); 4.02 (2H, triplet, J=7 Hz); 4.10 (2H, quartet, J=7 Hz); 6.30 (1H, singlet); 6.70–7.05 (3H, multiplet).

PREPARATION 88

(E)-3-(4-Butoxy-3-methoxyohenyl)cinnamate

Prepared as crystals, melting at 140°–143° C. (after recrystallization from a mixture of methylene chloride and hexane), in a yield of 92%.

Nuclear Magnetic Resonance Spectrum (CDCl$_3$, 270 MHz) δ ppm: 0.97 (3H, triplet, J=7.33 Hz); 1.40–1.60 (2H, multiplet); 1.75–1.90 (2H, multiplet); 3.79 (3H, singlet); 4.02 (2H, triplet, J=6.84 Hz); 6.28 (1H, singlet); 6.75 (1H, doublet of doublets, J=8.78 & 1.47 Hz); 6.78 (1H, doublet, J=8.78 Hz); 6.85 (1H, doublet, J=1.47 Hz); 7.17–7.24 (2H, multiplet); 7.30–7.40 (3H, multiplet).

Infrared Absorption Spectrum (CDCl$_3$) $v_{max}$ cm$^{-1}$: 2400–3600 (broad), 1690, 1610, 1595, 1580, 1510, 1500, 1470, 1420, 1320, 1250, 1135.

Mass Spectrum (m/z): 326 (M$^+$), 270, 253, 237.

PREPARATION 89

Ethyl (Z)-3-(3,4-dichlorophenyl)-3-(4-ethylphenyl)acrylate

Prepared as an oil, in a yield of 50%.

Nuclear Magnetic Resonance Spectrum (CDCl$_3$, 270 MHz) δ ppm: 1.16 (3H, triplet, J=7.32 Hz); 1.24 (3H, triplet, J=7.32 Hz); 2.66 (2H, quartet, J=7.32 Hz); 4.08 (2H, quartet, J=7.32 Hz); 6.37 (1H, singlet); 7.06 (1H, doublet of doublets, J=8.30 & 1.95 Hz); 7.12–7.24 (4H, multiplet); 7.30 (1H, doublet, J=1.95 Hz); 7.46 (1H, doublet, J=8.30 Hz).

Infrared Absorption Spectrum (CDCl$_3$) $v_{max}$ cm$^{-1}$: 1710, 1620, 1610, 1470, 1370, 1275, 1170, 1160.

Mass Spectrum (m/z): 48 (M$^+$, $^{35}$Cl) 319, 303, 276.

PREPARATION 90

Ethyl (E)-3-(3,4-dichlorophenyl)-3-(4-ethylphenyl)acrylate

Prepared as an oil, in a yield of 14%.

Nuclear Magnetic Resonance Spectrum (CDCl$_3$, 60 MHz) δ ppm: 1.10 (3H, triplet, J=7 Hz); 1.27 (3H, triplet, J=7 Hz); 2.70 (2H, quartet, J=7 Hz); 4.05 (2H, quartet, J=7 Hz); 6.27 (1H, singlet); 6.98–7.60 (7H, multiplet).

PREPARATION 91

(Z)-3-(3,4-Dichlorophenyl)-3-(4-ethylphenyl)acrylic acid

Prepared as crystals, melting at 172°–174° C. (after recrystallization from a mixture of methylene chloride and hexane), in a yield of 94%.

Nuclear Magnetic Resonance Spectrum (CDCl$_3$, 270 MHz) 1.24 (3H, triplet, J=7.32 Hz); 2.66 (2H, quartet, J=7.32 Hz); 6.35 (1H, singlet); 7.06 (1H, doublet of doublets, J=7.82 & 1.95 Hz); 7.12–7.24 (4H, multiplet); 7.29 (1H, doublet, J=1.95 Hz); 7.45 (1H, doublet, J=7.82 Hz).

Infrared Absorption Spectrum (CDCl$_3$) $v_{max}$ cm$^{-1}$: 2400–3600 (broad), 1690, 1620, 1605, 1470, 1280, 1180, 1160, 1120.

Mass Spectrum (m/z): 320 (M$^+$, $^{35}$Cl) 305, 291, 275.

PREPARATION 92

Ethyl (Z)-3-(4-propoxyphenyl)cinnamate

Prepared as an oil, in a yield of 35%.

Nuclear Magnetic Resonance Spectrum (CDCl$_3$, 270 MHz) δ ppm: 1.05 (3H, triplet, J=7.33 Hz); 1.67 (3H, triplet, J=7.33 Hz); 1.75–1.90 (2H, multiplet); 3.95 (2H, triplet, J=6.60 Hz); 4.09 (2H, quartet, J=7.33 Hz); 6.26 (1H, singlet); 6.89 (2H, doublet of multiplets, J=8.80 Hz); 7.14 (2H, doublet of multiplets, J=8.80 Hz); 7.26–7.40 (5H, multiplet).

Infrared Absorption Spectrum (CDCl$_3$) $v_{max}$ cm$^{-1}$: 1710, 1610, 1510, 1370, 1290, 1260, 1240, 1170.

Mass Spectrum (m/z): 310 (M$^+$), 268, 265, 238, 223, 196.

PREPARATION 93

Ethyl (E)-3-(4-propoxyphenyl)cinnamate

Prepared as an oil, in a yield of 35%.

Nuclear Magnetic Resonance Spectrum (CDCl$_3$, 270 MHz) δ ppm: 1.03 (3H, triplet, J=7.33 Hz); 1.10 (3H, triplet, J=7.33 Hz); 1.75–1.90 (2H, multiplet); 3.92 (2H, triplet, J=6.84 Hz); 4.03 (2H, quartet, J=7.33 Hz); 6.30 (1H, singlet); 6.82 (2H, doublet of multiplets, J=9.27 Hz); 7.15–7.28 (2H, multiplet); 7.23 (2H, doublet of multiplets, J=9.27 Hz); 7.28–7.43 (3H, multiplet).

Infrared Absorption Spectrum (CDCl$_3$) $v_{max}$ cm$^{-1}$: 1710, 1605, 1595, 1575, 1510, 1370, 1250, 1160, 1150.

Mass Spectrum (m/z): 310 (M$^+$), 268, 265, 238, 223, 196.

PREPARATION 94

(Z)-3-(4-Propoxyohenyl)cinnamic acid

Prepared as crystals, melting at 183°–185° C. (after recrystallization from a mixture of methylene chloride and hexane), in a yield of 93%.

Nuclear Magnetic Resonance Spectrum (CDCl$_3$, 270 MHz). δ ppm: 1.06 (3H, triplet, J=7.33 Hz); 1.75–1.90 (2H, multiplet); 3.95 (2H, triplet, J=6.84 Hz); 6.23 (1H, singlet); 6.88 (2H, doublet of multiplets, J=8.79 Hz); 7.15 (2H, doublet of multiplets, J=8.79 Hz); 7.26–7.42 (8H, multiplet).

Infrared Absorption Spectrum (CDCl$_3$) $v_{max}$ cm$^{-1}$: 2400–3600 (broad), 1695, 1610, 1515, 1290, 1280, 1250, 1175.

Mass Spectrum (m/z): 282 (M$^+$), 240, 223, 195.

PREPARATION 95

(E)-3, (4-Propoxyphenyl)cinnamic acid

Prepared as crystals, melting at 138°–140° C. (after recrystallization from a mixture of methylene chloride and hexane), in a yield of 92%.

Nuclear Magnetic Resonance Spectrum (CDCl$_3$, 60 MHz) δ ppm: 1.00 (2H, triplet, J=7 Hz); 1.45–2.20 (2H, multiplet); 3.90 (2H, quartet, J=7 Hz); 6.27 (1H, singlet); 6.83 (2H, doublet of multiplets, J=9 Hz); 7.05–7.60 (7H, multiplet); 10.00 (1H, broad multiplet).

PREPARATION 96

(E)-3-(3,4-Methylenedioxyphenyl)cinnamic acid

Prepared as crystals, melting at 222°–224° C. (after recrystallization from a mixture of diethyl ether and tetrahydrofuran), in a yield of 22%.

Nuclear Magnetic Resonance Spectrum (a 1:1 by volume mixture of $CDCl_3$ and $CD_3OD$, 60 MHz) δ ppm: 5.99 (2H, singlet); 6.29 (1H, singlet); 6.79 (3H, singlet); 7.05–7.60 (8H, multiplet).

PREPARATION 97

(Z)-3-(3,4-Methylenedioxyphenyl)cinnamic acid

Prepared as crystals, melting at 141°–143° C. (after recrystallization from a mixture of methylene chloride and hexane), in a yield of 51%.

Nuclear Magnetic Resonance Spectrum ($CDCl_3$, 60 MHz) δ ppm: 6.00 (2H, singlet); 6.26 (1H, singlet); 6.72–6.96 (3H, multiplet); 7.15–7.55 (5H, multiplet).

PREPARATION 98

Ethyl (E)-3-(3-methoxy-4-propoxyphenyl)-3-(3-methylphenyl)acrylate

Prepared as an oil, in a yield of 22%.

Nuclear Magnetic Resonance Spectrum ($CDCl_3$, 270 MHz) δ ppm: 1.03 (3H, triplet, J=7.32 Hz); 1.11 (3H, triplet, J=7.32 Hz); 1.80–1.95 (2H, multiplet); 2.35 (3H, singlet); 3.81 (3H, singlet); 3.98 (2H, triplet, J=6.84 Hz); 4.04 (2H, quartet, J=7.32 Hz); 6.29 (1H, singlet); 6.72–6.86 (2H, multiplet); 6.90 (1H, broad singlet); 6.98–7.05 (2H, multiplet); 7.15–7.24 (1H, multiplet); 7.30–7.42 (1H, multiplet).

Infrared Absorption Spectrum ($CDCl_3$) $v_{max}$ cm$^{-1}$: 1710, 1600, 1580, 1510, 1485, 1370, 1290, 1260, 1160, 1145, 1130.

Mass Spectrum (m/z): 354 (M$^+$), 312, 267, 240.

PREPARATION 99

Ethyl (Z)-3-(3-methoxy-4-propoxyphenyl)-3-(3-methylphenyl)acrylate

Prepared as an oil, in a yield of 40%.

Nuclear Magnetic Resonance Spectrum ($CDCl_3$, 270 MHz) 1.05 (3H, triplet, J=7.32 Hz); 1.15 (3H, triplet, J=7.32 Hz); 1.80–1.95 (2H, multiplet); 2.32 (3H, singlet); 3.80 (3H, singlet); 4.02 (2H, triplet, J=6.84 Hz); 4.08 (2H, quartet, J=7.32 Hz); 6.26 (1H, singlet); 6.72 (1H, doublet, J=1.–96 Hz); 6.78 (1H, doublet of doublets, J=7.82 & 1.96 Hz); 6.87 (1H, doublet, J=7.82 Hz); 7.06–7.25 (4H, multiplet).

Infrared Absorption Spectrum ($CDCl_3$) $v_{max}$ cm$^{-1}$: 1710, 1605, 1590, 1515, 1465, 1370, 1250, 1180, 1160, 1130.

Mass Spectrum (m/z): 54 (M$^+$), 312, 267, 240.

PREPARATION 100

(E)-3-(3-methoxy-4-propoxyphenyl)-3-(3-methylphenyl)acrylic acid

Prepared as crystals, melting at 123°–126° C. (after recrystallization from a mixture of methylene chloride and hexane), in a yield of 98%.

Nuclear Magnetic Resonance Spectrum ($CDCl_3$, 270 MHz) δ ppm: 1.03 (3H, triplet. J=7.33 Hz); 1.75–1.95 (2H, multiplet); 2.34 (3H, singlet); 3.80 (3H, singlet); 3.98 (2H, triplet, J=6.84 Hz); 6.26 (1H, singlet); 6.74 (1H, doublet of doublets, 8.79 & 1.93 Hz); 6.78 (1H, doublet, J=8.79 Hz); 6.86 (1H, doublet, J=1.95 Hz); 6.98–7.05 (2H, multiplet); 7.14–7.30 (2H, multiplet).

Infrared Absorption Spectrum ($CDCl_3$) $v_{max}$ cm$^{-1}$: 2400–3600 (broad), 1690, 1595, 1580, 1515, 1470, 1260, 1175, 1145, 1130.

Mass Spectrum (m/z): 326 (M$^+$), 284, 267, 239.

PREPARATION 101

(Z)-3-(3-methoxy-4-propoxyphenyl)-3-(3-methylphenyl)acrylic acid

Prepared as crystals, melting at 132°–135° C. (after recrystallization from a mixture of methylene chloride and nexane), in a yield of 97%.

PREPARATION 102

Ethyl 3,3-bis(3-methylphenyl)acrylate

Prepared as an oil, in a yield of 78%.

Nuclear Magnetic Resonance Spectrum ($CDCl_3$, 270 MHz) δ ppm: 1.11 (3H, triplet. J=7.32 Hz); 2.32 (3H, singlet); 2.35 (3H, singlet); 4.03 (2H, quartet, J=7.32 Hz); 6.31 (1H, singlet); 6.98–7.30 (8H, multiplet).

Infrared Absorption Spectrum ($CDCl_3$) $v_{max}$ cm$^{-1}$: 1710, 1620, 1600, 1580, 1370, 1350, 1280, 1190, 1160.

Mass Spectrum (m/z): 280 (M$^+$), 265, 251, 235, 208.

PREPARATION 103

3,3-Bis(3-methylphenyl)acrylic acid

Prepared as crystals, melting at 133°–135° C. (after recrystallization from a mixture of methylene chloride and hexane), in a yield of 94%.

Nuclear Magnetic Resonance Spectrum ($CDCl_3$, 270 MHz) δ ppm: 2.32 (3H, singlet); 2.34 (3H, singlet); 6.28 (1H, singlet); 6.98–7.12 (4H, multiplet); 7.14–7.30 (4H, multiplet).

Infrared Absorption Spectrum ($CHCl_3$) $v_{max}$ cm$^{-1}$: 2400–3600 (broad), 1690, 1615, 1600, 1580, 1430, 1285, 1170.

Mass Spectrum (m/z): 252 (M$^+$), 237, 235, 207.

PREPARATION 104

Methyl (E)-3,5-diphenylpent-2-en-4-ynoate 0.158 g of cuprous iodide and 0.424 g of phenylacetylene were added to 25 ml of a diethlyamine solution containing 1.000 g of methyl (A)-3-bromocinnamate and 0.029 g of bis(triphenylphosphine)dichloropalladium. The mixture was then stirred for 1 hour at room temperature, after which the solvent was distilled off under reduced pressure. Water was added to the residue, and the resulting mixture was extracted twice with benzene. The combined benzene extracts were washed with water, dried over anhydrous sodium sulfate and condensed by evaporation under reduced pressure. The residue was subjected to column chromatography through silica gel (70–230 Tyler mesh, 25 g). Those fractions eluted with a 39:1 by volume mixture of hexane and ethyl acetate were collected to afford 1.043 g of the title compound melting at 73°–75° C. (after recrystallisation from hexane).

Nuclear Magnetic Resonance Spectrum (CDCl$_3$, 270 MHz) δ ppm: 3.84 (3H, singlet); 6.60 (1H, singlet); 7.34–7.82 (10H, multiplet).

Mass spectrum (m/z): 262 (M$^+$); 247, 231.

Infrared Absorption Spectrum (CDCl$_3$) $v_{max}$ cm$^{-1}$: 2200, 1710, 1600, 1590, 1575, 1490, 1450, 1435, 1365, 1275, 1165.

PREPARATION 105

(E)-3,5-Diphenylpent-2-en-4-ynoic acid

A mixture of 1.000 g of methyl (E)-3,5-diphenylpent-2-en-4-ynoate (prepared as described in Preparation 104), 15 ml of methanol, 7.5 ml of tetrahydrofuran and 15 ml of a 10% w/v aqueous solution of sodium hydroxide was stirred for 18 hours an room temperature. At the end of this time. The solvent was distilled off under reduced pressure. The resulting residue was diluted with water and extracted twice with diethyl ether. The ethereal extracts were washed with water, dried over anhydrous sodium sulfate and condensed by evaporation under reduced pressure, to give 0.912 g of the title compound, melting at 124°–126° C. (after recrystallisation from a mixture of methylene chloride and hexane).

Nuclear Magnetic Resonance Spectrum (CDCl$_3$, 270 MHz) δ ppm: 6.65 (1H, singlet); 7.30–7.90 (10H, multiplet).

Mass spectrum (m/z): 248 (M$^+$), 231, 220.

Infrared Absorption Spectrum (CDCl$_3$) $v_{max}$ cm$^{-1}$: 2400–3600 (broad), 2200, 1685, 1600, 1590, 1575, 1490, 1450, 1280, 1180.

PREPARATION 106

Ethyl 3,3-bis(4-methoxyphenyl)-3-hydroxy-2-methylpropionyl

A mixture of 8.25 g of ethyl 2-bromopropionate, 11.81 g of 4,4'-dimethoxybenzophenone, 7.16 g of zinc and 70 ml of benzene was heated on an oil bath for 4 hours under reflux. The mixture was then allowed to stand to cool, after which the reaction solution was filtered. The filtrate was washed with 10% w/v aqueous sulfuric acid, with water and with a saturated aqueous solution of sodium chloride, in that order. After the mixture had been dried, the solvent was distilled off under reduced pressure. The residue was subjected to flash column chromatography through silica gel (about 400 mesh, 300 g). 7.92 g of the title compound were obtained as white crystals, melting at 67°–69° C. (after recrystallisation from a mixture of methylene chloride and hexane), from those fractions eluted with a 100:2 by volume mixture of hexane and ethyl acetate.

Nuclear Magnetic Resonance Spectrum (CDCl$_3$, 270 MHz) δ ppm: 1.14 (6H, triplet, J=6.84 Hz); 3.54 (1H, quartet, J=6.84 Hz); 3.75 (6H, singlet); 3.95–4.15 (2H, multiplet); 4.61 (1H, singlet); 6.80 (4H, doublet of multiplets, J=8.79 Hz); 7.33 (2H, doublet of multiplets, J=8.79 Hz); 7.44 (2H, doublet of multiplets, J=8.79 Hz).

Mass spectrum (m/z):. 344 (M$^+$), 326, 299, 281, 243.

Infrared Absorption Spectrum (CDCl$_3$) $v_{max}$ cm$^{-1}$: 1710, 1610, 1510, 1460, 1375, 1340, 1245, 1170.

Elemental analysis: Calculated for C$_{20}$H$_{24}$O$_5$: C, 69.75%; H, 7.02%. Found: C, 69.89%; H, 7.10%.

PREPARATION 107

Ethyl 3,3-bis(4-methoxyphenyl)-2-methylacrylate 4.10 ml of phosphorus oxychloride were dropped an from 5° to 10° C. onto 140 ml of a benzene solution containing 7.02 g of ethyl 3,3-bis(4-methoxyphenyl)-3-hydroxy-2-merthylpropionate (prepared as described in Preparation 106) on an ice bath. The reaction solution was then stirred for 3 hours at room temperature, after which it was poured into water and then extracted with diethyl ether three times. The combined ethereal extracts were washed with a saturated aqueous solution of sodium bicarbonate, with water and with a saturated aqueous solution of sodium chloride, after which it was dried over anhydrous sodium sulfate and condensed by evaporation under reduced pressure. The residue (6.72 g) was subjected to flash column chromatography through 100 g of silica gel. 6.04 g of the title compound were obtained as an oily substance from those fractions eluted with a 95:5 by volume mixture of hexane and ethyl acetate.

Nuclear Magnetic Resonance Spectrum (CDCl$_3$, 270 MHz) δ ppm: 0.95 (3H, triplet, J=7.32 Hz); 2.05 (3H, singlet); 3.78 (3H, singlet); 3.81 (2H, singlet); 3.97 (2H, quartet, J=7.32 Hz); 6.79 (2H, doublet of multiplets, J=8.30 Hz); 6.85 (2H, doublet of multiplets, J=8.30 Hz); 7.03 (2H, doublet of multiplets, J=8.30 Hz); 7.08 (2H, doublet of multiplets, J=8.30 Hz).

Mass spectrum (m/z): 326 (M$^+$), 297, 281, 271, 252.

Infrared Absorption Spectrum (CDCl$_3$) $v_{max}$ cm$^{-1}$: 1700, 1610, 1510, 1465, 1315, 1300, 1280, 1240, 1175, 1125.

Elemental analysis: Calculated for C$_{20}$H$_{22}$O$_4$: C, 73.60%; H, 6.79%. Found: C, 73.39%; H, 6.82%.

PREPARATION 108

3,3-Bis(4-methoxyphenyl)-2-methylacrylic acid

A mixture of 6.019 g of ethyl 3.3-bis(4-methoxyphenyl)acrylate (prepared as described in Preparation 107), 120 ml of ethanol and 80 ml of a 10% w/v aqueous solution of sodium hydroxide was stirred for 14 hours at room temperature. At the end of this time, the reaction mixture was heated on an oil bath at 100° C. for 4 hours, and then ethanol was distilled off. The residue was diluted with ice-water and washed with ethyl acetate. Concentrated hydrochloric acid was dropped onto the aqueous phase on an ice bath, to adjust the pH to a value of 2. The aqueous phase was extracted twice with methylene chloride. The combined methylene chloride extracts were washed with water dried over anhydrous sodium sulfate and condensed by evaporation under reduced pressure, to afford 5.117 g of the title compound as white crystals melting at 134°–135° C. (after recrystallisation from a mixture of methylene chloride and hexane).

Nuclear Magnetic Resonance Spectrum (CDCl$_3$, 270 MHz) δ ppm: 2.06 (3H, singlet); 3.80 (3H, singlet); 3.81 (3H, singlet); 6.79 (2H, doublet of multiplets, J=8.79 Hz); 6.86 (2H, doublet of multiplets, J=8.79 Hz); 7.06 (2H, doublet of multiplets, J=8.79 Hz); 7.07 (2H, doublet of multiplets, J=8.79 Hz).

Mass spectrum (m/z): 298 (M$^+$), 281. 253.

Infrared Absorption Spectrum (CHCl$_3$) $v_{max}$ cm$^{-1}$: 2400–3600 (broad), 1680, 1610, 1510, 1245, 1175.

Elemental analysis: Calculated for C$_{18}$H$_{18}$O$_4$: C, 72.47%; H, 6.081. Found: C, 72.11%; H, 6.15%.

PREPARATION 109

N-(3,4,5-Trimethoxybenzenesulfonyl)piperazine 75 ml of a methylene chloride solution containing 7.40 g of 3,4,5-trimethoxybenzenesulfonyl chloride were dropped into 150 ml of a methylene chloride solution containing 3.80 g of N-formylpiperazine and 7.73 ml of triethylamine in an ice bath. The mixture was stirred for 30 minutes at 0° to 5° C., after which it was poured into water and extracted twice with methylene chloride. The combined methylene chloride extracts were washed with 10% w/v aqueous hydrochloric acid and with a saturated aqueous solution of sodium chloride, dried over anhydrous sodium sulfate and condensed by evaporation under reduced pressure. The residue (9.86 g) was dissolved in a mixture of 150 ml of tetrahydrofuran, 75 ml of methanol and 50 ml of a w/v aqueous solution of sodium hydroxide, and then stirred for 14 hours at room temperature. At the end of this time the reaction solution was poured into water and extracted 4 times with methylene chloride. The combined methylene chloride extracts were washed with water dried over anhydrous sodium sulfate and condensed by evaporation under reduced pressure. The residue was crystallized from a mixture of hexane and ethyl acetate, to give 7.02 g of the title compound as crystals, melting as 131 to 133° C.

Nuclear Magnetic Resonance Spectrum ($CDCl_3$, 270 MHz) δ ppm: 2.90–3.10 (8H, multiplet); 3.91 (9H, singlet); 6.96 (2H, singlet).

Mass spectrum (m/z): 316 ($M^+$), 232, 85.

Elemental analysis: Calculated for $C_{13}H_{20}N_2O_5$: C, 49.35%; H, 6.37%; N, 8.85%; S, 10.13%. Found: C, 49.62%; H, 6.30%; N, 8.55%; S, 10.11%.

PREPARATION 110

3,3-Bis(3-chlorophenyl)acrylic acid

Following a procedure similar to that described in Preparation 1, but using 10.85 g of 3,3'-dichlorobenzophenone, 12.32 g of the title compound, melting at 114°–115° C., were obtained after recrystallization from a mixture of methylene chloride and hexane.

PREPARATION 111

1-[3,3-Bis(3-chlorophenyl)acryloyl]piperazine 5.51 ml of diphenylphosphoryl azide and 1.93 ml of N-formylpiperazine were added, in that order, to 100 ml of a methylene chloride solution containing 5.00 g of 3,3-bis(3-chlorophenyl)acrylic acid (prepared as described in Preparation 110) and 4.75 ml of triethylamine. The reaction mixture was then stirred at room temperature for 18 hours, after which it was washed with a saturated aqueous solution of sodium bicarbonate and then with water. It was then dried over anhydrous sodium sulfate and the solvent was removed by distillation under reduced pressure. The residue was dissolved in a mixture of 100 ml of ethanol and 50 ml of tetrahydrofuran, and 50 ml of a 10% w/v aqueous solution of sodium hydroxide were added. The resulting mixture was stirred for 8 hours at room temperature, after which it was poured into water. The solution was extracted twice, each time with methylene chloride, and the combined extracts were washed with water and dried over anhydrous sodium sulfate: the solvent was then removed by distillation under reduced pressure. The resulting residue was purified by column chromatography through 150 g of silica gel, using mixtures of methylene chloride and methanol ranging from 49:1 to 9:1 by volume as eluent, to give 5.23 g of the title compound as a viscous oil.

Nuclear Magnetic Resonance Spectrum ($CDCl_3$, 60 MHz) δ ppm: 2.21 (1H, singlet); 2.00–2.95 (4H, multiplet); 3.00–3.85 (4H, multiplet); 6.38 (1H, singlet); 6.90–7.50 (8H, multiplet).

Mass Spectrum (m/z): 360 ($M^+$, $^{35}Cl$) 325, 292, 275.

PREPARATION 112

Ethyl (Z) and (E)-3-(2-naphthyl)-3-phenylacrylate

A procedure similar to that described in the first half of Preparation 1 was repeated, except than 10.10 g of β-naphthyl phenyl ketone were used. The resulting crude compound was purified by column chromatography through 200 g of silica gel and then by medium pressure liquid chromatography through a Lobar C column, eluted with mixtures of hexane and ethyl acetate, no give 2.48 g of the Z-isomer of the title compound, melting at 91°–92° C., after recrystallization from hexane.

Further elution with the same solvent gave 4.44 g of the E-isomer, melting at 84°–85° C., after recrystallization from hexane.

PREPARATION 113

(Z)-3-(2-Naphthyl)-3-phenylacrylic acid 24 ml of a 10% w/v aqueous solution of sodium hydroxide were added to a solution of 2.411 g of ethyl (Z)-3-(2-naphthyl)-3-phenylacrylate (prepared as described in Preparation 112) in 48 ml of ethanol and 24 ml of tetrahydrofuran. The mixture was stirred for 15 hours at room temperature and then poured into water. The pH of the resulting mixture was adjusted to a value of 2 by the addition of concentrated hydrochloric acid, and the mixture was then extracted twice with methylene chloride. The combined extracts were washed with water and dried over anhydrous sodium sulfate: the solvent was then removed by evaporation under reduced pressure. The residue was recrystallized from a mixture of methylene chloride and hexane, to give 2.005 g of the title compound, melting at 170°–172° C.

Nuclear Magnetic Resonance Spectrum (a 1:1 by volume mixture of $CDCl_3$ and $CD_3OD$, 60 MHz) δ ppm: 6.44 (1H, singlet); 7.28–7.42 (6H, multiplet); 7.44–7.54 (2H, multiplet); 7.71 (1H, doublet, J=0.73 Hz); 7.76–7.91 (3H, multiplet).

Mass Spectrum (m/z): 274 ($M^+$), 257, 229.

Elemental analysis: Calculated for $C_{19}H_{14}O_2$: C, 83.19%; H, 5.14%. Found: C, 83.39%; H, 5.35%.

PREPARATION 114

(E)-3-(2-Naphthyl)-3-Phenylacrylic acid

A hydrolysis procedure similar to that described in Preparation 113 was repeated, except that 2.219 g of ethyl (E)-3-(2-naphthyl)-3-phenylacrylate (prepared as described in Preparation 112) were used, to give 1.685 g of the title compound, melting at C229°–231° C., after recrystallization from a mixture of diethyl ether and etrahydrofuran.

Nuclear Magnetic Resonance Spectrum (a 1:1 by volume mixture of $CDCl_3$ and $CD_3OD$, 60 MHz) δ ppm: 6.50 (1H, singlet); 7.23–7.32 (2H, multiplet); 7.36–7.43 (3H, multiplet); 7.43–7.54 (3H, multiplet); 7.67 (1H, doublet, J=1.83 Hz); 7.70–7.88 (3H, multiplet).

Mass Spectrum (m/z): 274 (M$^+$), 257, 229.

Elemental analysis: Calculated for $C_{19}H_{14}O_2$: C, 83.19%; H, 5.14%. Found: C, 83.45%; H, 5.33%.

PREPARATION 115

Ethyl (E)-p-isobutoxycinnamate 13.8 g of potassium carbonate and 7.50 g of sodium iodide were added to a solution of 9.61 g of ethyl (E)-p-hydroxycinnamate and 8.22 g of isobutylbromide in 100 ml of dimethyl sulfoxide. The reaction mixture was then stirred for 20 hours at 60° C., after which it was cooled to the room temperature. The reaction mixture was then poured into 1 liter of water and extracted twice with ethyl acetate. The combined extracts were washed with water and dried over anhydrous sodium sulfate: the solvent was then removed by evaporation under reduced pressure. The residue was purified by flash column chromatography using 300 g of silica gel, eluted with a 5:1 by volume solution of hexane and ethyl acetate, to give 10.71 g of the title compound as a colorless oil (which solidified at low temperature).

Nuclear Magnetic Resonance Spectrum (CDCl$_3$, 60 MHz) δ ppm: 0.98 (6H, doublet, J=7 Hz); 1.28 (3H, triplet, J=7 Hz); 1.60–2.50 (1H, multiplet); 3.70 (2H, doublet, J=7 Hz); 4.24 (2H, quartet, J=7 Hz); 6.26 (1H, doublet, J=16 Hz); 6.86 (2H, doublet of multiplets, J=9 Hz); 7.45 (2H, doublet of multiplets, J=9 Hz); 7.66 (1H, doublet, J=16 Hz).

PREPARATION 116

Ethyl (E)-p-propoxycinnamate

Following a procedure similar to that described in Preparation 115, but using 9.61 g of ethyl (E)-p-hydroxycinnamate and 10.20 g of propyl iodide and not using sodium iodide, 11.00 g of the title compound were obtained as a solid material.

Nuclear Magnetic Resonance Spectrum (CDCl$_3$, 60 MHz) δ ppm: 0.98 (3H, triplet, J=7 Hz); 1.26 (3H, triplet, J=7 Hz); 1.20–2.20 (2H, multiplet); 3.88 (2H, triplet, J=6.5 Hz); 4.21 (2H, quartet, J=7 Hz); 6.24 (1H, doublet, J=16 Hz); 6.85 (2H, doublet of multiplets, J=8 Hz); 7.44 (2H, doublet of multiplets, J=8 Hz); 7.62 (1H, doublet, J=16 Hz).

PREPARATION 117

Ethyl (E)-3,4-dipropoxycinnamate

Following a procedure similar to that described in Preparation 116, but using 10.41 g of ethyl (E)-3,4-dihydroxycinnamate and 20.40 g of propyl iodide, 10.20 g of the title compound were obtained as a solid material.

Nuclear Magnetic Resonance Spectrum (CDCl$_3$, 60 MHz) δ ppm: 1.02 (6H, triplet, J=7 Hz); 1.32 (3H, triplet, J=7 Hz); 1.50–2.20 (4H, multiplet); 3.99 (4H, triplet, J=7 Hz); 4.26 (2H, quartet, J=7 Hz); 6.30 (1H, doublet, J=16 Hz); 6.70–7.35 (3H, multiplet); 7.65 (1H, doublet, J=16 Hz).

PREPARATION 118

Ethyl (E)-4-ethoxy-3-methoxycinnamate

Following a procedure similar to that described in Preparation 116, but using 5.83 g of ethyl (E)-4-hydroxy-3-methoxycinnamate and 5.61 g of ethyl iodide, 5.55 g of the title compound were obtained as a solid material.

Nuclear Magnetic Resonance Spectrum (CDCl$_3$, 60 MHz) δ ppm: 1.30 (3H, triplet, J=7 Hz); 1.44 (3H, triplet, J=7 Hz); 3.89 (3H, singlet); 4.14 (2H, quartet, J=7 Hz); 4.24 (2H, quartet, J=7 Hz); 6.30 (1H, doublet, J=16 Hz); 6.75–7.35 (3H, multiplet); 7.66 (1H, doublet, J=7 Hz);

PREPARATION 119

Ethyl (E)-3methoxy-4-propoxycinnamate

Following a procedure similar to that described in Preparation 116, but using 11.11 g of ethyl (E)-4-hydroxy-3-methoxycinnamate and 10.20 g of propyl iodide, 12.08 g of the title compound were obtained.

Nuclear Magnetic Resonance Spectrum (CDCl$_3$, 60 MHz) 1.01 (3H, triplet, J=7 Hz); 1.30 (3H, triplet, J=7 Hz); 1.50–2.20 (2H, multiplet); 3.88 (3H, singlet); 3.98 (2H, triplet, J=7 Hz); 4.24 (2H, quartet, J=7 Hz); 6.28 (1H, doublet, J=16 Hz); 6.70–7.35 (3H, multiplet); 7.65 (1H, doublet, J=16 Hz).

PREPARATION 120

Ethyl (E)-4-butoxy-3-methoxycinnamate

Following a procedure similar to that described in Preparation 116, but using 6.66 g of ethyl (E)-4-hydroxy-3-methoxycinnamate and 6.62 g of butyl iodide, 7.00 g of the title compound were obtained as a solid material.

Nuclear Magnetic Resonance Spectrum (CDCl$_3$, 60 MHz) δ ppm: 0.96 (3H, triplet, J=7 Hz); 1.30 (3H, triplet, J=7 Hz); 1.20–2.10 (4H, multiplet); 3.88 (3H, singlet); 4.03 (3H, triplet, J=7 Hz); 4.24 (2H, quartet, J=7 Hz); 6.28 (1H, doublet, J=16 Hz); 6.75–7.35 (3H, multiplet); 7.65 (1H, doublet, J=16 Hz).

PREPARATION 121

Ethyl (Z)-3-(3-Propoxyphenyl)-3-(3-chlorophenyl)acrytate

Prepared as an oil, in a yield of 10%.

Nuclear Magnetic Resonance Spectrum (270 MHz, CDCl$_3$) δ ppm: 1.02 (3H, t, J=7.33 Hz), 1.12 (3H, t, J=7.33 Hz), 1.70–1.85 (2H, m), 3.88(2H, t, J=6.84 Hz), 4.06 (2H, q, J=7.33 Hz). 6.37 (1H, s), 6.80–6.86 (2H, m), 6.90 (1H, ddd, J=8.30,2.44, 0.97 Hz), 7.10 (1H, ddd, J=6.84,1.47,1.47 Hz), 7.19–7.38 (4H, m).

Mass Spectrum (m/z): 344 (M$^+$,$^{35}$Cl), 302, 299.

Infrared Absorption Spectrum $v_{max}$ (CHCl$_3$) cm$^{-1}$: 1710, 1620, 1600, 1580, 1485, 1475, 1440, 1370, 1350, 1290, 1170.

PREPARATION 122

Ethyl (E)-3-(3-Propoxyphenyl)-3-(3-chlorophenyl)acrylate

Prepared as an oil, in a yield of 18%

Nuclear Magnetic Resonance Spectrum (270 MHz, CDCl$_3$) δ ppm: 1.02 (3H, t, J=7.33 Hz), 1.12 (3H, t, J=7.32 Hz), 1.70–1.90 (2H, m), 3.89(2H, t, J=6.84 Hz), 4.06 (2H, q, J=7.33 Hz), 6.32 (1H, s), 6.71 (1H, m), 6.77 (1H, ddd, J=7.81,1.46, 0.98 Hz), 6.92 (1H, ddd, J=8.30, 2.93, 0.98 Hz), 7.16–7.35 (8H, m).

Mass Spectrum (m/z): 344 (M$^+$, $^{35}$Cl), 302, 299.

Infrared Absorption Spectrum $v_{max}$ (CDCl$_3$) cm$^{-1}$: 1710, 1600, 1580, 1570, 1475, 1440, 1370, 1350, 1280, 1260, 1170, 1030.

PREPARATION 123

(Z)-3-(3-Propoxyphenyl)-3-(3-chlorophenyl)acrylic acid

Prepared as crystals, melting at 118°–120° C. (after recrystallisation from a mixture of methylene chloride and hexane), in a yield of 94%.

Nuclear Magnetic Resonance Spectrum (270 MHz, CDCl$_3$) δ ppm: 1.02 (3H, t, J=7.33 Hz), 1.70–1.90 (2H, m), 3.88 (2H, t, J=6.84 Hz), 6.34 (1H, s), 6.77–6.85(2H, m), 6.92 (1H, ddd, J=7.32,2.44,0.98 Hz), 7.10 (1H, ddd, J=7.31,1.46, 1.46 Hz), 7.17–7.38 (4H, m).

Mass Spectrum (m/z): 316 (M$^+$, $^{35}$Cl), 274, 257.

Infrared Absorption Spectrum $v_{max}$ (CHCl$_3$) cm$^{-1}$: 1695, 1620, 1600, 1580, 1490, 1480, 1440, 1410, 1350, 1290, 1150.

PREPARATION 124

Ethyl (Z)-3-(4-Propoxyphenyl)-3-(3-chlorophenyl)acrylate

Prepared as an oil, in a yield of 10%

Nuclear Magnetic Resonance Spectrum (270 MHz, CDCl$_3$) δ ppm: 1.03 (3H, t, J=7.32 Hz), 1.12 (3H, t, J=7.32 Hz), 1.75–1.90 (2H, m), 3.95(2H, t, J=6.84 Hz), 4.04 (2H, q, J=7.32 Hz), 6.31(1H, s), 6.84(2H,dm, J=8.79 Hz), 7.09(1H, ddd, J=6.84, 1.95,1.95 Hz), 7.17–7.20 (1H, m); 7.21 (2H, dm, J=8.79 Hz), 7.28–7.40 (2H, m).

Mass Spectrum (m/z): 344 (M$^+$, $^{35}$Cl), 302, 299.

Infrared Absorption Spectrum $v_{max}$ (CHCl$_3$) cm$^{-1}$: 1710, 1600, 1590, 1570, 1510, 1470, 1370, 1275, 1255, 1170, 1155.

PREPARATION 125

Ethyl (E)-3-(4-Propoxyphenyl)-3-(3-chlorophenyl)acrylate

Prepared as an oil, in a yield of 14%

Nuclear Magnetic Resonance Spectrum (270 MHz, CDCl$_3$) δ ppm: 1.05 (3H, t, J=7.32 Hz), 1.17 (3H, t, J=7.32 Hz), 1.75–1.90 (2H, m), 3.95 (2H, t, J=6.84 Hz), 4.09 (2H, q, J=7.32 Hz), 6.24 (1H, s), 6.89 (2H, dm, J=8.79 Hz), 7.12 (1H, dm, J=8.79 Hz), 7.17 (1H, ddd, J=7.81,1.95,1.95 Hz), 7.25 (1H, dd, J=7.81,7.81 Hz), 7.28 (1H, dd J=1.95, 1.95 Hz), 7.33 (1H, ddd, J=7.81,1.95,1.95 Hz).

Mass Spectrum (m/z): 344 (M$^+$,$^{35}$Cl), 302, 299.

Infrared Absorption Spectrum $v_{max}$ (CHCl$_3$) cm$^{-1}$: 1710, 1610, 1510, 1470, 1290, 1240. 1170.

PREPARATION 126

(Z)-3-(4-Propoxyphenyl)-3-(3-chlorophenyl)acrylic acid

Prepared as crystals, melting at 174.5°–176.5° C. (after recrystallisation from a mixture of methylene chloride and hexane), in a yield of 92%.

Nuclear Magnetic Resonance Spectrum (270 MHz, CDCl$_3$) δ ppm: 1.03 (3H, t, J=7.32 Hz), 1.74–1.90 (2H, m), 3.93 (2H, t, J=6.83 Hz), 629 (1H, s), 6.84 ( 2H, dm, J=9.28 Hz), 7.09 (1H, ddd, J=7.33,1.95,1.95 Hz), 7.16–7.20 (1H, m), 7.20 (2H, dm, J=9.28 Hz), 7.27–7.38 (2H, m).

Mass Spectrum (m/z): 316 (M$^+$,$^{35}$Cl), 274, 257, 229.

Infrared Absorption Spectrum $v_{max}$ (KBr) cm$^{-1}$: 3400–2400, 1665, 1600, 1585, 1510, 1305, 1260, 1245, 1180.

PREPARATION 127

(E)-3-(4-Propoxyphenyl)-3-(3-chlorophenyl)acrylic acid

Prepared as crystals, melting at 147°–149° C. (after recrystallisation from a mixture of methylene chloride and hexane), in a yield of 95%.

Nuclear Magnetic Resonance Spectrum (270MHz. CDCl$_3$) δ ppm: 1.06 (3H, t, J=7.32 Hz), 1.75–1.90 (2H, m), 3.96 (2H, t, J=6.34 Hz), 6.20 (1H, s), 6.88 (2H, dm, J=8.79 Hz), 7.14 (2H, dm, J=8.79 Hz), 7.14–7.19 (1H, m), 7.23–7.38 (3H, m).

Mass Spectrum (m/z): 316 (M$^+$,$^{35}$Cl), 274, 257, 229.

Infrared Absorption Spectrum $v_{max}$ (CDCl$_3$) cm$^{-1}$: 3600–2400, 1690, 1610, 570, 1515, 1290, 1250, 1180.

PREPARATION 128

Ethyl (Z)-3-(2-Chlorophenyl)-3-(3-methoxyphenyl)acrylate

Prepared as crystals, melting at 82°–84° C. (after recrystallisation from a mixture of ethyl ether and hexane), in a yield of 63%.

Nuclear Magnetic Resonance Spectrum (270 MHz, CDCl$_3$) δ ppm: 1.10 (3H, t, J=7.32 Hz), 3.78 (3H, s), 4.04 (2H, q, J=7.32 Hz), 6.54 (1H, s), 6.84–6.94 ( 3H, m), 7.14–7.19 (1H, m), 7.21–7.36 (3H, m), 7.40–7.48 (1H, m).

Mass Spectrum (m/z): 316 (M$^+$, $^{35}$Cl), 281, 271, 253.

Infrared Absorption Spectrum $v_{max}$ (CDCl$_3$) cm$^{-1}$: 1715, 1615, 1600, 1580, 1490, 1470, 1435, 1370, 1350, 1290, 1170, 1050, 1035.

PREPARATION 129

(Z)-3-(2-Chlorophenyl)-3-(3-methoxyphenyl)acrylic acid

Prepared as crystals, melting at 140°–142° C. (after recrystallisation from a mixture of methylene chloride and hexane), in a yield of 96%.

Nuclear Magnetic Resonance Spectrum (270 MHz, CDCl$_3$) δ ppm: 3.77 (3H, s), 6.51 (1H, s), 6.83 (1H, dd, J=1.95,1.95 Hz), 6.86–6.94 (2H, m), 7.11–7.18 (1H, m), 7.21–7.35 (3H, m), 7.38–7.46 (1H, m).

Mass Spectrum (m/z): 288 (M$^+$, $^{35}$Cl), 253.

Infrared Absorption Spectrum $v_{max}$ (CHCl$_3$) cm$^{-1}$: 3600–2400, 1695, 1625, 1600, 1580, 1490, 1470, 1430, 1290, 1050.

PREPARATION 130

Ethyl (Z)-3-(4-Methoxyphenyl)-3-(3-bromophenyl)acrylate

Prepared as an oil, in a yield of 9%.

Nuclear Magnetic Resonance Spectrum (270 MHz, CDCl$_3$) δ ppm: 1.12 (3H, t, J=7.32 Hz), 3.82(3H, s), 4.05(2H, q, J=7.32 Hz), 6.31(1H, s), 6.85(2H, dm, J=8.79

Hz), 7.14 (1H, ddd, J=7.81,147,1.47 Hz), 7.22 (2H, dm J=8.79 Hz), 7.25 (1H, ddd J=7.81,7.81,1.47 Hz), 7.35 (1H, dd, J=1.47,1.47 Hz), 7.51 (1H, ddd, J=7.81,1.47, 1.47 Hz).

Mass Spectrum (m/z): 360 (M$^+$,$^{79}$Br), 333, 315, 288.

Infrared Absorption Spectrum $v_{max}$ (CHCl$_3$) cm$^{-1}$: 1710, 1600, 1510, 1370, 1290, 1270, 1250, 1165, 1025, 830.

PREPARATION 131

(E)-3-(4-Methoxyphenyl)-3-(3-bromophenyl)acrylate

Prepared as an oil, in a yield of 12%.

Nuclear Magnetic Resonance Spectrum (270 MHz, CDCl$_3$) δ ppm: 1.17 (3H, t, J=7.32 Hz), 3.84 (3H, s), 4.09 (2H, q, J=7.32 Hz), 6.24 (1H, s), 6.90 (2H, dm, J=8.79 Hz), 7.14 (2H, dm, J=8.79 Hz), 7.18–7.24 (2H, m), 7.43–7.52 (2H, m).

Mass Spectrum (m/z): 360 (M$^+$,$^{79}$Br), 333, 315, 288.

Infrared Absorption Spectrum $v_{max}$ (CHCl$_3$) cm$^{-1}$: 1715, 1610, 1515, 1375, 1295, 1250, 1175, 1030, 840.

PREPARATION 132

(Z)-3-(4-Methoxyphenyl)-3-(3-bromophenyl)acrylic acid

Prepared as crystals, melting at 169°–171° C. (after recrystallisation from a mixture of methylene chloride and hexane), in a yield of 97%.

Nuclear Magnetic Resonance Spectrum (270 MHz, CDCl$_3$) δ ppm: 3.82 (3H, s), 6.29 (1H, s), 6.85 (2H, dm, J=9.28 Hz), 7.14 (1H, ddd, J=7.81,1.95,0.98 Hz), 7.21 (2H, dm, J=9.28 Hz), 7.25 (1H, dd, J=7.81,7.81 Hz), 7.33 (1H, dd, J=1.95,1.95 Hz), 7.51 (1H, ddd, J=7.81,1.95, 0.98 Hz).

Mass Spectrum (m/z); 332 (M$^+$, $^{79}$Br), 315.

Infrared Absorption Spectrum $v_{max}$ (CHCl$_3$) cm$^{-1}$: 2400–3600, 1685, 1595, 1570, 1555, 1505, 1420, 1275, 1250, 1170, 1020, 825.

PREPARATION 133

(E) 3-(4-Methoxyphenyl)-3-(3-bromophenyl)acrylic acid

Prepared as crystals, melting at 131°–132° C. (after recrystallisation from a mixture of methylene chloride and hexane), in a yield of 96%.

Nuclear Magnetic Resonance Spectrum (270 MHz, CDCl$_3$) δ ppm: 3.82 (3H, s), 6.20 (1H, s), 6.90 (2H, dm, J=8.79 Hz), 7.15 (2H, dm, J=8.79 Hz), 7.18–7.24 (2H, m), 7.40–7.44 (1H, m), 7.46–7.54 (1H, m).

Mass Spectrum (m/z): 332 (M$^+$,$^{79}$Br), 315.

Infrared Absorption Spectrum $v_{max}$ (CHCl$_3$) cm$^{-1}$: 2400–3600, 1690, 1610, 1560, 1510, 1470, 1420, 1295, 1245, 1175, 1030, 835.

PREPARATION 134

Ethyl (Z)-3-(3-Fluorophenyl)-3-(4-methoxyphenyl)acrylate

Prepared as an oil, in a yield of 55%.

Nuclear Magnetic Resonance Spectrum (270 MHz, CDCl$_3$) δ ppm: 1.12 (3H, t, J=7.33 Hz), 3.82 (3H, s), 4.04 (2H, q, J=7.33 Hz), 6.32 (1H, s), 6.85 (2H, dm, J=8.79 Hz), 6.91 (1H, ddd, J=9.53,2.57,1.47 Hz), 6.99 (1H, dm, J=7.69 Hz), 7.03–7.11 (1H, m), 7.23 (2H, dm, J=8.79 Hz), 7.35 (1H, ddd, J=7.69,7.69,5.87 Hz).

Mass Spectrum (m/z): 300 (M$^+$) 271, 255, 228.

Infrared Absorption Spectrum $v_{max}$ (CHCl$_3$) cm$^{-1}$: 1705, 1600, 1585, 1510, 1440, 1370, 1275, 1250, 1160, 1030, 830.

PREPARATION 135

Ethyl (E)-3-(3-Fluorophenyl)-3-(4-methoxyphenyl)acrylate

Prepared as an oil, in a yield of 22%.

Nuclear Magnetic Resonance Spectrum (270 MHz, CDCl$_3$) δ ppm: 1.17 (3H, t, J=7.32 Hz), 3.84 (31H, s), 4.09 (2H, q, J=7.32 Hz), 6.27 (1H, s), 6.91 (2H, dm, J=8.79 Hz), 6.98 (1H, ddd, J=10.25,2.44,1.96 Hz), 7.05 (1H, dddd, J=8.30,8.30,2.44, 0.98 Hz), 7.08–7.12 (1H, m), 7.15 (2H, dm, J=8.79 Hz), 7.29 (1H, ddd, J=8.30,8.30, 5.86 Hz).

Mass Spectrum (m/z); 300 (M$^+$), 271, 255, 228.

Infrared Absorption Spectrum $v_{max}$ (CHCl$_3$) cm$^{-1}$: 1710, 1610, 1585, 1510, 1485, 1440, 1370, 1295, 1280, 1245, 1170, 1030, 1030, 870, 830.

PREPARATION 136

(Z)-3-(3-Fluorophenyl)-3-(4-methoxyphenyl)acrylic acid

Prepared as crystals, melting at 166°–167° C. (after recrystallisation from a mixture of methylene chloride and hexane), in a yield of 96%.

Nuclear Nagnetic Resonance Spectrum (270 MHz, CDCl$_3$) δ ppm: 3.82 (3H, s), 6.29 (1H, s), 6.85 (2H, dm, J=8.79 Hz), 6.91 (1H, ddd, J=9.76,2.44,1.46 Hz), 6.95–7.01 (1H, m), 7.07 (1H, dddd, J=8.30,8.30,2.44,0.97 Hz), 7.21 (2H, dm J=8.79 Hz), 7.33 (1H, ddd, J=8.30,8.30,5.86 Hz).

Mass Spectrum (m/z): 272 (M$^+$), 255, 227.

Infrared Absorption Spectrum $v_{max}$ (CHCl$_3$) cm$^{-1}$: 2400–3600, 1695, 1600, 1515, 1440, 1285, 1255, 1180, 1120, 1035.

PREPARATION 137

(E)-3-(3-Fluorophenyl)-3-(4-methoxyphenyl)acrylic acid

Prepared as crystals, melting at 133°–135° C. (after recrystallisation from a mixture of methylene chloride and hexane), in a yield of 95%.

Nuclear Magnetic Resonance Spectrum (270 MHz, CDCl$_3$) δ ppm: 3.85 (3H, s), 6.23 (1H, s), 6.89 (2H, dm, J=8.79 Hz), 6.96 (1H, ddd, J=9.77,1.96,1.96 Hz), 7.02–7.12 (2H, m), 7.15 (2H, dm, J=8.79 Hz), 7.30 (1H, ddd, J=8.30, 8.30,5.86 Hz).

Mass Spectrum (m/z): 272 (M$^+$), 255, 227.

Infrared Absorption Spectrum $v_{max}$ (CCDl$_3$) cm$^{-1}$: 2400–3600, 1690, 1610. 1580, 1510, 1485, 1440, 1290, 1245.

PREPARATION 138

Ethyl (Z)-3-(3-Trifluoromethylphenyl)-3-(4-methoxphenyl) acrylate

Prepared as an oil, in a yield of 56%.

Nuclear Magnetic Resonance Spectrum (270 MHz, CDCl₃) δ ppm: 1.08 (3H, t, J=7.32 Hz), 3.82(3H, s), 4.03(2H, q, J=7.32 Hz), 6.37(1H, s), 6.86(2H, dm, J=8.79 Hz), 7.21 (2H, dm, J=8.79 Hz), 7.37–7.43 (1H, m), 7.44–7.47 (1H, m), 7.48–7.55 (1H, m), 7.6–7.67 (1H, m).

Mass Spectrum (m/z): 350 (M⁺), 331, 321, 305, 278.

Infrared Absorption Spectrum $v_{max}$ (CHCl₃) cm⁻¹: 1710, 1600, 1510, 1325, 1255, 1165, 1130, 1070, 1030.

PREPARATION 139

Ethyl (E)-3-(3-Trifluoromethylphenyl)-3-(4-methoxyphenyl)acrylate

Prepared as an oil, in a yield of 15%.

Nuclear Magnetic Resonance Spectrum (270 MHz, CDCl₃) δ ppm: 1.18 (3H, t, J=7.33 Hz), 3.85 (3H, s), 411(2H, q, J=7.33 Hz), 6.28(1H, s), 6.91(2H, dm, J=8.79 Hz), 7.15 (2H, dm, J=8.79Hz), 7.37–7.53 (2H, m), 7.56–7.54 (2H, m).

Mass Spectrum (m/z): 350 (M⁺), 331, 321, 305, 278.

Infrared Absorption Spectrum $v_{max}$ (CDCl₃) cm⁻¹: 1710, 1610, 1510, 1370, 1330, 1295, 1245, 1170, 1150, 1130, 1070, 1030.

PREPARATION 140

(Z)-3-(3-Trifluoromethylphenyl)-3-(4-methoxyphenyl)acrylic acid

Prepared as crystals, melting at 165°–167° C. (after recrystallisation from a mixture of methylene chloride and hexane), in a yield of 91%.

Nuclear Magnetic Resonance Spectrum (270 MHz, CDCl₃) δ ppm: 3.82 (3H, s), 6.33 (1H, s), 6.86 (2H, dm, J=8.79 Hz), 7.19 (2H, dm J=8.79 Hz), 7.37 (1H, br, d, J=7.82 Hz), 7.45 (1H, br,s), 7.48 (1H, br.dd, J=7.82,7.82 Hz), 7.63 (1H, br.d, J=7.82 Hz).

Mass Spectrum (m/z): 322 (M⁺), 305, 277, 263.

Infrared Absorption Spectrum $v_{max}$ (CHCl₃) cm⁻¹: 2400–3600, 1690, 1600, 1575, 1510, 1440, 1325, 1310, 1290, 1260, 1180, 1150, 1130, 1070.

PREPARATION 141

Ethyl (E)-3-(3-Popoxyphenyl)-3-phenylacrylate

Prepared as an oil, in a yield of 23%.

Nuclear Magnetic Resonance Spectrum (270 MHz, CDCl₃) δ ppm: 1.01 (3H, t, J=7.32 Hz), 1.10 (3H, t, J=7.32 Hz), 1.70–190 (2H, m), 3.87 (2H, t, J=6.84 Hz), 4.04 (2H, q, J=7.32 Hz), 6.35 (1H, s), 6.82–6.92 (3H, m), 7.16–7.40 (6H, m).

PREPARATION 142

Ethyl (Z)-3-(3-Propoxpphenyl)-3-phenylacrylate

Prepared as an oil, in a yield of 47%.

Nuclear Magnetic Resonance Spectrum (270 MHz, CDCl₃) δ ppm: 1.01 (3H, t, J=7.32 Hz), 1.12 (3H, t, J=7.32 Hz), 1.70–1.90 (2H, m), 3.89(2H, t, J=6.84 Hz), 4.06 (2H, q, J=7.32 Hz), 6.34 (1H, s), 6.72–6.96 (3H, m), 7.23–7.38 (6H, m).

PREPARATION 143

(E)-3-(3-Propoxyphenyl)-3-phenylacrylic acid

Prepared as crystals melting at 120°–122° C. (after recrystallisation from a mixture of methylene chloride and hexane), in a yield of 51%.

Nuclear Magnetic Resonance Spectrum (270 MHz, CDCl₃) δ ppm: 1.00 (3H, t, J=7.33 Hz), 1.70–1.90 (2H, m), 3.86 (2H, t, J=6.70 Hz), 6.31 (1H, s), 6.78–6.85(2H, m), 6.88–6.94 (1H, m), 7.16–7.28 (3H, m), 7.28–7.40 (3H, m), Mass Spectrum (m/z): 282 (M⁺), 240, 223.

Infrared Absorption Spectrum $v_{max}$ (CHCl₃) cm⁻¹: 2400–3600, 1690, 1610, 1600, 1580, 1485, 1440, 1400, 1285.

PREPARATION 144

(Z)-3-(3-Propoxyphenyl)-3-phenylacrylic acid

Prepared as crystals, melting at 120°–122° C. (after recrystallisation from a mixture of methylene chloride and hexane), in a yield of 67%.

Nuclear Magnetic Resonance Spectrum (270 MHz, CDCl₃) δ ppm: 1.01 (3H, t, J=7.33 Hz), 1.70–1.90 (2H,m), 3.89 (2H, t, J=6.84 Hz), 6.31 (1H, s), 6.73 (1H, dd, J=2.44, 1.47 Hz), 6.78 (1H, ddd, J=7.32,1.47,0.98 Hz), 6.91 (1H, ddd, J=8.30, 2.44, 0.98 Hz), 7.22–7.40 (6H, m).

Mass Spectrum (m/z): 282 (M⁺), 240, 223.

Infrared Absorption Spectrum $v_{max}$ (CHCl₃) cm⁻¹: 2400–3600, 1680, 1590, 1570, 1480, 1440, 1425, 1390, 1275, 1100.

PREPARATION 145

Ethyl (Z)-3-(3,5-Dichlorophenyl)-3-(4-methoxyphenyl)acrylate

Prepared as crystals, melting at 116°–118° C. (after recrystallisation from hexane), in a yield of 64%.

Nuclear Magnetic Resonance Spectrum (270 MHz, CDCl₃) δ ppm: 1.14 (3), J=7.32Hz), 3.82 (3H, s), 4.06(2H, q, J=7.32 Hz), 6.33(1H, s), 6.86(2H, dm, J=8.79 Hz), 7.09 (2), d, J=1.83 Hz), 7.21 (2H, dm, J=8.79 Hz), 7.37 (1H, t, J=1.83 Hz).

Mass Spectrum (m/z): 350 (M⁺, ³⁵Cl), 321, 305, 278.

Infrared Absorption Spectrum $v_{max}$ (CHCl₃) cm⁻¹: 1710, 1600, 1585, 1560, 1510, 1370, 1345, 1290, 1270, 1250, 1170, 1160, 1030, 860, 830.

PREPARATION 146

(E)-3-(3,5-Dichlorophenyl)-3-(4-methoxyphenyl)acrylate

Prepared as an oil, in a yield of 19%.

Nuclear Magnetic Resonance Spectrum (270 MHz, CDCl₃) δ ppm: 1.17 (3H, t, J=7.32 Hz), 3.85 (3H, s), 4.09(2),q, J=7.32 Hz), 6.23(1H, s), 6.91(2H, dm, J=8.79 Hz), 7.13 (2H, dm, J=8.79 Hz), 7.16 (2H, d, J=1.96 Hz), 7.35 (1H, t, J=1.96 Hz).

Mass Spectrum (m/z): 350 (M⁺, ³⁵Cl), 321, 305, 278.

Infrared Absorption Spectrum $v_{max}$ (CHCl₃) cm⁻¹: 1710, 1610, 1580, 1560, 1510, 1415, 1370, 1350, 1290, 1245, 1170, 1030, 860, 835.

PREPARATION 147

(Z)-3-(3,5-Dichlorophenyl)-3-(4-methoxyphenyl)acrylic acid

Prepared as crystals, melting at 214°–216° C. (after recrystallisation from a mixture of THF and hexane), in a yield of 71%.

Nuclear Magnetic Resonance Spectrum (270 MHz, $CDCl_3$) δ ppm: 3.78 (3H, s), 6.37 (1H, s), 6.94 (2H, dm, J=8.79 Hz), 7.17 (2H, d, J=1.95 Hz), 7.23 (2H, dm, J=8.79 Hz), 7.57 (1H, t, J=1.95 Hz).

Mass Spectrum (m/z): 322 ($M^+$, $^{35}Cl$), 305, 277.

Infrared Absorption Spectrum $v_{max}$ (KBr) $cm^{-1}$: 2400–3400, 1695, 1670, 1600, 1580, 1560, 1510, 1290, 1260, 1215, 1185, 1170, 1035, 840, 800.

PREPARATION 148

(E)-3-(3,5-Dichlorothenyl)-3-(4-methoxyphenyl)acrylic acid

Prepared as crystals, melting at 169°–171° C. (after recrystallisation from a mixture of methylene chloride and hexane), in a yield of 80%.

Nuclear Magnetic Resonance Spectrum (270 MHz, $CDCl_3$) δ ppm: 3.85 (3H, s), 6.19 (1H, s), 6.90 (2H, dm, J=8.79 Hz), 7.13 (2H, dm, J=8.79 Hz), 7.14 (2H, d, J=1.95 Hz), 7.36 (1H, t, J=1.95 Hz).

Mass Spectrum (m/z): 322 ($M^+$, $^{35}Cl$), 305, 277.

Infrared Absorption Spectrum $v_{max}$ (KBr) $cm^{-1}$: 2400–3400, 1700, 1675, 1610, 1580, 1560, 1510, 1425, 1350, 1280, 1250, 1220, 1175, 1030, 850. 835, 805.

PREPARATION 149

Ethyl (Z)-3-(2,4-Dichlorophenyl)-3-(4-methoxythenyl)acrylate

Prepared as an oil, in a yield of 83%.

Nuclear Magnetic Resonance Spectrum (270 MHz, $CDCl_3$) δ ppm: 1.14 (3H, t, J=7.33 Hz), 3.81 (3H, s), 4.05 (2H, q, J=7.32 Hz), 6.48 (1H, s), 6.85 (2H, dm, J=8.80 Hz), 7.09 (1H, d, J=8.42 Hz), 7.24 (21t, dm J=8.8Hz), 7.30 (1H, dd. J=8.42, 1.84 Hz), 7.47 (1H, d, J=1.84 Hz).

Mass Spectrum (m/z): 350 ($M^+$, $^{35}Cl$), 315, 305, 287.

Infrared Absorption Spectrum $v_{max}$ ($CHCl_3$) $cm^{-1}$: 1710, 1605, 1590, 1510, 1280, 1255, 1170, 1030, 830.

PREPARATION 150

(Z)-3-(2,4-Dichlorophenyl)-3-(4-methoxyphenyl)acrylic acid

Prepared as crystals, melting at 162°–164° C. (after recrystallisation from a mixture of methylene chloride and hexane), in a yield of 90%.

NMR スペクトル (270 MHz, $CDCl_3$) δ ppm: 3.81 (3H, s), 6.44 (1H, s), 6.85 (2H, dm J=8.79 Hz), 7.07(1H, d, J=8.30 Hz), 7.22(2H, dm, J=8.79 Hz), 7.28(1H,dd, J=8.30,1.95 Hz), 7.45 (1H, d, J=1.95 Hz).

Mass Spectrum (m/z): 322 ($M^+$, $^{35}Cl$), 287.

Infrared Absorption Spectrum $v_{max}$ ($CHCl_3$) $cm^{-1}$: 1700, 1600, 1590, 1510, 1285, 1260, 1180, 1155, 830.

PREPARATION 151

Ethyl (Z)-3-(4-Methoxyphenyl)-3-(2,6-dichlorophenyl)acrylate

Prepared as crystals, melting at 119°–121° C. (after recrystallisation from a mixture of methylene chloride and hexane), in a yield of 60%.

NMR スペクトル (270 MHz, $CDCl_3$) δ ppm: 1.13 (3H, t, J=7.33 Hz), 3.81 (3H, s), 4.06 (2H, q, J=7.33 Hz), 6.56 (1H, s), 6.87 (2H, dm, J=9.28 Hz), 7.22–7.34 ( 1H, m), 7.30 (2H, dm, J=9.27 Hz), 7.35–7.41 (2H, m).

Mass Spectrum (m/z): 350 ($M^+$, $^{35}Cl$), 315, 305, 287.

Infrared Absorption Spectrum $v_{max}$ ($CHCl_3$) $cm^{-1}$: 1710, 1605, 1575, 1510, 1430, 1290, 1275, 1255, 1160, 1025, 830.

PREPARATION 152

(Z)-3-(4-Methoxyphenyl)-3-(2,6-dichlorophenyl)acrylic acid

Prepared as crystals, melting at 222°–224° C. (after recrystallisation from a mixture of methylene chloride and hexane), in a yield of 98%.

NMR スペクトル (270 MHz, $CDCl_3$) δ ppm: 3.81 (3H, s), 6.53 (1H, s), 6.87 (2H, dm, J=8.79 Hz), 7.20–7.40 (3H, m), 7.28 (2H, dm, J=8.79 Hz).

Mass Spectrum (m/z): 322 ($M^+$, $^{35}Cl$), 307, 305, 287, 272.

Infrared Absorption Spectrum $v_{max}$ ($CHCl_3$) $cm^{-1}$: 2400–3600, 1700, 1600, 1575, 1515, 1430, 1290, 1260, 1180, 1160, 835.

PREPARATION 153

Ethyl (Z)-3-(2,5-Dichlorophenyl)-3-(4-methoxyphenyl)acrylate

Prepared as crystals, melting at 98°–100° C. (after recrystallisation from hexane), in a yield of 82%.

NMR スペクトル (270 MHz, $CDCl_3$) δ ppm: 1.13 (3H, t, J=7.32 Hz), 3.82 (3H, s), 4.05 (2H, q, J=7.32 Hz), 6.47 (1H, s), 6.86 (2H, dm, J=8.79 Hz), 7.15 ( 1H, d, J=2.44 Hz), 7.25 (2H, dm, J=8.79 Hz), 7.29 (1H, dd, J=8.30,2.44 Hz), 7.37(1H, d, J=8.30 Hz).

Mass Spectrum (m/z): 350 ($M^+$, $^{35}Cl$), 315, 305, 287.

Infrared Absorption Spectrum $v_{max}$ ($CHCl_3$) $cm^{-1}$: 1715, 1605, 1515, 1470, 1295, 1280, 1280, 1170, 1165, 1100, 1030, 835.

PREPARATION 154

(Z)-3-(2,5-Dichlorophenyl)-3-(4-methoxyphenyl)acrylic acid

Prepared as crystals, melting at 201°–203° C. (after recrystallisation from a mixture of THF and hexane), yield of 97%.

NMR スペクトル (270 MHz, $d_6$-DMSO) δ ppm: 3.77 (3H, s), 6.53 (1H, s), 6.94 (2H, dm, J=8.79 Hz), 7.25 (2H, dm, J=8.79 Hz), 7.29 (1H, d, J=2.44 Hz), 7.46 (1H,dd, J=8.79, 2.44 Hz), 7.53 (1H, d, J=8.79 Hz), 12.13 (1H, br,s).

Mass Spectrum (m/z): 322 ($M^+$, $^{35}Cl$) 305, 287, 272.

Infrared Absorption Spectrum $v_{max}$ (KBr) $cm^{-1}$: 2200–3300, 1690, 1595, 1580, 1510, 1465, 1425, 1345, 1280, 1260, 1210, 1185, 1160, 1030, 835.

PREPARATION 155

Ethyl (Z)-3-(2,3-Dichlorophenyl)-3-(4-methoxyphenyl)acrylate

Prepared as crystals, melting at 88°–90° C. (after recrystallisation from a mixture of methylene chloride and hexane), in a yield of 70%.

NMR スペクトル (270 MHz, CDCl$_3$) δ ppm: 1.11 (3H, t, J=7.32 Hz), 3.81 (3H, s), 4.03 (2H, q, J=7.32 Hz), 6.47 (1H, s), 7.07 (1H, dd, J=7.70,1.47 Hz), 7.20–7.40(3H, m), 7.49 (1H, dd, J=8.06, 1.47 Hz).

Mass Spectrum (m/z): 350 (M$^+$,$^{35}$Cl), 315, 305, 287.

Infrared Absorption Spectrum ν$_{max}$ (CHCl$_3$) cm$^{-1}$: 1710, 1600, 1575, 1510, 1455, 1410, 1370, 1350, 1280, 1255, 1160, 1030, 830.

PREPAPRATION 156

(Z)-3-(2,3-Dichlorophenyl)-3-(4-methoylphenyl)acrylic acid

Prepared as crystals, melting at 129°–131° C. (after recrystallisation from a mixture of methylene chloride and hexane), in a yield of 89%.

NHR スペクトル (270 MHz, CDCl$_3$) δ ppm: 3.81 (3H, s), 6.44 (1H, s), 6.85 (2H, dm, J=8.78 Hz), 7.05 (1H, dd, J=7.81,147 Hz), 7.23 (1H, dd, J=7.81, 7.81 Hz), 7.24(2H, dm, J=8.78 Hz), 7.47 (1H, dd, J=7.81, 1.47 Hz).

Mass Spectrum (m/z): 322 (M$^+$,$^{35}$Cl), 287.

PREPARATION 157

Ethyl (Z)-3-(3,5-Dimethylphenyl)-3-(4-methoxyphenyl)acrylate

Prepared as an oil, in a yield of 57%.

NMR スペクトル (270 MHz, CDCl$_3$) δ ppm: 1.11 (3H, t, J=7.32 Hz), 2.31 (6H, s), 3.81 (3H, s), 4.04 (2H, q, J=7.32 Hz), 6.26 (1H, s), 6.80 (2H, br,s), 6.83(2H, dm, J=9.16 Hz), 6.99 (1H, t, J=0.73 Hz), 7.25 (2H, dm, J=9.16 Hz).

Mass Spectrum (m/z): 310 (M$^+$), 281, 265, 238.

Infrared Absorption Spectrum ν$_{max}$ (CHCl$_3$) cm$^{-1}$: 1710, 1610, 1510, 1460, 1440, 1370, 1350, 1290, 1245, 1170, 1030, 850, 840.

PREPARATION 158

Ethyl (E)-3-(3,5-Dimethylphenyl)-3-(4-methoxyphenol)acrylate

Prepared as an oil, in a yield of 24%.

NMR スペクトル (270 MHz, CDCl$_3$) δ ppm: 1.16 (3H, t, J=7.32 Hz), 2.27 (3H, s), 2.28 (3H, s), 3.84 (3H, s), 4.08 (2H, q, J=7.32 Hz), 6.24 (1H, s), 6.895 ( 2H, dm, J=8.79 Hz), 6.904 (2H, br,s), 6.99 (1H, br,s), 7.15 (2H, dm, J=8.79 Hz).

Mass Spectrum (m/z): 310 (M$^+$), 281, 265, 238.

Infrared Absorption Spectrum ν$_{max}$ (CHCl$_3$) cm$^{-1}$: 1710, 1610, 1510, 1460, 1440, 1370, 1350, 1290, 1245, 1170, 1030, 850, 840.

PREPARATION 159

(Z)-3-(3,5-Dimethylphenyl)-3-(4-methoxyphenyl)acrylic acid

Prepared as crystals, melting at 156°–158° C. (after recrystallisation from a mixture of methylene chloride and hexane), in a yield of 96%.

NMR スペクトル (270 MHz, CDCl$_3$) δ ppm: 2.31 (6H, s), 3.81 (3H, s), 6.24 (1H, s), 6.82 (2H, br,s), 6.84 (2H, dm, J=8.78 Hz), 701 (1H, br,s), 7.22 (2H, dm, J=8.78 Hz).

Mass Spectrum (m/z): 282 (M$^+$), 267, 237.

Infrared Absorption Spectrum ν$_{max}$ (CHCl$_3$) cm$^{-1}$: 2400–3600, 1690, 1600, 1570, 1510, 1285, 1250, 1175, 1030, 835.

PREPARATION 160

(E)-3-(3,5-Dimethylphenyl)-3-(4-methoxyphenyl)acrylic acid

Prepared as crystals, melting at 165°–166° C. (after recrystallisation from a mixture of methylene chloride and hexane), in a yield of 95%.

PREPARATION 161

Ethyl (E)-3-(3-Chlorophenyl)-3-(4-ethylphenyl)acrylate

Prepared as an oil, in a yield of 13%.

NMR スペクトル (270 MHz, CDCl$_3$) δ ppm: 1.12 (3H, t, J=7.33 Hz), 1.28 (3H, t, J=7.69 Hz), 2.70 (2H, q, J=7.69 Hz), 4.07 (2H, q, J=7.33 Hz), 6.29 (1H, s), 7.11 (2H, dm, J=8.43 Hz), 7.17 (1H, ddd, J=7.69,2.20,1.47 Hz), 7.21 (2H, dm, J=8.43 Hz, 7.25 (1H, dd, J=7.69,7.69 Hz), 7.29 (1H, dd, J=1.47,1.47 Hz), 7.32 (1H, ddd, J=7.69,2.20,1.47 Hz).

Mass Spectrum (m/z): 314 (M$^+$,$^{35}$Cl) 285, 269, 242.

Infrared Absorption Spectrum ν$_{max}$ (CHCl$_3$) cm$^{-1}$: 1710, 1610, 1570, 1475, 1370, 1350, 1260, 1170, 1030, 875, 840.

PREPARATION 162

Ethyl (Z) -3-(3-Chlorophenyl)-3-(4ethylphenyl)acrylate

Prepared as an oil, in a yield of 41%.

NMR スペクトル (270 MHz, CDCl$_3$) δ ppm: 1.12 (3H, t, J=7.32 Hz), 1.24 (3H, t, J=7.69 Hz), 2.66 (2H, q, J=7.69 Hz), 6.36 (1H, s), 7.10 (1H, ddd, J=6.96,1.83,1.83 Hz), 7.16 (2H, dm, J=8.43 Hz), 7.18–7.21 (1H, m), 7.21 (2H, dm, J=8.43 Hz), 7.27–7.34 (1H, m), 7.35 (ddd, J=8.06,1.83,1.83 Hz).

Mass Spectrum (m/z): 314 (M$^+$,$^{35}$Cl), 285, 269, 242.

Infrared Absorption Spectrum ν$_{max}$ (CHC$_3$) cm$^{-1}$: 1710, 1620, 1610, 1595, 1565, 1370, 1350, 1270, 1170, 1030, 880, 835.

PREPARATION 163

(E)-3-(3-Chlorophenyl)-3-(4-ethylphenyl)acrylic acid

Prepared as crystals, melting at 99°–100° C. (after recrystallisation from a mixture of methyllene chloride and hexane), in a yield of 95%.

NMR スペクトル (270 MHz, CDCl₃) δ ppm: 1.28 (3H, t, J=7.32 Hz), 2.70 (2H, q, J=7.32 Hz), 6.26 (1H, s), 7.11 (2H, dm, J=8.30 Hz), 7.15 (1H, ddd, J=7.81,1.46,1.46 Hz), 7.20 (2H, dm, J=8.30 Hz), 7.26 (1H, dd, J=7.81,7.81 Hz), 7.34 (1H, ddd, J=7.81,1.46,0.98 Hz).

Mass Spectrum (m/z): 286 (M$^+$,$^{35}$Cl), 271, 257, 241.

Infrared Absorption Spectrum $v_{max}$ (CHCl₃) cm$^{-1}$: 1690, 1610, 1570, 1420, 1270, 1180, 840.

PREPARATION 164

(Z)-3-Chlorophenyl)-3-(4-ethylphenyl)acrylic acid

Prepared as crystals, melting at 146°–148° C. (after recrystallisation from a mixture of methylene chloride and hexane), in a yield of 96%.

NMR スペクトル (270 MHz, CDCl₃) δ ppm: 1.23 (3H, t, 7.82 Hz), 2.66 (2H, q, J=7.82 Hz), 6.34 (1H, s), 7.10 (1H, ddd, J=6.84, 1.47,1.47 Hz), 7.13–7.22 (5H, m), 7.27–7.34 (1H, m), 7.35 (1H, ddd, J=8.30,1.47,1.47 Hz).

Mass Spectrum (m/z): 286 (M$^+$,$^{35}$Cl), 257, 241.

Infrared Absorption Spectrum $v_{max}$ (CHCl₃), cm$^{-1}$: 1690, 1610, 1570, 1420, 1270, 1180, 840.

PREPARATION 165

Ethyl (Z)-3-3,5-Ditrifluoromethylphenyl)-3-(4-methoxyphenyl)acrylate

Prepared as crystals, melting at 104°–105° C. (after recrystallisation from a mixture of ethyl ether and hexane), in a yield of 62%.

NMR スペクトル (270 MHz, CDCl₃) δ ppm: 1.08 (3H, t, J=7.33 Hz), 3.83 (3H, s), 4.02 (2H, q, J=7.33 Hz), 6.42 (1H, s), 6.88 (2H, dm, J=8.80 Hz), 7.18(2H, dm, J=8.80 Hz), 7.64–7.69 (2H, m), 7.88–7.92 (1m).

Mass Spectrum (m/z); 418 (M$^+$), 399, 390, 373, 346.

Infrared Absorption Spectrum $v_{max}$ (CHCl₃) cm$^{-1}$: 1710, 1600, 1510, 1460, 1390, 1330, 1280, 1175, 1140.

PREPARATION 166

Ethyl (E)-3-(3,5-Ditrifluoromethylphenyl)-3-(4-methoxyphenyl)acrylate

Prepared as an oil, in a yield of 14%.

NMR スペクトル (270 MHz, CDCl₃) δ ppm: 1.19 (3H, t, J=7.33 Hz), 3.86 (3H, s), 4.12 (2H, q, J=7.33 Hz), 6.31 (1H, s), 6.93 (2H, dm, J=8.79 Hz), 7.14 (2H, dm, J=8.79 Hz), 7.71–7.75 (2H, m), 7.85–7.89 (1H, m).

Mass Spectrum (m/z); 418 (M$^+$), 399, 389, 373, 346.

Infrared Absorption Spectrum $v_{max}$ (CHCl₃) cm$^{-1}$: 1720, 1610, 1515, 1460, 1370, 1350, 1280, 1245, 1175, 1140.

PREPARATION 167

(Z)-3-(3,5-Ditrifluoromethylphenyl)-3-(4-methoxyphenyl)acrylic acid

Prepared as crystals, melting at 197°–199° C. (after recrystallisation from a mixture of methylene chloride and hexane), in a yield of 92%.

NMR スペクトル (270 MHz, CDCl₃) δ ppm: 3.83 (3H, s), 6.40 (1H, s), 6.88 (2H, dm, J=8.79 Hz), 7.18 (2H, dm, J=8.79 Hz), 7.62–7.67 (2H, m), 7.87–7.92 (1m).

Mass Spectrum (m/z): 390 (M$^+$), 373, 345.

Infrared Absorption Spectrum $v_{max}$ (CHCl₃) cm$^{-1}$: 3700–2200, 1690, 1600, 1510, 1460, 1420, 1390, 1330, 1280, 1180, 1140.

PREPARATION 168

(E)-3-(3,5-Ditrifluoromethylphenyl)-3-(4-methoxyphenyl)acrylic acid

Prepared as crystals, melting at 144°–146° C. (after recrystallisation from a mixture of methylene chloride and hexane), in a yield of 95%.

NMR スペクトル (270 MHz CDCl₃) δ ppm: 3.87 (3H, s), 6.27 (1H, s), 6.93 (2H, dm, J=8.79 Hz), 7.16 (2H, dm, J=8.79 Hz), 7.69–7.74 (2H,m), 7.87–7.91 (1H, m).

Mass Spectrum (m/z): 390 (M$^+$), 373, 345.

Infrared Absorption Spectrum $v_{max}$ (CHCl₃) cm$^{-1}$1: 3200–2400, 11700, 1610. 1515, 1460, 1380, 1350, 1280, 1250, 1180, 1140.

PREPARATION 169

Ethyl (Z)-3-(3,5-Dichlorophenyl)-3-(4-ethoxyphenyl acrylate

Prepared as crystals, melting at 104°–106° C. (after recrystallisation from ethyl ether), in a yield of 41%.

NMR スペクトル (270 MHz, CDCl₃) δ ppm: 1.14 (3H, t, J=7.33Hz), 1.42 (3H, t, J=6.96 Hz), 4.05 (2H, q, J=6.96 Hz), 4.06 (2H, q, J=7.33 Hz), 6.32 (1H, s), 6.85 (2H, dm, J=8.79 Hz), 7.09 (2H, d, J=1.83 Hz), 7.20 (2H, dm, J=8.79 Hz), 7.37 (1H, t, J=1.83 Hz).

Mass Spectrum (m/z): 364 (M$^+$,$^{35}$Cl), 319, 292.

Infrared Absorption Spectrum $v_{max}$ (CHCl₃) m$^{-1}$: 1715, 1605, 1590, 1565, 1515, 1370, 1350, 1275, 1255, 1160, 1040.

PREPARATION 170

Ethyl (E)-3-13,5-Dichlorophenyl)-3-(4-ethoxyphenyl)acrylate

Prepared as an oil, in a yield of 12%

NMR スペクトル (270 MHz, CDCl₃) δ ppm: 1.17 (3H, t, J=7.32 Hz), 1.44 (3H, t, J=7.33 Hz), 4.07 (2H, q, J=7.33 Hz), 4.09 (2H, q, J=7.32 Hz), 6.22 (1H, s), 6.90 (2H, dm, J=8.79 Hz), 7.11 (2H, dm, J=8.79 Hz), 7.16 (2H, d, J=1.95 Hz), 7.34(1H, t, J=1.95 Hz).

Mass Spectrum (m/z): 364 (M$^+$,$^{35}$Cl), 319, 292.

Infrared Absorption Spectrum $v_{max}$ (CHCl₃) cm$^{-1}$: 1715, 1610, 1590 1560, 1515, 1395, 1370, 1350, 1290, 1245, 1175.

PREPARATION 171

(Z)-3-(3,5-Dichlorophenyl)-3-(4-ethoxyphenyl)acrylic acid

Prepared as crystals, melting at 220°–222° C. (after recrystallisation from a mixture of methanol and ethyl ether), in a yield of 86%.

NMR スペクトル (270 MHz, DMSO-d₆) δ ppm: 1.32 (3H, t, J=6.84 Hz), 4.04 (2H, q,J=6.84 Hz), 6.37 (1H, s), 6.92 (2H, dm, J=8.79 Hz), 7.18 (2H, d, J=1.95 Hz), 7.21(2H, dm, J=8.79 Hz), 7.60 (1H, t, J=1.95 Hz), 12.18 (1H, br,s).

Mass Spectrum (m/z) 336 (M$^+$,$^{35}$Cl), 308, 291.

Infrared Absorption Spectrum $v_{max}$ (KBr) cm$^{-1}$: 3400, 2200, 1695, 1670, 1625, 1600, 1585, 1560, 1515, 1440, 1290, 1260, 1215, 1185, 1165, 840.

PREPARATION 172

(E)-3-(3,5-Dichlorophenyl)-3-(4-ethoxyphenyl)acrylic acid

Prepared as crystals, melting at 174°–176° C. (after recrystallisation from a mixture of methylene chloride and hexane), in a yield of 89%.

NMR スペクトル (270 MHz, CDCl$_3$) δ ppm: 1.44 (3H, t, J=6.83 Hz), 4.08 (2H, q, J=6.83 Hz), 6.19 (1H, s), 6.89 (2H, dm, J=8.79 Hz), 7.12 (2H, dm, J=8.79 Hz), 7.15(2H, d, J=1.95 Hz), 7.36 (1H, t, J=1.95Hz).

Mass Spectrum (m/z): 336 (M$^+$,$^{35}$Cl, 308, 291.

Infrared Absorption Spectrum $v_{max}$ (CHCl$_3$) cm$^{-1}$: 3600–2200, 1690, 1610, 1585, 1560, 1510, 1420, 1390, 1290, 1245, 1175.

PREPARATION 173

Ethyl (Z)-3-(3,5-Dichlorophenyl)-3-(4-ethylphenyl)acrylate

Prepared as crystals, melting at 73°–75° C. (after recrystallisation from hexane), in a yield of 44%.

NMR スペクトル (270 MHz, CDCl$_3$) δ ppm: 1.15 (3H, t, J=7.32 Hz), 1.24 (3H, t, J=7.32 Hz), 2.66 (2H, q, J=7.32 Hz), 4.07 (2H, q, J=7.32 Hz), 6.38 (1H, s), 7.10 (2H, d, J=1.95 Hz), 7.13–7.23 (4H, m), 7.37 (1H, t, J=1.95 Hz).

Mass Spectrum (m/z): 348 (M$^+$, $^{35}$Cl), 319, 303, 276.

Infrared Absorption Spectrum $v_{max}$ (CHCl$_3$) cm$^{-1}$: 1710, 1620, 1605. 1585, 1560, 1410, 1370, 1345, 1270, 1160.

PREPARATION 174

Ethyl (E)-3-(3,5-Dichlorophenyl)-3-(4-ethylphenyl)acrylate

Prepared as an oil, in a yield of 13%.

NMR スペクトル (270 MHz, CDCl$_3$) δ ppm: 1.13 (3H, t, J=7.32 Hz), 1.28 (3H, t, J=7.32 Hz), 2.70 (2H, q, J=7.32 Hz), 4.07 (2H, q, J=7.32 Hz), 6.27 (1H, s), 7.09 (2H, dm, J=8.30 Hz), 7.17 (2H, d, J=1.95 Hz), 7.22 (2H, dm, J=8.30 Hz), 7.34(1H, t, J=1.95 Hz).

Mass Spectrum (m/z): 348 (M$^+$,$^{35}$Cl), 319, 303, 276.

Infrared Absorption Spectrum $v_{max}$ (CHCl$_3$) cm$^{-1}$: 1710, 1610, 1585, 1560, 1410, 1370, 1350, 1260, 1170.

PREPARATION 175

(Z)-3-(3,5-Dichlorophenyl)-3-(4-ethylphenyl)acrylic acid

Prepared as crystals, melting at 206°–208° C. (after recrystallisation from a mixture of THF and hexane), in a yield of 90%.

NMR スペクトル (270 MHz, DMSO-d$_6$) δ ppm: 1.17 (3H, t, J=7.32 Hz), 2.61 (2H, q, J=7.32 Hz), 6.43 (1H, s), 7.16–7.28 (4H,m), 7.20 (2H, d, J=1.95 Hz), 7.61 (1H, t, J=1.95 Hz), 12.32 (1H, br,s).

Mass Spectrum (m/z): 320 (M$^+$,$^{35}$Cl), 291, 275.

Infrared Absorption Spectrum $v_{max}$ (KBr) cm$^{-1}$: 3400–2200, 1695, 1670, 1620, 1605, 1580, 1560, 1415, 1275, 1220, 835, 805.

PREPARATION 176

(E)-3-(3,5-Dichlorophenyl)-3-(4-ethylphenyl)acrylic acid

Prepared as crystals, melting at 162°–164° C. (after recrystallisation from a mixture of methylene chloride and hexane), in a yield of 99%.

NMR スペクトル (270 MHz, CDCl$_3$) δ ppm: 1.28 (3H, t, J=7.32 Hz), 2.70 (2H, q, J=7.32 Hz), 6.23 (1H, s), 7.09 (2H, dm, J=8.30 Hz), 7.14 (2H, d, J=1.95 Hz), 7.21 (2H, dm, J=8.30 Hz), 7.36 (1H, t, J=1.95 Hz).

Mass Spectrum (m/z): 320 (M$^+$,$^{35}$Cl), 291, 275.

Infrared Absorption Spectrum $v_{max}$ (CHCl$_3$) cm$^{-1}$: 3600–2400, 1690, 1610, 1595, 1560, 1415, 1265, 1180, 860, 835.

PREPARATION 177

Ethyl (Z)-3-(3,5-Difluorophenyl)-3-(4-methoxyphenyl)acrylate

Prepared as crystals, melting at 65°–66° C. (after recrystallisation from hexane), in a yield of 48%.

NMR スペクトル (270 MHz, CDCl$_3$) δ ppm: 1.15 (3H, t, J=7.32 Hz), 3.82 (3H, s), 4.07 (2H, q, J=7.32 Hz), 6.33 (1H, 6.69–6.89 (3H, m), 6.86 (2H, dm, J=9.16 Hz), 7.22 (2H, dm, J=9.16 Hz).

Mass Spectrum (m/z): 318 (M$^+$), 289, 273, 246.

Infrared Absorption Spectrum $v_{max}$ (CHCl$_3$) cm$^{-1}$: 1715, 1605, 1515, 1435, 1375, 1290, 1255, 1170, 1120.

PREPARATION 178

Ethyl (E)-3-(3,5-Difluorophenyl)-3-(4-methoxyphenyl)acrylate

Prepared as an oil, in a yield of 20%.

NMR スペクトル (270 MHz, CDCl$_3$) δ ppm: 1.17 (3H, t, J=7.32 Hz), 3.85 (3H, s), 4.09 (2H, q, J=7.32 Hz), 6.26 (1H, s), 6.75–6.88 (3H, m), 6.91 (2H, dm, J=8.79 Hz), 7.13 (2H, dm, J=8.79 Hz).

Mass Spectrum (m/z): 318 (M$^+$), 289, 273, 246.

Infrared Absorption Spectrum $v_{max}$ (CHCl$_3$) cm$^{-1}$: 1715, 1620, 1610, 1595, 1515, 1435, 1370, 1295, 1250, 1170, 1120.

PREPARATION 179

(Z)-3-(3,5-Difluorophenyl)-3-(4-methoxyphenyl)acrylic acid

Prepared as crystals, melting at 1.70°–172° C. after recrystallisation from a mixture of THE and hexane), in a yield of 87%.

Nuclear Magnetic Resonance Spectrum (270 MHz, CDCl$_3$) δ ppm: 3.82 (3H, s), 6.30 (1H, s), 6.67–6.90 (3H, m), 6.86 (2H, dm, J=9.28 Hz), 7.21 (2H, dm, J=9.28 Hz).

Mass Spectrum (m/z): 290 (M$^+$), 273, 245.

PREPARATION 180

(E)-3-(3,5-Difluorophenyl)-3-(4-methoxyphenyl) acrylic acid

Prepared as crystals, melting at 140°–142° C. (after recrystallisation from a mixture of methylene chloride and hexane), in a yield of 90%.

Nuclear Magnetic Resonance Spectrum (270 MHz, CDCl$_3$) δ ppm: 3.85 (3H, s), 6.22 (1H, s), 6.75–6.94 (3H, m), 6.90 (2H, dm, J=8.79 Hz), 7.14 (2H, dm, J=8.79 Hz).

Mass Spectrum (m/z): 290 (M$^+$), 273, 245.

Infrared Absorption Spectrum $v_{max}$ (CHCl$_3$) cm$^{-1}$: 3600–2400, 1695, 1625, 1610, 1595, 1515, 1435, 1295, 1250, 1175, 1125.

PREPARATION 181

Ethyl (Z)-3-(3-Cyanophenyl)-3-(4-methoxyphenyl)acrylate

Prepared as crystals, melting at 105°–106° C. (after recrystallisation from hexane), in a yield of 43%.

Nuclear Magnetic Resonance Spectrum (270 MHz, CDCl$_3$) δ ppm: 1.15 (3H, t, J=7.32 Hz), 3.83 (3H, s), 4.05 (2H, q, J=7.32 Hz), 6.38 (1H, s), 6.86(2H, dm, J=8.79 Hz), 7.19 (2H, dm, J=8.79 Hz), 7.45 (1H, ddd, J=7.69,1.47,1.47 Hz), 7.48–7.52 (1H, m), 7.51 (1H, ddd, J=7.69,7.69,0.73 Hz),7.68 (1H, ddd, J=7.69,1.47,1.47 Hz).

Mass Soectrum (m/z): 307 (M$^+$), 278, 262, 235.

Infrared Absorption Spectrum $v_{max}$ (CHCl$_3$) cm$^{-1}$: 2240, 1715, 1610. 1515, 1375, 1280, 1260, 1170, 1030, 835.

PREPARATION 182

(Z)-3-(3-Cyanophenyl)-3-(4-methoxyphenyl)acrylic acid

Prepared as crystals, melting at 193°–194° C. (after recrystallisation from a mixture of THF and hexane), in a yield of 8%.

Nuclear Magnetic Resonance Spectrum (270 MHz, CDCl$_3$) δ ppm: 3.83 (3H, s), 6.34 (1H, s), 6.86 (2H, dm, J=8.79 Hz), 7.17 (2H, dm, J=8.79 Hz), 7.44 (1H, ddd, J=7.82,1.47,1.47 Hz), 7.45–7.50 (1H, m), 7.48 (1H, dd, J=7.82, 7.82 Hz), 7.67 (1H, ddd, J=7.82,1.47,1.47 Hz).

Mass Spectrum (m/z): 279 (M$^+$), 262, 234.

Infrared Absorption Spectrum $v_{max}$ (CHCl$_3$) cm$^{-1}$: 3600–2400, 2240, 1690, 1600, 1570, 1510, 1425, 1285, 1260, 1180, 1035, 835.

PREPARATION 183

Ethyl (Z)-3-(3-Fluorophenyl)-3-(4-ethoxyphenyl)acrylate

Prepared as an oil, in a yield of 16%.

Nuclear Magnetic Resonance Spectrum (270 MHz, CDCl$_3$) δ ppm: 1.12 (3H, t, J=7.33 Hz), 1.41 (3H, t, J=6.96 Hz), 4.038 (2H, q, J=6.96 Hz), 4.042 (2H, q, J=7.33 Hz), 6.32 (1H, s), 6.83 (2H, dm, J=8.79 Hz), 6.91 (1H, ddd, J=9.53,2.56,146 Hz), 6.95–7.02 (1H, m), 7.07 (1H, dddd, J=8.43,8.43,2.56,1.10 Hz), 7.22 (2H, dm, J=8.79 Hz), 7.34 (1H, ddd, J=8.43,8.43,5.86 Hz).

Mass Spectrum (m/z): 314 (M$^+$), 285, 269, 242.

Infrared Absorption Spectrum $v_{max}$ (CHCl$_3$) cm$^{-1}$: 1705, 1600, 1580. 1510, 1475, 1370, 1270, 1250, 1160, 1115, 1035.

PREPARATION 184

Ethyl (E)-3-(3-Fluorophenyl)-3-(4-ethoxyphenyl)acrylate

Prepared as an oil, in a yield of 8%.

Nuclear Magnetic Resonance Spectrum (270 MHz, CDCl$_3$) δ ppm: 1.16 (3H, t, J=7.32 Hz), 1.43 (3H, t, J=6.83 Hz), 4.07 (2H, q, J=6.83 Hz), 4.09 (2H, q, J=7.32 Hz), 6.26(1H, s), 6.89(2H, dm, J=8.79 Hz), 6.94–7.13(3H,m), 7.13(2H, dm, J=8.79 Hz), 7.28 (1H, ddd, J=8.30,8.30,5.86 Hz).

Mass Spectrum (m/z): 314 (M$^+$), 285, 269, 242.

Infrared Absorption Spectrum $v_{max}$ (CHCl$_3$) cm$^{-1}$: 1710, 1605, 1580, 1510, 1485, 1475, 1440, 1370, 1240, 1170, 1130, 1035.

PREPARATION 185

(Z)-3-(3-Fluorophenyl)-3-(4-ethoxyphenyl)acrylic acid

Prepared as crystals, melting at 154°–155°C. (after recrystallisation from a mixture of THF and hexane), in a yield of 91%.

Nuclear Magnetic Resonance Spectrum (270 MHz, CDCl$_3$) δ ppm: 1.41 (3H, t, J=6.831 Hz), 4.04 (2H, q, J=6.83 Hz), 6.28 (1H, s), 6.83 (2H, dm, J=8.79 Hz), 6.90 (1H, ddd, J=9.28,2.44,1.46 Hz), 6.94–7.00 (1H, m), 7.06 (1H, dddd, J=8.30, 8.30, 2.44,0.98 Hz), 7.20 (2H, dm, J=8.79 Hz), 7.33 (1H, ddd, J=8.30,8.30,5.86 Hz).

Mass Spectrum (m/z): 286 (M$^+$), 269, 257, 241.

Infrared Absorption Spectrum $v_{max}$ (CHCl$_3$) cm$^{-1}$: 3600–2400, 1690, 1595, 1510, 1435, 1285, 1250, 1175, 1115, 1035.

PREPARATION 186

(E)-3-(3-Fluorophenyl)-3-(4-ethoxyphenyl)acrylic acid

Prepared as crystals, melting at 148°–149° C. (after recrystallisation from a mixture of methylene chloride and hexane), in a yield of 95%.

Nuclear Magnetic Resonance Spectrum (270 MHz, CDCl$_3$) δ ppm: 1.44 (3H, t, J=6.83 Hz), 4.07 (2H, q, J=6.83 Hz), 6.22 (1H, s), 6.88 (2H, dm, J=8.79), 6.92–7.00 (1H, m), 7.01–7.12 (2H, m), 7.14 (2H, dm, J=8.79 Hz), 7.29(1H, ddd, J=8.30, 8.30, 5.86 Hz).

Mass Spectrum (m/z): 286 (M$^+$), 269, 257, 241.

Infrared Absorption Spectrum $v_{max}$ (CHCl$_3$) cm-1: 3600–2400, 1690, 1605, 1580, 1510, 1485, 1440, 1285, 1265, 1240, 1170, 1035.

PREPARATION 187

Ethyl (Z)-3-(3-Chloro-5-methylphenyl)-3-(4-methoxyphenyl)acrylate

Prepared as crystals, melting at 83°–85° C. (after recrystallisation from hexane), in a yield of 49%.

Nuclear Magnetic Resonance Spectrum (270 MHz, $CDCl_3$) δ ppm: 1.12 (3H, t, J=7.33 Hz), 2.33 (3H, s), 3.82 (3H, s), 4.05 (2H, q, J=7.33 Hz), 6.29 (1H, s), 6.85 (2H, dm, J=8.79 Hz), 6.86–6.90 (1H, m), 6.98–7.03 (1H, m), 7.14–7.20 (1H, m), 7.23 (2H, dm, J=8.79 Hz).

Mass Spectrum (m/z): 330 ($M^+$, $^{35}Cl$), 301, 285, 258.

Infrared Absorption Spectrum $\nu_{max}$ ($CHCl_3$) $cm^{-1}$: 1710, 1600, 1575, 1510, 1290, 1275, 1250, 1165, 1030, 830.

PREPARATION 188

Ethyl (E)-3-(3-Chloro-5-methylphenyl)-3-(4-methoxyphenyl)acrylate

Prepared as an oil, in a yield of 17%.

Nuclear Magnetic Resonance Spectrum (270 MHz, $CDCl_3$) δ ppm: 1.17 (3H, t, J=7.33 Hz), 2.30 (3H, s), 3.85 (3H, s), 4.09 (2H, q, J=7.33 Hz), 6.23 (1H, s), 6.90 (2H, dm, J=8.79 Hz), 6.95–7.02 (1H, m), 7.04–7.09 (1H, m), 7.13–7.19 (1H, m), 7.14 (2H, dm J=8.79 Hz).

Mass Spectrum (m/z): 330 ($M^+$, $^{35}Cl$), 301, 285, 258.

Infrared Absorption Spectrum $\nu_{max}$ ($CDCl_3$) $cm^{-1}$: 1710, 1610, 1570, 1510, 1290, 1280, 1245, 1170, 1140, 1030.

PREPARATION 189

(Z)-3-(3-Chloro-5-methylphenyl)-3-(4-methoxyphenyl)acrylic acid

Prepared as crystals, melting at 190°–192° C. (after recrtstailisation from a mixture of THE and hexane), in a yield of 93%.

Nuclear Magnetic Resonance Spectrum (270 MHz, $CDCl_3$) δ ppm: 2.33 (3H, s), 3.82 (3H, s), 6.26 (1H, s), 6.85 (2H, dm, J=8.79 Hz), 6.85–6.90 (1H, m), 6.96–7.01 (1H, m), 7.14–7.20 (1H, m), 7.21 (2H, dm, J=8.79 Hz).

Mass Spectrum (m/z): 302 ($M^+$, $^{35}Cl$), 285, 257.

Infrared Absorption Spectrum $\nu_{max}$ ($CDCl_3$) $cm^{-1}$: 3600–2400, 1690, 1600, 1570, 1510, 1280, 1250, 1175, 1030, 830.

PREPARATION 190

(E)-3-(3-Chloro-5-methylphenyl)-3-(4-methoxyphenyl)acrylic acid

Prepared as crystals, melting at 156°–158° C. (after recrystallisation from a mixture of methylene chloride and hexane), in a yield of 91%.

Nuclear Magnetic Resonance Spectrum (270 MHz, $CDC_3$) δ ppm: 2.30 (3H, s). 3.85 (3H, s), 6.18 (1H, s), 6.89 (2H, dm, J=8.791 Hz). 6.94–6.99 (1H, m), 7.00–7.06 (1H, m), 7.14–7.20 (1H, m), 7.14 (2H, dm, J=8.79 Hz).

Mass Spectrum (m/z): 302 ($M^+$, $^{35}Cl$), 285, 257.

Infrared Absorption Spectrum $\nu_{max}$ ($CHCl_2$) $cm^{-1}$: 3600–2400, 1690, 1605, 1570, 1510, 1290, 1245, 1170, 1030, 870, 850, 830.

PREPARATION 191

Ethyl (Z)3-(3-Chloro-5-methylphenyl)-3-(4-ethoxyphenyl)acrylate

Prepared as an oil, in a yield of 17%.

Nuclear Magnetic Resonance Spectrum (270 MHz, $CDCl_3$) δ ppm: 1.12 (3H, t, J=7.32 Hz) 1.41 (3H, t. J=6.96 Hz), 2.33 (3H, s), 4.04 (2H, q, J=6.96 Hz), 4.05 (2H, q, J=7.32Hz), 6.29 (1H, s), 6.83 (2H, dm, J=8.79 Hz), 6.85–6.91 (1H, m), 6.98–14 7.02 (1H, m), 7.15–7.19 (1H, m). 7.21 (2H, dm, J=8.79 Hz).

Mass Spectrum (m/z): 344 ($M^+$, $^{35}Cl$), 315, 299, 272.

Infrared Absorption Spectrum $\nu_{max}$ ($CDCl_3$) $cm^{-1}$: 1705, 1600, 1570, 1510, 1475, 1365, 1270, 1250, 1160, 1035, 850, 830.

PREPARATION 192

Ethyl (E)-3-(3-Chloro-5-methylphenyl)-3-(4-ethoxyphenyl)acrylate

Prepared as an oil, in a yield of 6%.

Nuclear Magnetic Resonance Spectrum (270 MHz, $CDCl_3$) δ ppm: 1.16 (3H, t, J=7.32 Hz), 1.43 (3H, t. J=6.84 Hz), 2.30 (3H, s), 4.07 (2H, q, J=6.84 Hz), 4.08 (2H, q, J=7.32 Hz), 6.22 (1H, s), 6.89 (2H, dm, J=8.79 Hz), 6.95–7.01 (1H, m), 7.04–7.09 (1H, m), 7.12–7.18 (1H, m), 7.12 (2H, dm J=8.79 Hz).

Mass Spectrum (m/z): 344 ($M^+$, $^{35}Cl$), 315, 299, 272.

Infrared Absorption Spectrum $\nu_{max}$ ($CHCl_3$) $cm^{-1}$: 1705, 1605, 1570, 1510, 1475, 1365, 1280, 1240, 1165, 1140, 1110, 1035, 850.

PREPARATION 193

(Z)-3-(3-Chlorro-5-methylphenyl)-3-(4-ethoxyphenyl)acrylic acid

Prepared as crystals, melting at 197°–199° C. (after recrystallisation from a mixture of THF and hexane), in a yield of 89%.

Nuclear Magnetic Resonance Spectrum (270 MHz, $CDCl_3$) δ ppm: 1.41 (3H, t, J=6.84 Hz), 2.32 (3H, s), 4.04 (2H, q, J=6.84 Hz), 6.26 (1H, s), 6.83 (2H, dm, J=9.28 Hz), 6.85–6.91 (1H, m), 6.96–7.02 (1H, m), 7.14–7.20 (1H, m), 7.20 (2H, dm, J=9.28 Hz).

Mass Spectrum (m/z): 316 ($M^+$, $^{35}Cl$), 287, 271.

PREPARATION 194

(E)-3-(3-Chloro-5-methylphenyl)-3-(4-ethoxyphenyl)acrylic acid

Prepared as crystals, melting at 163°–165° C. (after recrystallisation from a mixture of methylene chloride and hexane), in a yield of 86%.

Nuclear Magnetic Resonance Spectrum (270 MHz, $CDCl_3$) δ ppm: 1.44 (3H, t, J=6.84 Hz). 2.30 (3H, s), 4.07 (2H, q, J=6.84 Hz), 6.17 (1H, s), 6.87 (2H, dm, J=8.79 Hz), 6.93–7.00 (1H, m), 7.00–7.07 (1H, m), 7.14–7.20 (1H, m), 7.13 (2H, dm, J=8.79 Hz).

Mass Spectrum (m/z): 316 ($M^+$, $^{35}Cl$), 287, 271.

PREPARATION 195

1-[(E)-3-(2-Chlorophenyl)-3-(4-methoxyphenyl) acryloyl]piperazine

By similar reaction and purification as those of PREPARATION 111, using a compound of PREPARATION 76 (5.65 g), there was obtained the title compound (6.37 g) as a powder, melting at 108°–110° C.

Nuclear Magnetic Resonance Spectrum (270 MHz, $CDCl_3$) δ ppm: 1.75 (1H, s). 2.35–2.45 (2H, m), 2.65–2.75 (2H, m), 3.25–3.35 (2H, m), 3.45–3.55 (2H, m), 3.82 (3H, s), 6.28 (1H, s), 6.86 (2H, dm, J=8.79 Hz), 7.16–7.36 (6H, m).

Elemental Analysis for $C_{20}H_{21}N_2O_2Cl$: Calcd.: C,67.32; H, 5.93; N,7.85; Cl,9.93. Found: C,67.09; H, 5.81; N,7.81; Cl,10.10.

PREPARATION 196

4-Acetoxy-3,5-dimethoxybenzoic acid

To a mixture of 3,5-dimethoxy-4-hydroxybenzoic acid (3.00 g) and acetic anhydride (30 ml) was dropwise added pyridine (15 ml) with ice-cooling over a 5 minutes period. After stirring at room temperature for 30 minutes, the reaction mixture was poured into water and stirred at room temperature for 30 minutes followed by extracting thrice with ethyl acetate. The combined extract was washed with 10% hydrochloric acid, dried and concentrated. The residue was recrystallized from a mixture of methylene chloride and hexane to afford the title compound (3.13 g), melting at 192°–194° C.

Nuclear Magnetic Resonance Spectrum (270 MHz, $CDCl_3$) δ ppm: 2.36 (3H, s), 3.90 (6H, s). 7.40 (2H, s).

Elemental Analysis for $C_{11}H_{12}O_5$: Calcd.: C,55.00; H, 5.04. Found: C.55.02; H, 5.04.

PREPARATION 197

Ethyl 3,5-dichlorocinnamate

To a mixture of sodium hydride (0.84 g: 55% dispersion in mineral oil) and tetrahydrofuran (40 ml) was dropwise added a solution of ethyl diethylphosphonoacetate (4.33 g) in tetrahydrofuran (20 ml) with ice-cooling of 6° to 12° C. over a 12 minutes period. After stirring at room temperature for 30 minutes, to the mixture thus obtained was dropwise added a solution of 3,5-dichlorobenzaldehyde (3.07 g) in tetrahydrofuran (20 ml) with ice-cooling of 8° to 11° C. over a 10 minutes period. After stirring at room temperature for 4 hours, the reaction mixture was poured into water and extracted twice with ethyl acetate. The combined extract was washed with water, dried and concentrated. The residue was purified by flash column chromatography through silica gel (100 g). Fractions eluted with a 99:1 mixture of hexane and ethyl acetate were collected and worked up to afford the title compound (3.33 g), melting at 71°–73° C.

Nuclear Haaneric Resonance Spectrum (270 MHz, $CDCl_3$) δ ppm: 1.34 (3H, t, J=7.32 Hz), 4.27 (2H, q, J=7.32 Hz), 6.43 (1H, d, J=16.11 Hz), 7.36 (1H, t, J=1.95 Hz), 7.38 (2H, d, J=1.95 Hz), 7.54 (1H, d, J=16.11 Hz).

Mass Spectrum (m/z): 244 ($M^+$, $^{35}Cl$), 216, 199, 171.

Infrared Absorption Spectrum $\nu_{max}$ ($CHCl_3$) $cm^{-1}$: 1770, 1640, 1580, 1560, 1415, 1360, 1310, 1280, 1270, 1170, 1020, 970, 845.

Elemental Analysis for $C_{11}H_{10}O_2Cl_2$: Calcd.: C,53.90; H, 4.11; Cl28.93. Found : C,54.01; H, 4.16; Cl28.76.

PREPARATION 198

Ethyl 2,5-dichlorocinnamate

Following the procedure described in PREPARATION 197, but using 2,5-dichlorobenzaldehyde (9.74 g), there was obtained the title compound (12.17 g), melting at 34°–36° C.

Nuclear Magnetic Resonance Spectrum (270 MHz, $CDCl_3$) δ ppm: 1.35 (3H, t, J=7.32 Hz), 4.29 (2H, q, J=7.32 Hz), 6.42 (1H, d, J=16.12 Hz), 7.27 (1H, dd, J=8.31, 2.44 Hz), 7.35 (1H, d, J=8.30 Hz), 7.59 (1H, d. J=2.44 Hz), 7.99 (1H, d, J=16.12 Hz).

Mass Spectrum (m/z): 244 ($M^+$, $^{35}Cl$), 209, 199.

Elemental Analysis for $C_{11}H_{10}O_2Cl_2$: Calcd.: C,53.90; H, 4.11; Cl,28.93. Found: C,54.14; H, 4.24; Cl, 28.77.

PREPARATION 199

Ethyl 2,3-dichlorocinnamate

Following the procedure described in PREPARATION 197, but using 2,3-dichlorobenzaldehyde (20.00 g), there was obtained the title compound (23.46 g), melting at 69°–70° C.

Nuclear Magnetic Resonance Spectrum (270 MHz, $CDCl_3$) δ ppm: 1.35 (3H, t, J=7.32 Hz), 4.29 (2H, q, J=7.32 Hz), 6.41 (1H, d, J=16.12 Hz), 7.22 (1H, dd, J=8.30, 8.30 Hz), 7.48 (1H, dd, J=8.30,1.47 Hz), 7.51 (1H, dd, J=8.30, 1.47 Hz), 8.08 (1H, d, J=16.12 Hz).

Mass Spectrum (m/z): 244 ($M^+$, $^{35}Cl$), 209, 199.

Elemental Analysis for $C_{11}H_{10}O_2Cl_2$: Calcd.: C,53.90; H, 4.11; Cl,28.93. Found : C,54.10; H, 4.31; Cl,28.65.

PREPARATION 200

Ethyl 3,5-dimethylcinnamate

The procedure described in PREPARATION 197 was repeated, but using 3,5-dimethylbenzaldehyde (11.44 g). The crude product was purified by flash column chromatography through silica gel (300 g). Fractions eluted with a 9:1 mixture of hexane and ethyl acetate were collected and worked up to afford the title compound (15.22 g).

Nuclear Magnetic Resonance Spectrum (270 MHz, $CDCl_3$) δ ppm: 1.33 (3H, t, J=7.32 Hz), 2.33 (6H, S), 4.26 (2H, q, J=7.32 Hz), 6.41 (1H, d, J=16.12 Hz), 7.02 (1H, br,s), 7.14 (2H, br,s), 7.63 (1H, d, J=16.12 Hz).

Mass Spectrum (m/z): 204 ($M^+$), 189, 175, 159.

Elemental Analysis for $C_{13}H_{15}O_2$: Calcd.: C,76.44; H, 7.90. Found : C,76.67; H, 8.14.

PREPARATION 201

1-[(Z)-3-(3,5-Dichlorophenyl)-3-(4-methoxyphenyl) acryloyl]piperazine

By similar reaction and purification as those of PREPARATION 111, using a compound of PREPARATION 147 (1.00 g), there was obtained the title compound (1.07 g) as a powder.

Nuclear Magnetic Resonance Spectrum (270 MHz, $CDCl_3$) δ ppm: 1.89 (1H, s), 2.45–2.65 (2H, m), 2.65–2.85 (2H, m), 3.25–3.45 (2H, m), 3.45–3.65 (2H, m), 3.83 (3H, s), 6.33 (1H, s), 6.87 (2H, dm, J=8.79 Hz), 7.17 (2H, d, J=1.95 Hz), 7.19 (2H, dm, J=8.79 Hz), 7.35 (1H, J=1.95 Hz).

Mass Spectrum (m/z): 390 (M$^+$, $^{35}$Cl), 305, 85.

Infrared Absorption Spectrum $v_{max}$ (CHCl$_3$) cm$^{-1}$: 1630, 1610, 1565, 1515, 1465, 1445, 1250, 1180.

Elemental Analysis for $C_{20}H_{20}N_2O_2Cl_2$: Calcd.: C,51.39; H, 5.15; N,7.16; Cl,18.12. Found: C,61.44; H, 5.39: N,7.04; Cl,17.93.

EXPERIMENT 1

Inhibition of PAF-induced hypotension

The test animals used were Wistar-Imamichi rats, each weighing from 350 to 450 g, anesthetized with Inactin (90 mg/kg, intraperitoneally).

Blood pressure was continuously measured throughout the experiment through a cannula inserted into the femoral artery. Each drug sample to be tested was intravenously injected through a cannula inserted into the femoral vein.

At first, 1-$C_{16:0}$ PAF was injected intravenously in amounts of 10 ng/kg at each injection at intervals of 5 minutes until the degree of the hypotensive response became constant. Then, each drug sample to be tested was intravenously injected. After one minute, the same dose of PAF was administered again. The drug sample was cumulatively administered. From its inhibition rate against the PAF-induced hypotensive effect, the 50% inhibitive dose (ID$_{50}$) was determined, and is regarded as an index of PAF-antagonist activity. For administration, the PAF was dissolved in physiological saline solution containing 0.25% w/v of bovine serum albumin (BSA). The compounds under test were dissolved in dimethylformamide for use.

In addition to the compounds of the invention that were tested, we also tested a prior art compound, CV-3988, under the same conditions, so as to show the extent of the improvement in activity achieved by the compounds of the invention as compared with what is recognised to be one of the most effective of the available prior art compounds. CV-3988 is disclosed in U.S. Pat. No. 4,408,052, and is structurally related to PAF itself.

Table 4 below shows the results. In this Table, the compounds of the invention are identified by the number of the foregoing Example in which they were prepared.

TABLE 4

| Compound of Example | Inhibitory Effect ID$_{50}$ (mg/kg) |
|---|---|
| 1 | 0.057 |
| 2 | 0.039 |
| 3 | 0.048 |
| 4 | 0.074 |
| 5 | 0.054 |
| 7 | 0.014 |
| 8 | 0.058 |
| 15 | 0.022 |
| 16 | 0.074 |
| 17 | 0.0083 |
| 18 | 0.026 |
| 25 | 0.052 |
| 28 | 0.039 |
| 29 | 0.048 |
| 30 | 0.044 |
| 31 | 0.0067 |
| 33 | 0.0078 |
| 34 | 0.021 |
| 35 | 0.012 |
| 36 | 0.039 |
| 39 | 0.0080 |
| 41 | 0.0071 |

TABLE 4-continued

| Compound of Example | Inhibitory Effect ID$_{50}$ (mg/kg) |
|---|---|
| 42 | 0.0050 |
| 43 | 0.0044 |
| 44 | 0.0075 |
| 45 | 0.0066 |
| 48 | 0.012 |
| 49 | 0.0080 |
| 52 | 0.0084 |
| 53 | 0.0074 |
| 56 | 0.011 |
| 70 | 0.0033 |
| 71 | 0.0074 |
| 72 | 0.0097 |
| 73 | 0.0084 |
| 74 | 0.0055 |
| 75 | 0.0051 |
| 76 | 0.0092 |
| 77 | 0.0037 |
| 78 | 0.0073 |
| 79 | 0.0066 |
| 80 | 0.0065 |
| 82 | 0.013 |
| 83 | 0.011 |
| 84 | 0.0086 |
| 85 | 0.0061 |
| 86 | 0.015 |
| 87 | 0.011 |
| 88 | 0.092 |
| Prior art compound, CV-3988 | 0.42 |

EXPERIMENT 2

Inhibitory effect in vitro against PAF-induced blood platelet aggregation

Blood samples were drawn from a rabbit and one part by volume of each sample was immediately mixed with ⅑ part of a 3.8% w/v aqueous solution of sodium citrate. The samples were centrifuged at 150× G at room temperature for 15 minutes to obtain a platelet rich plasma (PRP) fraction from the upper layer. The remains were further centrifuged at 1,000× G for 15 minutes to obtain a platelet poor plasma (PPP) fraction from the upper layer. The PRP and PPP fractions were mixed appropriately, to obtain a sample in which the final count of blood platelets was adjusted to be 6×10$^5$ per µl. According to the method reported by Born et al. [G. V. R. Born et al.: J. Physiol. 62, 67–68 (1962)], blood platelet aggregation was determined by an increase in light transmission measured using an aggregometer. 3 µl of a solution of the test compound in dimethyl sulfoxide were added to 272 µl of PRP, and, after 1 minute, 25 µl of a physiological saline solution containing 1-$C_{16:0}$ PAF (at a final concentration of 10$^{-8}$~3×10$^{-8}$M) were added. Inhibition of aggregation was observed for 5 minutes. At the end of this time, the inhibition rate was calculated from this value and the value of PAF-induced aggregation which was observed when dimethyl sulfoxide only was used without the addition of any test compound. IC$_{50}$ values were calculated from the dose-response curve.

Table 5 below shows the results.

TABLE 5

| Compound of Example | Inhibitory effect IC$_{50}$ (M) |
|---|---|
| 1 | 3.2 × 10$^{-7}$ |
| 2 | 2.0 × 10$^{-7}$ |

TABLE 5-continued

| Compound of Example | Inhibitory effect $IC_{50}$ (M) |
|---|---|
| 3 | $2.2 \times 10^{-7}$ |
| 5 | $2.6 \times 10^{-7}$ |
| 15 | $6.8 \times 10^{-8}$ |
| 17 | $6.3 \times 10^{-8}$ |
| 28 | $2.3 \times 10^{-7}$ |
| 29 | $1.8 \times 10^{-7}$ |
| 30 | $1.5 \times 10^{-7}$ |
| 31 | $4.4 \times 10^{-8}$ |
| 33 | $4.3 \times 10^{-8}$ |
| 35 | $1.1 \times 10^{-7}$ |
| 36 | $2.2 \times 10^{-7}$ |
| 37 | $1.1 \times 10^{-7}$ |
| 40 | $1.1 \times 10^{-7}$ |
| 41 | $6.7 \times 10^{-8}$ |
| 45 | $3.9 \times 10^{-8}$ |
| 49 | $6.6 \times 10^{-8}$ |
| 52 | $3.0 \times 10^{-8}$ |
| 53 | $5.2 \times 10^{-8}$ |
| 70 | $3.0 \times 10^{-8}$ |
| 71 | $3.8 \times 10^{-8}$ |
| 73 | $8.6 \times 10^{-8}$ |
| 74 | $5.8 \times 10^{-8}$ |
| 75 | $9.9 \times 10^{-8}$ |
| 76 | $8.3 \times 10^{-8}$ |
| 77 | $2.6 \times 10^{-8}$ |
| 78 | $2.9 \times 10^{-8}$ |
| 80 | $2.8 \times 10^{-8}$ |
| 81 | $3.1 \times 10^{-8}$ |
| 82 | $9.9 \times 10^{-9}$ |
| 87 | $6.5 \times 10^{-8}$ |

EXPERIMENT 3

Inhibitory effect on PAF-receptor binding

Blood samples were drawn from the heart of a rabbit. 1 part by volume of each sample was mixed immediately with ⅑ part of 0.77M solution of disodium ethylenediaminetetraacetate. After a similar procedure than described in Experiment 2, a precipitated blood platelet sample was obtained. This blood platelet sample was washed, and, after repeated freezing and thawing for cellular breakdown, it was laid on top of double layers consisting of 0.25M and 1.5M sucrose solutions. By centrifugation at 63,500× G, for 2 hours at 4° C., the fraction obtained from the interface between the 0.25M and 1.5M sucrose solutions was collected and is regarded as a PAF-receptor membrane fraction. A receptor binding experiment was conducted according to a method very similar to that reported by Hwang et al. [San-Bao Hwang et al.: J. Biol. Chem. 260, 15639–15645 (1985)]. The specific binding of $^3$H-PAF was measured using a Wattman GF/C filter. A test compound was dissolved in dimethyl sulfoxide and diluted 100 fold with a buffer solution containing 0.5% bovine serum albumin. Nine parks by weight of the solution, for a receptor binding experiment, was mixed with one park of the test compound solution prepared above. The percent inhibition of the specific binding was plotted for a log concentration of the test compound, and the 50% inhibitory concentration ($IC_{50}$) was calculated from the linear line connecting all the plotted points.

The results are shown in Table 6.

TABLE 6

| Compound of Example | Inhibition of receptor binding ($IC_{50}$, M) |
|---|---|
| 1 | $4.7 \times 10^{-8}$ |
| 5 | $4.7 \times 10^{-8}$ |
| 15 | $4.3 \times 10^{-8}$ |
| 31 | $1.4 \times 10^{-8}$ |
| 41 | $1.7 \times 10^{-7}$ |
| 42 | $2.0 \times 10^{-8}$ |
| 43 | $1.3 \times 10^{-8}$ |
| 44 | $1.5 \times 10^{-8}$ |
| 45 | $1.6 \times 10^{-8}$ |
| 49 | $2.1 \times 10^{-8}$ |
| 56 | $3.5 \times 10^{-8}$ |
| 72 | $2.6 \times 10^{-8}$ |
| 75 | $2.3 \times 10^{-8}$ |
| 77 | $1.4 \times 10^{-8}$ |
| 81 | $3.2 \times 10^{-8}$ |
| 83 | $1.4 \times 10^{-8}$ |
| 84 | $4.0 \times 10^{-8}$ |
| 85 | $2.0 \times 10^{-8}$ |
| 87 | $7.6 \times 10^{-8}$ |
| Prior art compound, CV-3988 | $1.6 \times 10^{-6}$ |

As can be seen from this table, the novel N-acryloylpiperazine derivatives of the present invention have an excellent PAF-antagonist activity.

EXPERIMENT 4

Acute toxicity

Each of the compounds prepared as described in Examples 2, 7 and 15 was separately administered orally in a dose of 300 mg/kg to each of a group of 3 male ddy mice (5 weeks old). The mice were observed for a period of one week, during which time all mice survived, indicating that the compounds of the present invention have a very low toxicity.

FORMULATION 1

Tablets

The composition was as follows:

| | |
|---|---|
| Compound of Example 3 | 50 mg |
| Lactose | 98 mg |
| Corn starch | 30 mg |
| Microcrystalline cellulose | 20 mg |
| Magnesium stearate | 2 mg |
| | 200 mg |

All of the above ingredients, except for the magnesium stearate, were blended for 30 minutes, after which the magnesium stearate was added through a screen, and the mixture was blended for a further 5 minutes. The mixture was then compressed to form tablets of diameter 8 min.

FORMULATION 2

Capsules

The composition was as follows:

| | |
|---|---|
| Compound of Example 3 | 50 mg |
| Lactose | 98 mg |
| Corn starch | 50 mg |
| Magnesium stearate | 2 mg |
| | 200 mg |

All of the above ingredients were blended for 5 minutes, after which the mixture was filled into No. 3 capsules.

131

FORMULATION 3

Granules

The composition was as follows:

| | |
|---|---|
| Compound of Example 3 | 50 mg |
| Lactose | 730 mg |
| Corn starch | 200 mg |
| Hydroxypropyl cellulose | 20 mg |
| | 1000 mg |

The first three of the above ingredients were mixed, and then the mixture was moistened with a 10% aqueous solution of the hydroxypropyl cellulose. The moistened mixture was then granulated by passing it through a basket with an extruder of diameter 0.5 mm. The granules were dried at 60° C. and sized through a 16 mesh screen (Tyler standard mesh).

FORMULATION 4

Suppositories 50 mg of the Compound of Example 3 were dispersed in 1950 mg of Witepsol (trade mark) at 50° C. and poured into an appropriate mold.

FORMULATION 5

Syrups

The composition was as follows:

| | |
|---|---|
| Compound of Example 3 | 1 g |
| Sucrose | 50 g |
| Carboxymethylcellulose sodium | 0.25 g |
| Citric acid | 0.15 g |
| Sodium citrate | 1 g |
| Sodium benzoate | 0.5 g |
| Purified Water | 100 ml |

The sucrose, citric acid, sodium citrate and sodium benzoate were dissolved in purified water; the carboxymethylcellulose sodium was dispersed in the resulting solution with the active compound, and then the volume was adjusted with more purified water.

FORMULATION 6

Injections

The composition was as follows:

| | |
|---|---|
| Compound of Example 3 | 1.0 mg |
| Propylene glycol | 150.0 mg |
| Polysorbate 80 | 0.5 mg |
| Sodium dihydrogen phosphate (dihydrate) | 1.6 mg |
| Disodium hydrogen phosphate (anhydrous) | 1.4 mg |
| Purified water for injection | 1.0 ml |

The active compound was dissolved in a mixture of the propylene glycol and the Polysorbate 80, and the resulting solution was mixed with water for injection. The phosphates were then dissolved in the solution and the volume was adjusted. The solution was filled into an ampoule, which was then sealed and sterilized at 121° C. for 20 minutes.

We claim:

1. A compound of formula (I):

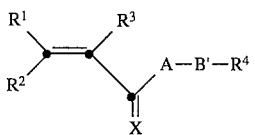

wherein:

$R^1$ and $R^2$ are the same or different, and each represents a group having the formula —$R^5$, —CH=CH—$R^5$ or —C≡C—$R^5$, wherein $R^5$ represents a $C_6$–$C_{14}$ carbocyclic aryl group which is unsubstituted or has at least one substituent selected from the group consisting of substituents (a), defined below, or an aromatic heterocyclic group having from 5 to 14 ring atoms, of which from 1 to 5 are hetero-atoms selected from the group consisting of nitrogen, oxygen and sulfur hereto-atoms, said heterocyclic group being unsubstituted or having at least one substituent selected from the group consisting of substituents (a), defined below;

$R^3$ represents a hydrogen atom, a $C_1$–$C_6$ alkyl group, a cyano group, or a group having the formula —$R^5$, in which $R^5$ is as defined above;

X represents an oxygen atom or a sulfur atom;

A represents a 1,4-piperazin-1,4-diyl group or a 1,4-homopiperazin-1,4-diyl group;

B represents a $C_1$–$C_6$ alkylene group, a carbonyl group, a thiocarbonyl group, a sulfinyl group or a sulfonyl group;

$R^4$ represents an unsubstituted phenyl group or a substituted phenyl group having from 1 to 5 substituents selected from the group consisting of substituents (a) and substituents (b), defined below:

substituents (a):

$C_1$–$C_{22}$ alkyl groups: $C_1$–$C_{22}$ alkoxy groups;

$C_1$–$C_6$ haloalkyl groups; hydroxy groups;

$C_{1-4}$ alkylenedioxy groups; $C_1$–$C_{22}$ aliphatic carboxylic acyloxy groups; substituted $C_1$–$C_6$ aliphatic carboxylic acyloxy groups having at least one substituent selected from the group consisting of substituents (c), defined below; $C_7$–$C_{15}$ carbocyclic aromatic carboxylic acyloxy groups; substituted $C_7$–$C_{15}$ carbocyclic aromatic carboxylic acyloxy groups having at least one substituent selected from the group consisting of substituents (d), defined below; $C_8$–$C_{15}$ aralkyloxycarbonyloxy groups in which the aryl part is unsubstituted or has at least one substituent selected from the group consisting of substituents (d), defined below; $C_1$–$C_6$ alkanesulfonyloxy groups in which the alkane part is unsubstituted or has at least one substituent selected from the group consisting of substituents (c), defined below; arylsulfonyloxy groups in which the aryl part is unsubstituted or has at least one substituent selected from the group consisting of substituents (d), defined below; halogen atoms; and nitro groups;

substituents (b):

$C_1$–$C_6$ alkylsulfonyl groups; $C_1$–$C_6$ alkylsulfinyl groups; and $C_1$–$C_6$ alkylthio groups;

substituents (c):

$C_1$–$C_6$ alkyl groups; $C_1$–$C_6$ haloalkyl groups; halogen atoms; $C_1$–$C_6$ alkoxy groups; and ($C_1$–$C_6$ alkanoyloxy)methoxycarbonyl groups;

substituents (d):

$C_1$–$C_6$ alkyl groups; $C_1$–$C_6$ alkoxy groups; halogen atoms; unsubstituted $C_6$–$C_{10}$ aryl groups; nitro groups, and ($C_1$–$C_6$ alkoxy)carbonyl groups;

and pharmaceutically acceptable salts thereof.

2. A pharmaceutical composition comprising an effective amount of a PAF antagonist in combination with a pharmaceutically acceptable carrier or diluent, wherein the PAF antagonist is selected from the group consisting of the compound of formula (I), as defined in claim 1, and pharmaceutically acceptable salts thereof.

3. A method of treating a PAF-mediated pathology in a mammal susceptible to such pathology by administering to said mammal an effective amount of a PAF antagonist selected from the group consisting of the compound of formula (I), as defined in claim 1, and pharmaceutically acceptable salts thereof.

4. A method for the treatment or prophylaxis of psoriasis, nephritis, asthma, inflammation or shock comprising administering an amount of a PAF antagonist to an animal sufficient to effect treatment or prophylaxis of psoriasis, nephritis, asthma, inflammation or shock, wherein said PAF antagonist is selected from the group consisting of the compound of formula (I), as defined in claim 1, and pharmaceutically acceptable salts thereof.

5. The compound of claim 1, wherein $R^2$ represents a substituted phenyl group having one to three substituents selected from the group consisting of $C_1$–$C_{22}$ alkyl groups, $C_1$–$C_6$ haloalkyl groups and halogen atoms.

* * * * *